US009029295B2

(12) United States Patent
Kuragano et al.

(10) Patent No.: US 9,029,295 B2
(45) Date of Patent: May 12, 2015

(54) PYRIDAZINONE COMPOUND AND HERBICIDE AND NOXIOUS ARTHROPOD CONTROLLING AGENT COMPRISING IT

(75) Inventors: Takashi Kuragano, Tsukuba (JP); Shin-ichiro Souma, Takarazuka (JP); Yoshinobu Jin, Kasai (JP); Tomohiro Araki, Takarazuka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 13/995,273

(22) PCT Filed: Dec. 26, 2011

(86) PCT No.: PCT/JP2011/080571

§ 371 (c)(1), (2), (4) Date: Jun. 18, 2013

(87) PCT Pub. No.: WO2012/091156

PCT Pub. Date: Jul. 5, 2012

(65) Prior Publication Data

US 2013/0281299 A1 Oct. 24, 2013

(30) Foreign Application Priority Data

Dec. 27, 2010 (JP) ................................ 2010-289621

(51) Int. Cl.

| | |
|---|---|
| ***A01N 43/58*** | (2006.01) |
| *C07D 237/14* | (2006.01) |
| *C07D 237/16* | (2006.01) |
| *C07D 237/18* | (2006.01) |
| *C07D 237/22* | (2006.01) |
| *C07D 237/24* | (2006.01) |

(52) U.S. Cl.

CPC .............. *A01N 43/58* (2013.01); *C07D 237/14* (2013.01); *C07D 237/16* (2013.01); *C07D 237/18* (2013.01); *C07D 237/22* (2013.01); *C07D 237/24* (2013.01)

(58) Field of Classification Search

CPC .. C07D 237/16; C07D 237/18; C07D 237/22; A01N 43/58

USPC ........... 424/405; 504/238; 514/247; 544/240, 544/241

See application file for complete search history.

(56) References Cited

U.S. PATENT DOCUMENTS

2012/0028988 A1 2/2012 Sakamoto et al.

FOREIGN PATENT DOCUMENTS

| | | |
|---|---|---|
| EP | 2 204 366 | 7/2010 |
| WO | 2007/119434 | 10/2007 |
| WO | 2009/035145 | 3/2009 |
| WO | 2009/035150 | 3/2009 |
| WO | WO2009/035145 A2 * | 3/2009 |
| WO | 2009/086041 | 7/2009 |
| WO | WO2009/086041 A1 * | 7/2009 |
| WO | 2010/069525 | 6/2010 |
| WO | 2010/069526 | 6/2010 |
| WO | WO2010/069526 A1 * | 6/2010 |
| WO | 2010/078912 | 7/2010 |
| WO | 2010/104217 | 9/2010 |
| WO | WO2010/104217 A1 * | 9/2010 |
| WO | 2010/113986 | 10/2010 |

OTHER PUBLICATIONS

International Search Report issued Mar. 26, 2012 in International (PCT) Application No. PCT/JP2011/080571.

International Preliminary Report on Patentability issued Jul. 2, 2013 and Written Opinion of the International Searching Authority issued Mar. 26, 2012 in International Application No. PCT/JP2011/080571.

Stevenson et al., "Application of Cross-Coupling and Metalation Chemistry of 3(2H)-Pyridazinones to Fungicide and Herbicide Discovery", Journal of Heterocyclic Chemistry, vol. 42, 2005, pp. 427-435.

* cited by examiner

*Primary Examiner* — Jane C Oswecki

(74) *Attorney, Agent, or Firm* — Wenderoth, Lind & Ponack, L.L.P.

(57) ABSTRACT

The present invention relates to a pyridazinone compound of the formula (I): wherein $R^1$ represents hydrogen, a $C_{1-6}$ alkyl group, and the like, $R^2$ represents halogen, a cyano group, a nitro group, a $C_{1-6}$ alkoxy group, and the like, G represents hydrogen, and the like, Z represents halogen, a cyano group, a nitro group, a $C_{1-6}$ alkyl group, and the like, and n represents an integer of 1-5 useful as an active ingredient in a herbicide and a noxious arthropod controlling agent.

(I)

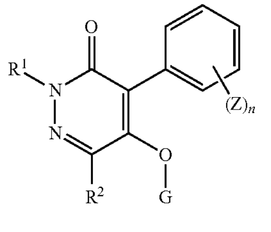

8 Claims, No Drawings

PYRIDAZINONE COMPOUND AND HERBICIDE AND NOXIOUS ARTHROPOD CONTROLLING AGENT COMPRISING IT

TECHNICAL FIELD

The present invention relates to a pyridazinone compound and a herbicide and a noxious arthropod controlling agent comprising it.

BACKGROUND ART

To date, compounds having potential to be an active ingredient in a herbicide for controlling weeds has been developed, and compounds having an activity of controlling weeds were found.

For controlling noxious arthropods, various compounds have heretofore been developed and used practically.

Pyridazinone compounds having an activity of controlling weeds and noxious arthropods are known (see, Patent Literatures 1-8 and Non patent Literature 1).

CITATION LIST

Patent Literature

Patent Literature 1: WO 2007/119434
Patent Literature 2: WO 2009/035150
Patent Literature 3: WO 2009/086041
Patent Literature 4: WO 2010/069525
Patent Literature 5: WO 2010/069526
Patent Literature 6: WO 2010/078912
Patent Literature 7: WO 2010/104217
Patent Literature 8: WO 2010/113986

Non Patent Literature

Non patent Literature 1: Journal of Heterocyclic Chemistry, vol. 42, pp. 427-435, 2005

SUMMARY OF INVENTION

Technical Problem

An object of the present invention is to provide a compound having an excellent activity of controlling weeds and a compound having an excellent activity of controlling noxious arthropods.

The present inventors have studied so as to resolve the above problem and found that a pyridazinone compound of the following formula (I) has an excellent activity of controlling weeds and an excellent activity of controlling noxious arthropods, thus leading to the present invention.

That is, the present invention provides:

<1> A pyridazinone compound of the formula (I):

(I)

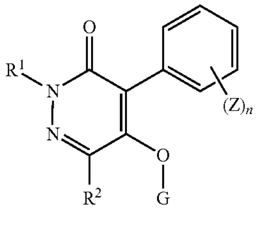

wherein:

$R^1$ represents hydrogen, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl)$C_{3-8}$ cycloalkyl group, a ($C_{3-8}$ cycloalkyl)$C_{1-6}$ alkyl group, a ($C_{3-8}$ cycloalkyl)$C_{3-8}$ cycloalkyl group, a ($C_{3-8}$ halocycloalkyl)$C_{1-6}$ alkyl group, a {($C_{1-6}$ alkyl)$C_{3-8}$ cycloalkyl}$C_{1-6}$ alkyl group, a ($C_{1-6}$ alkoxy)$C_{1-6}$ alkyl group, a ($C_{3-8}$ cycloalkoxy)$C_{1-6}$ alkyl group, a {($C_{1-6}$ alkoxy)$C_{1-6}$ alkoxy}$C_{1-6}$ alkyl group, a ($C_{1-6}$ alkylthio)$C_{1-6}$ alkyl group, a ($C_{1-6}$ alkylsulfinyl)$C_{1-6}$ alkyl group, a ($C_{1-6}$ alkylsulfonyl) $C_{1-6}$ alkyl group, a phenyl$C_{1-6}$ alkyl group optionally substituted with one or more substituents selected from Group A, a $C_{3-6}$ alkenyl group, a $C_{3-6}$ alkynyl group, or a tetrahydropyranyl group;

$R^2$ represents halogen, a cyano group, a nitro group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, a $C_{1-6}$ haloalkylsulfonyl group, a $C_{3-8}$ cycloalkoxy group, a ($C_{3-8}$ cycloalkyl)$C_{1-6}$ alkoxy group, a $C_{1-6}$ alkylthio$C_{1-6}$ alkoxy group, a $C_{1-6}$ alkoxy$C_{1-6}$ alkoxy group, a $C_{3-6}$ alkenyloxy group, a $C_{3-6}$ alkynyloxy group, a cyano$C_{1-6}$ alkoxy group, a ($C_{1-6}$ alkoxycarbonyl)$C_{1-6}$ alkoxy group, a carbamoyl$C_{1-6}$ alkoxy group, a ($C_{1-6}$ alkylaminocarbonyl)$C_{1-6}$ alkoxy group, a (di$C_{1-6}$ alkylaminocarbonyl)$C_{1-6}$ alkoxy group, an amino group, a $C_{1-6}$ alkylamino group, a di($C_{1-6}$ alkyl)amino group, a formylamino group, a ($C_{1-6}$ alkyl)carbonylamino group, a hydroxy$C_{1-6}$ alkyl group, a ($C_{1-6}$ alkoxy)$C_{1-6}$ alkyl group, a ($C_{1-6}$ haloalkoxy)$C_{1-6}$ alkyl group, a ($C_{3-8}$ cycloalkoxy)$C_{1-6}$ alkyl group, a {($C_{3-8}$ cycloalkyl) $C_{1-6}$ alkoxy}$C_{1-6}$ alkyl group, a ($C_{1-6}$ alkylthio)$C_{1-6}$ alkyl group, a ($C_{1-6}$ haloalkylthio)$C_{1-6}$ alkyl group, a cyano$C_{1-6}$ alkyl group, a hydroxyimino$C_{1-6}$ alkyl group, a ($C_{1-6}$ alkoxyimino)$C_{1-6}$ alkyl group, a formyl group, or a ($C_{1-6}$ alkyl) carbonyl group;

G represents hydrogen or a group of the following formula:

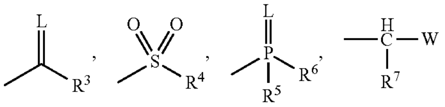

wherein, L represents oxygen or sulfur;

$R^3$ represents a $C_{1-6}$ alkyl group, a $C_{3-8}$ cycloalkyl group, a $C_{2-6}$alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl)$C_{1-6}$ alkoxy group, a di($C_{1-6}$ alkyl)amino group, a di($C_{3-6}$ alkenyl)amino group, a ($C_{1-6}$ alkyl)($C_{6-10}$ aryl)amino group, or a 5-6 membered heteroaryl group;

$R^4$ represents a $C_{1-6}$ alkyl group, a $C_{6-10}$ aryl group, or a di($C_{1-6}$ alkyl)amino group;

$R^5$ and $R^6$ may be same or different and represent independently a $C_{1-6}$ alkyl group, a $C_{3-8}$ cycloalkyl group, a $C_{6-10}$ aryl group, a $C_{1-6}$ alkoxy group, a $C_{3-8}$ cycloalkoxy group, a $C_{6-10}$ aryloxy group, a ($C_{6-10}$ aryl)$C_{1-6}$ alkoxy group, a $C_{1-6}$ alkylthio group, or a di($C_{1-6}$ alkyl)amino group;

$R^7$ represents hydrogen or a $C_{1-6}$ alkyl group; and

W represents a $C_{1-6}$ alkoxy group, a $C_{1-6}$ alkylthio group, a $C_{1-6}$ alkylsulfinyl group, a $C_{1-6}$ alkylsulfonyl group, or a phenyl group optionally substituted with one or more substituents selected from Group A: provided that any of $R^3$, $R^4$, $R^5$, $R^6$, and W may be optionally substituted with halogens, and any of the $C_{3-8}$ cycloalkyl group, the $C_{6-10}$ aryl group, the aryl part of the ($C_{6-10}$ aryl)$C_{1-6}$ alkyl group, the $C_{3-8}$ cycloalkoxy group, the $C_{6-10}$ aryloxy group, the aryl part of the ($C_{6-10}$ aryl)$C_{1-6}$ alkoxy group, the aryl part of the ($C_{1-6}$ alkyl)($C_{6-10}$ aryl)amino group, and the 5-6 membered heteroaryl group may be optionally substituted with a $C_{1-6}$ alkyl group;

Z represents halogen, a cyano group, a nitro group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, or a $C_{3-8}$ cycloalkyl group: provided that for the Z group, the $C_{1-6}$ alkyl group, the $C_{2-6}$ alkenyl group, the $C_{2-6}$ alkynyl group, the $C_{1-6}$ alkoxy group, and the $C_{1-6}$ alkylthio group may be optionally substituted with halogens, and the $C_{3-8}$ cycloalkyl group may be optionally substituted with at least one group selected from the group consisting of halogen and a $C_{1-6}$ alkyl group;

n represents an integer of 1-5: provided that when n is 2 or more, each of Z may be same or different; and the Group A consists of halogen, a $C_{1-6}$ alkyl group, or a $C_{1-6}$ alkoxy group (hereinafter referred to as the present compound);

<2> The pyridazinone compound according to the above <1> wherein $R^1$ is hydrogen, a $C_{1-3}$ alkyl group, a $C_{1-3}$ haloalkyl group, a ($C_{3-6}$ cycloalkyl)methyl group, a $C_{3-6}$ alkenyl group, a $C_{3-6}$ alkynyl group, or a benzyl group;

$R^2$ is a $C_{1-3}$ alkoxy group, a $C_{1-3}$ alkylthio group, a $C_{1-3}$ alkylsulfinyl group, a $C_{1-3}$ alkylsulfonyl group, a di($C_{1-3}$ alkyl)amino group, a halogen, a cyano group, a nitro group, a $C_{1-3}$ haloalkoxy group, a cyclopropyl$C_{1-3}$ alkoxy group, a ($C_{1-3}$ alkylthio)$C_{1-3}$ alkoxy group, a ($C_{1-3}$ alkoxy)$C_{1-3}$ alkoxy group, a $C_{3-6}$ alkenyloxy group, a $C_{3-6}$ alkynyloxy group, a cyano$C_{1-3}$ alkoxy group, an amino group, a formylamino group, a ($C_{1-3}$ alkyl)carbonylamino group, a hydroxy$C_{1-3}$ alkyl group, a ($C_{1-3}$ alkoxy)$C_{1-3}$ alkyl group, a cyano$C_{1-3}$ alkyl group, a hydroxyiminomethyl group, a methoxyiminomethyl group, or a formyl group;

G is hydrogen or a group of the following formula:

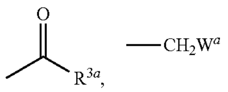

wherein, $R^{3a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group, or a $C_{6-10}$ aryloxy group; and $W^a$ is a $C_{1-3}$ alkoxy group;

Z is a $C_{1-3}$ alkyl group, a $C_{2-6}$ alkenyl group, or a $C_{2-6}$ alkynyl group; and n is an integer of 1-3: wherein when n is 2 or more, each of Z may be same or different;

<3> The pyridazinone compound according to the above <2> wherein $R^1$ is a methyl group;

$R^2$ is a methoxy group, an ethoxy group, a methylthio group, a methylsulfinyl group, a methylsulfonyl group, a dimethylamino group, a fluorine atom, a chlorine atom, a bromine atom, a cyano group, a nitro group, a cyclopropylmethyloxy group, a methylthiomethoxy group, a methoxymethoxy group, an allyloxy group, a propargyloxy group, a cyanomethyloxy group, an amino group, an acetamide group, a hydroxymethyl group, a methoxymethyl group, a cyanomethyl group, a hydroxyiminomethyl group, or a formyl group;

G is hydrogen, an acetyl group, a propionyl group, a benzoyl group, a methoxycarbonyl group, an ethoxycarbonyl group, an allyloxycarbonyl group, a phenoxycarbonyl group, a methoxymethyl group, or an ethoxymethyl group; and Z is a methyl group, an ethyl group, a vinyl group, or an ethynyl group;

<4> The pyridazinone compound according to any one of the above <1>-<3> wherein G is hydrogen;

<5> A herbicide comprising the pyridazinone compound according to any one of the above <1>-<4> as an active ingredient;

<6> A method of controlling a weed which comprises applying an effective amount of the pyridazinone compound according to any one of the above <1>-<4> to a weed or soil where a weed is grown;

<7> Use of the pyridazinone compound according to any one of the above <1>-<4> for controlling a weed;

<8> A noxious arthropod controlling agent which comprises the pyridazinone compound according to any one of the above <1>-<4> as an active ingredient;

<9> A method of controlling a noxious arthropod which comprises applying an effective amount of the pyridazinone compound according to any one of the above <1>-<4> to a noxious arthropod or to a habitat of a noxious arthropod; and <10> Use of the pyridazinone compound according to any one of the above <1>-<4> for controlling a noxious arthropod.

Effect of Invention

The present compound has an excellent activity of controlling weeds and noxious arthropods, and is useful as an active ingredient in a herbicide and a noxious arthropod controlling agent.

DESCRIPTION OF EMBODIMENTS

Various substituents used in the present specification will be illustrated bellow.

The term "$C_{1-6}$ alkyl group" means an alkyl group of 1 to 6 carbons, and includes, for example, a methyl group, an ethyl group, a n-propyl group, an isopropyl group, a n-butyl group, an isobutyl group, a sec-butyl group, a tert-butyl group, a n-pentyl group, a sec-pentyl group, an isopentyl group, a neopentyl group, a n-hexyl group, and an isohexyl group.

The term "$C_{2-6}$ alkenyl group" means an alkenyl group of 2 to 6 carbons, and includes, for example, a vinyl group, an allyl group, a 1-buten-3-yl group, and a 3-buten-1-yl group.

The term "$C_{2-6}$ alkynyl group" means an alkynyl group of 2 to 6 carbons, and includes, for example, an ethinyl group, a propargyl group, and a 2-butynyl group.

The term "$C_{1-6}$ haloalkyl group" means a $C_{1-6}$ alkyl group substituted with halogens such as fluorine, chlorine, bromine, and iodine, and includes, for example, a trifluoromethyl group, a chloromethyl group, a 2,2-difluoroethyl group, a 2,2,2-trichloroethyl group, a 2,2,2-trifluoroethyl group, and a 2,2,2-trifluoro-1,1-dichloroethyl group.

The term "$C_{3-8}$ cycloalkyl group" means a cycloalkyl group of 3 to 8 carbons, and includes, for example, a cyclopropyl group, a cyclopentyl group, and a cyclohexyl group.

The term "$C_{3-8}$ halocycloalkyl group" means a cycloalkyl group of 3 to 8 carbons substituted with halogens such as fluorine, chlorine, bromine, and iodine, and includes, for example, a 2-chlorocyclopropyl group and a 4,4-difluorocyclohexyl group.

The term "($C_{1-6}$ alkyl)$C_{3-8}$ cycloalkyl group" means a cycloalkyl group of 3 to 8 carbons substituted with an alkyl group of 1 to 6 carbons, and includes, for example, an ethylcyclopropyl group, an isobutylcyclopropyl group, a 3-methylcyclopentyl group, and a 4-methylcyclohexyl group.

The term "($C_{3-8}$ cycloalkyl)$C_{1-6}$ alkyl group" means an alkyl group of 1 to 6 carbons substituted with a cycloalkyl group of 3 to 8 carbons, and includes, for example, a cyclopropylmethyl group and a cyclopentylmethyl group.

The term "($C_{3-8}$ cycloalkyl)$C_{3-8}$ cycloalkyl group" means a cycloalkyl group of 3 to 8 carbons substituted with a cycloalkyl group of 3 to 8 carbons, and includes, for example, a 2-cyclopropylcyclopropyl group and a 3-cyclopropylcyclopentyl group.

The term "($C_{3-8}$ halocycloalkyl)$C_{1-6}$ alkyl group" means an alkyl group of 1 to 6 carbons substituted with a cycloalkyl group of 3 to 8 carbons substituted with halogens such as fluorine, chlorine, bromine, and iodine, and includes, for example, a 2-chlorocyclopropylmethyl group and a 3-chlorocyclopentylethyl group.

The term "{($C_{1-6}$ alkyl)$C_{3-8}$ cycloalkyl}$C_{1-6}$ alkyl group" means an alkyl group of 1 to 6 carbons substituted with (a cycloalkyl group of 3 to 8 carbons substituted with an alkyl of 1 to 6 carbons), and includes, for example, a 2-methylcyclopropylmethyl group and a 3-methylcyclopentylmethyl group.

The term "hydroxy$C_{1-6}$ alkyl group" means an alkyl group of 1 to 6 carbons substituted with a hydroxyl group, and includes, for example, a hydroxymethyl group, a 1-hydroxyethyl group, a 2-hydroxyethyl group, and a 3-hydroxypropyl group.

The term "($C_{1-6}$ haloalkoxy)$C_{1-6}$ alkyl group" means an alkyl group of 1 to 6 carbons substituted with (an alkoxy group of 1 to 6 carbons substituted with halogens such as fluorine, chlorine, bromine, and iodine), and includes, for example, a 2,2-difluoroethoxymethyl group, a 2,2,2-trifluoroethoxymethyl group, a 2,2-difluoroethoxyethyl group, and a 2,2,2-trifluoroethoxyethyl group.

The term "{($C_{3-8}$ cycloalkyl)$C_{1-6}$ alkoxy}$C_{1-6}$ alkyl group" means an alkyl group of 1 to 6 carbons substituted with (an alkoxy group of 1 to 6 carbons substituted with a cycloalkyl group of 3 to 8 carbons), and includes, for example, a cyclopropylmethoxymethyl group.

The term "($C_{1-6}$ haloalkylthio)$C_{1-6}$ alkyl group" means an alkyl group of 1 to 6 carbons substituted with (an alkylthio group of 1 to 6 carbons substituted with halogens such as fluorine, chlorine, bromine, and iodine), and includes, for example, a trifluoromethylthiomethyl group, a 2,2-difluoroethylthiomethyl group, and a 2,2,2-trifluoroethylthiomethyl group.

The term "cyano$C_{1-6}$ alkyl group" means an alkyl group of 1 to 6 carbons substituted with a cyano group, and includes, for example, a cyanomethyl group, a 1-cyanoethyl group, a 2-cyanoethyl group, and a 3-cyanoethyl group.

The term "hydroxyimino$C_{1-6}$ alkyl group" means an alkyl group of 1 to 6 carbons substituted with a hydroxyimino group, and includes, for example, a hydroxyiminomethyl group.

The term "($C_{1-6}$ alkoxyimino)$C_{1-6}$ alkyl group" means an alkyl group of 1 to 6 carbons substituted with an alkoxyimino group of 1 to 6 carbons, and includes, for example, a methoxyiminomethyl group and an ethoxyiminomethyl group.

The term "($C_{1-6}$ alkoxy)$C_{1-6}$ alkyl group" means an alkyl group of 1 to 6 carbons substituted with an alkoxy group of 1 to 6 carbons, and includes, for example, a methoxymethyl group, a 1-methoxyethyl group, an ethoxymethyl group, a butoxymethyl group, and a 2-ethoxyethyl group.

The term "($C_{3-8}$ cycloalkoxy)$C_{1-6}$ alkyl group" means an alkyl group of 1 to 6 carbons substituted with a cycloalkoxy group of 3 to 8 carbons, and includes, for example, a cyclopropyloxymethyl group and a cyclopentyloxymethyl group.

The term "{($C_{1-6}$ alkoxy)$C_{1-6}$ alkoxy}$C_{1-6}$ alkyl group" means an alkyl group of 1 to 6 carbons substituted with (an alkoxy group of 1 to 6 carbons substituted with an alkoxy group of 1 to 6 carbons), and includes, for example, a methoxymethoxymethyl group and a (1-ethoxyethoxy)methyl group.

The term "($C_{1-6}$ alkylthio)$C_{1-6}$ alkyl group" means an alkyl group of 1 to 6 carbons substituted with an alkylthio group of 1 to 6 carbons, and includes, for example, a methylthiomethyl group, a 1-(methylthio)ethyl group, an ethylthiomethyl group, a butylthiomethyl group, and a 2-(ethylthio)ethyl group.

The term "($C_{1-6}$ alkylsulfinyl)$C_{1-6}$ alkyl group" means an alkyl group of 1 to 6 carbons substituted with an alkylsulfinyl group of 1 to 6 carbons, and includes, for example, a methylsulfinylmethyl group, a 1-(methylsulfinyl)ethyl group, an ethylsulfinylmethyl group, a butylsulfinylmethyl group, and a 2-(ethylsulfinyl)ethyl group.

The term "($C_{1-6}$ alkylsulfonyl)$C_{1-6}$ alkyl group" means an alkyl group of 1 to 6 carbons substituted with an alkylsulfonyl group of 1 to 6 carbons, and includes, for example, a methylsulfonylmethyl group, a 1-(methylsulfonyl)ethyl group, an ethylsulfonylmethyl group, a butylsulfonylmethyl group, and a 2-(ethylsulfonyl)ethyl group.

The term "phenyl$C_{1-6}$ alkyl group optionally substituted with one or more substituents selected from Group A" means an alkyl group of 1 to 6 carbons substituted with a phenyl optionally substituted with one or more substituents selected from Group A, and includes, for example, a benzyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-methylbenzyl group, a 3-methylbenzyl group, a 4-methylbenzyl group, a 2-methoxybenzyl group, a 3-methoxybenzyl group, a 4-methoxybenzyl group, a phenethyl group, a 4-phenylbutyl group, and a 6-phenylhexyl group.

The term "$C_{1-6}$ alkoxy group" means an alkoxy group of 1 to 6 carbons, and includes, for example, a methoxy group, an ethoxy group, a n-propyloxy group, an isopropyloxy group, a n-butoxy group, an isobutoxy group, a sec-butoxy group, a tert-butoxy group, a n-pentoxy group, a sec-pentoxy group, an isopentoxy group, a neopentoxy group, a n-hexyloxy group, and an isohexyloxy group.

The term "$C_{1-6}$ haloalkoxy group" means an alkoxy group of 1 to 6 carbons substituted with halogens such as fluorine, chlorine, bromine, and iodine, and includes, for example, a trifluoromethoxy group, a 2,2-difluoroethoxy group, a 2,2,2-trichloroethoxy group, a 3,3-difluoropropyloxy group, and a 2,2,2-trifluoroethoxy group.

The term "($C_{3-6}$ cycloalkyl)$C_{1-6}$ alkoxy group" means an alkoxy group of 1 to 6 carbons substituted with a cycloalkyl group of 3 to 8 carbons, and includes, for example, a cyclopropylmethoxy group, a 1-cyclopropylethoxy group, and a cyclopentylmethoxy group.

The term "($C_{1-6}$ alkylthio)$C_{1-6}$ alkoxy group" means an alkoxy group of 1 to 6 carbons substituted with an alkylthio group of 1 to 6 carbons, and includes, for example, a methylthiomethoxy group, a methylthioethoxy group, a methylthiopropoxy group, an ethylthiomethoxy group, and an ethylthioethoxy group.

The term "($C_{1-6}$ alkoxy)$C_{1-6}$ alkoxy group" means an alkoxy group of 1 to 6 carbons substituted with an alkoxy group of 1 to 6 carbons, and includes, for example, a methoxymethoxy group, an ethoxymethoxy group, a n-propyloxymethoxy group, an isopropyloxymethoxy group, a 2-methoxyethoxy group, a 2-ethoxyethoxy group, and a 3-methoxypropyloxy group.

The term "cyano$C_{1-6}$ alkoxy group" means an alkoxy group of 1 to 6 carbons substituted with a cyano group, and includes, for example, a cyanomethoxy group, a 1-cyanomethoxy group, a 2-cyanoethoxy group, and a 3-cyanopropyloxy group.

The term "($C_{1-6}$ alkoxycarbonyl)$C_{1-6}$ alkoxy group" means an alkoxy group of 1 to 6 carbons substituted with (a carbonyl group substituted with an alkoxy group of 1 to 6 carbons), and includes, for example, a methoxycarbonylmethoxy group and an ethoxycarbonylmethoxy group.

The term "carbamoyl$C_{1-6}$ alkoxy group" means an alkoxy group of 1 to 6 carbons substituted with a carbamoyl group, and includes, for example, a carbamoylmethoxy group.

The term "($C_{1-6}$ alkylaminocarbonyl)$C_{1-6}$ alkoxy group" means an alkoxy group of 1 to 6 carbons substituted with (a carbonyl group substituted with an amino group substituted with an alkyl group of 1 to 6 carbons), and includes, for example, a methylaminocarbonylmethoxy group.

The term "{di($C_{1-6}$ alkyl)aminocarbonyl}$C_{1-6}$ alkoxy group" means an alkoxy group of 1 to 6 carbons substituted with {a carbonyl group substituted with (an amino group substituted with two alkyl groups of 1 to 6 carbons which may be same or different)}, and includes, for example, a dimethylaminocarbonylmethoxy group.

The term "$C_{1-6}$ alkylthio group" means an alkylthio group of 1 to 6 carbons, and includes, for example, a methylthio group, an ethylthio group, and an isopropylthio group.

The term "$C_{1-6}$ alkylsulfinyl group" means an alkylsulfinyl group of 1 to 6 carbons, and includes, for example, a methylsulfinyl group, an ethylsulfinyl group, and an isopropylsulfinyl group.

The term "$C_{1-6}$ alkylsulfonyl group" means an alkylsulfonyl group of 1 to 6 carbons, and includes, for example, a methylsulfonyl group, an ethylsulfonyl group, and an isopropylsulfonyl group.

The term "$C_{1-6}$ haloalkylthio group" means an alkylthio group of 1 to 6 carbons substituted with halogens such as fluorine, chlorine, bromine, and iodine, and includes, for example, a trichloromethylthio group, a trifluoromethylthio group, a 2,2-difluoroethylthio group, a 2,2,2-trifluoroethylthio group, a 2,2,2-trichloroethylthio group, and a 3-chloropropylthio group.

The term "$C_{1-6}$ haloalkylsulfinyl group" means an alkylsulfinyl group of 1 to 6 carbons substituted with halogens such as fluorine, chlorine, bromine, and iodine, and includes, for example, a trichloromethylsulfinyl group, a trifluoromethylsulfinyl group, a 2,2-difluoroethylsulfinyl group, a 2,2,2-trifluoroethylsulfinyl group, a 2,2,2-trichloroethylsulfinyl group, and a 3-chloropropylsulfinyl group.

The term "$C_{1-6}$ haloalkylsulfonyl group" means an alkylsulfonyl group of 1 to 6 carbons substituted with halogens such as fluorine, chlorine, bromine, and iodine, and includes, for example, a trichloromethylsulfonyl group, a trifluoromethylsulfonyl group, a 2,2-difluoroethylsulfonyl group, a 2,2,2-trifluoroethylsulfonyl group, a 2,2,2-trichloroethylsulfonyl group, and a 3-chloropropylsulfonyl group.

The term "$C_{3-8}$ cycloalkoxy group" means a cycloalkoxy group of 3 to 8 carbons, and includes, for example, a cyclopropyloxy group, a cyclopentyloxy group, and a cyclohexyloxy.

The term "$C_{1-6}$ alkylamino group" means an alkylamino group of 1 to 6 carbons, and includes, for example, a methylamino group, an ethylamino group, and an isopropylamino group.

The term "di($C_{1-6}$ alkyl)amino group" means an amino group substituted with two alkyl groups of 1 to 6 carbons which may be same or different, and includes, for example, a dimethylamino group, a diethylamino group, and an ethylmethylamino group.

The term "($C_{1-6}$ alkyl)carbonylamino group" means an amino group substituted with a carbonyl group substituted with an alkyl group of 1 to 6 carbons, and includes, for example, an acetamide group, and a propionylamino group.

The term "($C_{1-6}$ alkyl)carbonyl group" means a carbonyl group substituted with an alkyl group of 1 to 6 carbons, and includes, for example, an acetyl group, a propionyl group, and a butyryl group.

The term "$C_{6-10}$ aryl group" means an aryl group of 6 to 10 carbons, and includes, for example, a phenyl group and a naphthyl group.

The term "($C_{6-10}$ aryl)$C_{1-6}$ alkyl group" means an alkyl group of 1 to 6 carbons substituted with an aryl group of 6 to 10 carbons, and includes, for example, a benzyl group and a phenethyl group.

The term "$C_{3-6}$ alkenyloxy group" means an alkenyloxy group of 3 to 6 carbons, and includes, for example, an allyloxy group and a 2-butenyloxy group.

The term "$C_{3-6}$ alkynyloxy group" means an alkynyloxy group of 3 to 6 carbons, and includes, for example, a propargyloxy group and a 2-butynyloxy group.

The term "$C_{6-10}$ aryloxy group" means an aryloxy group of 6 to 10 carbons, and includes, for example, a phenoxy group and a naphthyloxy group.

The term "($C_{6-10}$ aryl)$C_{1-6}$ alkoxy group" means an alkoxy group of 1 to 6 carbons substituted with an aryl group of 6 to 10 carbons, and includes, for example, a benzyloxy group and a phenethyloxy group.

The term "di($C_{3-6}$ alkenyl)amino group" means an amino group substituted with two alkenyl groups of 3 to 6 carbons which may be same or different, and includes, for example, a diallylamino group and a di(3-butenyl)amino group.

The term "($C_{1-6}$ alkyl)($C_{6-10}$ aryl)amino group" means an amino group substituted with an alkyl group of 1 to 6 carbons and an aryl group of 6 to 10 carbons, and includes, for example, a methylphenylamino group and an ethylphenylamino group.

The term "5-6 membered heteroaryl group" means an aromatic 5 or 6-membered heterocyclic group containing 1-3 heteroatoms selected from nitrogen, oxygen, and sulfur, and includes, for example, a 3-pyridyl group, a 3-thienyl group, and a 1-pyrazolyl group.

The term "$C_{1-3}$ alkyl group" means an alkyl group of 1 to 3 carbons, and includes, for example, a methyl group, an ethyl group, a n-propyl group, and an isopropyl group.

The term "$C_{1-3}$ alkoxy group" means an alkoxy group of 1 to 3 carbons, and includes, for example, a methoxy group, an ethoxy group, a n-propyloxy group, and an isopropyloxy group.

The term "$C_{1-3}$ alkylthio group" means an alkylthio group of 1 to 3 carbons, and includes, for example, a methylthio group, an ethylthio group, and a propylthio group.

The term "$C_{1-3}$ alkylsulfinyl group" means an alkylsulfinyl group of 1 to 3 carbons, and includes, for example, a methylsulfinyl group, an ethylsulfinyl group, and a propylsulfinyl group.

The term "$C_{1-3}$ alkylsulfonyl group" means an alkylsulfonyl group of 1 to 3 carbons, and includes, for example, a methylsulfonyl group, an ethylsulfonyl group, and a propylsulfonyl group.

The term "di($C_{1-3}$ alkyl)amino group" means an amino group substituted with two alkyl groups of 1 to 3 carbons which may be same or different, and includes, for example, a dimethylamino group, a diethylamino group, and an ethylmethylamino group.

The term "$C_{1-3}$ haloalkyl group" means a $C_{1-6}$ alkyl group substituted with halogens such as fluorine, chlorine, bromine, and iodine, and includes, for example, a trifluoromethyl group, a chloromethyl group, a 2,2-difluoroethyl group, a 2,2,2-trichloroethyl group, a 2,2,2-trifluoroethyl group, and a 2,2,2-trifluoro-1,1-dichloroethyl group.

The term "($C_{3-6}$ cycloalkyl)methyl group" means a methyl group substituted with a cycloalkyl group of 3 to 6 carbons, and includes, for example, a cyclopropylmethyl group and a cyclopentylmethyl group.

The term "$C_{3-6}$ alkenyl group" means an alkenyl group of 3 to 6 carbons, and includes, for example, an allyl group, a 1-buten-3-yl group, and a 3-buten-1-yl group.

The term "$C_{3-6}$ alkynyl group" means an alkynyl group of to 6 carbons, and includes, for example, a propargyl group and a 2-butynyl group.

The term "$C_{1-3}$ haloalkoxy group" means an alkoxy group of 1 to 3 carbons substituted with halogens such as fluorine, chlorine, bromine, and iodine, and includes, for example, a trifluoromethoxy group, a 2,2-difluoroethoxy group, a 2,2,2-trichloroethoxy group, a 3,3-difluoropropyloxy group, and a 2,2,2-trifluoroethoxy group.

The term "cyclopropyl$C_{1-3}$ alkoxy group" means an alkoxy group of 1 to 3 carbons substituted with a cyclopropyl group, and includes, for example, a cyclopropylmethoxy group, a 1-cyclopropylethoxy group, and a 2-cyclopropylethoxy group.

The term "($C_{1-3}$ alkylthio)$C_{1-3}$ alkoxy group" means an alkoxy group of 1 to 3 carbons substituted with an alkylthio group of 1 to 3 carbons, and includes, for example, a methylthiomethoxy group, a methylthioethoxy group, a methylthiopropoxy group, an ethylthiomethoxy group, and an ethylthioethoxy group.

The term "($C_{1-3}$ alkoxy)$C_{1-3}$ alkoxy group" means an alkoxy group of 1 to 3 carbons substituted with an alkoxy group of 1 to 3 carbons, and includes, for example, a methoxymethoxy group, an ethoxymethoxy group, a n-propyloxymethoxy group, an isopropyloxymethoxy group, a 2-methoxyethoxy group, a 2-ethoxyethoxy group, and a 3-methoxypropyloxy group.

The term "cyano$C_{1-3}$ alkoxy group" means an alkoxy group of 1 to 3 carbons substituted with a cyano group, and includes, for example, a cyanomethoxy group, a 1-cyanomethoxy group, a 2-cyanoethoxy group, and a 3-cyanopropyloxy group.

The term "($C_{1-3}$ alkyl)carbonylamino group" means an amino group substituted with a carbonyl group substituted with an alkyl group of 1 to 3 carbons, and includes, for example, an acetamide group and a propionylamino group.

The term "hydroxy$C_{1-3}$ alkyl group" means an alkyl group of 1 to 3 carbons substituted with a hydroxyl group, and includes, for example, a hydroxymethyl group, a 1-hydroxyethyl group, a 2-hydroxyethyl group, and a 3-hydroxypropyl group.

The term "($C_{1-3}$ alkoxy)$C_{1-3}$ alkyl group" means an alkyl group of 1 to 3 carbons substituted with an alkoxy group of 1 to 3 carbons, and includes, for example, a methoxymethyl group, a 1-methoxyethyl group, an ethoxymethyl group, and a 2-ethoxyethyl group.

The term "cyano$C_{1-3}$ alkyl group" means an alkyl group of 1 to 3 carbons substituted with a cyano group, and includes, for example, a cyanomethyl group, a 1-cyanoethyl group, a 2-cyanoethyl group, and a 3-cyanoethyl group.

Examples of halogen include fluorine, chlorine, bromine and iodine.

In the present compound, a pyridazinone compound of the formula (I) may be in the form of an agriculturally acceptable salt with an inorganic base or an organic base. The present invention includes said salt of a pyridazinone compound.

Examples of the salt include a salt produced by mixing the present compound with an inorganic base (e.g. hydroxides, carbonates, hydrogen carbonates, acetates, and hydrides of an alkali metal (lithium, sodium, potassium, and the like); hydroxides and hydrides of an alkali earth metal (magnesium, calcium, barium, and the like); ammonia), an organic base (e.g. dimethylamine, triethylamine, piperazine, pyrrolidine, piperidine, 2-phenylethylamine, benzylamine, ethanolamine, diethanolamine, pyridine, collidine), or a metal alkoxide (e.g. sodium methoxide, potassium tert-butoxide, magnesium methoxide).

When the present compound has one or more asymmetric centers, there are two or more stereoisomers (e.g., enantiomer and diastereomer) of the present compound. The compound of the present invention includes all of such stereoisomers and a mixture of two or more of them.

When the present compound has geometric isomerism based on a double bond or the like, there are two or more geometric isomers (e.g., E/Z or trans/cis isomers, and S-trans/S-cis isomers) of the present compound. The present compound includes all of such geometric isomers and a mixture of two or more of them.

Examples of the present compound include the following compounds:

[1]: A compound of the formula (I) wherein $R^1$ is hydrogen, a $C_{1-6}$ alkyl group, a $C_{1-6}$ haloalkyl group, a $C_{3-8}$ cycloalkyl group, a ($C_{3-8}$ cycloalkyl)$C_{1-6}$ alkyl group, a ($C_{1-6}$ alkoxy) $C_{1-6}$ alkyl group, a $C_{3-6}$ alkenyl group, or a $C_{3-6}$ alkynyl group;

[2]: A compound of the above [1] wherein $R^1$ is hydrogen, a $C_{1-3}$ alkyl group, a $C_{1-3}$ haloalkyl group, a cyclopropyl group, a cyclopropylmethyl group, $C_{3-6}$ alkenyl group, or a $C_{1-3}$ alkoxymethyl group;

[3]: A compound of the above [2] wherein $R^1$ is hydrogen or a $C_{1-3}$ alkyl group;

[4]: A compound of the above [3] wherein $R^1$ is a methyl group;

[5]: A compound of the above [3] wherein $R^1$ is hydrogen;

[6]: A compound of the formula (I) or a compound of the above [1]-[5] wherein $R^2$ is halogen, a cyano group, a nitro group, a $C_{1-3}$ alkoxy group, a $C_{1-3}$ haloalkoxy group, a $C_{1-3}$ alkylthio group, a $C_{1-3}$ alkylsulfinyl group, a $C_{1-3}$ alkylsulfonyl group, a $C_{1-3}$ haloalkylthio group, a $C_{1-3}$ haloalkylsulfinyl group, a $C_{1-3}$ haloalkylsulfonyl group, a $C_{3-6}$ cycloalkoxy group, a ($C_{3-6}$ cycloalkyl)$C_{1-3}$ alkoxy group, an amino group, a $C_{1-3}$ alkylamino group, a di($C_{1-3}$ alkyl)amino group, a $C_{1-6}$ alkylthio$C_{1-6}$ alkoxy group, a $C_{1-6}$ alkoxy$C_{1-6}$ alkoxy group, a $C_{3-6}$ alkenyloxy group, a $C_{3-6}$ alkynyloxy group, a cyano$C_{1-6}$ alkoxy group, a ($C_{1-6}$ alkoxycarbonyl)$C_{1-6}$ alkoxy group, a carbamoyl$C_{1-6}$ alkoxy group, a ($C_{1-6}$ alkylaminocarbonyl) $C_{1-6}$ alkoxy group, a (di$C_{1-6}$ alkylaminocarbonyl)$C_{1-6}$ alkoxy group, a formylamino group, a ($C_{1-6}$ alkyl)carbonylamino group, a hydroxy$C_{1-6}$ alkyl group, a ($C_{1-6}$ alkoxy)$C_{1-6}$ alkyl group, a ($C_{1-6}$ haloalkoxy)$C_{1-6}$ alkyl group, a ($C_{3-8}$ cycloalkoxy)$C_{1-6}$ alkyl group, a {($C_{3-8}$ cycloalkyl)$C_{1-6}$ alkoxy}$C_{1-6}$ alkyl group, a ($C_{1-6}$ alkylthio)$C_{1-6}$ alkyl group, a ($C_{1-6}$ haloalkylthio)$C_{1-6}$ alkyl group, a cyano$C_{1-6}$ alkyl group, a hydroxyimino$C_{1-6}$ alkyl group, a ($C_{1-6}$ alkoxyimino)$C_{1-6}$ alkyl group, a formyl group, or a ($C_{1-6}$ alkyl)carbonyl group;

[7]: A compound of the above [6] wherein $R^2$ is halogen, a $C_{1-3}$ alkoxy group, a $C_{1-3}$ alkylthio group, a $C_{1-3}$ alkylsulfinyl group, a $C_{1-3}$ alkylsulfonyl group, a di($C_{1-3}$ alkyl)amino group, a $C_{1-6}$ alkylthio$C_{1-6}$ alkoxy group, a $C_{1-6}$ alkoxy$C_{1-6}$ alkoxy group, a $C_{3-6}$ alkenyloxy group, a $C_{3-6}$ alkynyloxy group, a cyano$C_{1-6}$ alkoxy group, a hydroxy$C_{1-6}$ alkyl group, a ($C_{1-6}$ alkoxy)$C_{1-6}$ alkyl group, a ($C_{3-8}$ cycloalkoxy)

$C_{1-6}$ alkyl group, a cyano$C_{1-6}$ alkyl group, a hydroxyiminо$C_{1-6}$ alkyl group, or a formyl group;

[8]: A compound of the above [7] wherein $R^2$ is a $C_{1-3}$ alkoxy group;

[9]: A compound of the above [8] wherein $R^2$ is a methoxy group;

[10]: A compound of the above [8] wherein $R^2$ is an ethoxy group;

[11]: A compound of the above [7] wherein $R^2$ is a $C_{1-3}$ alkylthio group;

[12]: A compound of the above [11] wherein $R^2$ is a methylthio group;

[13]: A compound of the above [11] wherein $R^2$ is an ethylthio group;

[14]: A compound of the above [7] wherein $R^2$ is a $C_{1-3}$ alkylsulfinyl group;

[15]: A compound of the above [14] wherein $R^2$ is a methylsulfinyl group;

[16]: A compound of the above [14] wherein $R^2$ is an ethylsulfinyl group;

[17]: A compound of the above [7] wherein $R^2$ is a $C_{1-3}$ alkylsulfonyl group;

[18]: A compound of the above [17] wherein $R^2$ is a methylsulfonyl group;

[19]: A compound of the above [17] wherein $R^2$ is an ethylsulfonyl group;

[20]: A compound of the above [7] wherein $R^2$ is a di($C_{1-3}$ alkyl)amino group;

[21]: A compound of the above [20] wherein $R^2$ is a dimethylamino group;

[22]: A compound of the above [7] wherein $R^2$ is halogen;

[23]: A compound of the above [22] wherein $R^2$ is fluorine;

[24]: A compound of the above [22] wherein $R^2$ is chlorine;

[25]: A compound of the above [22] wherein $R^2$ is bromine;

[26]: A compound of the above [7] wherein $R^2$ is a $C_{1-6}$ alkylthio$C_{1-6}$ alkoxy group;

[27]: A compound of the above [26] wherein $R^2$ is a methylthiomethoxy group;

[28]: A compound of the above [26] wherein $R^2$ is a methylthioethoxy group;

[29]: A compound of the above [7] wherein $R^2$ is a $C_{1-6}$ alkoxy$C_{1-6}$ alkoxy group;

[30]: A compound of the above [29] wherein $R^2$ is a methoxymethoxy group;

[31]: A compound of the above [29] wherein $R^2$ is an ethoxymethoxy group;

[32]: A compound of the above [7] wherein $R^2$ is a $C_{3-6}$ alkenyloxy group;

[33]: A compound of the above [32] wherein $R^2$ is an allyloxy group;

[34]: A compound of the above [7] wherein $R^2$ is a $C_{3-6}$ alkynyloxy group;

[35]: A compound of the above [34] wherein $R^2$ is a propargyloxy group;

[36]: A compound of the above [7] wherein $R^2$ is a cyano$C_{1-6}$ alkoxy group;

[37]: A compound of the above [36] wherein $R^2$ is a cyanomethoxy group;

[38]: A compound of the above [7] wherein $R^2$ is a hydroxy$C_{1-6}$ alkyl group;

[39]: A compound of the above [38] wherein $R^2$ is a hydroxymethyl group;

[40]: A compound of the above [7] wherein $R^2$ is a ($C_{1-6}$ alkoxy)$C_{1-6}$ alkyl group;

[41]: A compound of the above [40] wherein $R^2$ is a methoxymethyl group;

[43]: A compound of the above [7] wherein $R^2$ is a ($C_{3-8}$ cycloalkoxy)$C_{1-6}$ alkyl group;

[44]: A compound of the above [43] wherein $R^2$ is a (cyclopropyloxy)methyl group;

[45]: A compound of the above [7] wherein $R^2$ is a cyano$C_{1-6}$ alkyl group;

[46]: A compound of the above [45] wherein $R^2$ is a cyanomethyl group;

[47]: A compound of the above [7] wherein $R^2$ is a hydroxyimino$C_{1-6}$ alkyl group;

[48]: A compound of the above [47] wherein $R^2$ is a hydroxyiminomethyl group;

[49]: A compound of the above [7] wherein $R^2$ is a formyl group;

[50]: A compound of the above [6] wherein $R^2$ is a ($C_{1-6}$ alkoxycarbonyl)$C_{1-6}$ alkoxy group;

[51]: A compound of the above [50] wherein $R^2$ is a (methoxycarbonyl)methoxy group;

[52]: A compound of the above [50] wherein $R^2$ is an (ethoxycarbonyl)methoxy group;

[53]: A compound of the above [6] wherein $R^2$ is a carbamoyl$C_{1-6}$ alkoxy group;

[54]: A compound of the above [53] wherein $R^2$ is a carbamoylmethoxy group;

[55]: A compound of the above [6] wherein $R^2$ is a (di$C_{1-6}$ alkylaminocarbonyl)$C_{1-6}$ alkoxy group;

[56]: A compound of the above [55] wherein $R^2$ is a (dimethylaminocarbonyl)methoxy group;

[57]: A compound of the above [6] wherein $R^2$ is a ($C_{1-6}$ alkyl)carbonylamino group;

[58]: A compound of the above [57] wherein $R^2$ is an acetamide group;

[59]: A compound of the above [6] wherein $R^2$ is a ($C_{1-6}$ alkylthio)$C_{1-6}$ alkyl group;

[60]: A compound of the above [59] wherein $R^2$ is a methylthiomethyl group;

[61]: A compound of the above [6] wherein $R^2$ is a ($C_{1-6}$ alkoxyimino)$C_{1-6}$ alkyl group;

[62]: A compound of the above [61] wherein $R^2$ is a (methoxyimino)methyl group;

[63]: A compound of the above [6] wherein $R^2$ is a cyano group;

[64]: A compound of the above [6] wherein $R^2$ is a nitro group;

[65]: A compound of the above [6] wherein $R^2$ is an amino group;

[66]: A compound of the formula (I) or a compound of the above [1]-[65] wherein G is hydrogen or a group of the following formula:

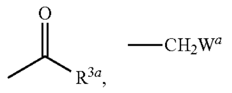

wherein, $R^{3a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group, or a $C_{6-10}$ aryloxy group; and $W^a$ represents a $C_{1-3}$ alkoxy group or a phenyl group optionally substituted with one or more substituents selected from Group A;

[67]: A compound of the above [66] wherein G is hydrogen or a group of the following formula:

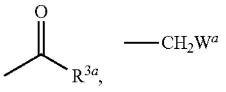

wherein, $R^{3a}$ represents a $C_{1-3}$ alkyl group, a phenyl group, a $C_{1-3}$ alkoxy group, an allyloxy group, a propargyloxy group, or a phenoxy group; and $W^a$ represent a $C_{1-2}$alkoxy group or a phenyl group optionally substituted with one or more substituents selected from Group A;

[68]: A compound of the above [67] wherein G is hydrogen;

[69]: A compound of the above [67] wherein G is a ($C_{1-3}$ alkyl)carbonyl group;

[70]: A compound of the above [69] wherein G is an acetyl group;

[71]: A compound of the above [69] wherein G is a propionyl group;

[72]: A compound of the above [67] wherein G is a benzoyl group;

[73]: A compound of the above [67] wherein G is a $C_{1-3}$ alkoxycarbonyl group;

[74]: A compound of the above [73] wherein G is a methoxycarbonyl group;

[75]: A compound of the above [73] wherein G is an ethoxycarbonyl group;

[76]: A compound of the above [67] wherein G is an allyloxycarbonyl group;

[77]: A compound of the above [67] wherein G is a propargyloxycarbonyl group;

[78]: A compound of the above [67] wherein G is a phenoxycarbonyl group;

[79]: A compound of the above [67] wherein G is a $C_{1-2}$alkoxymethyl group;

[80]: A compound of the above [79] wherein G is a methoxymethyl group;

[81]: A compound of the above [79] wherein G is an ethoxymethyl group;

[82]: A compound of the above [67] wherein G is a phenyl group;

[83]: A compound of the above [67] wherein G is a 4-methoxyphenyl group;

[84]: A compound of the formula (I) or a compound of the above [1]-[83] wherein Z is halogen, a cyano group, a nitro group, a $C_{1-3}$ alkyl group, a $C_{2-3}$alkenyl group, a $C_{2-3}$alkynyl group, a $C_{1-3}$ alkoxy group, a $C_{1-3}$ alkylthio group, or a cyclopropyl group, wherein for the Z group, the $C_{1-3}$ alkyl group, the $C_{2-3}$alkenyl group, the $C_{2-3}$alkynyl group, the $C_{1-3}$ alkoxy group, and the $C_{1-3}$ alkylthio group may be optionally substituted with halogen, and the cyclopropyl group may be optionally substituted with at least one selected from the group consisting of halogen and a methyl group;

n represent an integer of 1-3, when n is 2 or more, each of Z may be same or different;

[85]: A compound of the above [84] wherein Z is halogen, a cyano group, a nitro group, a methyl group, an ethyl group, a vinyl group, an allyl group, an ethinyl group, a propargyl group, a methoxy group, an ethoxy group, a methylthio group, an ethylthio group, or a cyclopropyl group, wherein for the Z group, the methyl group, the ethyl group, the vinyl group, the allyl group, the ethinyl group, the propargyl group, the methoxy group, the ethoxy group, the methylthio group, and the ethylthio group may be optionally substituted with halogen, and the cyclopropyl group may be optionally substituted with at least one selected from the group consisting of halogen and a methyl group; and n represents an integer of 1-3, when n is 2 or more, each of Z may be same or different;

[86]: A compound of the above [85] wherein Z is halogen, a cyano group, a nitro group, a methyl group, a trifluoromethyl group, an ethyl group, a 2,2,2-trifluoroethyl group, a vinyl group, an allyl group, an ethinyl group, a propargyl group, a methoxy group, a trifluoromethoxy group, an ethoxy group, a methylthio group, a trifluoromethylthio group, an ethylthio group, or a cyclopropyl group, and n is an integer of 1-3, when n is 2 or more, each of Z may be same or different;

[87]: A compound of the above [86] wherein Z is fluorine, chlorine, bromine, a cyano group, a methyl group, a trifluoromethyl group, an ethyl group, a vinyl group, an allyl group, an ethinyl group, a methoxy group, an ethoxy group, or a methylthio group, and n is an integer of 1-3, when n is 2 or more, each of Z may be same or different;

[88]: A compound of the above [87] wherein Z is a $C_{1-3}$ alkyl group, and n is an integer of 1-3, when n is 2 or more, each of Z may be same or different;

[89]: A compound of the above [88] wherein Z is a methyl group or an ethyl group, and n is an integer of 1-3, when n is 2 or more, each of Z may be same or different;

[90]: A compound of the above [89] wherein $(Z)_n$ is a 2,4,6-trimethyl group;

[91]: A compound of the above [89] wherein $(Z)_n$ is a 2,4-dimethyl-6-ethyl group;

[92]: A compound of the above [89] wherein $(Z)_n$ is a 2,6-diethyl-4-methyl group;

[93]: A compound of the above [89] wherein $(Z)_n$ is a 2,4,6-triethyl group;

[94]: A compound of the above [89] wherein $(Z)_n$ is a 2-ethyl-4,6-dimethyl group;

[95]: A compound of the above [86] wherein Z is a methyl group, an ethyl group, a vinyl group, an ethinyl group, a trifluoromethyl group, a trifluoromethoxy group, or halogen, and n is an integer of 1-3, when n is 2 or more, each of Z may be same or different;

[96]: A compound of the above [95] wherein $(Z)_n$ is a 2-vinyl-4,6-dimethyl group;

[97]: A compound of the above [95] wherein $(Z)_n$ is a 2-ethinyl-4,6-dimethyl group;

[98]: A compound of the above [95] wherein $(Z)_n$ is a 2-trifluoromethoxy group;

[99]: A compound of the above [95] wherein $(Z)_n$ is a 2-trifluoromethyl-4-chloro group;

[100]: A compound of the formula (I) wherein $R^1$ is a phenyl$C_{1-6}$ alkyl group optionally having a $C_{1-6}$ alkoxy group, a $C_{1-6}$ alkyl group, a $C_{3-6}$ alkenyl group or a ($C_{3-8}$ cycloalkyl) $C_{1-6}$ alkyl group, $R^2$ is halogen, a cyano group, a nitro group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a ($C_{3-8}$ cycloalkyl)$C_{1-6}$ alkoxy group, a ($C_{1-6}$ alkylthio)$C_{1-6}$ alkoxy group, a ($C_{1-6}$ alkoxy)$C_{1-6}$ alkoxy group, a $C_{3-6}$ alkenyloxy group, a $C_{3-6}$ alkynyloxy group, a cyano$C_{1-6}$ alkoxy group, a ($C_{1-6}$ alkoxycarbonyl)$C_{1-6}$ alkoxy group, a carbamoyl$C_{1-6}$ alkoxy group, a (di$C_{1-6}$ alkylaminocarbonyl)$C_{1-6}$ alkoxy group, an amino group, a di($C_{1-6}$ alkyl)amino group, a ($C_{1-6}$ alkyl)carbonylamino group, a hydroxy$C_{1-6}$ alkyl group, a ($C_{1-6}$ alkoxy)$C_{1-6}$ alkyl group, a cyano$C_{1-6}$ alkyl group, a hydroxyimino$C_{1-6}$ alkyl group or a formyl group, G is hydrogen or a group of the following formula:

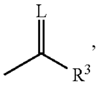,
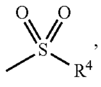,
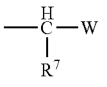

wherein L is oxygen, $R^3$ is a $C_{1-6}$ alkyl group optionally substituted with halogens, a $C_{6-10}$ aryl group optionally substituted with halogens or a $C_{1-6}$ alkyl group, a $C_{1-6}$ alkoxy group optionally substituted with halogens or a $C_{3-6}$ alkenyloxy group optionally substituted with halogens, $R^4$ is a $C_{1-6}$ alkyl group optionally substituted with halogens, $R^7$ is hydrogen, and W is a phenyl group optionally having at least one group selected from the group consisting of a $C_{1-6}$ alkoxy group and halogen, Z is halogen, a $C_{1-6}$ alkyl group optionally substituted with halogens, a $C_{2-6}$ alkenyl group optionally substituted with halogens, a $C_{2-6}$ alkynyl group optionally substituted with halogens, or a $C_{1-6}$ alkoxy group optionally substituted with halogens, and n is an integer of 1-3: provided that when n is 2 or 3, each of Z may be same or different;

[101] A compound of the formula (I-II):

(I-II)

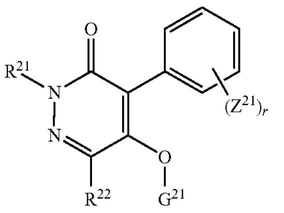

wherein $R^{21}$ represents hydrogen, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl)$C_{3-8}$ cycloalkyl group, a ($C_{3-8}$ cycloalkyl)$C_{1-6}$ alkyl group, a ($C_{3-8}$ cycloalkyl)$C_{3-8}$ cycloalkyl group, a ($C_{3-8}$ halocycloalkyl)$C_{1-6}$ alkyl group, a {($C_{1-6}$ alkyl)$C_{3-8}$ cycloalkyl}$C_{1-6}$ alkyl group, a ($C_{1-6}$ alkoxy)$C_{1-8}$ alkyl group, a ($C_{3-8}$ cycloalkoxy)$C_{1-8}$ alkyl group, a {($C_{1-6}$ alkoxy)$C_{1-6}$ alkoxy}$C_{1-6}$ alkyl group, a ($C_{1-6}$ alkylthio)$C_{1-8}$ alkyl group, a ($C_{1-8}$ alkylsulfinyl)$C_{1-8}$ alkyl group, a ($C_{1-6}$ alkylsulfonyl)$C_{1-6}$ alkyl group, or a tetrahydropyranyl group;

$R^{22}$ represents halogen, a cyano group, a nitro group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, a $C_{1-6}$ haloalkylsulfonyl group, a $C_{3-8}$ cycloalkoxy group, a ($C_{3-8}$ cycloalkyl)$C_{1-6}$ alkoxy group, an amino group, a $C_{1-6}$ alkylamino group, or a di($C_{1-8}$ alkyl)amino group;

$G^{21}$ represents hydrogen or a group of the following formula:

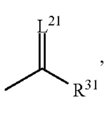,
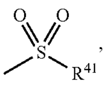,
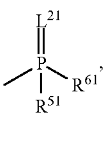,
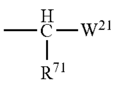

wherein, $L^{21}$ represents oxygen or sulfur;

$R^{31}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl)$C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl)$C_{1-6}$ alkoxy group, a di($C_{1-6}$ alkyl)amino group, a di($C_{3-6}$ alkenyl)amino group, a ($C_{1-6}$ alkyl)($C_{6-10}$ aryl)amino group, or a 5-6 membered heteroaryl group;

$R^{41}$ represents a $C_{1-6}$ alkyl group, a $C_{6-10}$ aryl group, or a di($C_{1-6}$ alkyl)amino group;

$R^{51}$ and $R^{61}$ may be same or different and represent independently a $C_{1-6}$ alkyl group, a $C_{3-8}$ cycloalkyl group, a $C_{6-10}$ aryl group, a $C_{1-6}$ alkoxy group, a $C_{3-8}$ cycloalkoxy group, a $C_{6-10}$ aryloxy group, a ($C_{6-10}$ aryl) $C_{1-6}$ alkoxy group, a $C_{1-6}$ alkylthio group, or a di($C_{1-6}$ alkyl)amino group;

$R^{71}$ represents hydrogen or a $C_{1-6}$ alkyl group; and $R^{21}$ represents a $C_{1-6}$ alkoxy group, a $C_{1-6}$ alkylthio group, a $C_{1-6}$ alkylsulfinyl group, or a $C_{1-6}$ alkylsulfonyl group: provided that any of $R^{31}$, $R^{41}$, $R^{51}$, $R^{61}$, and $W^{21}$ may be optionally substituted with halogens, and any of the $C_{3-8}$ cycloalkyl group, the $C_{6-10}$ aryl group, the aryl part of the ($C_{6-10}$ aryl) $C_{1-6}$ alkyl group, the $C_{3-8}$ cycloalkoxy group, the $C_{6-10}$ aryloxy group, the aryl part of the ($C_{6-10}$ aryl)$C_{1-6}$ alkoxy group, the aryl part of the ($C_{1-6}$ alkyl)($C_{6-10}$ aryl)amino group, and the 5-6 membered heteroaryl group may be optionally substituted with a $C_{1-6}$ alkyl group;

$Z^{21}$ represents halogen, a cyano group, a nitro group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, or a $C_{3-8}$ cycloalkyl group: provided that for the $Z^{21}$ group, the $C_{1-6}$ alkyl group, the $C_{2-6}$ alkenyl group, the $C_{2-6}$ alkynyl group, the $C_{1-6}$ alkoxy group, and the $C_{1-6}$ alkylthio group may be optionally substituted with halogens, and the $C_{3-8}$ cycloalkyl group may be optionally substituted with at least one group selected from the group consisting of halogen and a $C_{1-6}$ alkyl group;

r represents an integer of 1-5: provided that when r is 2 or more, each of $Z^{21}$ may be same or different;

[102] A compound of the above [101] wherein $R^{21}$ is hydrogen or a $C_{1-3}$ alkyl group, $R^{22}$ is a $C_{1-3}$ alkoxy group, a $C_{1-3}$ alkylthio group, a $C_{1-3}$ alkylsulfinyl group, a $C_{1-3}$ alkyl sulfonyl group, or a di($C_{1-3}$ alkyl)amino group, $G^{21}$ is hydrogen or a group of the following formula:

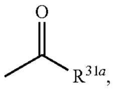,
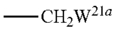

wherein $R^{31a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group, or a $C_{6-10}$ aryloxy group, and $W^{21a}$ represents a $C_{1-3}$ alkoxy group;

$Z^{21}$ is a $C_{1-3}$ alkyl group, and r is an integer 1-3: provided that when r is 2 or more, each $Z^{21}$ may be same or different;

[103]: A compound of the above [102] wherein $R^{21}$ is a methyl group, $R^{22}$ is a methoxy group, an ethoxy group, a methylthio group, a methylsulfinyl group, a methylsulfonyl group, or a dimethylamino group, $G^{21}$ is hydrogen, an acetyl group, a propionyl group, a benzoyl group, a methoxycarbonyl group, an ethoxycarbonyl group, an allyloxycarbonyl group, a phenoxycarbonyl group, a methoxymethyl group or an ethoxycarbonyl group, and $Z^{21}$ is a methyl group, or an ethyl group;

[104]: A compound of the above one of [101]-[103] wherein $G^{21}$ is hydrogen;

[105]A compound of the above [101] wherein $R^{21}$ is hydrogen, a $C_{1-6}$ alkyl group, a $C_{1-6}$ haloalkyl group, a $C_{3-8}$ cycloalkyl group, a ($C_{3-8}$ cycloalkyl)$C_{1-6}$ alkyl group, or a ($C_{1-6}$ alkoxy)$C_{1-6}$ alkyl group;

[106] A compound of the above [105] wherein $R^{21}$ is hydrogen, a alkyl group, a haloalkyl group, a cyclopropyl group, a cyclopropyl group, or a ($C_{1-3}$ alkoxy)methyl group;

[107] A compound of the above [106] wherein $R^{21}$ is hydrogen, or a $C_{1-3}$ alkyl group;

[108] A compound of the above [107] wherein $R^{21}$ is a methyl group;

[109] A compound of the above [107] wherein $R^{21}$ is hydrogen;

[110] A compound of the above [101] or one of [105]-[109] wherein $R^{22}$ is halogen, a cyano group, a nitro group, a $C_{1-3}$ alkoxy group, a $C_{1-3}$ haloalkoxy group, a $C_{1-3}$ alkylthio group, a $C_{1-3}$ alkylsulfinyl group, a $C_{1-3}$ alkylsulfonyl group, a $C_{1-3}$ haloalkylthio group, a $C_{1-3}$ haloalkylsulfinyl group, a $C_{1-3}$ haloalkylsulfonyl group, a $C_{3-6}$ cycloalkoxy group, a ($C_{3-6}$ cycloalkyl)$C_{1-3}$ alkoxy group, an amino group, a $C_{1-3}$ alkylamino group, or a di($C_{1-3}$ alkyl)amino group;

[111] A compound of the above [110] wherein $R^{22}$ is a $C_{1-3}$ alkoxy group, a $C_{1-3}$ alkylthio group, a $C_{1-3}$ alkylsulfinyl group, a $C_{1-3}$ alkylsulfonyl group, or a di($C_{1-3}$ alkyl)amino group;

[112] A compound of the above [111] wherein $R^{22}$ is a $C_{1-3}$ alkoxy group;

[113] A compound of the above [112] wherein $R^{22}$ is a methoxy group;

[114] A compound of the above [112] wherein $R^{22}$ is an ethoxy group;

[115] A compound of the above [111] wherein $R^{22}$ is a $C_{1-3}$ alkylthio group;

[116] A compound of the above [115] wherein $R^{22}$ is a methylthio group;

[117] A compound of the above [115] wherein $R^{22}$ is an ethylthio group;

[118] A compound of the above [111] wherein $R^{22}$ is a $C_{1-3}$ alkylsulfinyl group;

[119] A compound of the above [118] wherein $R^{22}$ is a methylsulfinyl group;

[120] A compound of the above [118] wherein $R^{22}$ is an ethylsulfinyl group;

[121] A compound of the above [111] wherein $R^{22}$ is a $C_{1-3}$ alkylsulfonyl group;

[122] A compound of the above [121] wherein $R^{22}$ is a methylsulfonyl group;

[123] A compound of the above [121] wherein $R^{22}$ is an ethylsulfonyl group;

[124] A compound of the above [111] wherein $R^{22}$ is a di($C_{1-3}$ alkylamino group;

[125] A compound of the above [124] wherein $R^{22}$ is a dimethylamino group;

[126] A compound of the above [101] or one of [105]-[125] wherein $G^{21}$ is hydrogen or a group of the following formula:

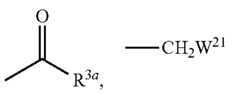

wherein:

$R^{3a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group, or a $C_{6-10}$ aryloxy group, and $W^{21}$ represents a $C_{1-3}$ alkyl group;

[127] A compound of the above [126] wherein $R^{3a}$ is a $C_{1-3}$ alkyl group, a phenyl group, a $C_{1-3}$ alkoxy group, an allyloxy group, a propargyloxy group, or a phenoxy group, and $W^{21}$ is a $C_{1-2}$ alkyl group;

[128] A compound of the above [127] wherein $G^{21}$ is hydrogen;

[129] A compound of the above [127] wherein $G^{21}$ is a ($C_{1-3}$ alkyl)carbonyl group;

[130] A compound of the above [129] wherein $G^{21}$ is an acetyl group;

[131] A compound of the above [129] wherein $G^{21}$ is a propionyl group;

[132] A compound of the above [127] wherein $G^{21}$ is a benzoyl group;

[133] A compound of the above [127] wherein $G^{21}$ is a $C_{1-3}$ alkoxycarbonyl group;

[134] A compound of the above [133] wherein $G^{21}$ is a methoxycarbonyl group;

[135] A compound of the above [133] wherein $G^{21}$ is an ethoxycarbonyl group;

[136] A compound of the above [133] wherein $G^{21}$ is an allyloxycarbonyl group;

[137] A compound of the above [127] wherein $G^{21}$ is a propargyloxycarbonyl group;

[138] A compound of the above [127] wherein $G^{21}$ is a phenoxycarbonyl group;

[139] A compound of the above [127] wherein $G^{21}$ is a $C_{1-2}$ alkoxymethyl group;

[140] A compound of the above [139] wherein $G^{21}$ is a methoxymethyl group;

[141] A compound of the above [139] wherein $G^{21}$ is an ethoxymethyl group;

[142] A compound of the above [101] or one of [105]-[141] wherein $Z^{21}$ is halogen, a cyano group, a nitro group, a $C_{1-3}$ alkyl group, a $C_{2-3}$ alkenyl group, a $C_{2-3}$ alkynyl group, a $C_{1-3}$ alkoxy group, a $C_{1-3}$ alkylthio group, or a cyclopropyl group, and r is an integer of 1-3: provided that any of the $C_{1-3}$ alkyl group, the $C_{2-3}$ alkenyl group, the $C_{2-3}$ alkynyl group, the $C_{1-3}$ alkoxy group, and the $C_{1-3}$ alkylthio group may be optionally substituted with halogen, the cyclopropyl group may be substituted with at least one group consisting of halogen and a methyl group, and when r is 2 or more, each of $Z^{21}$ may be same or different;

[143] A compound of the above [142] wherein $Z^{21}$ is halogen, a cyano group, a nitro group, a methyl group, an ethyl group, a vinyl group, an allyl group, an ethynyl group, a propargyl group, a methoxy group, an ethoxy group, a methylthio group, an ethylthio group, or a cyclopropyl group, and r is an integer of 1-3: provided that any of the methyl group, the ethyl group, the vinyl group, the alllyl group, the ethynyl group, the propargyl group, the methoxy group, the methylthio group, and the ethylthio group may be optionally substituted with halogen, the cyclopropyl group may be optionally substituted with at least one group selected from the group consisting of halogen and a methyl group, and when r is 2 or more, each of $Z^{21}$ may be same or different;

[144] A compound of the above [143] wherein $Z^{21}$ is halogen, a cyano group, a nitro group, a methyl group, a trifluoromethyl group, an ethyl group, a 2,2,2-trifluoroethyl group, a vinyl group, an allyl group, an ethynyl group, a propargyl group, a methoxy group, a trifluoromethoxy group, an ethoxy group, a methylthio group, a trifluoromethylthio group, an ethylthio group, or a cyclopropyl group, and r is an integer of 1-3: provided that when r is 2 or more, each of $Z^{21}$ may be same or different;

[145] A compound of the above [134] wherein $Z^{21}$ is fluorine, chlorine, bromine, a cyano group, a methyl group, a trifluoromethyl group, an ethyl group, a vinyl group, an allyl group, an ethylnyl group, a methoxy group, an ethoxy group, or a methylthio group, and r is an integer of 1-3: provided that when r is 2 or more, each of $Z^{21}$ may be same or different;

[146] A compound of the above [142] wherein $Z^{21}$ is a $C_{1-3}$ alkyl group, and r is an integer of 1-3: provided that when r is 2 or more, each of $Z^{21}$ may be same or different;

[147] A compound of the above [146] wherein $Z^{21}$ is a methyl group or an ethyl group, and r is an integer of 1-3: provided that when r is 2 or more, each of $Z^{21}$ may be same or different;

[148] A compound of the above [147] wherein $(Z^{21})_r$ is a 2,4,6-trimethyl group;

[149] A compound of the above [147] wherein $(Z^{21})_r$ is a 2,4-dimethyl-6-ethyl group;

[150] A compound of the above [147] wherein $(Z^{21})_r$ is a 2,6-diethyl-4-methyl group; and

[151] A compound of the above [147] wherein $(Z^{21})_r$ is a 2,4,6-triethyl group.

The herbicide and the noxious arthropod controlling agent of the present invention contain the present compound and an inert carrier. Examples of the inert carrier include a solid carrier, a liquid carrier, and a gaseous carrier. The herbicide and the noxious arthropod controlling agent of the present invention are usually a formulation such as a wettable powder, a wettable granule, a flowable formulation, a granule, a dryflowable formulation, an emulsion, an aqueous liquid formulation, an oil solution, a smoking agent, an aerosol, and a microcapsule by adding further adjuvants for formulation such as a surfactant, binders, dispersants, and stabilizers. The herbicide and noxious arthropod controlling agent of the present invention usually contain the present compound in an amount of 0.1-80% by weight.

Examples of the inert carrier include a solid carrier, a liquid carrier, and a gaseous carrier.

Examples of the solid carrier include a fine power and a granule of clays (such as kaolin, diatomite, synthetic hydrated silicon oxide, Fubasami clay, bentonite, and acid clay), talcs, other inorganic minerals (such as sericite, quartz powder, sulfur powder, activated carbon, calcium carbonate, and hydrated silica). Examples of the liquid carrier include, water, alcohols (such as methanol and ethanol), ketones (such as acetone and methylethylketone), aromatic hydrocarbons (such as benzene, toluene, xylene, ethylbenzene, and methylnaphthalene), aliphatic hydrocarbons (such as n-hexane, cyclohexane, and light oil), esters (such as ethyl acetate and butyl acetate), nitriles (such as acetonitrile and isobutylnitrile), ethers (such as dioxane and diisopropylether), acid amides (such as N,N-dimethylformamide and dimethylacetamide), halogenated hydrocarbons (such as dichloroethane, trichloroethylene, and carbon tetrachloride).

Examples of the surfactant include alkylsulfuric acidesters, alkylsulfonic acid salts, alkylarylsulfonic acid salts, alkyl aryl ethers and polyoxyethylene thereof, polyoxyethylene glycol ethers, polyalcoholesters, and sugar alcohol derivatives.

Examples of the other adjuvant for formulation include binders and dispersants, particurally, casein, gelatin, polysaccharides (such as starch, gum arabic, cellulose derivatives, and alginic acid), lignin derivatives, bentonite, sugars, synthetic water-soluble polymers (such as polyvinyl alcohol, polyvinylpyrrolidone, and polyacrylic acid), PAP (acidic isopropyl phosphate), BHT (a mixture of 2-t-butyl-4-methoxyphenol and 3-t-butyl-4-methoxyphenol), vegetable oil, mineral oil, fatty acid and esters thereof.

The method of controlling weeds of the present invention comprises the step of applying an effective amount of the present compound to weeds or soil where weeds grow. For the method of controlling weeds of the present invention, the herbicidal composition of the present invention is usually used. Examples of application method of the herbicidal composition of the present invention include foliage treatment of weeds with the herbicidal composition of the present invention, treatment of the surface of soil where weeds grow with the herbicidal composition of the present invention, or soil incorporation of the herbicidal composition of the present invention into the soil where weeds grow. In the method of controlling weeds of the present invention, the present compound is used in an amount of usually 1 to 5,000 g, preferably 10 to 1,000 g per 10,000 $m^2$ of an area where weed control is desired.

The method of controlling noxious arthropods of the present invention comprises applying an effective amount of the present compound to noxious arthropods or habitats of noxious arthropods. For the method of controlling arthropods of the present invention, a formulation which contains the present compound is usually used.

When the present compound is used for controlling arthropods in agriculture and forestry, the application amount is usually 1 to 10,000 g, preferably 10 to 1,000 g of the present compound per 10,000 $m^2$. In the method of controlling noxious arthropods of the present invention, for example, a formulation which contains the present compound can be applied to plants to be protected from noxious arthropods by spraying. Also, soil can be treated with a formulation which contains the present compound to control noxious arthropods living in the soil.

When the present compound is used for the control of arthropods in public and environmental health area, the application amount is usually 0.001 to 10 mg/$m^3$ of the present compound for application to space, and 0.001 to 100 mg/$m^2$ of the present compound for application to a plane.

The pest controlling agent of the present invention could be used in farmlands on which "plants" shown below are cultivated. "plants":

Agricultural crops: corn, rice, wheat, barley, rye, oat, sorghum, cotton, soybean, peanut, sarrazin, sugar beet, rapeseed, sunflower, sugar cane, and tobacco;

Vegetables: Solanaceae vegetables (such as eggplant, tomato, green pepper, hot pepper, and potato), Cucurbitaceae vegetables (such as cucumber, pumpkin, zucchini, watermelon, and melon), Cruciferae vegetables (such as Japanese radish, turnip, horseradish, kohlrabi, Chinese cabbage, cabbage, brown mustard, broccoli, and cauliflower), Compositae vegetables (such as burdock, garland chrysanthemum, artichoke, and lettuce), Liliaceae vegetables (such as Welsh onion, onion, garlic, and asparagus), Umbelliferae vegetables (such as carrot, parsley, celery, and parsnip), Chenopodiaceae vegetables (such as spinach, and Swiss chard), Labiatae vegetables (such as Japanese basil, mint, and basil), strawberry, sweat potato, yam, and aroid;

Fruit trees: pomaceous fruits (such as apple, common pear, Japanese pear, Chinese quince, and quince), stone fleshy fruits (such as peach, plum, nectarine, Japanese plum, cherry, apricot, and prune), citrus plants (such as Satsuma mandarin, orange, lemon, lime, and grapefruit), nuts (such as chestnut, walnut, hazel nut, almond, pistachio, cashew nut, and macadamia nut), berry fruits (such as blueberry, cranberry, blackberry, and raspberry), grape, persimmon, olive, loquat, banana, coffee, date, coconut palm, and oil palm;

Trees other fruit trees: tea, mulberry, flowering trees (such as azalea, japonica, hydrangea, sasanqua, Illicium anisatum, cherry tree, tulip poplar, crepe myetle, and orange osmanthus), street trees (such as ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, and horse-chestnut), sweet viburnum, *Podocarpus macrophyllus*, Japanese cedar, Japanese cypress, croton, spindle tree, and Chainese howthorn.

Others: flowers (such as rose, carnation, chrysanthemum, *Eustoma grandiflorum* Shinners, gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, and begonia), biofuel plants (such as *Jatropha*, safflower, Camelina alyssum, switchgrass, miscanthus, reed canary grass, *Arundo donax*, kenaf, cassava, and willow), and foliage plant.

The aforementioned "plants" include plants, to which resistance to 4-hydroxyphenyl pyruvate dioxygenase inhibitors such as isoxaflutole; acetolactate synthase (hereinafter referred to as ALS) inhibitors such as imazethapyr and thifensulfuron-methyl; 5-enolpyruvylshikimate-3-phosphate synthetase (hereinafter referred to as EPSPS) inhibitors such as glyphosate; glutamine synthetase inhibitors such as the glufosinate; acetyl-CoA carboxylase inhibitors such as sethoxydim; protoporphyrinogen oxidase inhibitors such as flumioxazin; auxin herbicides such as dicamba and 2,4-D; or herbicides such as bromoxynil, etc. has been conferred by a classical breeding method or genetic engineering technique.

Examples of a "plant" on which resistance has been conferred by a classical breeding method include rapeseed, wheat, sunflower, rice and corn resistant to imidazolinone ALS inhibitory herbicides such as imazethapyr, which are already commercially available under a product name of Clearfield®. Similarly, there is STS® soybean on which resistance to sulfonylurea ALS inhibitory herbicides such as thifensulfuron-methyl has been conferred by a classical breeding method. Similarly, there is Express® sunflower on which resistance to ALS inhibitory herbicides such as tribenuron methyl has been conferred by a classical breeding method. Similarly, examples of plants on which resistance to acetyl-CoA carboxylase inhibitors such as trione oxime or aryloxy phenoxypropionic acid herbicides has been conferred by a classical breeding method include SR corn. The plants on which resistance to acetyl-CoA carboxylase inhibitors has been conferred is described in Proc. Natl. Acad. Sci. USA, vol. 87, pp. 7175-7179 (1990).

Examples of a "plant" on which resistance has been conferred by genetic engineering technique include corn, soybean, cotton, rapeseed, and sugar beet resistant to glyphosate which has an EPSPS gene resistant to EPSPS inhibitors. The plants are already commercially available under a product name of RoundupReady®, Agrisure®GT, Gly-Tol, etc. Similarly, there are corn, soybean, cotton, and rapeseed on which resistance to glufosinate has been conferred by genetic engineering technique. The plants are already commercially available under a product name of LibertyLink®, etc. Similarly, cotton on which resistance tobromoxynil has been conferred by genetic engineering technique is already commercially available under a product name of BXN. Similarly, there are corn and soybean resistant to both glyphosate and ALS inhibitors has been released as a product name of Optimum®GAT®. Soybean on which resistance toimazapyr has been conferred by genetic engineering technique has been released as Cultivance®.

A variation of acetyl-CoA carboxylase resistant to acetyl-CoA carboxylase inhibitors is reported in Weed Science, vol. 53, pp. 728-746 (2005) and a plant resistant to acetyl-CoA carboxylase inhibitors can be generated by introducing a gene of such acetyl-CoA carboxylase variation into a plant by genetic engineering technique, or by introducing a variation conferring resistance into a plant acetyl-CoA carboxylase. Furthermore, a plant resistant to acetyl-CoA carboxylase inhibitors or ALS inhibitors can be generated by introducing a site-directed amino acid substitution variation into an acetyl-CoA carboxylase gene or an ALS gene of a plant by introducing a nucleic acid into which a base substitution variation has been introduced represented Chimeraplasty Technique (Gura T., Repairing the Genome's Spelling Mistakes. Science 285: pp. 316-318 (1999)) into a plant cell.

A crop such as soybean resistant to dicamba can be generated by introducing a gene encoding a degrading enzyme of dicamba, which includes dicamba monooxygenase isolated from *Pseudomonas maltophilia* (Behrens et al. 2007 Dicamba Resistance: Enlarging and Preserving Biotechnology-Based Weed Management Strategies. Science 316, pp. 1185-1188).

A crop resistant to both herbicide systems, phenoxy herbicides such as 2,4-D, MCPA, dichlorpropand mecoprop; and pyridineoxy acetic acid herbicides such as fluoroxypyr and trichlopyr; and aryloxyphenoxypropionic acid herbicides such as quizalofop-P-ethyl, haloxyfop-P-methyl, fluazifop-P-butyl, diclofop, fenoxaprop-P-ethyl, metamifop, cyhalofop-buthyl and clodinafop-propargyl can be generated by introducing a gene encoding aryloxyalkanoate dioxygenase (WO 05/107437, WO 07/053,482, WO 08/141,154), which is called a DHT crop.

Furthermore, a plant resistant to HPPD inhibitors can be generated by introducing a gene encoding HPPD resistant to HPPD inhibitors (US 2004/0058427). A plant resistant to HPPD inhibitors can be generated by introducing a gene which, even if HPPD is inhibited by HPPD inhibitors, can synthesize homogentisic acid being a production of HPPD via other metabolic pathway (WO 02/036787). A plant resistant to HPPD inhibitors can be generated by introducing a gene expressing excessive HPPD and making the plant produce HPPD up to amounts which do not affect the growth of the plant (WO 96/38567). A plant resistant to HPPD inhibitors can be generated by introducing the above gene expressing excessive HPPD, further introducing a gene encoding prephenate dehydrogenase in order to increase the production of p-hydroxyphenylpyruvic acid being a substrate for HPPD (Rippert P et. al., Engineering plant shikimate pathway for production of tocotrienol and improving herbicide resistance. Plant Physiol. 134: pp. 92-100 (2004)).

The aforementioned "plant" includes a plant on which resistance to nematodes and aphid has been conferred by a classical breeding method. Examples thereof include soybean having a Ragl (Resistance Aphid Gene 1) gene capable of conferring resistance to aphid.

The aforementioned "plant" includes a plant on which the ability to synthesize, for example, selective toxins as known in genus *Bacillus* has been conferred by genetic engineering techniques.

Examples of toxins expressed in such genetically engineered plant include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3, or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crop also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. In a modified toxin, one or multiple amino acids of natural toxins are substituted. Examples of such toxins and genetically engineered plants capable of synthesizing the toxins are described in EP-A-0 374 753, WO 93/07278, WO 95/34656, EP-A-0 427 529, EP-A-451 878, WO 03/052073, etc. Toxins contained in the genetically engineered plants are able to confer resistance particularly to insect pests belonging to Coleoptera, Hemiptera, Diptera, Lepidoptera and Nematodes, on the plant.

Genetically engineered plants, which comprise one or multiple insecticidal pest-resistant genes and which express one or multiple toxins, have already been known, and some of the genetically engineered plants have already been on the market. Examples of the genetically engineered plants include YieldGard® (a corn variety for expressing Cry1Ab toxin), YieldGard Rootworm® (a corn variety for expressing Cry3Bb1 toxin), YieldGard Plus® (a corn variety for expressing Cry1Ab and Cry3Bb1 toxins), Herculex I® (a corn variety for expressing phosphinotricine N-acetyl transferase (PAT) so as to confer resistance to Cry1Fa2 toxin and glufosinate), NuCOTN33B® (a cotton variety for expressing Cry1Ac toxin), Bollgard I® (a cotton variety for expressing Cry1Ac toxin), Bollgard II® (a cotton variety for expressing Cry1Ac and Cry2Ab toxins), VIPCOT® (a cotton variety for expressing VIP toxin), NewLeaf® (a potato variety for expressing Cry3A toxin), NatureGard® Agrisure® GT Advantage (GA21 glyphosate-resistant trait), Agrisure®CB Advantage (Btll corn borer (CB). trait), and Protecta®. There is genetically engineered papaya into which has been introduced a capsid protein gene of papaya ringspot virus (PRSV), which is already commercially available under a product name of Rainbow Papayaa®.

The aforementioned "plant" also includes a plant on which the ability to produce antipathogenic substances having selective action has been conferred by genetic engineering techniques.

Examples of antipathogenic substances expressed in the genetically engineered plant include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein (PRPs, EP-A-0 392 225); and antipathogenic substances generated by microorganisms, such as a peptide antibiotic, an antibiotic having a hetero ring, a protein factor associated with resistance to plant diseases. The antipathogenic substances and genetically engineered plants producing the substances are described in EP-A-0392225, WO95/33818, EP-A-0353191, etc.

The aforementioned "plant" also includes a plant on which resistances to environmental stress such as cold resistance, heat resistance, drought resistance and salt resistance have been conferred by a classical breeding method or genetic engineering technology. Examples of craps on which drought resistance has been conferred include cspB-introduced crops.

The aforementioned "plant" includes a plant on which advantageous characters such as characters improved in oil stuff ingredients or characters having reinforced amino acid content have been conferred by genetic engineering technology. Examples thereof include VISTIVE® (low linolenic soybean having reduced linolenic content) or high-lysine (high-oil) corn (corn with increased lysine or oil content).

Stack varieties are also included in which are combined a plurality of advantageous characters such as the classic herbicide tolerance characters mentioned above or herbicide tolerance genes, harmful insect resistance genes, antipathogenic substance producing genes, environmental stress tolerance genes, and characters improved in oil stuff ingredients or characters having reinforced amino acid content.

When the present compound is used for a herbicide-resistant crops, the crops are treated sequentially with the present compound and the herbicide (such as glyphosate or a salt thereof, glufosinate or a salt thereof, dicamba or a salt thereof, imazethapyr or a salt thereof, and isoxaflutole) to which the crops is resistant, or with a mixture of both, and thereby comprehensive weed control can be attained.

The present compound can be used as a mixture with or together with other insecticides, acaricides, nematocides, fungicides, and/or synergists.

Examples of the active ingredients of insecticides include as follows:

(1) Organic Phosphorus Compounds:

Acephate, butathiofos, chlorethoxyfos, chlorfenvinphos, chlorpyrifos, chlorpyrifos-methyl, cyanophos: CYAP, dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds:

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, oxamyl, pirimicarb, propoxur: PHC, XMC, thiodicarb, xylylcarb, and aldicarb.

(3) Pyrethroid Compounds:

Acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethyl cyclopropanecarboxylate, and protrifenbute.

(4) Nereistoxin Compounds:

Cartap, bensultap, thiocyclam, monosultap, and bisultap.

(5) Neonicotinoid Compounds:

Imidacloprid, nitenpyram, acetamiprid, thiamethoxam, thiacloprid, dinotefuran, and clothianidin.

(6) Benzoylurea Compounds:

Chlorfluazuron, bistrifluoron, diflubenzuron, fluazuron, flucycloxuron, flufenoxuron, hexaflumuron, lufenuron, novaluron, noviflumuron, teflubenzuron, and triflumuron.

(7) Phenylpyrazole Compounds:

Acetoprole, ethiprole, fipronil, vaniliprole, pyriprole, and pyrafluprole.

(8) Bt Toxines:

Live spores derived from and crystal toxins produced from *Bacillus* thuringiesis and a mixture thereof;

(9) Hydrazine Compounds:

Chromafenozide, halofenozide, methoxyfenozide, and tebufenozide.

(10) Organic Chlorine Compounds:

Aaldrin, dieldrin, chlordane, DDT, dienochlor, endosulfan, and methoxychlor.

(11) Other Insecticidal Active Ingredients:

Mmachine oil, nicotine-sulfate; avermectin-B, bromopropylate, buprofezin, chlorphenapyr, cyromazine, DCIP (dichlorodiisopropyl ether), D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, aluminium phosphide, arsenic acid, benclothiaz, calcium cyanamide, calcium polysulfide, DSP, flonicamid, flurimfen, formetanate, metam-ammonium, metam-sodium, Methyl bromide, Potassium oleate, spiromesifen, sulfur, metaflumizone, spirotetramat, pyrifluquinazone, spinetoram, chlorantraniliprole, tralopyril, diafenthiuron, a compound of the formula (A):

(A)

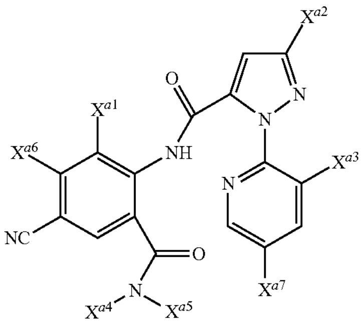

wherein $X^{a1}$ represents a methyl group, chlorine, bromine, or fluorine, $X^{a2}$ represents fluorine, chlorine, bromine, a $C_1$-$C_4$ haloalkyl group, or a $C_1$-$C_4$haloalkoxy group, $X^{a3}$ represents fluorine, chlorine, or bromine, $X^{a4}$ represents an optionally substituted $C_1$-$C_4$ alkyl, an optionally substituted $C_3$-$C_4$ alkenyl, an optionally substituted $C_3$-$C_4$ alkynyl, an optionally substituted $C_3$-$C_5$ cycloalkylalkyl, or hydrogen, $X^{a5}$ represents hydrogen or a methyl group, $X^{a6}$ represents hydrogen, fluorine, or chlorine, and $X^{a7}$ represents hydrogen, fluorine, or chlorine, a compound of the formula (B):

(B)

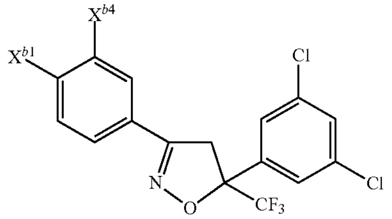

wherein $X^{b1}$ represents a $X^{b2}$—NH—C(═O) group, a $X^{b2}$—C(═O)—NH—$CH_2$ group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted $C_1$-$C_4$ haloalkyl group such as a 2,2,2-trifluoroethyl group or an optionally substituted $C_3$-$C_6$ cycloalkyl group such as a cyclopropyl group, $X^{b3}$ represents an optionally substituted $C_1$-$C_4$ alkyl group such as a methyl group, and $X^{b4}$ represents hydrogen, chlorine, cyano group, or a methyl group; and a compound of the formula (C)

(C)

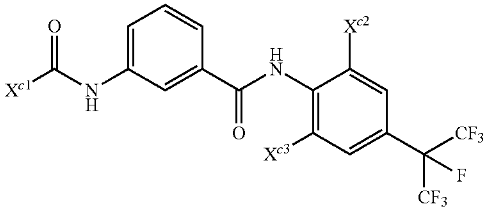

wherein $X^{c1}$ represents an optionally substituted $C_1$-$C_4$ alkyl group such as a 3,3,3-trifluoropropyl group, an optionally substituted $C_1$-$C_4$ alkoxy group such as a 2,2,2-trichloroethoxy group, an optionally substituted phenyl group such as a 4-cyanophenyl group, or an optionally substituted pyridyl group such as a 2-chloro-3-pyridyl group, $X^{c2}$ represents a methyl group, or a trifluoromethylthio group, and $X^{c3}$ represents a methyl group or halogen.

Examples of the active ingredients of acardides include as follows:

Acequinocyl, amitraz, benzoximate, bifenazate, bromopropylate, chinomethionat, chlorobenzilate, CPCBS (chlorfenson), clofentezine, cyflumetofen, Kelthane (dicofol), etoxazole, fenbutatin oxide, fenothiocarb, fenpyroximate, fluacrypyrim, halfenprox, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Examples of the active ingredients of nematocides include as follows:

DCIP, fosthiazate, levamisole hydrochloride (levamisole), methylsothiocyanate, morantel tartarate, and imicyafos.

Examples of the active ingredients of fungicides include as follows:

(1) Polyhaloalkylthio Compounds:

Captan and folpet.

(2) Organic Phosphorus Compounds:

IBP, EDDP, and tolclofos-methyl.

(3) Benzimidazole Compounds:

Benomyl, carbendazim, thiophanate-methyl, and thiabendazole.

(4) Carboxyamide Compounds:

Carboxin, mepronil, flutolanil, thifluzamid, furametpyr, boscalid), and penthiopyrad.

(5) Dicarboxylmide Compounds:

Procymidone, iprodione, and vinclozolin.

(6) Acyl Alanine Compounds:

Metalaxyl.

(7) Azole Compounds:

Triadimefon, triadimenol, propiconazole, tebuconazole, cyproconazole, epoxiconazole, prothioconazole, ipconazole, triflumizole, prochloraz, penconazole, flusilazole, diniconazole, bromuconazole, difenoconazole, metconazole, tetraconazole, myclobutanil, fenbuconazole, hexaconazole, fluquinconazole, triticonazole, bitertanol, imazalil, and flutriafol.

(8) Morpholine Compounds:

Dodemorph, tridemorph, and fenpropimorph.

(9) Strobilurin Compounds:

Azoxystrobin, kresoxim-methyl, metominostrobin, trifloxystrobin, picoxystrobin, pyraclostrobin, fluoxastrobin, and dimoxystrobin.

(10) Antibiotics

Validamycin A, blasticidin S, kasugamycin, and polyoxin.

(11) Dithiocarbamate Compounds:

Mancozeb, maneb, and thiuram.

(12) Other Fungicidal Active Ingredients:

Fthalide, probenazole, isoprothiolane, tricyclazole, pyroquilon, ferimzone, acibenzolar S-methyl, carpropamid, diclocymet, fenoxanil, tiadinil, diclomezine, teclofthalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, basic copper calcium sulfate (bordeaux mixture), dichlofluanid, cyprodinil, pyrimethanil, mepanipyrim, diethofencarb, pyribencarb, famoxadone, fenamidone, zoxamide, ethaboxam, amisulbrom, iprovalicarb, benthiavalicarb, cyazofamid, mandipropamid, metrafenone, fluopiram, and bixafen.

Examples of the active ingredients of synergists include as follows:

Piperonyl butoxide, sesamex, sulfoxide, N-(2-ethylhexyl)-8,9,10-trinorborn-5-ene-2,3-dicarboxylmide (MGK 264), N-declyimidazole, WARF-antiresistant, TBPT, TPP, IBP, PSCP, methyl iodide ($CH_3I$), t-phenylbutenone, diethyl maleate, DMC, FDMC, ETP, and ETN.

Examples of the subjects to be controlled by the herbicide of the present invention include as follows:

Weeds such as *Digitaria ciliaris, Eleusine indica, Setaria viridis, Setaria faberi, Setaria glauca, Echinochloa crus-galli, Panicum dichotomiflorum, Panicum texanum, Brachiaria platyphylla, Brachiaria plantaginea, Brachiaria decumbens, Sorghum halepense, Andropogon sorghum, Cynodon dactylon, Avena fatua, Lolium multiflorum, Alopecurus myosuroides, Bromus tectorum, Bromus sterilis, Phalaris minor, Apera spica-venti, Poa annua, Agropyron repens, Cyperus iria, Cyperus rotundus, Cyperus esculentus, Portulaca oleracea, Amaranthus retroflexus, Amaranthus hybridus, Amaranthus palmeri, Amaranthus rudis, Abutilon theophrasti, Sida spinosa, Fallopia convolvulus, Polygonum scabrum, Persicaria pennsylvanica, Persicaria vulgaris, Rumex crispus, Rumex obtusifolius, Fallopia japonica, Chenopodium album, Kochia scoparia, Polygonum longisetum, Solanum nigrum, Datura stramonium, Ipomoea purpurea, Ipomoea hederacea, Ipomoea hederacea* var. *integriuscula, Ipomoea lacunosa, Convolvulus arvensis, Lamium purpureum, Lamium amplexicaule, Xanthium pensylvanicum, Helianthus annuus, Matricaria perforata* or *inodora, Matricaria chamomilla, Chrysanthemum segetum, Matricaria matricarioides, Ambrosia artemisiifolia, Ambrosia trifida, Erigeron canadensis, Artemisia princeps, Solidago altissima, Conyza bonariensis, Sesbania exaltata, Cassia obtusifolia, Desmodium tortuosum, Trifolium repens, Pueraria lobata, Vicia angustifolia, Commelina communis, Commelina benghalensis, Galium aparine, Stellaria media, Raphanus raphanistrum, Sinapis arvensis, Capsella bursa-pastoris, Veronica persica, Veronica hederifolia, Viola arvensis, Viola tricolor, Papaver rhoeas, Myosotis scorpioides, Asclepias syriaca, Euphorbia helioscopia, Chamaesyce nutans, Geranium carolinianum, Erodium cicutarium, Equisetum arvense, Leersia japonica, Echinochloa oryzicola, Echinochloa crus-galli* var. *formosensis, Leptochloa chinensis, Cyperus difformis, Fimbristylis miliacea, Eleocharis acicularis, Scirpus juncoides, Scirpus wallichii, Cyperus serotinus, Eleocharis kuroguwai, Bolboschoenus koshevnikovii, Schoenoplectus nipponicus, Monochoria vaginalis, Lindernia procumbens, Dopatrium junceum, Rotala indica, Ammannia multiflora, Elatine triandra, Ludwigia epilobioides, Sagittaria pygmaea, Alisma canaliculatum, Sagittaria trifolia, Potamogeton distinctus, Oenanthe javanica, Callitriche palustris, Lindernia micrantha, Lindernia dubia, Eclipta prostrata, Murdannia keisak, Paspalum distichum*, and *Leersia oryzoides*; aquatic plants such as *Alternanthera philoxeroides, Limnobium spongia*, water fern (Genus *Salvinia*), *Pistia stratiotes*, water pennywort (Genus *Hydrocotyle*), conferva (Genus *Pithophora*, Genus *Cladophora*), *Ceratophyllum demersum*, duckweed (Genus *Lemna*), *Cabomba caroliniana, Hydrilla verticillata, Najas guadalupensis*, pondweeds (*Potamogeton crispus, Potamogeton illinoensis, Potamogeton pectinatus*, etc.), watermeals (Genus *Wolffia*), water milfoils {*Myriophyllum spicatum, Myriophyllum heterophyllum*, etc.), and *Eichhornia crassipes; Bryopsida, Hepaticopsida, Anthocerotopsida; Cyanobacteria; Pteridopsida*; and suckers of perennial crops (pomaceous fruits, stone fleshy fruits, berry fruits, nuts, citrus plants, hop, grape, etc.).

Examples of noxious arthropods against which the present compound has an activity include noxious arthropods such as noxious insects and noxious acarines. Specific examples theseof include as follows:

Hemiptera: *Delphacidae* such as *Laodelphax striatellus, Nilaparvata lugens*, and *Sogatella furcifera*; Deltocephalidae such as *Nephotettix cincticeps, Nephotettix virescens*, and *Empoasca onukii*; Aphididae such as *Aphis gossypii, Myzus persicae, Brevicoryne brassicae, Aphis spiraecola, Macrosiphum euphorbiae, Aulacorthum solani, Rhopalosiphum padi, Toxoptera citricidus*, and *Hyalopterus pruni*; Pentatomidae such as *Nezara antennata, Riptortus clavetus, Leptocorisa chinensis, Eysarcoris parvus*, and *Halyomorpha mista*; Aleyrodidae such as *Trialeurodes vaporariorum, Bemisia tabaci, Bemisia argentifolii, Dialeurodes citri*, and *Aleurocanthus spiniferus*; Coccidae such as *Aonidiella aurantii, Comstockaspis perniciosa, Unaspis citri, Ceroplastes rubens, Icerya purchasi, Planococcus kraunhiae, Pseudococcus longispinis*, and *Pseudaulacaspis pentagona*; Tingidae; Cimices such as *Cimex lectularius*; and Psyllidae.

Lepidoptera: Pyralidae such as *Chilo suppressalis, Tryporyza incertulas, Cnaphalocrocis medinalis, Notarcha derogata, Plodia interpunctella, Ostrinia furnacalis, Hellula undalis*, and *Pediasia teterrellus*; Noctuidae such as *Spodoptera litura, Spodoptera exigua, Pseudaletia separata, Mamestra brassicae, Agrotis ipsilon, Plusia nigrisigna, Thoricoplusia* spp., *Heliothis* spp., and *Helicoverpa* spp.; Pieridae such as *Pieris rapae*; Tortricidae such as *Adoxophyes* spp., *Grapholita molesta, Leguminivora glycinivorella, Matsumuraeses azukivora, Adoxophyes orana fasciata, Adoxo-*

*phyes honmai, Homona magnanima, Archips fuscocupreanus*, and *Cydia pomonella*; Gracillariidae such as *Caloptilia theivora* and *Phyllonorycter ringoneella*; Carposinidae such as *Carposina niponensis*; Lyonetiidae such as *Lyonetia* spp.; Lymantriidae such as *Lymantria* spp. and *Euproctis* spp; Yponomeutidae such as *Plutella xylostella*; Gelechiidae such as *Pectinophora gossypiella* and *Phthorimaea operculella*; Arctiidae such as *Hyphantria cunea*; and Tineidae such as *Tinea translucens* and *Tineola bisselliella.*

Thysanoptera: Thripidae such as *Frankliniella occidentalis, Thrips palmi, Scirtothrips dorsalis, Thrips tabaci*, and *Frankliniella intonsa.*

Diptera: Culices such as *Culex pipiens pallens, Culex tritaeniorhynchus*, and *Culex quinquefasciatus; Aedes* spp. such as *Aedes aegypti* and *Aedes albopictus; Anopheles* spp. such as *Anopheles sinensis*; Chironomidae; Muscidae such as *Musca domestica* and *Muscina stabulans*; Calliphoridae; Sarcophagidae; Fanniidae; Anthomyiidae such as *Delia platura* and *Delia antiqua*; Agromyzidae such as *Agromyza oryzae, Hydrellia griseola, Liriomyza sativae, Liriomyza trifolii*, and *Chromatomyia horticol*; Chloropidae such as *Chlorops oryzae*; Tephritidae such as *Dacus cucurbitae* and *Ceratitis capitata*; Drosophilidae; Phoridae such as *Megaselia spiracularis*; Psychodidae such as *Clogmia albipunctata*; Simuliidae; Tabanidae such as *Tabanus trigonus*; and stable flies.

Coleoptera: *Diabrotica* spp. such as *Diabrotica virgifera virgifera* and *Diabrotica undecimpunctata howardi*; Scarabaeidae such as *Anomala cuprea, Anomala rufocuprea*, and *Popillia japonica*; weevils such as *Sitophilus zeamais, Lissorhoptrus oryzophilus, Callosobruchuys chienensis, Echinocnemus squameus, Anthonomus grandis*, and *Sphenophorus venatus*; Tenebrionidae such as *Tenebrio molitor* and *Tribolium castaneum*; Chrysomelidae such as *Oulema oryzae, Aulacophora femoralis, Phyllotreta striolata*, and *Leptinotarsa decemlineata*; Dermestidae such as *Anthrenus verbasci* and Dermestes maculates; Anobiidae such as *Lasioderma serricorne; Epilachna* such as *Epilachn vigintioctopunctata*; Scolytidae such as *Lyctus brunneus* and *Tomicus piniperda*; Bostrychidae; Ptinidae; Cerambycidae such as *Anoplophora malasiaca; Agriotes* spp., and *Paederus fuscipes.*

Orthoptera: *Locusta migratoria, Gryllotalpa africana, Oxya yezoensis, Oxya japonica*, and Gryllidae.

Siphonaptera: *Ctenocephalides felis, Ctenocephalides canis, Pulex irritans, Xenopsylla cheopis.*

Anoplura: *Pediculus humanus corporis, Phthirus pubis, Haematopinus eurysternus, Dalmalinia ovis, Haematopinus suis.*

Hymenoptera: Formicidae such as *Monomorium pharaosis, Formica fusca japonica, Ochetellus glaber, Pristomyrmex pungens, Pheidole noda, Acromyrmex* spp., and *Solenopsis* spp.; Vespidae; Betylidae; and Tenthredinidae such as *Athalia rosae* and *Athalia japonica.*

Nematoda: *Aphelenchoides besseyi, Nothotylenchus acris, Meloidogyne incognita, Meloidogyne hapla, Meloidogyne javanica, Heterodera glycines, Globodera rostochiensis, Pratylenchus coffeae*, and *Pratylenchus neglectus*; Termitidae such as *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae*), *Reticuliterumes flavipes, Reticulitermes hesperus, Reticulitermes virginicus, Reticulitermes tibialis, Heterotermes aureus, Zootermopsis nevadensis.*

Acarina: Tetranychidae such as *Tetranychus urticae, Tetranychus kanzawai, Panonychus citri, Panonychus ulmi*, and *Oligonychus* spp.; Eriophyidae such as *Aculops pelekassi, Phyllocoptruta citri, Aculops lycopersici, Calacarus carinatus, Acaphylla theavagrans, Eriophyes chibaensis*, and *Aculus schlechtendali*; Tarsonemidae such as *Polyphagotarsonemus latus*; Tenuipalpidae such as *Brevipalpus phoenicis*; Tuckerellidae; Ixodidae such as *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus*, and *Rhipicephalus sanguineus*; Psoroptidae such as *Octodectes cynotis*; Sarcoptidae such as *Sacroptes scabiei*; Demodicidae such as *Demodex canis*; Acaridae such as *Tyrophagus putrescentiae* and *Tyrophagus similis*; Pyroglyphidae such as *Dermatophagoides farinae* and *Dermatophagoides ptrenyssnus*; Cheyletidae such as *Cheyletus eruditus, Cheyletus malaccensis*, and *Cheyletus moorei*; Dermanyssidae such as *Ornithonyssus bacoti, Ornithonyssus sylvairum*, and *Dermanyssus gallinae*; Trombiculidae such as *Leptotrombidium akamushi*; and Araneae such as *Chiracanthium japonicum* and *Latrodectus hasseltii.*

Chilopoda: *Thereuonema hilgendorfi, Scolopendra subspinipes.*

Diplopoda: *Oxidus gracilis, Nedyopus tambanus*);

Isopoda: *Armadillidium vulgare.*

The present compound can also be used for the control of parasites.

The present compound can be produced, for example, by the following Production methods.

Production Method 1

The present compound of the formula (I-a) wherein G is hydrogen can be produced by treating the compound of the formula (II-a) with a base:

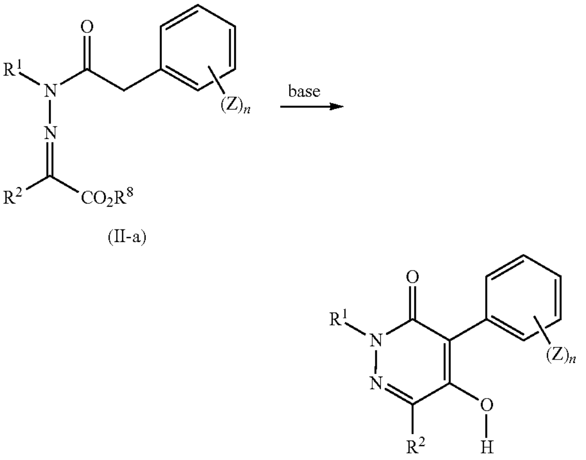

(II-a)

(I-a)

wherein $R^8$ represents a $C_{1-6}$ alkyl group (e.g. a methyl group, an ethyl group), and $R^1$, $R^2$, Z, and n are as defined above.

The reaction is performed in a solvent.

Examples of the solvent to be used in the reaction include aromatic hydrocarbons such as benzene, toluene, and xylene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfones such as sulfolane; and mixtures thereof.

Examples of the base to be used in the reaction include metal alkoxides such as potassium tert-butoxide; alkali metal hydrides such as sodium hydride; and organic bases such as triethylamine, tributylamine, and N,N-diisopropylethylamine.

The amount of the base to be used in the reaction is usually 1 to 10 moles, preferably 2 to 5 moles based on 1 mole of the compound of the formula (II-a).

The reaction temperature of the reaction is usually within a range of −60 to 180° C., preferably −10 to 100° C. The reaction time of the reaction is usually within a range of 10 minutes to 30 hours.

The completion of the reaction can be confirmed by an analytical means such as thin layer chromatography and high performance liquid chromatography after sampling a part of the reaction mixture. After the completion of the reaction, the compound of the formula (I-a) can be isolated, for example, by neutralizing the reaction mixture with an addition of an acid, mixing the reaction mixture with water, and extracting the reaction mixture with an organic solvent, and then drying and concentrating the resulting organic layer.

Production Method 2

A present compound of the formula (I-b) wherein G is not hydrogen can be produced from a compound of the formula (I-a) and a compound of the formula (III):

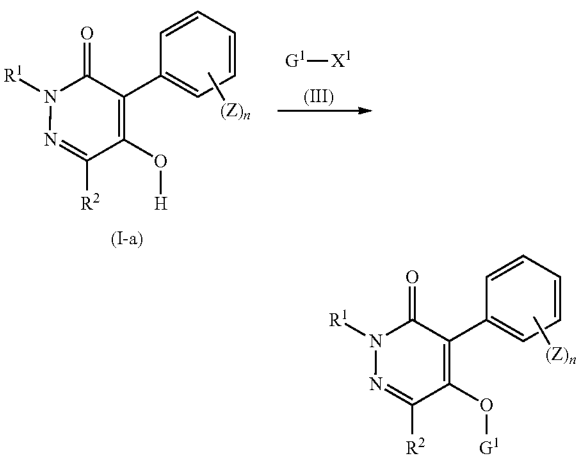

(I-a)

(I-b)

wherein $G^1$ represents are as defined for G excluding hydrogen, $X^1$ represents halogen (e.g. chlorine, bromine, iodine), a $C_{1-3}$ alkylsulfonyloxy group optionally substituted with halogens (e.g. a methylsulfonyloxy group, a trifluoromethylsulfonyloxy group), a benzenesulfonyl group, or a p-toluenesulfonyl group, when $G^1$ represents any group of the formula:

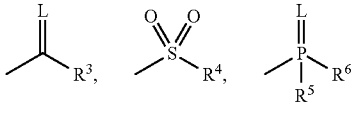

wherein L, $R^3$, $R^4$, $R^5$, and $R^6$ are as defined above; $X^1$ may represent a formula $OG^1$, and $R^1$, $R^2$, Z, and n are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethylsulfoxide; sulfones such as sulfolane; ketones such as acetone; and mixtures thereof.

Examples of the compound of the formula (III) to be used in the reaction include carboxylic acid halides such as acetyl chloride, propionyl chloride, isobutyryl chloride, pivaloyl chloride, benzoyl chloride, and cyclohexanecarboxylic acid chloride; carboxylic acid anhydrides such as acetic anhydride, and anhydrous trifluoroacetic acid; carbonic acid half esters such as methyl chloroformate, ethyl chloroformate, and phenyl chloroformate; carbamic acid halides such as dimethylcarbamoyl chloride; sulfonic acid halides such as methanesulfonyl chloride and p-toluenesulfonyl chloride; sulfonic acid anhydrides such as methanesulfonic acid anhydride and trifluoromethanesulfonic acid anhydride; phosphate ester halides such as dimethylchlorophosphate; halogenoalkyl alkyl ethers such as chloromethyl methyl ether and chloromethyl ethyl ether; and halogenobenzyls such as benzyl bromide and 4-methoxybenzyl chloride.

The amount of the compound of the formula (III) to be used in the reaction is usually 1 or more moles, preferably 1 to 3 moles based on 1 mole of the compound of the formula (I-a).

The reaction is usually performed in the presence of a base.

Examples of the base to be used in the reaction include organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate, and sodium hydride.

The amount of the base to be used in the reaction is usually 0.5 to 10 moles, preferably 1 to 5 moles based on 1 mole of the compound of the formula (I-a).

The reaction temperature of the reaction is usually within a range of −30 to 180° C., preferably −10 to 80° C. The reaction time of the reaction is usually within a range of 10 minutes to 30 hours.

The completion of the reaction can be confirmed by an analytical means such as thin layer chromatography and high performance liquid chromatography after sampling a part of the reaction mixture. After the completion of the reaction, the compound of the formula (I-b) can be isolated, for example, by mixing the reaction mixture with water, and extracting the reaction mixture with an organic solvent, and then drying and concentrating the resulting organic layer.

The compound of the formula (III) is a known compound or can be produced from a known compound.

Production Method 3

A present compound of the formula (I-d) wherein $R^2$ is a $C_{1-6}$ alkylsulfinyl group or a $C_{1-6}$ haloalkylsulfinyl group can be produced by oxidizing a compound of the formula (I-c) wherein $R^2$ is a $C_{1-6}$ alkylthio group or a $C_{1-6}$ haloalkylthio group. When a group other than $R^2$ in the compound of the formula (I-c) contains an alkylthio group, an alkylsulfinyl group, a haloalkylthio group and/or a haloalkylsulfinyl group, these groups may be oxidized:

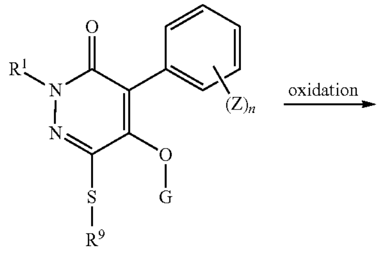

(I-c)

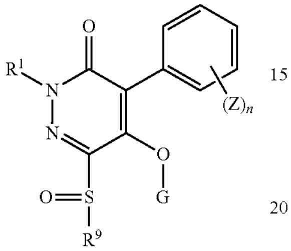

(I-d)

wherein $R^9$ represents a $C_{1-6}$ alkyl group or a $C_{1-6}$ haloalkyl group, and $R^1$, G, Z, and n are as defined above.

An oxidizing agent is used in the reaction.

Examples of the oxidizing agent include hydrogen peroxide; peracids such as peracetic acid, perbenzoic acid, and m-chloroperbenzoic acid; sodium metaperiodate, ozone, selenium dioxide, chromic acid, dinitrogen tetraoxide, acetyl nitrate, iodine, bromine, N-bromosuccinimide, and iodosylbenzene.

The amount of the oxidizing agent to be used in the reaction is usually 0.8 to 1.2 moles based on 1 mole of the compound of the formula (I-c).

The reaction is performed in a solvent.

Examples of the solvent to be used in the reaction include saturated hydrocarbons such as hexane, heptane, octane, and cyclohexane; aromatic hydrocarbons such as benzene, toluene, xylene, chlorobenzene; and dichlorobenzene; saturated halogenated hydrocarbons such as dichloromethane, chloroform, 1,2-dichloroethane, and carbon tetrachloride; alcohols such as methanol, ethanol, and propanol; nitriles such as acetonitrile; amides such as dimethylformamide and dimethylacetamide; sulfones such as sulfolane; organic acids such as acetic acid and propionic acid; water, and mixtures thereof.

The reaction temperature of the reaction is usually within a range of −50 to 100° C., preferably 0 to 50° C. The reaction time of the reaction is usually within a range of 10 minutes to 100 hours.

The progress of the reaction can be confirmed by analyzing a port of the reaction mixture by thin layer chromatography, high performance liquid chromatography, and the like. After the completion of the reaction, the compound of the formula (I-d) can be isolated, for example, by mixing the reaction mixture with water, and extracting the reaction mixture with an organic solvent, and then drying and concentrating the resulting organic layer.

Production Method 4

A present compound of the formula (I-e) wherein $R^2$ is a $C_{1-6}$ alkylsulfonyl group or a $C_{1-6}$ haloalkylsulfonyl group can be produced by oxidizing a compound of the formula (I-c) or a compound of the formula (I-d). When a group other than $R^2$ in the compound of the formula (I-c) or the compound of the formula (I-d) contains an alkylthio group, an alkylsulfinyl group, a haloalkylthio group and/or a haloalkylsulfinyl group, these groups may be oxidized:

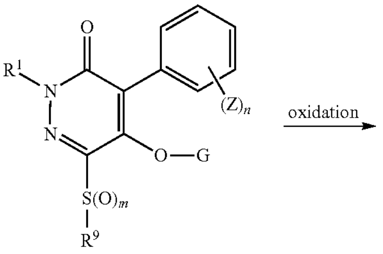

(I-c) (m = 0)
(I-d) (m = 1)

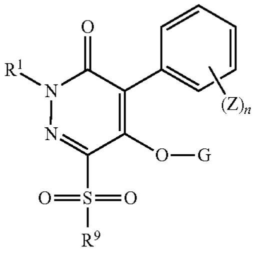

(I-e)

wherein m represents 0 or 1, and $R^1$, $R^9$, G, Z, and n are as defined above.

An oxidizing agent is used in the reaction.

Examples of the oxidizing agent include hydrogen peroxide; peracids such as peracetic acid, perbenzoic acid, and m-chloroperbenzoic acid; sodium metaperiodate, ozone, selenium dioxide, chromic acid, dinitrogen tetraoxide, acetyl nitrate, iodine, bromine, N-bromosuccinimide, iodosylbenzene, a combination of hydrogen peroxide with tungsten catalyst, a combination of hydrogen peroxide with vanadium catalyst, and potassium permanganate.

When the compound of the formula (I-c) is used as a starting material, the amount of the oxidizing agent to be used in the reaction is usually 2 to 10 moles, preferably 2 to 4 moles based on 1 mole of the compound of the formula (I-c). When the compound of the formula (I-d) is used as a starting material, the amount of the oxidizing agent to be used in the reaction is usually 1 to 10 moles, preferably 1 to 3 moles based on 1 mole of the compound of the formula (I-d).

The reaction is performed in a solvent.

Examples of the solvent to be used in the reaction include saturated hydrocarbons such as hexane, heptane, octane, and cyclohexane; aromatic hydrocarbons such as benzene, toluene, xylene, chlorobenzene, and dichlorobenzene; saturated halogenated hydrocarbons such as dichloromethane, chloroform, 1,2-dichloroethane, and carbon tetrachloride; alcohols such as methanol, ethanol, and propanol; nitriles such as acetonitrile; amides such as dimethylformamide and dimethylacetamide; sulfones such as sulfolane; organic acids such as acetic acid and propionic acid; water, and mixtures thereof.

The reaction temperature of the reaction is usually within a range of 0 to 200° C., preferably 20 to 150° C. The reaction time of the reaction is usually within a range of 30 minutes to 100 hours.

The progress of the reaction can be confirmed by analyzing a port of the reaction mixture by thin layer chromatography, high performance liquid chromatography, and the like. After the completion of the reaction, the compound of the formula (I-e) can be isolated, for example, by mixing the reaction mixture with water, and extracting the reaction mixture with an organic solvent, and then drying and concentrating the resulting organic layer.

Production Method 5

The present compound of the formula (I-g) wherein $R^2$ is a cyano group, a $C_{1-6}$ alkoxy group, a $C_{1-6}$ haloalkoxy group, a $C_{1-6}$ alkylthio group, a $C_{1-6}$ haloalkylthio group, a $C_{3-8}$ cycloalkoxy group, a $(C_{3-8}$ cycloalkyl$)C_{1-6}$ alkoxy group can be produced by reacting a compound of the formula (I-f) wherein $R^2$ is halogen, a $C_{1-6}$ alkylsulfonyl group, or a $C_{1-6}$ haloalkylsulfonyl group with a compound of the formula (IV) in the presence of a base or reacting the compound of the formula (I-f) with a compound of the formula (IV'):

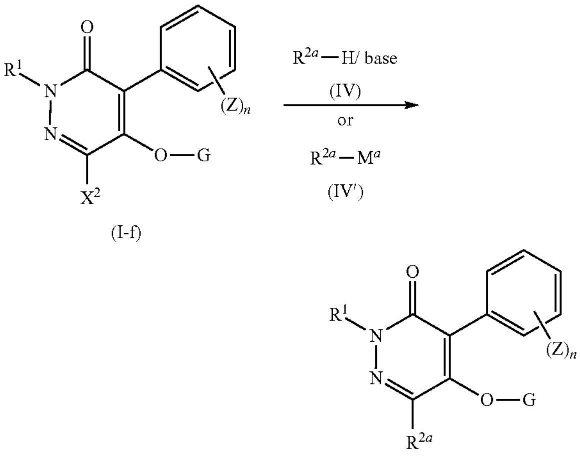

(I-f)

(I-g)

wherein $X^2$ represents halogen, a $C_{1-12}$ alkylsulfonyl group, or a $C_{1-12}$ haloalkylsulfonyl group, $R^{2a}$ represents a cyano group, a $C_{1-6}$ alkoxy group, a $C_{1-6}$ haloalkoxy group, a $C_{1-6}$ alkylthio group, a $C_{1-6}$ haloalkylthio group, a $C_{3-8}$ cycloalkoxy group, a $(C_{3-8}$ cycloalkyl$)C_{1-6}$ alkoxy group, $M^a$ represents an alkali metal (e.g. lithium, sodium, potassium), and $R^1$, G, Z, and n are as defined above.

When a compound of the formula (IV) and a base are used, the amount of the compound of the formula (IV) to be used in the reaction is usually 1 or more moles, preferably 1 to 3 moles, possibly excessive amount double as a solvent based on 1 mole of the compound of the formula (I-f).

Examples of the base to be used in the reaction include inorganic bases such as sodium hydroxide, potassium hydroxide, sodium hydride, sodium methoxide, sodium ethoxide, and potassium t-butoxide.

When a compound of the formula (IV') is used, the amount of the compound of the formula (IV') to be used in the reaction is usually 1 or more moles, preferably 1 to 3 moles, possibly about 10 moles based on 1 mole of the compound of the formula (I-f).

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethylsulfoxide; sulfones such as sulfolane; and mixtures thereof. The compound of the formula (IV) may be used as a solvent.

The reaction temperature of the reaction is usually within a range of 0 to 200° C., preferably 20 to 150° C. The reaction time of the reaction is usually within a range of 10 minutes to 100 hours.

The progress of the reaction can be confirmed by analyzing a port of the reaction mixture by thin layer chromatography, high performance liquid chromatography, and the like. After the completion of the reaction, the compound of the formula (I-g) can be isolated, for example, by mixing the reaction mixture with water, and extracting the reaction mixture with an organic solvent, and then drying and concentrating the resulting organic layer.

The compound of the formula (IV) and the compound of the formula (IV') are a known compound, or can be produced from a known compound.

Production Method 6

A present compound of the formula (I-h) wherein G is hydrogen can be produced by treating a compound of the formula (II-b) with a base:

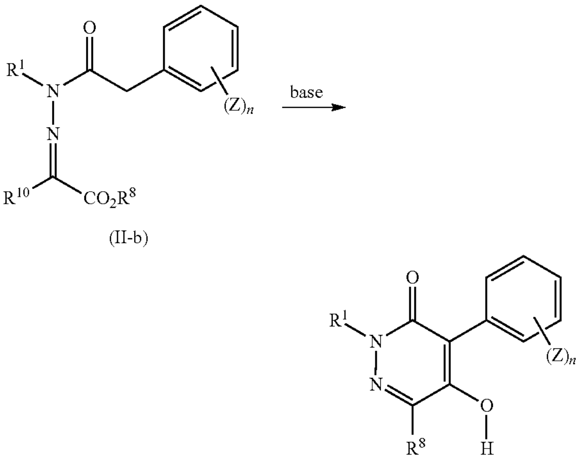

(II-b)

(I-h)

wherein $R^{10}$ represents a $C_{1-12}$ alkylthio group (e.g. a methylthio group, a hexylthio group, a dodecylthio), and $R^1$, $R^8$, Z, and n are as defined above.

The reaction can be performed under the condition described in Production method 1

Production Method 7

A present compound of the formula (I-i) can be produced by reacting a compound of the formula (XVIII) with a compound of the formula (XIX):

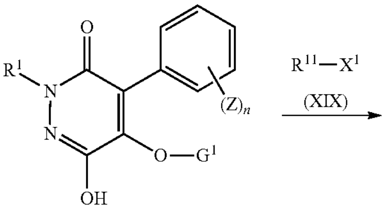

(XVIII)

-continued

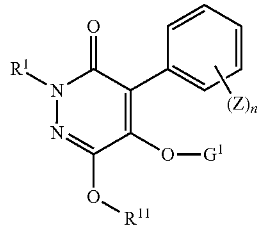

(I-i)

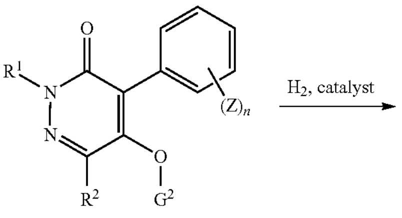

(I-j)

wherein $R^{11}$ represents a $C_{1-6}$ alkyl group, a $C_{1-6}$ haloalkyl group, a $C_{3-8}$ cycloalkyl group, a $(C_{3-8}$ cycloalkyl)$C_{1-6}$ alkyl group, a $C_{1-6}$ alkylthio$C_{1-6}$ alkyl group, a $C_{1-6}$ alkoxy$C_{1-6}$ alkyl group, a $C_{1-6}$ alkenyl group, a $C_{1-6}$ alkynyl group, a cyano$C_{1-6}$ alkyl group, a $C_{1-6}$ alkoxycarbonyl$C_{1-6}$ alkyl group, and $G^1$, $R^1$, $X^1$, Z, and n are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethylsulfoxide; sulfones such as sulfolane; ketones such as acetone; and mixtures thereof.

The amount of the compound of the formula (XIX) to be used in the reaction is usually 1 or more moles, preferably 1 to 3 moles based on 1 mole of the compound of the formula (XVIII).

The reaction is usually performed in the presence of a base.

Examples of the base to be used in the reaction include organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate, and sodium hydride.

The amount of the base to be used in the reaction is usually 0.5 to 10 moles, preferably 1 to 5 moles based on 1 mole of the compound of the formula (XIX).

The reaction temperature of the reaction is usually within a range of −30 to 180° C., preferably −10 to 80° C. The reaction time of the reaction is usually within a range of 10 minutes to 30 hours.

The completion of the reaction can be confirmed by an analytical means such as thin layer chromatography and high performance liquid chromatography after sampling a part of the reaction mixture. After the completion of the reaction, the compound of the formula (I-i) can be isolated, for example, by mixing the reaction mixture with water, and extracting the reaction mixture with an organic solvent, and then drying and concentrating the resulting organic layer.

The compound of the formula (XIX) is a known compound, or can be produced from a known compound.

Production Method 8

A present compound of the formula (I-a) can be produced by reacting a compound of the formula (I-j) under hydrogen atmosphere in the presence of catalyst:

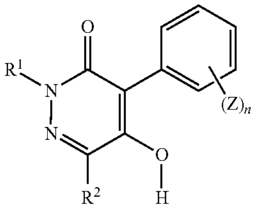

(I-a)

wherein $G^2$ represent a benzyl group optionally substituted with one or more substituents selected from Group A, and $R^1$, $R^2$, Z, and n are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; alcohols such as methanol and ethanol; esters such as methyl acetate and ethyl acetate; organic acids such as acetic acid and propionic acid; and mixtures thereof.

Examples of the catalyst to be used in the reaction include palladium, platinum, and nickel.

The amount of the catalyst to be used in the reaction is usually 0.001 to 0.3 moles, preferably 0.01 to 0.1 moles based on 1 mole of the compound of the formula (I-j).

The reaction temperature of the reaction is usually within a range of 0 to 180° C., preferably 20 to 80° C. The reaction time of the reaction is usually within a range of 10 minutes to 100 hours.

An acid can be used in order to facilitate the reaction rate. Examples of the catalyst to be used in the reaction include hydrochloric acid and hydrobromic acid.

The amount of the acid to be used in the reaction is usually 0.01 to 5 moles, preferably 0.1 to 2 moles based on 1 mole of the compound of the formula (I-j).

The completion of the reaction can be confirmed by an analytical means such as thin layer chromatography and high performance liquid chromatography after sampling a part of the reaction mixture. After the completion of the reaction, the compound of the formula (I-a) can be isolated, for example, by filtering the catalyst and concentrating the filtrate.

Production Method 9

A present compound of the formula (I-a) can be produced by reacting a compound of the formula (I-k) with ammonium cerium(IV) nitrate (CAN):

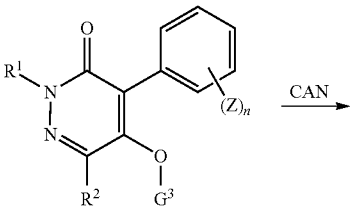

(I-k)

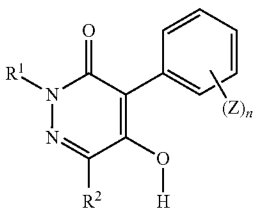

(I-a)

wherein $G^3$ represents a 4-methoxybenzyl group, and $R^1$, $R^2$, Z, and n are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethylsulfoxide; sulfones such as sulfolane; ketones such as acetone; alcohols such as methanol and ethanol; esters such as methyl acetate and ethyl acetate; nitriles such as acetonitrile; water and mixtures thereof.

The amount of CAN to be used in the reaction is usually 1 to 5 moles based on 1 mole of the compound of the formula (I-k).

The reaction temperature of the reaction is usually within a range of −20 to 100° C., preferably 0 to 50° C. The reaction time of the reaction is usually within a range of 10 minutes to 100 hours.

The completion of the reaction can be confirmed by an analytical means such as thin layer chromatography and high performance liquid chromatography after sampling a part of the reaction mixture. After the completion of the reaction, the compound of the formula (I-i) can be isolated, for example, by mixing the reaction mixture with water, and extracting the reaction mixture with an organic solvent, and then drying and concentrating the resulting organic layer.

Production Method 10

A present compound of the formula (I-m) can be produced from a compound of the formula (XX) and a compound of the formula (XXI):

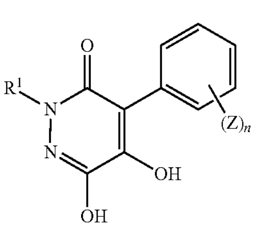

(XX)

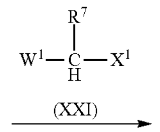

-continued

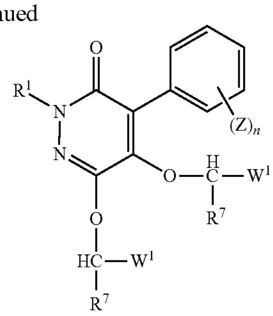

(I-m)

wherein $W^1$ represent a $C_{1-6}$ alkoxy group or a $C_{1-6}$ alkylthio group, and $R^1$, $X^1$, Z, and n are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethylsulfoxide; sulfones such as sulfolane; and mixtures thereof.

Examples of the compound of the formula (XXI) to be used in the reaction include halogenoalkyl alkyl ethers such as chloromethyl methyl ether and chloromethyl ethyl ether; halogenoalkyl alkyl sulfides such as chloromethyl methyl sulfide and chloromethyl ethyl sulfide.

The amount of the compound of the formula (XXI) to be used in the reaction is usually 2 to 10 moles based on 1 mole of the compound of the formula (XX).

The reaction is usually performed in the presence of a base.

Examples of the base to be used in the reaction include organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate, and sodium hydride.

The amount of the base to be used in the reaction is usually 2 to 10 moles based on 1 mole of the compound of the formula (XX).

The reaction temperature of the reaction is usually within a range of −30 to 180° C., preferably −10 to 50° C. The reaction time of the reaction is usually within a range of 10 minutes to 30 hours.

The completion of the reaction can be confirmed by an analytical means such as thin layer chromatography and high performance liquid chromatography after sampling a part of the reaction mixture. After the completion of the reaction, the compound of the formula (I-m) can be isolated, for example, by mixing the reaction mixture with water, and extracting the reaction mixture with an organic solvent, and then drying and concentrating the resulting organic layer.

The compound of the formula (XXI) is a known compound, or can be produced from a known compound.

Production Method 11

A present compound of the formula (I-p) can be produced from a compound of the formula (I-o) and a compound of the formula (XXII):

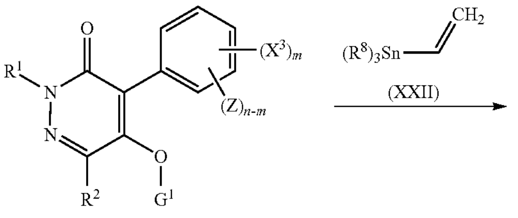

(I-o)

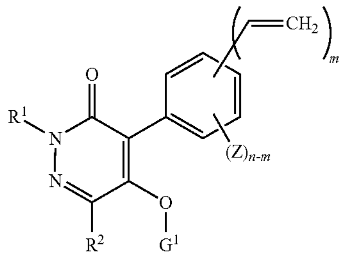

(I-p)

wherein $X^3$ represents a halogen atom (e.g. fluorine atom, chlorine atom, bromine atom, and iodine atom), m represents an integer of 1-3, and $R^1$, $R^2$, $R^8$, $G^1$, Z, and n are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as chloroform and 1,2-dichloroethane; amides such as dimethylformamide and dimethylacetamide; and mixtures thereof.

The amount of the organometallic agent of the formula (XXII) to be used in the reaction is usually 1 or more moles, preferably 1 to 10 moles based on 1 mole of the compound of the formula (I-o).

The reaction is performed in the presence of a catalyst. Examples of the catalyst to be used in the reaction include palladium catalysts such as tetrakis(triphenylphosphine)palladium and dichlorobis(triphenylphosphine)palladium.

The amount of the catalyst to be used in the reaction is usually 0.001 to 0.5 moles, preferably 0.01 to 0.2 moles based on 1 mole of the compound of the formula (I-o).

The reaction temperature of the reaction is usually within a range of −80 to 180° C., preferably −30 to 150° C. The reaction time of the reaction is usually within a range of 30 minutes to 100 hours.

The completion of the reaction can be confirmed by an analytical means such as thin layer chromatography and high performance liquid chromatography after sampling a part of the reaction mixture. After the completion of the reaction, The production of the reaction can be isolated, for example, by concentrating the reaction mixture, and subjecting to chromatographic purification.

The organometallic agent of the formula (XXII) is a known compound or can be produced from a known compound according to a known method.

The compound of the formula (XXII) is a known compound, or can be produced from a known compound.

Production Method 12

A present compound of the formula (I-r) can be produced by the first step of reacting a compound of the formula (I-q) with a compound of the formula (XXIII) and the second step of treating with an alkali metal salt:

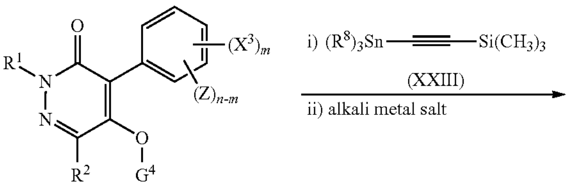

(I-q)

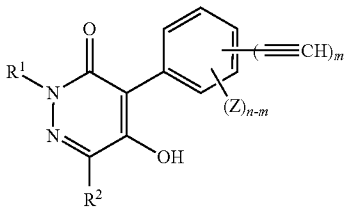

(I-r)

wherein $G^4$ represents a $(C_{1-6}$ alkyl)carbonyl group or a $C_{1-6}$ alkoxycarbonyl group, and $R^1$, $R^2$, $R^8$, $X^3$, Z, m, and n are as defined above.

The first step is illustrated.

The reaction can be performed in a solvent. Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as chloroform and 1,2-dichloroethane; amides such as dimethylformamide and dimethylacetamide; and mixtures thereof.

The amount of the compound of the formula (XXIII) to be used in the reaction is usually 1 to 10 moles based on 1 mole of the compound of the formula (I-q).

The reaction is performed in the presence of a catalyst. Examples of the catalyst to be used in the reaction include palladium catalysts such as tetrakis(triphenylphosphine)palladium and dichlorobis(triphenylphosphine)palladium The amount of the catalyst to be used in the reaction is usually 0.001 or 0.5 moles, preferably 0.01 to 0.2 moles based on 1 mole of the compound of the formula (I-q).

The reaction temperature of the reaction is usually within a range of −80 to 180° C., preferably −30 to 150° C. The reaction time of the reaction is usually within a range of 30 minutes to 100 hours.

The completion of the reaction can be confirmed by an analytical means such as thin layer chromatography and high performance liquid chromatography after sampling a part of the reaction mixture. After the completion of the reaction, The product in the first step can be isolated, for example, by concentrating the reaction mixture, and subjecting to chromatographic purification.

The second step is illustrated.

The reaction can be performed in a solvent. Examples of the solvent to be used in the reaction include water; alcohols such as methanol and ethanol; ethers such as dioxane, tetrahydrofuran, and dimethoxyethane; and mixtures thereof.

Examples of the alkali metal salt to be used in the reaction include alkali metal hydroxides such as sodium hydroxide and potassium hydroxide; and alkali metal carbonates such as sodium carbonate and potassium carbonate.

The amount of the alkali metal salt to be used in the reaction is usually 2 to 10 moles based on 1 mole of the compound of the formula (I-q).

The reaction temperature of the reaction of the second step is usually within a range of −30 to 180° C., preferably −10 to 50° C. The reaction time of the reaction is usually within a range of 30 minutes to 100 hours.

The completion of the reaction can be confirmed by an analytical means such as thin layer chromatography and high performance liquid chromatography after sampling a part of the reaction mixture. After the completion of the reaction, the compound of the formula (I-r) can be isolated, for example, by mixing the reaction mixture with water, neutralizing the reaction mixture with an addition of an acid, and extracting the reaction mixture with an organic solvent, and then drying and concentrating the resulting organic layer.

The compound of the formula (XXIII) is a known compound, or can be produced from a known compound.

Production Method 13

A present compound of the formula (I-a) can be produced by reacting a compound of the formula (I-s) with an alkali metal salt:

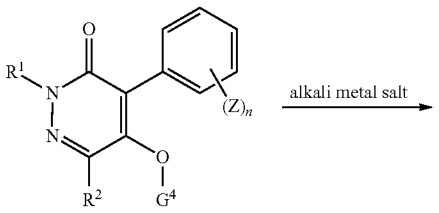

(I-s)

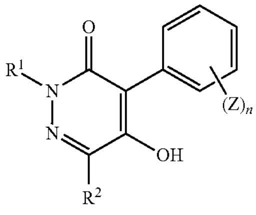

(I-a)

wherein $R^1$, $R^2$, $G^4$, Z, and n are as defined above.

The reaction can be performed in a solvent. Examples of the solvent to be used in the reaction include water; alcohols such as methanol and ethanol; ethers such as dioxane, tetrahydrofuran, and dimethoxyethane; and mixtures thereof.

Examples of the alkali metal salt to be used in the reaction include alkali metal hydroxides such as sodium hydroxide and potassium hydroxide; and alkali metal carbonates such as sodium carbonate and potassium carbonate.

The amount of the alkali metal salt to be used in the reaction is usually 1 or more moles, preferably 1 to 5 moles based on 1 mole of the compound of the formula (I-s).

The reaction temperature of the reaction is usually within a range of −30 to 180° C., preferably −10 to 50° C. The reaction time of the reaction is usually within a range of 5 minutes to 100 hours.

The completion of the reaction can be confirmed by an analytical means such as thin layer chromatography and high performance liquid chromatography after sampling a part of the reaction mixture. After the completion of the reaction, the compound of the formula (I-a) can be isolated, for example, by mixing the reaction mixture with water, neutralizing the reaction mixture with an addition of an acid, and extracting the reaction mixture with an organic solvent, and then drying and concentrating the resulting organic layer.

Production Method 14

A present compound of the formula (I-O) can be produced from a compound of the formula (XXXIII):

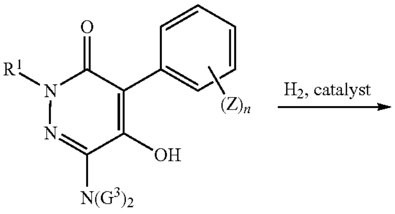

(XXXIII)

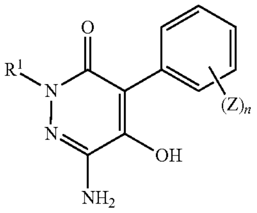

(I-O)

wherein $G^3$, $R^1$, Z, and n are as defined above.

The reaction can be performed under the condition described in Production method 8.

Production Method 15

A present compound of the formula (I-v) can be produced by reacting a compound of the formula (I-u) with a nitrite salt in the presence of an acid:

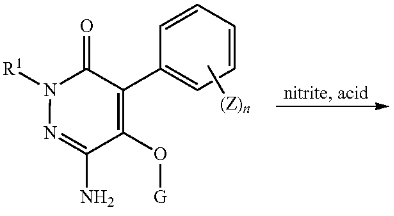

(I-u)

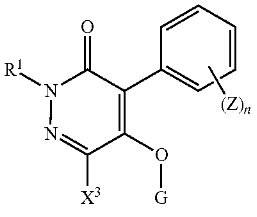

(I-v)

wherein $R^1$, $X^3$, Z, and n are as defined above.

The reaction can be performed in a solvent. Examples of the solvent to be used in the reaction include water; ethers such as dioxane and tetrahydrofuran; nitriles such as acetonitrile; and mixtures thereof.

Examples of the nitrite salt to be used in the reaction include sodium nitrite, and potassium nitrite.

The amount of the nitrite salt to be used in the reaction is usually 1 to 10 moles, preferably 1 to 5 moles based on 1 mole of the compound of the formula (I-u).

Examples of the acid to be used in the reaction include HF-pyridine, hydrochloric acid, hydrobromic acid, and hydroiodic acid.

The amount of the acid to be used in the reaction is usually 1 or more moles, possibly excessive amount double as a solvent.

The reaction temperature of the reaction is usually within a range of −30 to 100° C., preferably −10 to 50° C. The reaction time of the reaction is usually within a range of 5 minutes to 30 hours.

The completion of the reaction can be confirmed by an analytical means such as thin layer chromatography and high performance liquid chromatography after sampling a part of the reaction mixture. After the completion of the reaction, the compound of the formula (I-v) can be isolated, for example, by mixing the reaction mixture with water, and extracting the reaction mixture with an organic solvent, and then drying and concentrating the resulting organic layer.

Production Method 16

A present compound of the formula (I-x) can be produced by the first step of reacting a compound of the formula (I-w) with a compound of the formula (XXIV) or a compound of the formula (XXV), and the second step of treating with an alkali metal salt:

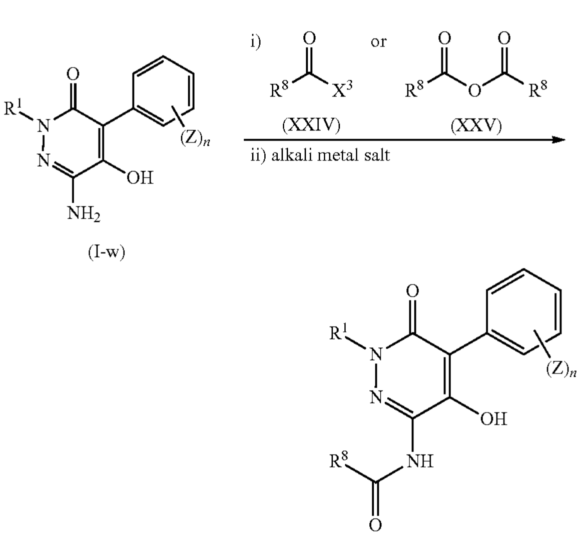

(I-w)
(I-x)

wherein $R^1$, $R^8$, $X^3$, Z, and n are as defined above.

The first step is illustrated.

The reaction can be performed in a solvent.

Examples of the solvent to be used in the reaction include aromatic hydrocarbons such as benzene and toluene; hydrocarbons such as hexane and heptane; ethers such as diethyl ether, diisopropylether, dioxane, tetrahydrofuran, dimethoxyethane, and t-butyl methyl ether; halogenated hydrocarbons such as chloroform and 1,2-dichloroethane; amides such as dimethylformamide and dimethylacetamide; nitriles such as acetonitrile; sulfoxides such as dimethylsulfoxide; sulfones such as sulfolane; and mixtures thereof.

The amount of the compound of the formula (XXIV) or the compound of the formula (XXV) to be used in the reaction is usually 3 to 20 moles, preferably 3 to 10 moles based on 1 mole of the compound of the formula (I-w).

The reaction is usually performed in the presence of a base. Examples of the base to be used in the reaction include organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate, and sodium hydride.

The amount of the base to be used in the reaction is usually 3 to 30 moles, preferably 3 to 10 moles based on 1 mole of the compound of the formula (I-w).

The reaction temperature of the reaction is usually within a range of −80 to 180° C., preferably −10 to 100° C. The reaction time of the reaction is usually 10 minutes to 100 hours.

The completion of the reaction can be confirmed by an analytical means such as thin layer chromatography and high performance liquid chromatography after sampling a part of the reaction mixture. After the completion of the reaction, the reaction mixture can be directly used in the next reaction.

The second step is illustrated.

The reaction in the second step can be performed by the method similar to Production method 13.

The compound of the formula (XXIV) and the compound of the formula (XXV) are a known compound, or can be produced from a known compound.

Production Method 17

A present compound of the formula (I-y) can be produced by oxidizing a compound of the formula (I-u):

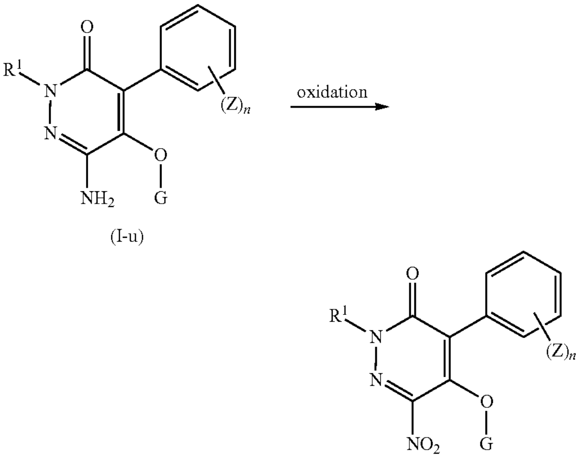

(I-u)
(I-y)

wherein $R^1$, Z, and n are as defined above.

Examples of the oxidizing agent to be used in the reaction include a combination of hydrogen peroxide and tungsten catalyst, a combination of hydrogen peroxide and vanadium catalyst; peracids such as peracetic acid, perbenzoic acid, and m-chloroperbenzoic acid.

The amount of the oxidizing agent to be used in the reaction is usually 2 to 10 moles, preferably 2 to 4 moles based on 1 mole of the compound of the formula (I-u).

The reaction can be performed in a solvent.

Examples of the solvent to be used in the reaction include saturated hydrocarbons such as hexane, heptane, octane, and cyclohexane; aromatic hydrocarbons such as benzene, toluene, xylene, chlorobenzene, and dichlorobenzene; saturated halogenated hydrocarbons such as dichloromethane, chloroform, 1,2-dichloroethane, and carbon tetrachloride; alcohols such as methanol, ethanol, and propanol; nitriles such as acetonitrile; amides such as dimethylformamide and dimethylacetamide; sulfones such as sulfolane; organic acids such as acetic acid and propionic acid; water; and mixtures thereof.

The reaction temperature of the reaction is usually within a range of 0 to 200° C., preferably 20 to 150° C. The reaction time of the reaction is usually within a range of 30 minutes to 100 hours.

The progress of the reaction can be confirmed by analyzing a port of the reaction mixture by thin layer chromatography, high performance liquid chromatography, and the like. After the completion of the reaction, the compound of the formula (I-y) can be isolated, for example, by mixing the reaction mixture with water, and extracting the reaction mixture with an organic solvent, and then drying and concentrating the resulting organic layer.

Production Method 18

A present compound of the formula (I-z) can be produced by reacting a compound of the formula (XXVI) with an alkali metal salt:

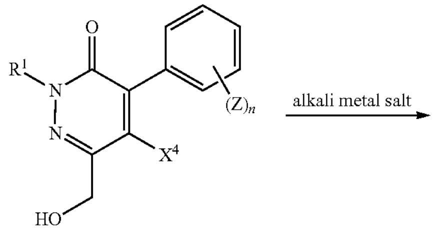

(XXVI)

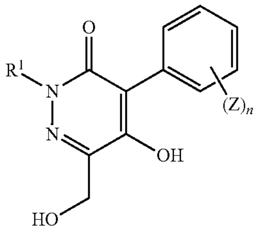

(I-z)

wherein $X^4$ represents a $C_{1-6}$ alkylsulfonyl group, a benzenesulfonyl group, or a p-toluenesulfonyl group, and $R^1$, Z, and n are as defined above.

The reaction can be performed in a solvent.

Examples of the solvent to be used in the reaction include water; ethers such as dioxane, tetrahydrofuran, and dimethoxyethane; amides such as dimethylformamide and N-methylpyrrolidone; 1,3-dimethylimidazolidinone; sulfoxides such as dimethylsulfoxide; and mixtures thereof.

Examples of the alkali metal salt to be used in the reaction include alkali metal hydroxides such as sodium hydroxide, and potassium hydroxide; and alkali metal carbonates such as sodium carbonate and potassium carbonate.

The amount of the alkali metal salt to be used in the reaction is usually 1 to 20 moles, preferably 2 to 5 moles based on 1 mole of the compound of the formula (XXVI).

The reaction temperature of the reaction is usually within a range of 30 to 180° C. The reaction time of the reaction is usually within a range of 5 minutes to 100 hours.

The completion of the reaction can be confirmed by an analytical means such as thin layer chromatography and high performance liquid chromatography after sampling a part of the reaction mixture. After the completion of the reaction, the compound of the formula (I-z) can be isolated, for example, by mixing the reaction mixture with water, neutralizing the reaction mixture with an addition of an acid, and extracting the reaction mixture with an organic solvent, and then drying and concentrating the resulting organic layer.

Production Method 19

A present compound of the formula (I-B) can be produced by oxidizing a compound of the formula (I-A):

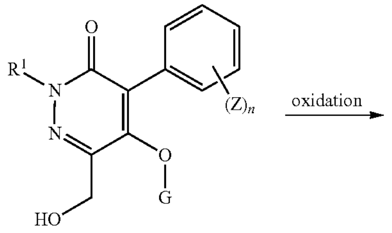

(I-A)

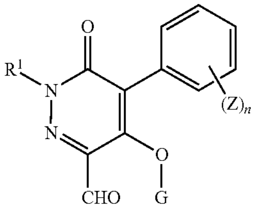

(I-B)

wherein $R^1$, G, Z, and n are as defined above.

Examples of the oxidizing agent to be used in the reaction include manganese oxide, PCC, PDC, a combination of iodobenzene diacetate and 2,2,6,6-tetramethylpiperidine 1-oxyl.

The amount of the oxidizing agent to be used in the reaction is usually 1 to 10 moles based on 1 mole of the compound of the formula (I-A).

The reaction can be performed in a solvent. Examples of the solvent to be used in the reaction include aromatic hydrocarbons such as benzene and toluene; saturated halogenated hydrocarbons such as dichloromethane and chloroform; and mixtures thereof.

The reaction temperature of the reaction is usually within a range of 0 to 150° C. The reaction time of the reaction is usually within a range of 5 minutes to 100 hours.

The progress of the reaction can be confirmed by analyzing a port of the reaction mixture by thin layer chromatography, high performance liquid chromatography, and the like. After the completion of the reaction, the compound of the formula (I-B) can be isolated, for example, by mixing the reaction mixture with water, and extracting the reaction mixture with an organic solvent, and then drying and concentrating the resulting organic layer.

Production Method 20

A present compound of the formula (I-C) can be produced from a compound of the formula (I-B) and a compound of the formula (XXVII):

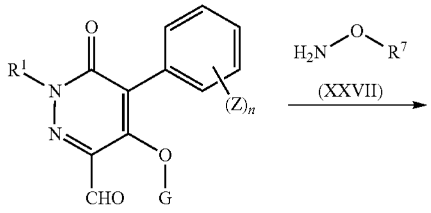

(I-B)

-continued

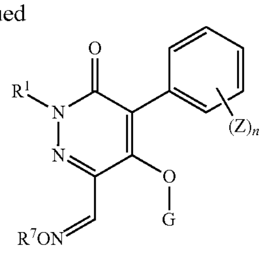

(I-C)

wherein G, $R^1$, $R^7$, Z, and n are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethylsulfoxide; sulfones such as sulfolane; water; and mixtures thereof.

The amount of the compound of the formula (XXVII) to be used in the reaction is usually 1 to 5 moles based on 1 mole of the compound of the formula (I-B).

The reaction temperature of the reaction is usually within a range of −30 to 180° C., preferably −10 to 80° C. The reaction time of the reaction is usually within a range of 5 minutes to 30 hours.

The completion of the reaction can be confirmed by an analytical means such as thin layer chromatography and high performance liquid chromatography after sampling a part of the reaction mixture. After the completion of the reaction, the compound of the formula (I-C) can be isolated, for example, by mixing the reaction mixture with water, and extracting the reaction mixture with an organic solvent, and then drying and concentrating the resulting organic layer.

The compound of the formula (XXVII) is a known compound, or can be produced from a known compound.

Production Method 21

A present compound of the formula (I-E) can be produced from a compound of the formula (I-D) and a compound of the formula (XXV):

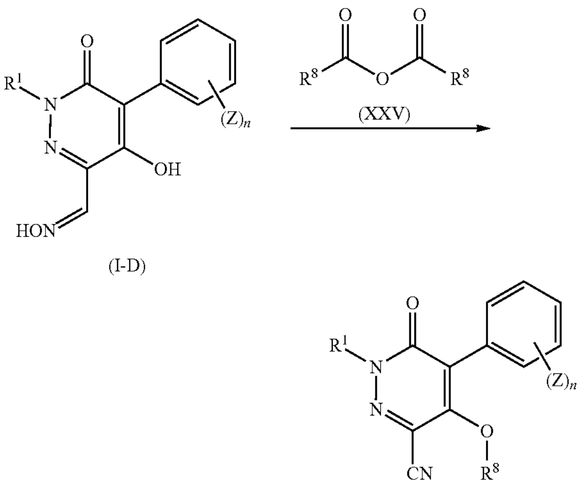

(I-D)

(XXV)

(I-E)

wherein $R^1$, $R^8$, Z, and n are as defined above.

The reaction can be performed in a solvent.

Examples of the solvent to be used in the reaction include aromatic hydrocarbons such as benzene and toluene; amides such as dimethylformamide and dimethylacetamide; sulfoxides such as dimethylsulfoxide; and mixtures thereof.

The amount of the compound of the formula (XXV) to be used in the reaction is usually 2 or more moles, possibly excessive amount double as a solvent based on 1 mole of the compound of the formula (I-D).

The reaction temperature of the reaction is usually within a range of 50 to 200° C. The reaction time of the reaction is usually within a range of 30 minutes to 100 hours.

The completion of the reaction can be confirmed by an analytical means such as thin layer chromatography and high performance liquid chromatography after sampling a part of the reaction mixture. After the completion of the reaction, the compound of the formula (I-E) can be isolated, for example, by mixing the reaction mixture with water, and extracting the reaction mixture with an organic solvent, and then drying and concentrating the resulting organic layer.

Production Method 22

A present compound of the formula (I-F) can be produced from a compound of the formula (XXVIII):

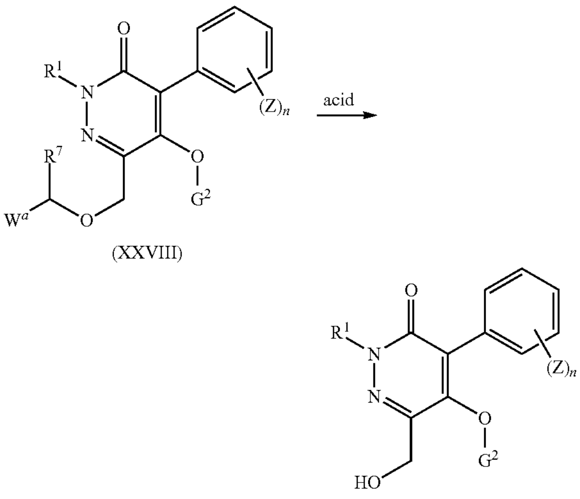

(XXVIII)

(I-F)

wherein $G^2$, $R^1$, $R^7$, $W^a$, Z, and n are as defined above.

The reaction can be performed in a solvent. Examples of the solvent to be used in the reaction include water; alcohols such as methanol, and ethanol; and mixtures thereof.

An acid is used in the reaction. Examples of the acid to be used in the reaction include hydrochloric acid, nitric acid, sulfuric acid, and hydrobromic acid.

The amount of the acid to be used in the reaction is usually 1 to 100 moles based on 1 mole of the compound of the formula (XXVIII).

The reaction is performed in the presence of water. The amount of water to be used in the reaction is usually 1 or more moles, preferably 10 to 100 moles.

The reaction temperature of the reaction is usually within a range of 0 to 150° C. The reaction time of the reaction is usually within a range of 5 minutes to 100 hours.

The completion of the reaction can be confirmed by an analytical means such as thin layer chromatography and high performance liquid chromatography after sampling a part of the reaction mixture. After the completion of the reaction, the compound of the formula (I-F) can be isolated, for example, by mixing the reaction mixture with water, and extracting the reaction mixture with an organic solvent, and then drying and concentrating the resulting organic layer.

Production Method 23

A present compound of the formula (I-G) can be produced from a compound of the formula (XXIX):

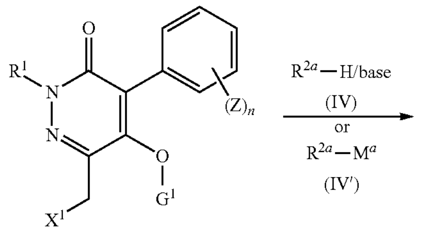

(XXIX)

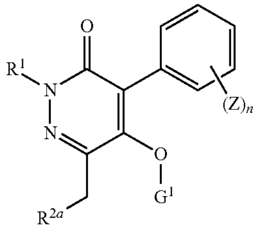

(I-G)

wherein $G^1$, $R^1$, $R^{2a}$, $M^a$, $X^1$, Zm and n are as defined above.

The reaction can be performed under the condition described in Production method 5.

Production Method 24

A present compound of the formula (I-J) can be produced by reacting a compound of the formula (I-H) with a compound of the formula (XXX):

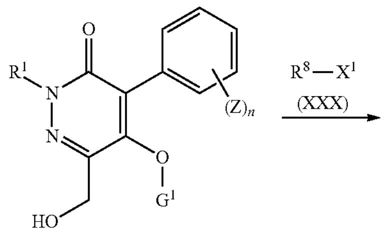

(I-H)

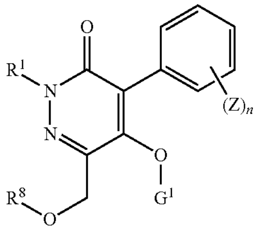

(I-J)

wherein $G^1$, $R^1$, $R^8$, $X^1$, Z and n, are as defined above.

The reaction can be performed in a solvent.

Examples of the solvent to be used in the reaction include aromatic hydrocarbons such as benzene and toluene; ethers such as diethyl ether, diisopropylether, dioxane, tetrahydrofuran, and dimethoxyethane; halogenated hydrocarbons such as dichloromethane, chloroform, and 1,2-dichloroethane; amides such as dimethylformamide and dimethylacetamide; sulfoxides such as dimethylsulfoxide; sulfones such as sulfolane; and mixtures thereof.

The amount of the compound of the formula (XXX) to be used in the reaction is usually 1 or more moles, preferably 1 to 3 moles based on 1 mole of the compound of the formula (I-H).

The reaction is usually performed in the presence of a base. Examples of the base to be used in the reaction include inorganic bases such as sodium hydroxide, potassium hydroxide, and sodium hydride.

The amount of the base to be used in the reaction is usually 1 to 10 moles, preferably 1 to 5 moles based on 1 mole of the compound of the formula (I-H).

The reaction temperature of the reaction is usually within a range of −30 to 180° C., preferably −10 to 80° C. The reaction time of the reaction is usually within a range of 5 minutes to 30 hours.

The completion of the reaction can be confirmed by an analytical means such as thin layer chromatography and high performance liquid chromatography after sampling a part of the reaction mixture. After the completion of the reaction, the compound of the formula (I-J) can be isolated, for example, by mixing the reaction mixture with water, and extracting the reaction mixture with an organic solvent, and then drying and concentrating the resulting organic layer.

The compound of the formula (XXX) is a known compound, or can be produced from a known compound.

Production Method 25

A present compound of the formula (I-L) can be produced by reacting a compound of the formula (I-K) with an acid:

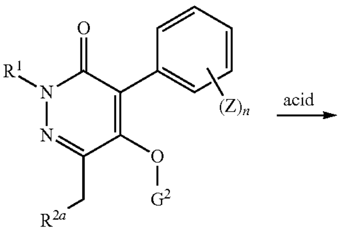

(I-K)

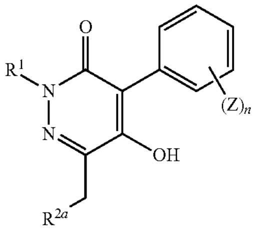

(I-L)

wherein $G^2$, $R^1$, $R^{2a}$, Z, and n are as defined above.

The reaction can be performed in a solvent. Examples of the solvent to be used in the reaction include water; organic acids such as acetic acid and propionic acid; and mixtures thereof.

The amount of the acid to be used in the reaction is usually 1 or more moles, preferably 1 to 20 moles based on 1 mole of the compound of the formula (I-K).

The reaction temperature of the reaction is usually within a range of 30 to 180° C., preferably 60 to 120° C. The reaction time of the reaction is usually within a range of 5 minutes to 30 hours.

The completion of the reaction can be confirmed by an analytical means such as thin layer chromatography and high performance liquid chromatography after sampling a part of the reaction mixture. After the completion of the reaction, the compound of the formula (I-L) can be isolated, for example, by mixing the reaction mixture with water, and extracting the reaction mixture with an organic solvent, and then drying and concentrating the resulting organic layer.

Production Method 26

A present compound of the formula (I-M) can be produced by the first step of reacting a compound of the formula (XXXI) with a chlorinating agent, and the second step of reacting the product with a compound of the formula (XXXII):

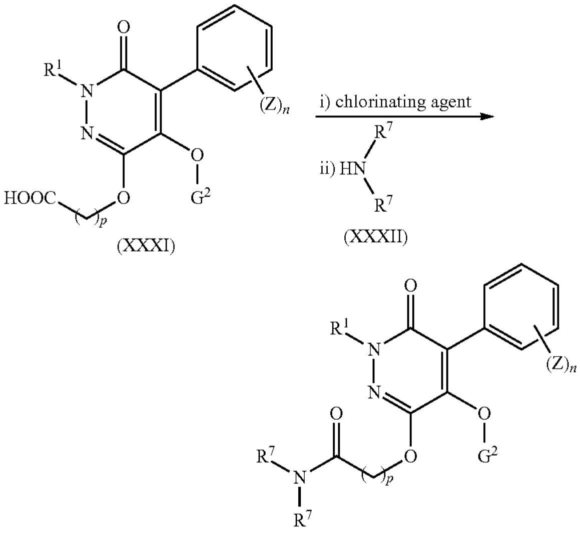

(XXXI) (XXXII)

(I-M)

wherein p represents an integer of 1-6, and $G^2$, $R^1$, $R^7$, Z, and n are as defined above.

The first step is illustrated.

The reaction can be performed in a solvent.

Examples of the solvent to be used in the reaction include aromatic hydrocarbons such as benzene and toluene; saturated hydrocarbons such as hexane and heptane; ethers such as diethyl ether, diisopropylether, dioxane, tetrahydrofuran, dimethoxyethane, and t-butyl methyl ether; halogenated hydrocarbons such as chloroform and 1,2-dichloroethane; and mixtures thereof.

Examples of the chlorinating agent to be used in the reaction include thionyl chloride, oxalyl chloride, and phosphorous pentachloride.

The amount of the chlorinating agent to be used in the reaction is usually 0.2 to 20 moles, preferably 1 to 10 moles based on 1 mole of the compound of the formula (XXXI).

The reaction temperature of the reaction is usually within a range of −20 to 180° C., preferably 10 to 130° C. The reaction time of the reaction is usually within a range of 5 minutes to 100 hours.

The completion of the reaction can be confirmed by an analytical means such as thin layer chromatography, gas chromatography, and NMR after sampling a part of the reaction mixture. After the completion of the reaction, the acid chloride of the compound of the formula (XXXI) can be isolated by concentrating the reaction mixture.

The second step is illustrated.

The reaction can be performed in a solvent.

Examples of the solvent to be used in the reaction include aromatic hydrocarbons such as benzene and toluene; saturated hydrocarbons such as hexane and heptane; ethers such as diethyl ether, diisopropylether, dioxane, tetrahydrofuran, dimethoxyethane, and t-butyl methyl ether; halogenated hydrocarbons such as chloroform and 1,2-dichloroethane; nitriles such as acetonitrile and mixtures thereof.

The amount of the compound of the formula (XXXII) to be used in the reaction is usually 1 to 20 moles based on 1 mole of the compound of the formula (XXXI).

The reaction temperature of the reaction is usually within a range of −20 to 100° C., preferably −10 to 50° C. The reaction time of the reaction is usually within a range of 5 minutes to 100 hours.

The reaction can be performed in the presence of a base.

Examples of the base to be used in the reaction include organic bases such as triethylamine, tripropylamine, pyridine, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate, and sodium hydride.

The amount of the base to be used in the reaction is usually 1 to 20 moles, preferably 1 to 10 moles based on 1 mole of the compound of the formula (XXXI).

The completion of the reaction can be confirmed by an analytical means such as thin layer chromatography and high performance liquid chromatography after sampling a part of the reaction mixture. After the completion of the reaction, the compound of the formula (I-M) can be isolated, for example, by mixing the reaction mixture with water, and extracting the reaction mixture with an organic solvent, and then drying and concentrating the resulting organic layer.

The compound of the formula (XXXII) is a known compound, or can be produced from a known compound.

Each compound produced by Production methods 1-26 can be isolated and purified by other known means such as concentration, concentration under reduced pressure, extraction, re-extraction, crystallization, recrystallization, and chromatography.

Specific examples of the present compound are as follows:

($I^1$)

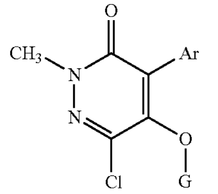

($I^2$)

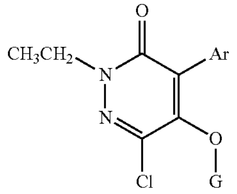

-continued
(I$^{3}$)
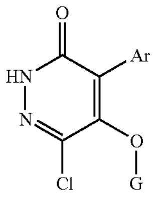
(I$^{4}$)
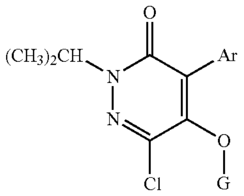
(I$^{5}$)
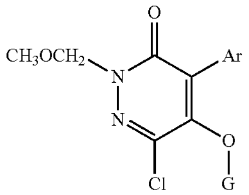
(I$^{6}$)
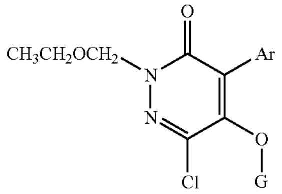
(I$^{7}$)
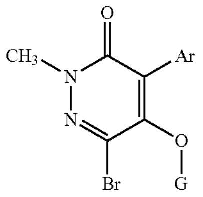
(I$^{8}$)
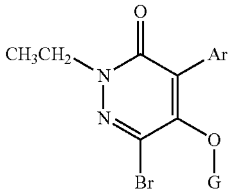
(I$^{9}$)
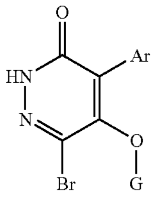
-continued
(I$^{10}$)
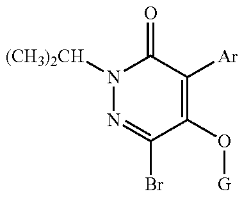
(I$^{11}$)
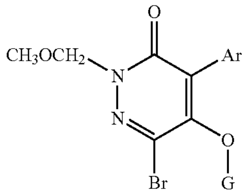
(I$^{12}$)
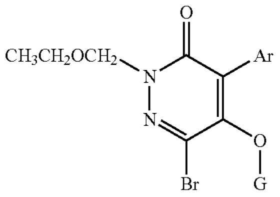
(I$^{13}$)
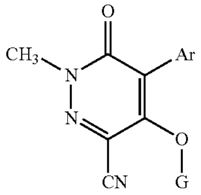
(I$^{14}$)
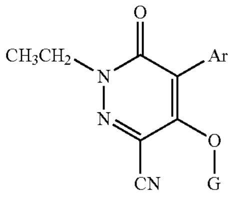
(I$^{15}$)
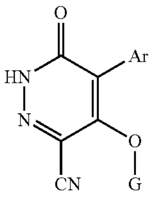
(I$^{16}$)
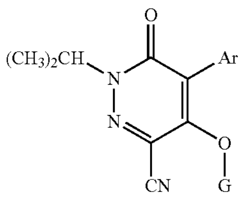

-continued
(I[17])
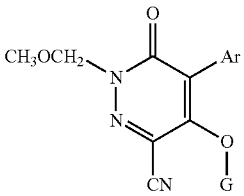
(I[18])
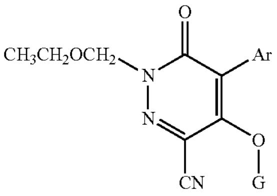
(I[19])
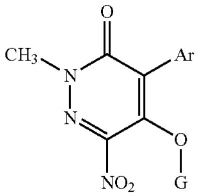
(I[20])
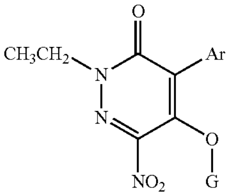
(I[21])
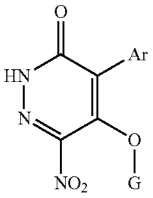
(I[22])
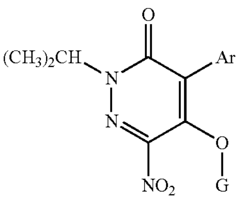
(I[23])
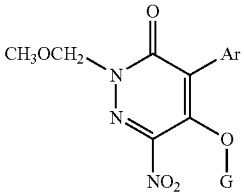
-continued
(I[24])
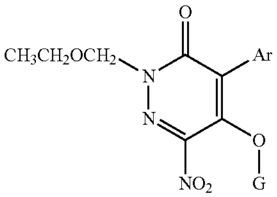
(I[25])
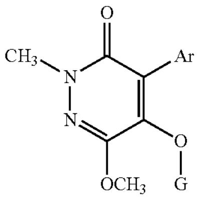
(I[26])
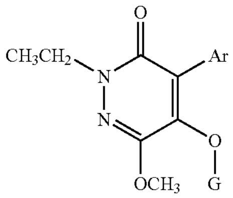
(I[27])
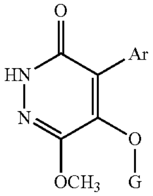
(I[28])
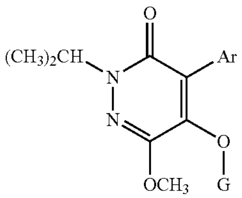
(I[29])
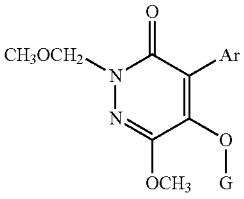
(I[30])
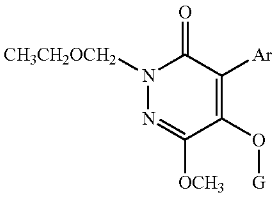

-continued
$(I^{31})$
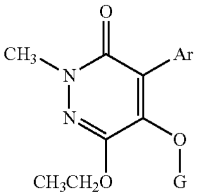
$(I^{32})$
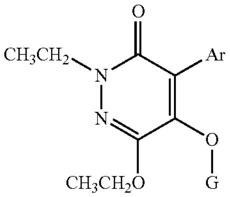
$(I^{33})$
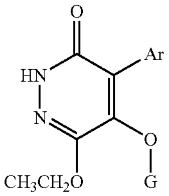
$(I^{34})$
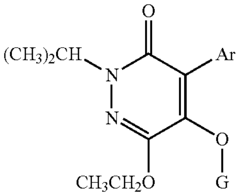
$(I^{35})$
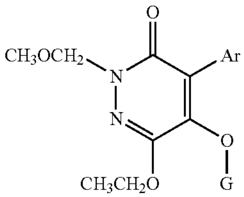
$(I^{36})$
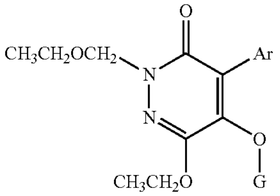
$(I^{37})$
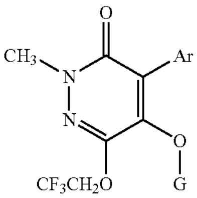
-continued
$(I^{38})$
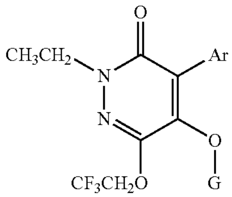
$(I^{39})$
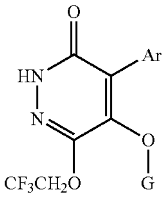
$(I^{40})$
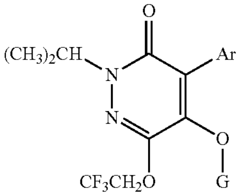
$(I^{41})$
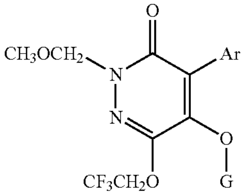
$(I^{42})$
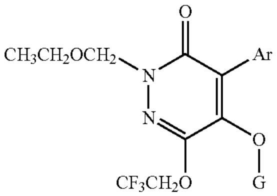
$(I^{43})$
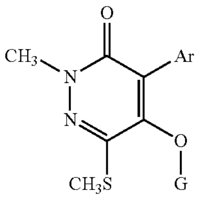
$(I^{44})$
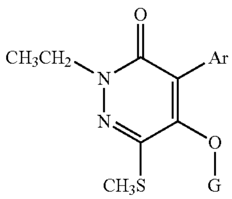

-continued
($I^{45}$)
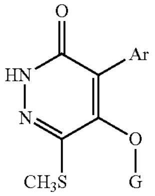
($I^{46}$)
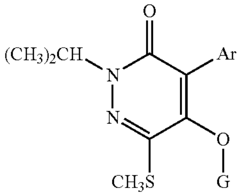
($I^{47}$)
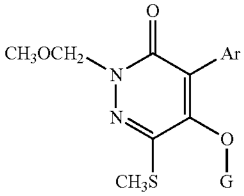
($I^{48}$)
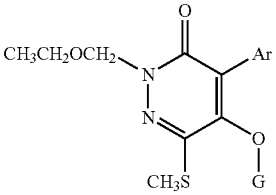
($I^{49}$)
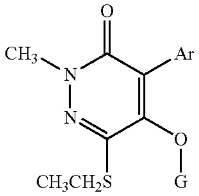
($I^{50}$)
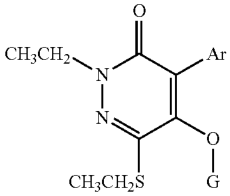
($I^{51}$)
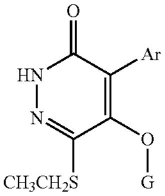
-continued
($I^{52}$)
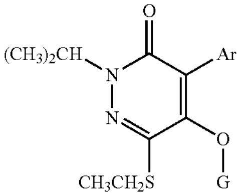
($I^{53}$)
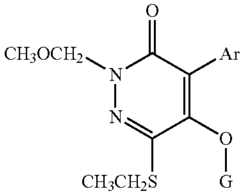
($I^{54}$)
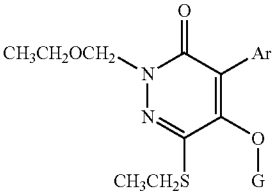
($I^{55}$)
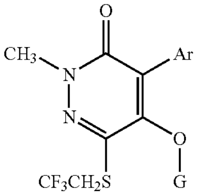
($I^{56}$)
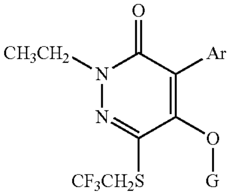
($I^{57}$)
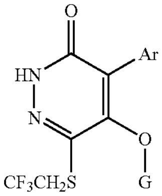
($I^{58}$)
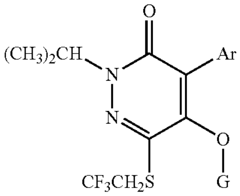

-continued
$(I^{59})$
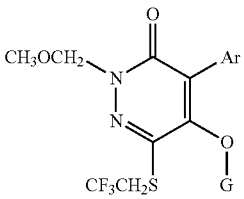
$(I^{60})$
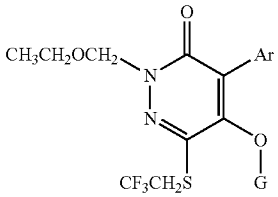
$(I^{61})$
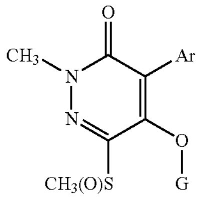
$(I^{62})$
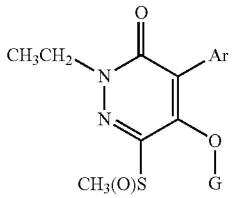
$(I^{63})$
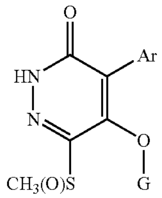
$(I^{64})$
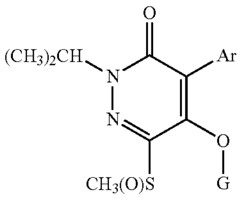
$(I^{65})$
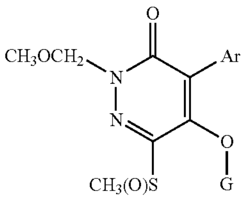
-continued
$(I^{66})$
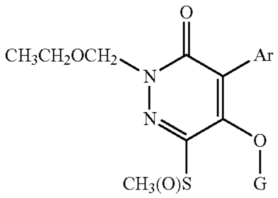
$(I^{67})$
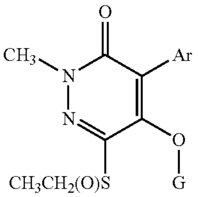
$(I^{68})$
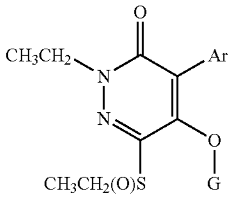
$(I^{69})$
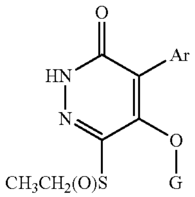
$(I^{70})$
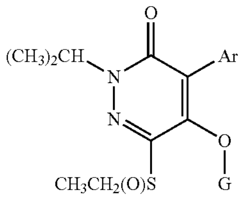
$(I^{71})$
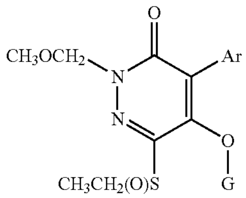
$(I^{72})$
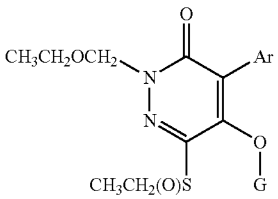

-continued
$(I^{73})$
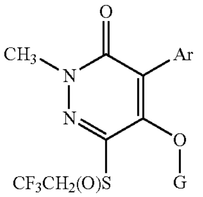
$(I^{74})$
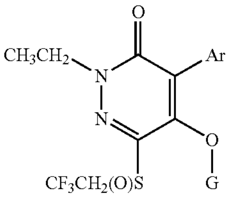
$(I^{75})$
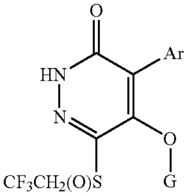
$(I^{76})$
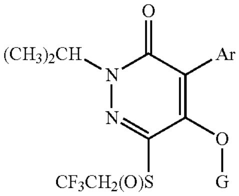
$(I^{77})$
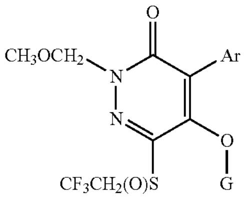
$(I^{78})$
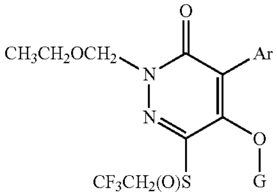
$(I^{79})$
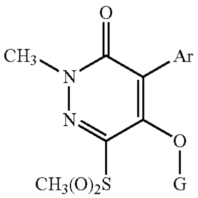
-continued
$(I^{80})$
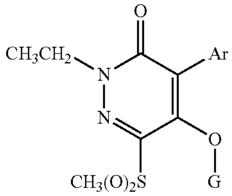
$(I^{81})$
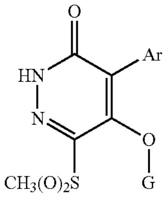
$(I^{82})$
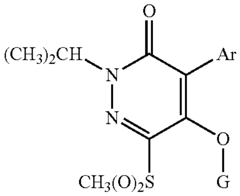
$(I^{83})$
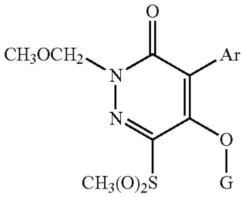
$(I^{84})$
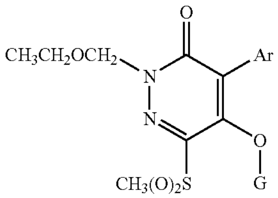
$(I^{85})$
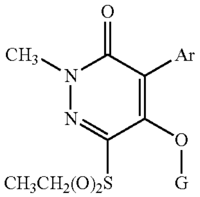
$(I^{86})$
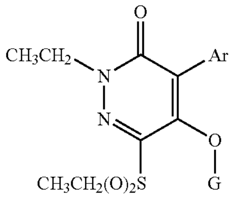

-continued
(I87)
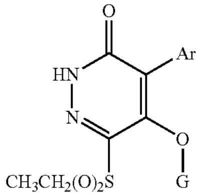
(I88)
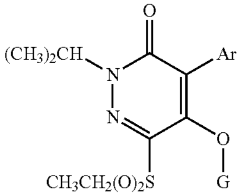
(I89)
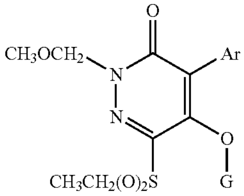
(I90)
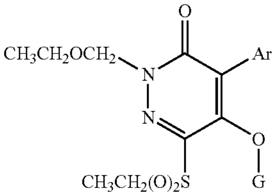
(I91)
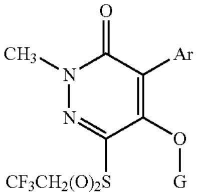
(I92)
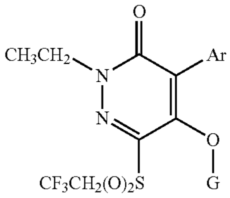
(I93)
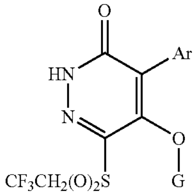
-continued
(I94)
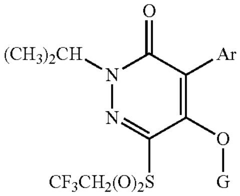
(I95)
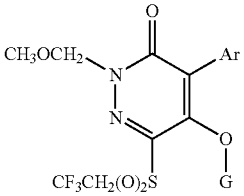
(I96)
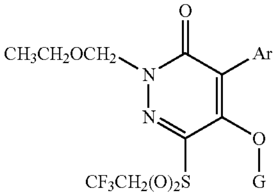
(I97)
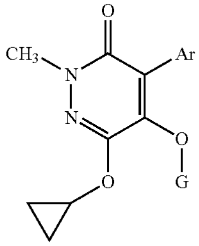
(I98)
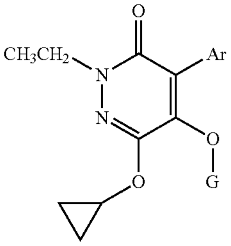
(I99)
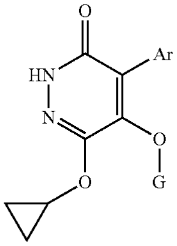

-continued
($I^{100}$)
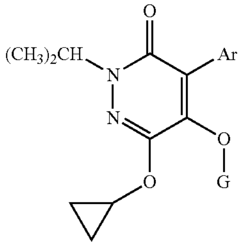
($I^{101}$)
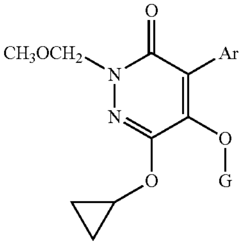
($I^{102}$)
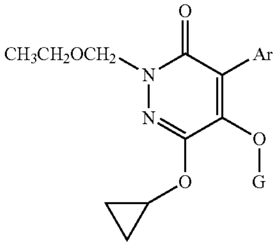
($I^{103}$)
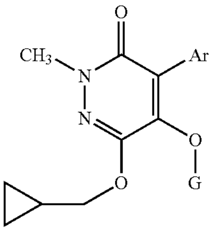
($I^{104}$)
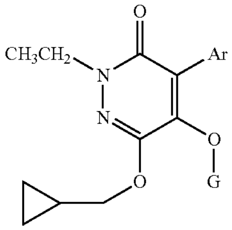
($I^{105}$)
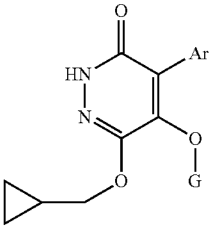
-continued
($I^{106}$)
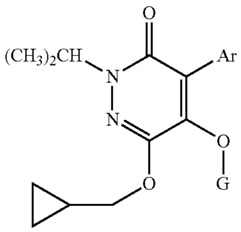
($I^{107}$)
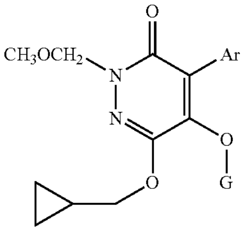
($I^{108}$)
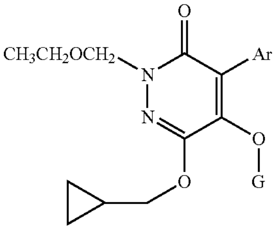
($I^{109}$)
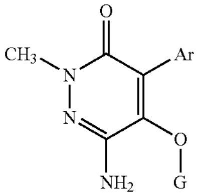
($I^{110}$)
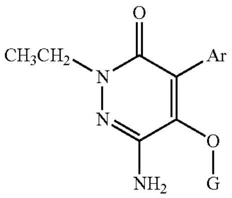
($I^{111}$)
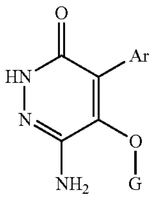
($I^{112}$)
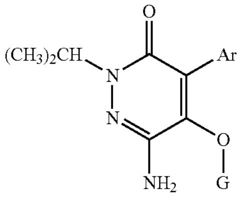

-continued
(I113)
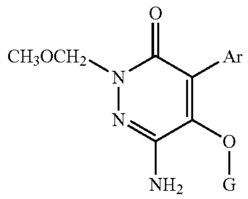
(I114)
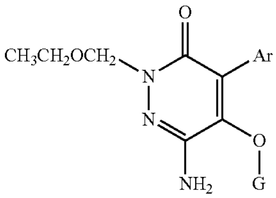
(I115)
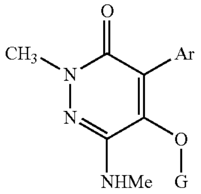
(I116)
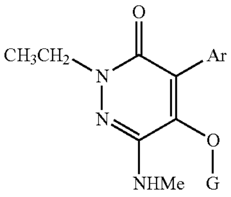
(I117)
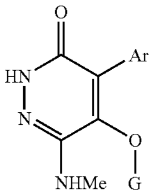
(I118)
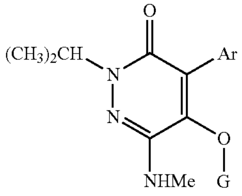
(I119)
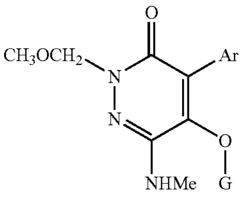
-continued
(I120)
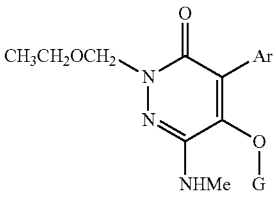
(I121)
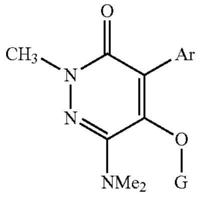
(I122)
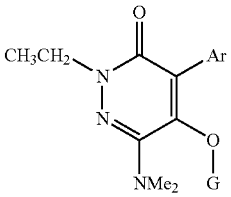
(I123)
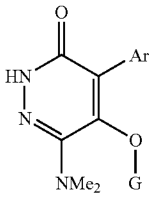
(I124)
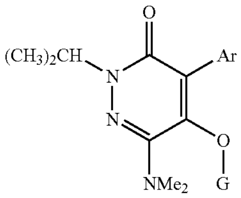
(I125)
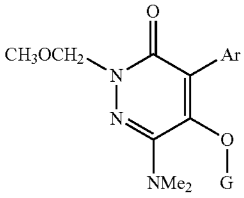
(I126)
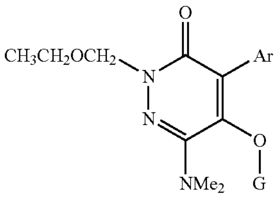

-continued
$(I^{127})$
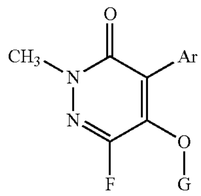
$(I^{128})$
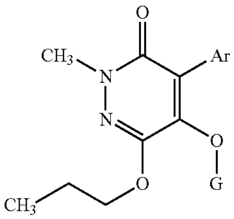
$(I^{129})$
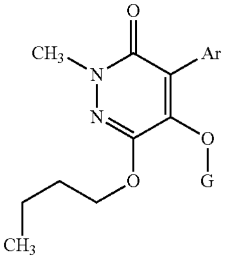
$(I^{130})$
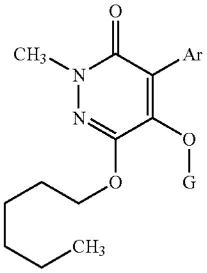
$(I^{131})$
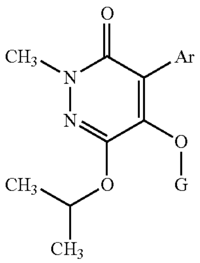
$(I^{132})$
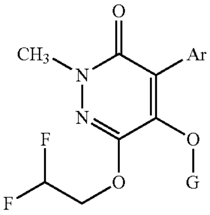
-continued
$(I^{133})$
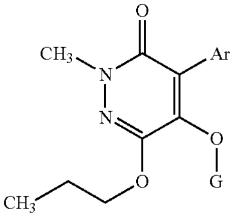
$(I^{134})$
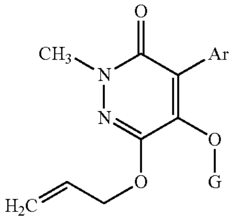
$(I^{135})$
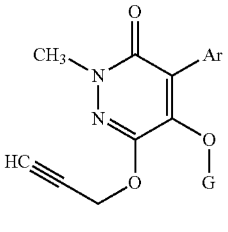
$(I^{136})$
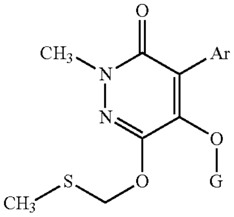
$(I^{137})$
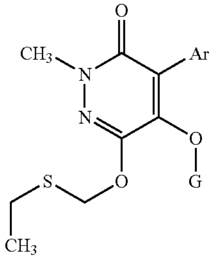
$(I^{138})$
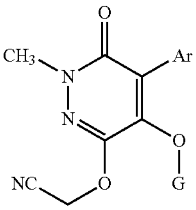
$(I^{139})$
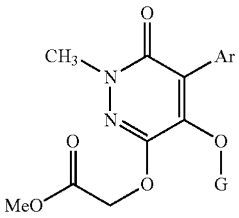

-continued
(I140)
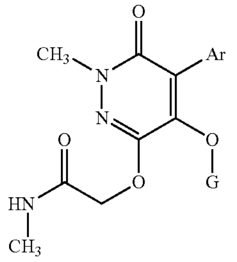
(I141)
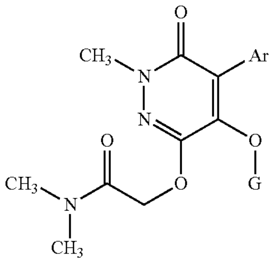
(I142)
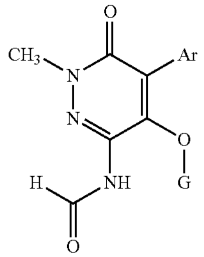
(I143)
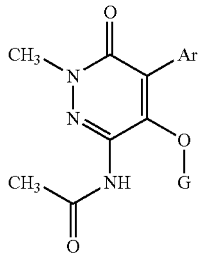
(I144)
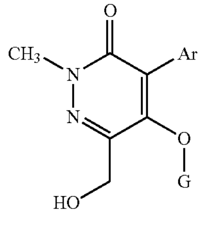
(I145)
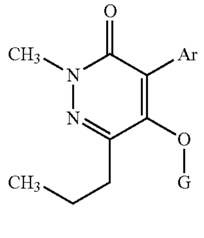
-continued
(I146)
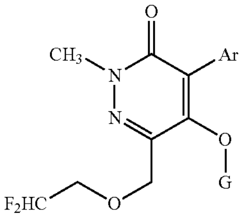
(I147)
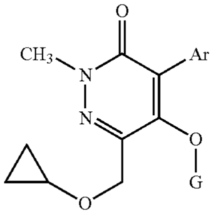
(I148)
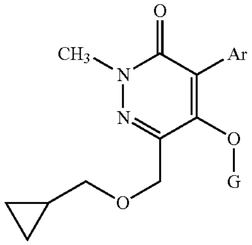
(I149)
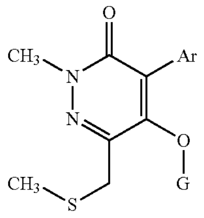
(I150)
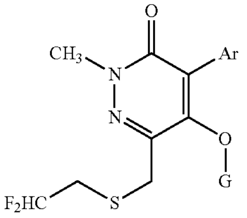
(I151)
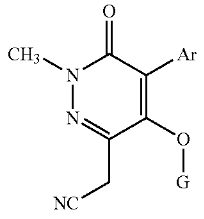

-continued
$(I^{152})$
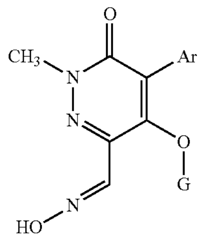
$(I^{153})$
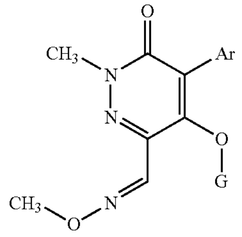
$(I^{154})$
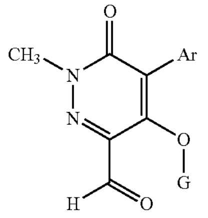
$(I^{155})$
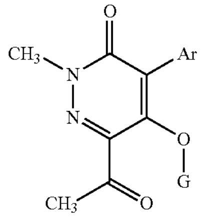
$(I^{156})$
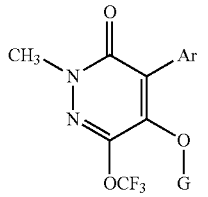
$(I^{157})$
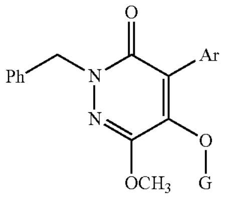
$(I^{158})$
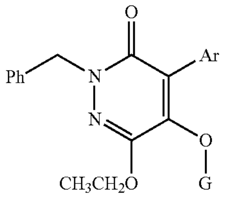
-continued
$(I^{159})$
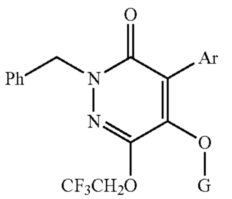
$(I^{160})$
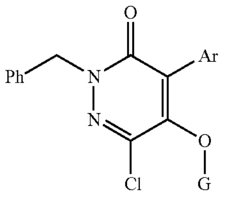
$(I^{161})$
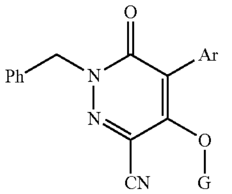
$(I^{162})$
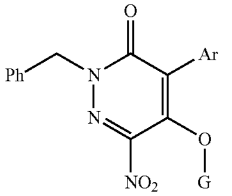
$(I^{163})$
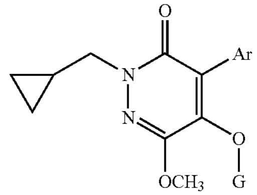
$(I^{164})$
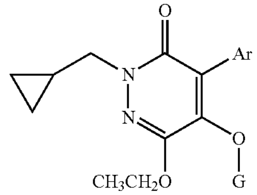
$(I^{165})$
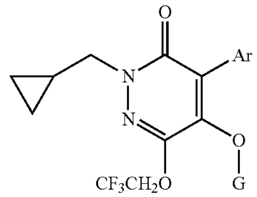

-continued
(I166)
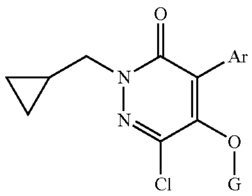
(I167)
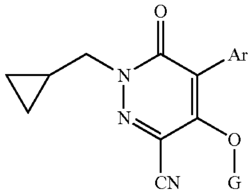
(I168)
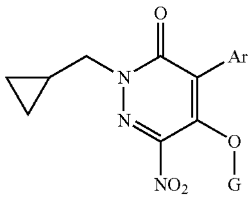
(I169)
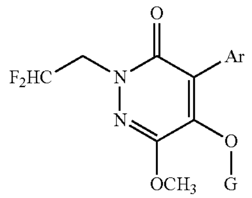
(I170)
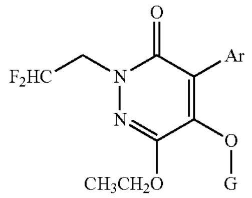
(I171)
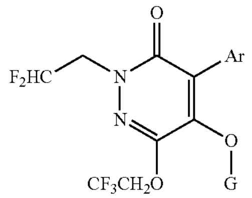
(I172)
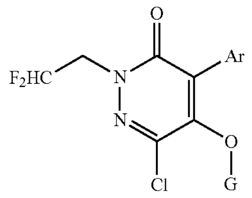
-continued
(I173)
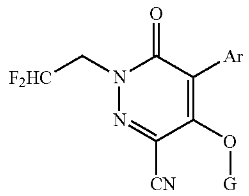
(I174)
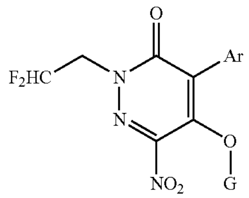
(I175)
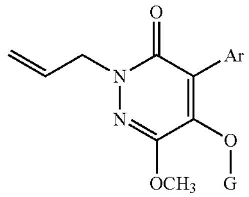
(I176)
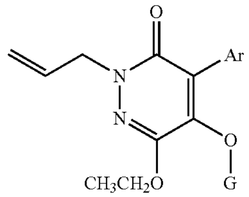
(I177)
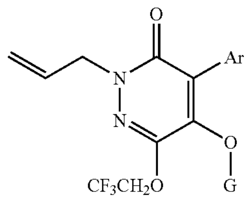
(I178)
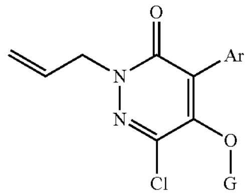
(I179)
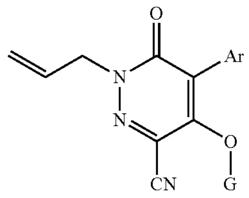

-continued (I[180])

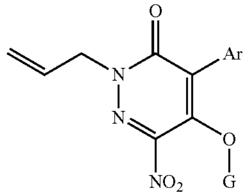

(I[181])

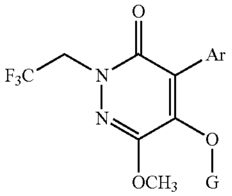

(I[182])

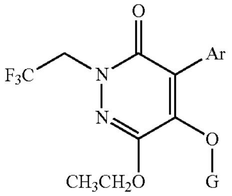

(I[183])

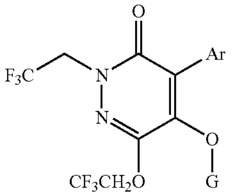

(I[184])

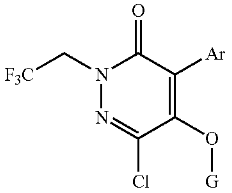

(I[185])

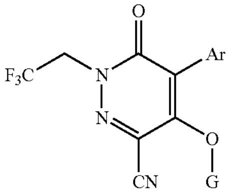

(I[186])

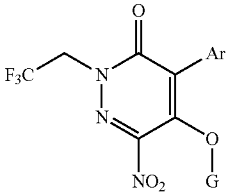

1) A pyridazinone compound of the formulae ($I^1$)-($I^{186}$) wherein Ar is a 2-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

2) A pyridazinone compound of the formulae ($I^1$)-($I^{186}$) wherein Ar is a 2-ethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

3) A pyridazinone compound of the formulae ($I^1$)-($I^{186}$) wherein Ar is a 2-propylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

4) A pyridazinone compound of the formulae ($I^1$)-($I^{186}$) wherein Ar is a 2,2-dimethylphenyl group, G is hydrogen, an acetyl group, a trifluoroacetyl group, a propionyl group, a butyryl group, an isobutyryl group, an isovaleryl group, a pivaloyl group, 2,4-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

5) A pyridazinone compound of the formulae ($I^1$)-($I^{186}$) wherein Ar is a 2,6-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group group, a methoxymethyl group, an ethoxymethyl group, a benzyl group, or a 4-methoxybenzyl group.

6) A pyridazinone compound of the formulae ($I^1$)-($I^{186}$) wherein Ar is a 2-ethyl-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

7) A pyridazinone compound of the formulae ($I^1$)-($I^{186}$) wherein Ar is a 2-ethyl-6-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

8) A pyridazinone compound of the formulae ($I^1$)-($I^{186}$) wherein Ar is a 2,6-diethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

9) A pyridazinone compound of the formulae ($I^1$)-($I^{186}$) wherein Ar is a 2,4,6-trimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

10) A pyridazinone compound of the formulae ($I^1$)-($I^{186}$) wherein Ar is a 2-ethyl-4,6-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

11) A pyridazinone compound of the formulae ($I^1$)-($I^{186}$) wherein Ar is a 2,6-diethyl-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

12) A pyridazinone compound of the formulae ($I^1$)-($I^{186}$) wherein Ar is a 2,4,6-triethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

13) A pyridazinone compound of the formulae ($I^1$)-($I^{186}$) wherein Ar is a 2,4-diethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

14) A pyridazinone compound of the formulae ($I^1$)-($I^{186}$) wherein Ar is a 2,4-diethyl-6-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, nyl group, a benzenesulfonyl group, a p-toluenesulfonyl group, a methoxymethyl group, an ethoxymethyl group, a benzyl group, or a 4-methoxybenzyl group.

15) A pyridazinone compound of the formulae ($I^1$)-($I^{186}$) wherein Ar is a 4-chloro-2,6-diethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

16) A pyridazinone compound of the formulae ($I^1$)-($I^{186}$) wherein Ar is a 4-bromo-2,6-diethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

17) A pyridazinone compound of the formulae ($I^1$)-($I^{186}$) wherein Ar is a 4-cyano-2,6-diethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

18) A pyridazinone compound of the formulae ($I^1$)-($I^{186}$) wherein Ar is a 2,6-diethyl-4-methoxyphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

19) A pyridazinone compound of the formulae ($I^1$)-($I^{186}$) wherein Ar is a 2,6-diethyl-4-nitrophenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

20) A pyridazinone compound of the formulae ($I^1$)-($I^{186}$) wherein Ar is a 2,5-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

21) A pyridazinone compound of the formulae ($I^1$)-($I^{186}$) wherein Ar is a 2,6-diethyl-4-ethinylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

22) A pyridazinone compound of the formulae ($I^1$)-($I^{186}$) wherein Ar is a 2-cyano-4,6-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

23) A pyridazinone compound of the formulae ($I^1$)-($I^{186}$) wherein Ar is a 2-cyano-6-ethyl-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

24) A pyridazinone compound of the formulae ($I^1$)-($I^{186}$) wherein Ar is a 2,4-dichloro-6-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

25) A pyridazinone compound of the formulae ($I^1$)-($I^{186}$) wherein Ar is a 2-chloro-4,6-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

26) A pyridazinone compound of the formulae ($I^1$)-($I^{186}$) wherein Ar is a 2-chloro-6-ethyl-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

27) A pyridazinone compound of the formulae ($I^1$)-($I^{186}$) wherein Ar is a 2,4-dichloro-6-ethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

28) A pyridazinone compound of the formulae ($I^1$)-($I^{186}$) wherein Ar is a 2-bromo-6-ethyl-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

29) A pyridazinone compound of the formulae ($I^1$)-($I^{186}$) wherein Ar is a 4-chloro-2-ethyl-6-methoxyphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

30) A pyridazinone compound of the formulae ($I^1$)-($I^{186}$) wherein Ar is a 2-chloro-6-methoxy-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

31) A pyridazinone compound of the formulae ($I^1$)-($I^{186}$) wherein Ar is a 2-ethyl-6-methoxy-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

32) A pyridazinone compound of the formulae ($I^1$)-($I^{186}$) wherein Ar is a 2,6-diethyl-4-trifluoromethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

33) A pyridazinone compound of the formulae ($I^1$)-($I^{186}$) wherein Ar is a 2,6-diethyl-4-trifluoromethoxyphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

34) A pyridazinone compound of the formulae ($I^1$)-($I^{186}$) wherein Ar is a 2-ethyl-6-ethinyl-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

35) A pyridazinone compound of the formulae ($I^1$)-($I^{186}$) wherein Ar is a 2-chloro-6-ethyl-4-methoxyphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

36) A pyridazinone compound of the formulae ($I^1$)-($I^{186}$) wherein Ar is a 2-cyclopropyl-6-ethyl-4-methylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

37) A pyridazinone compound of the formulae ($I^1$)-($I^{186}$) wherein Ar is a 4-cyclopropyl-2,6-diethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

38) A pyridazinone compound of the formulae ($I^1$)-($I^{186}$) wherein Ar is a 2-bromo-4,6-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

39) A pyridazinone compound of the formulae ($I^1$)-($I^{186}$) wherein Ar is a 2-methoxy-4,6-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

40) A pyridazinone compound of the formulae ($I^1$)-($I^{186}$) wherein Ar is a 2-ethinyl-4,6-dimethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

41) A pyridazinone compound of the formulae ($I^1$)-($I^{186}$) wherein Ar is a 2-trifluoromethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

42) A pyridazinone compound of the formulae ($I^1$)-($I^{186}$) wherein Ar is a 2,6-dichloro-4-trifluoromethylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

43) A pyridazinone compound of the formulae ($I^1$)-($I^{186}$) wherein Ar is a 2,6-dichloro-4-trifluoromethoxyphenyl group,
G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

44) A pyridazinone compound of the formulae ($I^1$)-($I^{186}$) wherein Ar is a 2,6-dimethyl-4-(2,2,2-trifluoroethoxy)phenyl group,
G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

45) A pyridazinone compound of the formulae ($I^1$)-($I^{186}$) wherein Ar is a 2-chloro-4-methyl-6-trifluoromethoxyphenyl group,
G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

46) A pyridazinone compound of the formulae ($I^1$)-($I^{186}$) wherein Ar is a 2-chloro-6-trifluoromethylphenyl group,
G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

47) A pyridazinone compound of the formulae ($I^1$)-($I^{186}$) wherein Ar is a 5-chloro-2-trifluoromethylphenyl group,
G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

48) A pyridazinone compound of the formulae ($I^1$)-($I^{186}$) wherein Ar is a 4-chloro-2-trifluoromethylphenyl group,
G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

49) A pyridazinone compound of the formulae ($I^1$)-($I^{186}$) wherein Ar is a 3-bromo-2-chloro-6-fluorophenyl group,
G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

50) A pyridazinone compound of the formulae ($I^1$)-($I^{186}$) wherein Ar is a 2,6-dichlorophenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

51) A pyridazinone compound of the formulae $(I^1)$-$(I^{186})$ wherein Ar is a 2,5-dichlorophenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

52) A pyridazinone compound of the formulae $(I^1)$-$(I^{186})$ wherein Ar is a 2,3,6-trichlorophenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

53) A pyridazinone compound of the formulae $(I^1)$-$(I^{186})$ wherein Ar is a 2,4-dimethyl-6-vinylphenyl group, G is hydrogen, an acetyl group, a trifluoroacetyl group, a propionyl group, a butyryl group, an isobutyryl group, an isovaleryl group, a pivaloyl group, a 2,2-dimethylbutyryl group, a 3,3-dimethylbutyryl group, a cyclohexylcarbonyl group, a benzoyl group, a benzylcarbonyl group, a methoxycarbonyl group, an ethoxycarbonyl group, an isopropoxycarbonyl group, a tert-butoxycarbonyl group, a phenoxycarbonyl group, an allyloxycarbonyl group, a dimethylaminocarbonyl group, a dimethylaminothiocarbonyl group, a methanesulfonyl group, a trifluoromethanesulfonyl group, a benzenesulfonyl group, a p-toluenesulfonyl group, a methoxymethyl group, an ethoxymethyl group, a benzyl group, or a 4-methoxybenzyl group.

Reference Production Method 1

A compound of the formula (II) can be produced, for example, by reacting a compound of the formula (V) with a compound of the formula (VI):

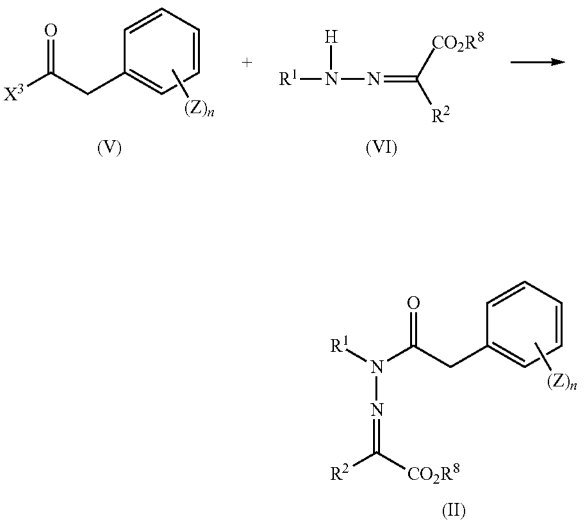

(V) (VI) (II)

wherein $R^1$, $R^2$, $R^8$, $X^3$, Z and n are as defined above.

The reaction is usually performed in a solvent.

Examples of the solvent to be used in the reaction include aromatic hydrocarbons such as benzene, toluene, and xylene; ethers such as diethyl ether, diisopropylether, dioxane, tetrahydrofuran, and dimethoxyethane; halogenated hydrocarbons such as dichloromethane, chloroform, and 1,2-dichloroethane; ketones such as acetone and methylethylketone; nitriles such as acetonitrile; amides such as dimethylformamide and dimethylacetamide; sulfones such as sulfolane; and mixtures thereof.

The reaction is usually performed in the presence of a base.

Examples of the base to be used in the reaction include organic bases such as triethylamine, tripropylamine, pyridine, dimethylaminopyridine, 1,8-diazabicyclo[5.4.0]-7-undecene, and 1,4-diazabicyclo[2.2.2]octane; and inorganic bases such as sodium hydroxide, potassium hydroxide, calcium hydroxide, sodium carbonate, potassium carbonate, sodium hydrogen carbonate, calcium carbonate, and sodium hydride.

The amount of the compound of the formula (V) to be used in the reaction is usually 0.5 or more moles, preferably 0.8 to 2 moles based on 1 mole of the compound of the formula (VI). The amount of the base to be used in the reaction is usually 0.5 or 10 moles, preferably 1 to 5 moles based on 1 mole of the compound of the formula (VI).

The reaction temperature of the reaction is usually within a range of −30 to 180° C., preferably −10 to 50° C. The reaction time of the reaction is usually within a range of 10 minutes to 30 hours.

The progress of the reaction can be confirmed by analyzing a port of the reaction mixture by thin layer chromatography, high performance liquid chromatography, and the like. After the completion of the reaction, the compound of the formula (II) can be isolated, for example, by mixing the reaction mixture with water, and extracting the reaction mixture with an organic solvent, and then drying and concentrating the resulting organic layer.

Reference Production Method 2

The compound of the formula (V) can be produced, for example, by the following production method:

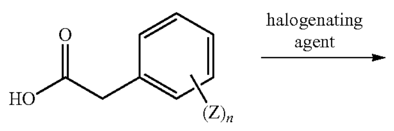

(VII)

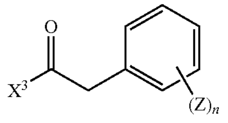

(V)

wherein $X^3$, Z and n are as defined above.

Examples of the halogenating agent to be used in the reaction include thionyl chloride, thionyl bromide, phosphorous oxychloride, and oxalyl chloride.

The compound of the formula (VII) is a known compound, or can be produced from a known compound, for example according to the method described in WO 96/25395, WO 96/35664, WO 97/02243, WO 99/43649, WO 2001/017973, WO 2004/065366, WO 2004/080962, WO 2005/016873, WO 2005/044796, WO 2005/092897, and WO 2006/056281 or the method similar to them.

Reference Production Method 3

A compound of the formula (VI-a) which is the formula (VI) wherein $R^2$ is a cyano group, a $C_{1-6}$ alkoxy group, a $C_{1-6}$ haloalkoxy group, a $C_{1-6}$ alkylthio group, a $C_{1-6}$ haloalkylthio group, a $C_{3-8}$ cycloalkoxy group, a ($C_{3-8}$ cycloalkyl)$C_{1-6}$ alkoxy group, or a di($C_{1-6}$ alkyl)amino group can be produced, for example, according to the following scheme:

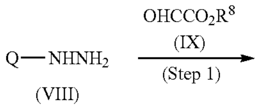

(VIII)

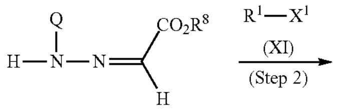

(X)

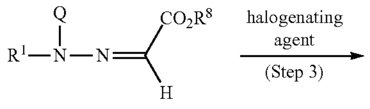

(XII)

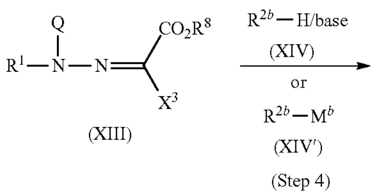

(XIII)

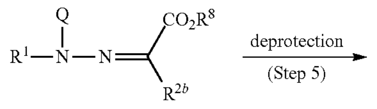

(XV)

-continued

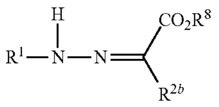

(VI-a)

wherein Q represents a protecting group (e.g. a t-butoxycarbonyl group, a benzylcarbonyl group), $R^{2b}$ represents a cyano group, a $C_{1-6}$ alkoxy group, a $C_{1-6}$ haloalkoxy group, a $C_{1-6}$ alkylthio group, a $C_{1-6}$ haloalkylthio group, a $C_{3-6}$ cycloalkoxy group, a ($C_{3-8}$ cycloalkyl)$C_{1-6}$ alkoxy group, or a di($C_{1-6}$ alkyl)amino group among the definition of $R^2$, $M^b$ represents an alkali metal (e.g. lithium, sodium, potassium), and $R^1$, $X^1$, $X^3$, and $R^8$ are as defined above.

Step 1 is a dehydration-condensation of a compound of the formula (VIII) and a compound of the formula (IX). The reaction can be performed according to the usual reaction condition for producing a hydrazone compound from a hydrazine compound and a carbonyl compound.

Step 2 is a reaction in which a compound of the formula (X) is reacted with a compound of the formula (XI) to give a compound of the formula (XII). For example, the reaction can be performed under the reaction condition described in Production method 2.

Step 3 is a reaction in which a compound of the formula (XII) is reacted with a halogenating agent (e.g. N-chlorosuccinimide, N-bromosuccinimide, N-iodosuccinimide) to give a compound of the formula (XIII). The reaction can be performed under the known reaction condition for halogenating with the halogenating agent.

Step 4 is a reaction in which a compound of the formula (XIII) is reacted with a compound of the formula (XIV) or a compound of the formula (XIV') to give a compound of the formula (XV). For examples, the reaction can be performed under the reaction condition described in Production method 5.

Step 5 is a reaction in which a compound of the formula (XV) is deprotected to give a compound of the formula (VI). The reaction can be performed under the specific known reaction condition for the protecting group Q.

All of the compound of the formula (VIII), the compound of the formula (IX), the compound of the formula (XI), the compound of the formula (XIV) and the compound of the formula (XIV') are a known compound, or can be produced from a known compound.

Reference Production Method 4

Alternatively, in Reference production method 3, a compound of the formula (VI-a) can be produced without a protecting group Q:

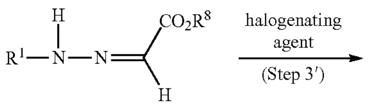

(XVI)

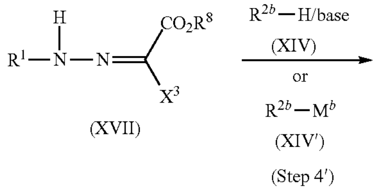

(XVII)

-continued

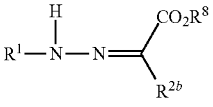

(VI-a)

wherein $M^b$, $R^1$, $R^{2b}$, $R^8$, and $X^3$ are as defined above.

Step 3' and Step 4' can be performed under the reaction conditions of Step 3 and Step 4 in Reference production method 3, respectively.

The compound of the formula (XVI) is a known compound, or can be produced from a known compound.

Reference Production Method 5

A compound of the formula (II-b) and a compound of the formula (XVIII) can be produced, for example, according to the following scheme:

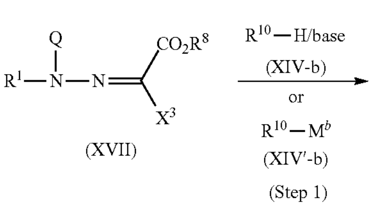

(XVII)

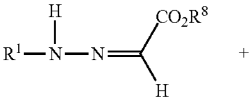

(VI-b)

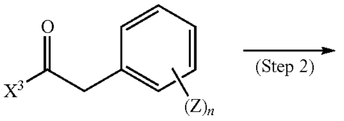

(V)

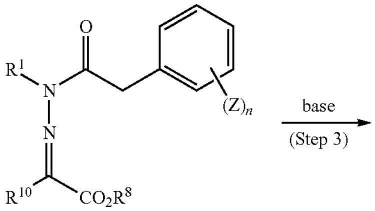

(II-b)

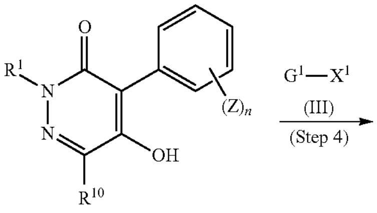

(XXXIV)

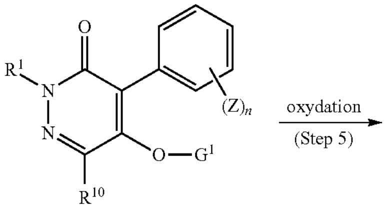

(XXXV)

-continued

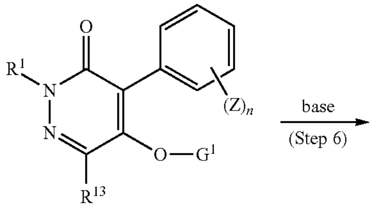

(XXXVI)

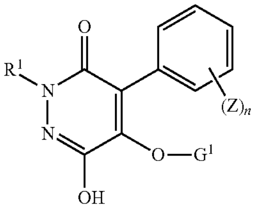

(XVIII)

wherein $R^{13}$ represents a $C_{1-12}$ alkylsulfonyl group, and $G^1$, $M^b$, $R^1$, $R^8$, $R^{10}$, $X^3$, Z, and n are as defined above.

A compound of the formula (VI-b) can be produced, for example, by reacting a compound of the formula (XVII) with a compound of the formula (XIV-b) under the reaction condition described in Step 4 of Reference production method 3. A compound of the formula (II-b) can be produced, for example, under the reaction condition described in Reference production method 1. A compound of the formula (XXXIV) can be produced, for example, under the reaction condition described in Production method 1. A compound of the formula (XXXV) can be produced, for example, under the reaction condition described in Production method 2. A compound of the formula (XXXVI) can be produced, for example, under the reaction condition described in Production method 4. A compound of the formula (XVIII) can be produced, for example, under the reaction condition described in Production method 18.

The compound of the formula (XIV-b) and the compound of the formula (XIV'-b) are a known compound, or can be produced from a known compound.

Reference Production Method 6

A compound of the formula (XX) can be produced, for example, by reacting a compound of the formula (I-N) with Lewis acid:

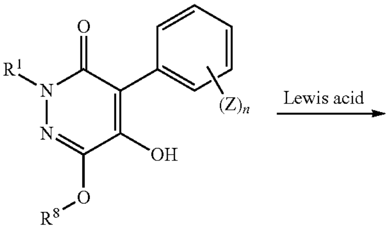

(I-N)

-continued

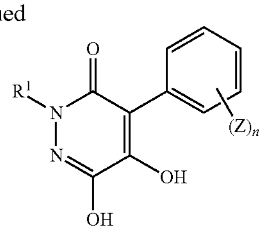

(XX)

wherein $R^1$, $R^8$, Z, and n are as defined above.

Examples of Lewis acid to be used in the reaction include aluminum chloride, boron trichloride, and boron tribromide. The reaction can be performed under the known dealkylation condition with Lewis acid.

Reference Production Method 7

A compound of the formula (XXXIII) can be produced, for example, according to the following scheme:

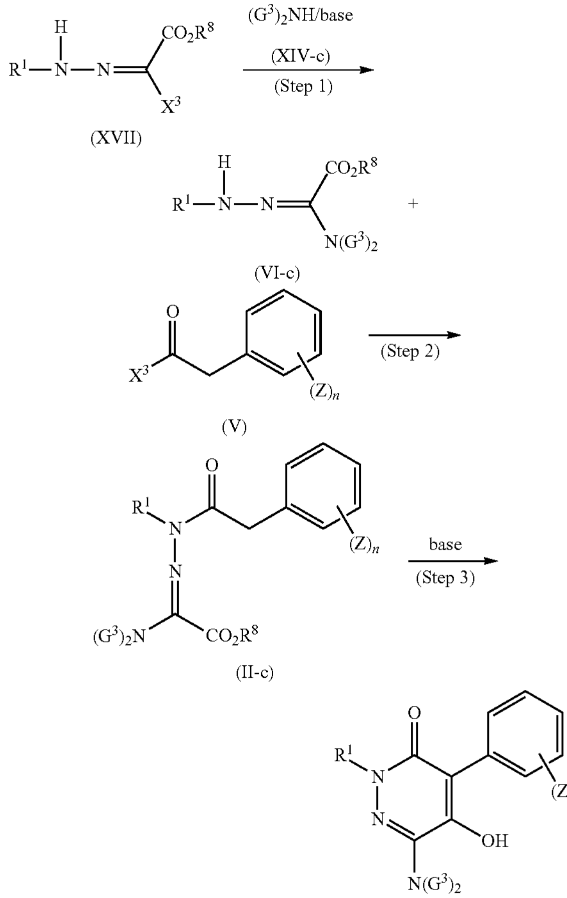

(XVII) (VI-c) (V) (II-c) (XXXIII)

wherein $G^3$, $R^1$, $R^8$, $X^3$, Z, and n are as defined above.

A compound of the formula (VI-c) can be produced by reacting a compound of the formula (XVII) with the compound of the formula (XIV-c) under the reaction condition described in Step 4 of Reference production method 3. A compound of the formula (II-c) can be produced, for example, under the reaction condition described in Reference production method 1. A compound of the formula (XXXIII) can be produced, for example, under the reaction condition described in Production method 1.

The compound of the formula (XIV-c) is a known compound, or can be produced from a known compound.

Reference Production Method 8

A compound of the formula (XXVI) can be produced, for example, according to the following scheme:

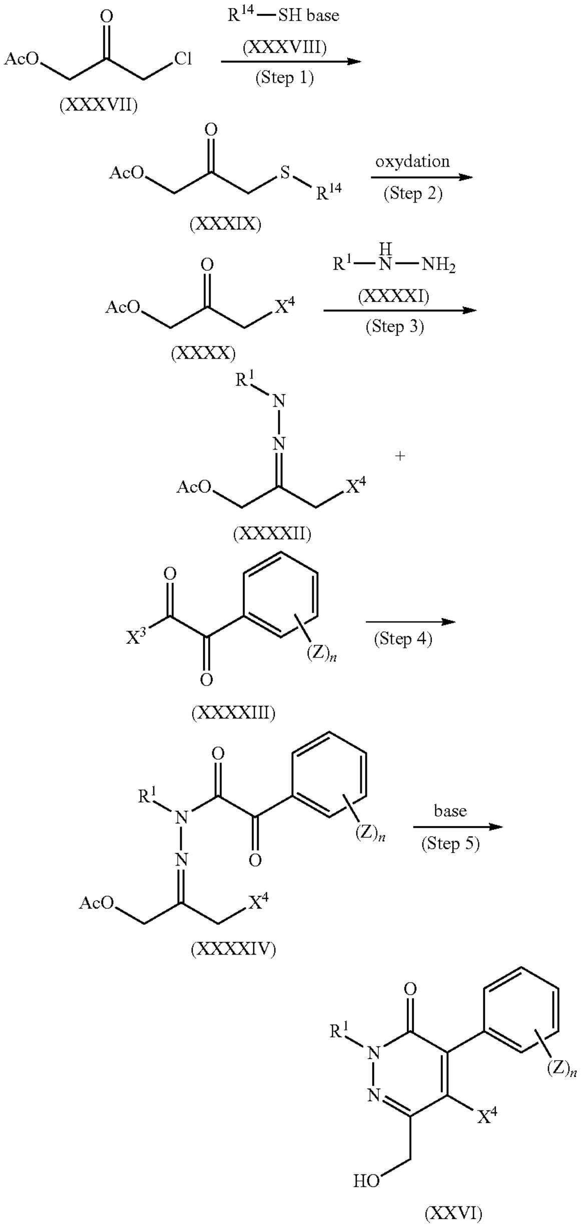

(XXXVII) (XXXIX) (XXXX) (XXXXII) (XXXXIII) (XXXXIV) (XXVI)

wherein $R^{14}$ represents a $C_{1-6}$ alkyl group, a phenyl group, and a 4-methylphenyl group, and $R^1$, $X^4$, Z, and n are as defined above.

Step 1 is illustrated.

A compound of the formula (XXXIX) can be produced by reacting a compound of the formula (XXXVII) with a compound of the formula (XXXXVIII) in the presence of a base.

The reaction can be performed in a solvent. Examples of the solvent to be used in the reaction include aromatic hydrocarbons such as benzene and toluene; ethers such as diethyl ether, tetrahydrofuran, and t-butyl methyl ether; halogenated hydrocarbons such as dichloromethane and chloroform; amides such as dimethylformamide and dimethylacetamide; sulfoxides such as dimethylsulfoxide; and mixtures thereof.

The amount of the compound of the formula (XXXVIII) to be used in the reaction is usually 1 to 3 moles based on 1 mole of the compound of the formula (XXXVII).

The reaction is usually performed in the presence of a base. Examples of the base to be used in the reaction include organic bases such as triethylamine, tripropylamine, pyridine, dimethylaminopyridine, and 1,8-diazabicyclo[5.4.0]-7-undecene.

The amount of the base to be used in the reaction is usually 1 to 5 moles based on 1 mole of the compound of the formula (XXXVII).

The reaction temperature of the reaction is usually within a range of −30 to 100° C., preferably −10 to 50° C.

The reaction time of the reaction is usually within a range of 5 minutes to 30 hours.

The completion of the reaction can be confirmed by an analytical means such as thin layer chromatography and high performance liquid chromatography after sampling a part of the reaction mixture. After the completion of the reaction, the compound of the formula (XXXIX) can be isolated, for example, by mixing the reaction mixture with water, and extracting the reaction mixture with an organic solvent, and then drying and concentrating the resulting organic layer.

Step 2 is performed, for example, under the same reaction condition as in Production method 4.

Step 3 is a dehydration-condensation of a compound of the formula (XXXX) and a compound of the formula (XXXXI). The reaction can be performed according to the usual reaction condition for producing a hydrazone compound from a hydrazine compound and a carbonyl compound.

Step 4 is performed, for example, under the same reaction condition as in Reference production method 1.

Step 5 is illustrated.

A compound of the formula (XXVI) can be produced by reacting a compound of the formula (XXXXIV) in the presence of a base.

The reaction can be performed in a solvent. Examples of the solvent to be used in the reaction include alcohols such as methanol and ethanol; amides such as dimethylformamide and dimethylacetamide; sulfoxides such as dimethylsulfoxide; and mixtures thereof.

Examples of the base to be used in the reaction include alkali metal hydroxides such as lithium hydroxide, sodium hydroxide, and potassium hydroxide.

The amount of the base to be used in the reaction is usually 1 to 10 moles based on 1 mole of the compound of the formula (XXXXIV).

The reaction temperature of the reaction is usually within a range of −30 to 50° C. The reaction time of the reaction is usually within a range of 5 minutes to 30 hours.

The completion of the reaction can be confirmed by an analytical means such as thin layer chromatography and high performance liquid chromatography after sampling a part of the reaction mixture. After the completion of the reaction, the compound of the formula (XXVI) can be isolated, for example, by mixing the reaction mixture with water, and extracting the reaction mixture with an organic solvent, and then drying and concentrating the resulting organic layer.

The compound of the formula (XXXVII), the compound of the formula (XXXVIII), the compound of the formula (XXXXI) and the compound of the formula (XXXXIII) are a known compound, or can be produced from a known compound.

Reference Production Method 9

A compound of the formula (XXVIII) can be produced, for example, according to the following scheme:

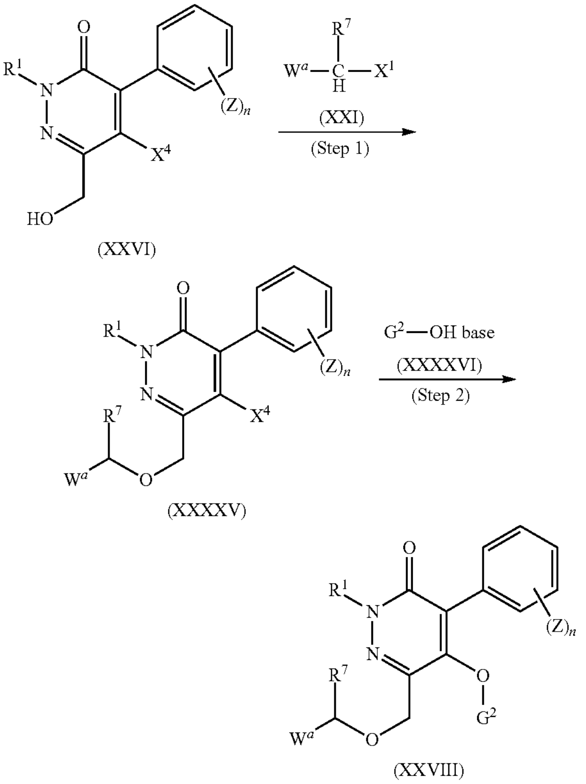

(XXVI) (XXXXV) (XXVIII)

wherein $G^2$, $R^1$, $R^7$, $X^1$, $X^4$, $W^a$, Z, and n are as defined above.

Step 1 is illustrated. A compound of the formula (XXXXV) can be produced by etherification using a compound of the formula (XXVI) and a compound of the formula (XXI). The reaction can be performed under a usual reaction condition for producing an ether compound from an alcohol compound and an alkylating agent.

Step 2 is illustrated. A compound of the formula (XXVIII) can be produced by reacting the compound of the formula (XXXXV) with the compound of the formula (XXXXVI) in the presence of a base. The reaction can be performed under the reaction condition similar to Production method 24.

The compound of the formula (XXXXVI) is a known compound, or can be produced from a known compound.

Reference Production Method 10

A compound of the formula (XXIX) can be produced, for example, from a compound of the formula (I-H):

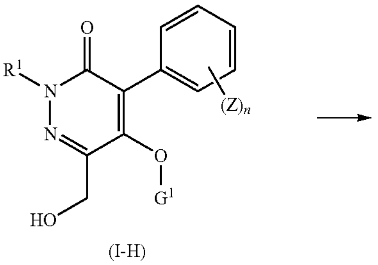

(I-H)

-continued

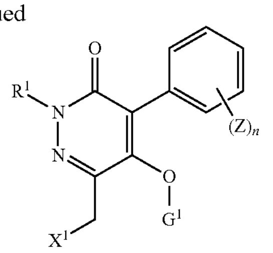

(XXIX)

wherein $G^1$, $R^1$, $X^1$, Z, and n are as defined above.

The reaction is to convert the alcohol part of a compound of the formula (I-H) to a leaving group and can be performed under a usual reaction condition.

Reference Production Method 11

A compound of the formula (XXXI) can be produced, for example, by hydrolyzing a compound of the formula (XXXXVII):

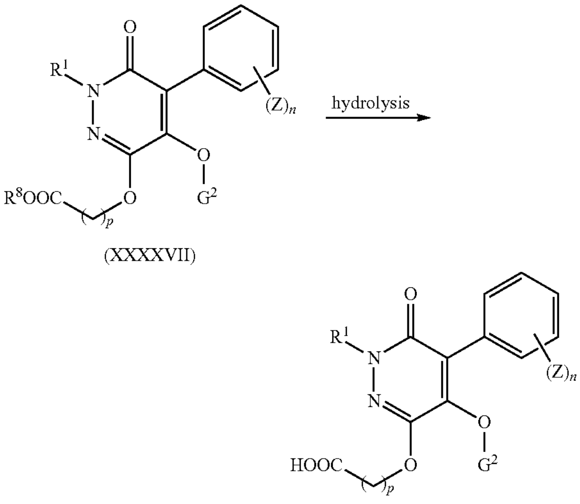

(XXXXVII)

(XXXI)

wherein $G^2$, $R^1$, $R^8$, Z, n, and p are as defined above.

The reaction is a hydrolysis of ester and can be performed under a usual reaction condition.

Reference Production Method 12

A compound of the formula (XVI) can be produced, for example, by deprotecting a compound of the formula (XII):

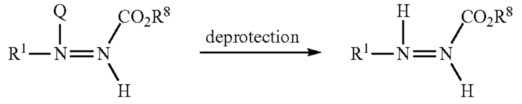

(XII) (XVI)

wherein Q, $R^1$, and $R^8$ are as defined above.

The reaction can be performed under the specific known reaction condition for the protecting group Q.

EXAMPLES

The present invention will be illustrated in detail by the following Production Examples, Reference Examples, Formulation Examples and Test Examples, however, the present invention is not limited to these examples.

In Production Examples and Reference Examples, room temperature usually means 10 to 30° C. $^1$H NMR means proton nuclear magnetic resonance spectrum. Tetramethylsilane is used as an internal standard, and chemical shift (δ) is expressed in ppm.

Abbreviations used in Production Examples and Reference Examples have the following meanings:

$CDCl_3$: chloroform-d, s: singlet, d: doublet, t: triplet, q: quartet, brs: broad singlet, m: multiplet, J: coupling constant, Me: a methyl group, Et: an ethyl group, Pr: a propyl group, i-Pr: an i-propyl group, c-Pr: a cyclopropyl group, t-Bu: a t-butyl group, Ph: a phenyl group, OMe: a methoxy group, OEt: an ethoxy group, OPr: a propoxy group, OBu: a butoxy group, Ac: an acetyl group, Bn: a benzyl group, Boc: a t-butoxycarbonyl group, TMS: a trimethylsilyl group, PMB: a p-methoxybenzyl group, MOM: a methoxymethyl group.

Production Example 1

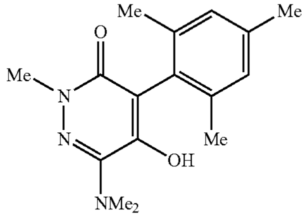

Production of 4-(2,6-diethyl-4-methylphenyl)-6-dimethylamino-5-hydroxy-2-methyl-3(2H)-pyridazinone (Compound (I-1-2))

To a solution of potassium t-butoxide (380 mg, 3.38 mmol) in dry THF (10 ml) was slowly added a solution of ethyl 2-[2-(2,6-diethyl-4-methylphenyl)acetyl-2-methylhydrazono]-2-dimethylaminoacetate (Compound (II-2)) (280 mg, 0.840 mmol) in dry THF (3 ml) dropwise. The mixture was stirred at room temperature for 15 minutes. The reaction solution was diluted with water, and extracted with ethyl acetate 2 times. The combined organic layer was washed with saturated brine, dried over anhydrous magnesium sulfate, and concentrated under reduced pressure. The resulting solid was washed with hexane, filtered, and dried to give 230 mg of Compound (I-1-2).

$^1$H NMR ($CDCl_3$): δ ppm: 1.08 (6H, t, J=7.6 Hz), 2.25-2.45 (4H, m), 2.36 (3H, s), 2.84 (6H, s), 3.71 (3H, s), 7.02 (2H, s).

The present compounds produced according to Production Example 1 and Compound (I-1-2) are shown in Table 1.

TABLE 1

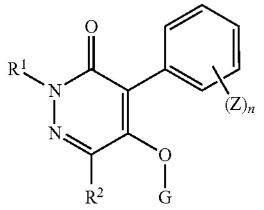

| No. | $R^1$ | $R^2$ | $(Z)_n$ | G | Melting point (° C.)/ $^1$H NMR |
|---|---|---|---|---|---|
| (I-1-1) | Me | $NMe_2$ | 2, 4, 6-$Me_3$ | H | 177-180 |
| (I-1-2) | Me | $NMe_2$ | 2, 6-$Et_2$-4-Me | H | 179-181 |
| (I-1-3) | Me | $NMe_2$ | 2, 4, 6-$Et_3$ | H | 146-148 |
| (I-1-4) | Me | SMe | 2, 4, 6-$Me_3$ | H | 188-190 |
| (I-1-5) | Me | SMe | 2, 6-$Et_2$-4-Me | H | 1) |
| (I-1-6) | Me | SMe | 2, 4, 6-$Et_3$ | H | 2) |
| (I-1-7) | Me | SMe | 2-Et-4, 6-$Me_2$ | H | 3) |

1) $^1$H NMR ($CDCl_3$): δ ppm: 1.08 (6H, t, J = 7.6 Hz), 2.25-2.43 (4H, m), 2.36 (3H, s), 2.51 (3H, s), 3.81 (3H, s), 5.75 (1H, brs), 7.03 (2H, s).

2) $^1$H NMR ($CDCl_3$): δ ppm: 1.08 (6H, t, J = 7.6 Hz), 1.27 (3H, t, J = 7.6 Hz), 2.27-2.45 (4H, m), 2.51 (3H, s), 2.66 (2H, q, J = 7.6 Hz), 3.81 (3H, s), 5.69 (1H, brs), 7.05 (2H, s).

3) $^1$H NMR ($CDCl_3$): δ ppm: 1.08 (3H, t, J = 7.5 Hz), 2.06 (3H, s), 2.27-2.43 (2H, m), 2.34 (3H, s), 2.51 (3H, s), 3.80 (3H, s), 5.42 (1H, brs), 7.00 (1H, s), 7.02 (1H, s).

Production Example 2

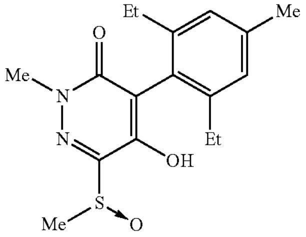 [SMILES: CCc1cc(C)cc(CC)c1-c1c(O)c(S(C)=O)nn(C)c1=O]

Production of 4-(2,6-diethyl-4-methylphenyl)-5-hydroxy-2-methyl-6-methylsulfinyl-3(2H)-pyridazinone (Compound (I-2-1))

To a solution of Compound (I-1-5) (0.15 g, 0.468 mmol) in chloroform (5 ml) was added m-chloroperbenzoic acid (0.081 g, 0.468 mmol) under ice-cooling. After ice-bath was removed, the mixture was stirred at room temperature for 5.5 hours. To the reaction mixture was added ethyl acetate, washed with aqueous sodium hydrogen sulfite solution, then saturated brine, dried over anhydrous magnesium sulfate, and concentrated under reduced pressure. The residue was purified by silica gel column chromatography (ethyl acetate) to give 0.10 g of Compound (I-2-1) as solid (yield: 63%).

$^1$H NMR ($CDCl_3$): δ ppm: 1.07-1.16 (6H, m), 2.30-2.45 (4H, m), 2.35 (3H, s), 3.11 (3H, s), 3.80 (3H, s), 7.00 (2H, s).

The present compounds produced according to Production Example 2 and Compound (I-2-1) are shown in Table 2.

TABLE 2

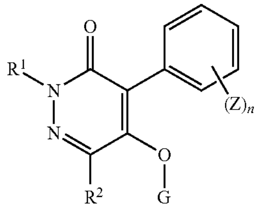

| No. | $R^1$ | R2 | $(Z)_n$ | G | $^1$H NMR |
|---|---|---|---|---|---|
| (I-2-1) | Me | S(O)Me | 2, 6-$Et_2$-4-Me | H | 1) |
| (I-2-2) | Me | S(O)Me | 2, 4, 6-$Et_3$ | H | 2) |
| (I-2-3) | Me | S(O)Me | 2-Et-4, 6-$Me_2$ | H | 3) |

1) $^1$H NMR: described in the above Production Example.

2) $^1$H NMR ($CDCl_3$): δ ppm: 1.08-1.15 (6H, m), 1.26 (3H, t, J = 7.6 Hz), 2.32-2.46 (4H, m), 2.65 (2H, q, J = 7.6 Hz), 3.11 (3H, s), 3.81 (3H, s), 7.01 (2H, s).

3) $^1$H NMR ($CDCl_3$): δ ppm: 1.07-1.16 (3H, m), 2.09 (1.5H, s), 2.10 (1.5H, s), 2.29-2.47 (2H, m), 2.32 (3H, s), 3.11 (3H, s), 3.80 (3H, s), 6.96 (1H, s), 6.98 (1H, s), 10.37 (1H, brs).

Production Example 3

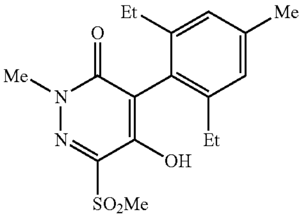

Production of 4-(2,6-diethyl-4-methylphenyl)-5-hydroxy-2-methyl-6-methylsulfonyl-3(2H)-pyridazinone (Compound (I-3-1))

To a solution of Compound (I-1-5) (9.64 g, 30.3 mmol) in chloroform (300 ml) was slowly added m-chloroperbenzoic acid (21.28 g, 123 mmol) portionwise under ice-cooling. After ice-bath was removed, the mixture was stirred at room temperature for 4 hours. To the reaction mixture was added ethyl acetate, washed with aqueous sodium hydrogen sulfite solution, then saturated brine, dried over anhydrous magnesium sulfate, and concentrated under reduced pressure. The residue was purified by silica gel column chromatography (hexane:ethyl acetate=1:1 to ethyl acetate) to give 5.72 g of Compound (I-3-1) as solid (yield: 54%).

$^1$H NMR ($CDCl_3$): δ ppm: 1.10 (6H, t, J=7.6 Hz), 2.26-2.41 (4H, m), 2.36 (3H, s), 3.86 (3H, s), 3.90 (3H, s), 7.02 (2H, s).

The present compounds produced according to Production Example 3 and Compound (I-3-1) are shown in Table 3.

TABLE 3

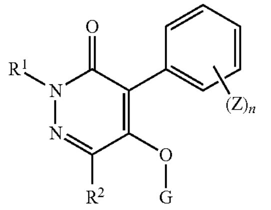

| No. | $R^1$ | $R^2$ | $(Z)_n$ | G | $^1$H NMR |
|---|---|---|---|---|---|
| (I-3-1) | Me | $S(O)_2Me$ | 2, 6-$Et_2$-4-Me | H | 1) |
| (I-3-2) | Me | $S(O)_2Me$ | 2,4, 6-$Et_3$ | H | 2) |
| (I-3-3) | Me | $S(O)_2Me$ | 2-Et-4, 6-$Me_2$ | H | 3) |
| (I-3-4) | Me | $S(O)_2Me$ | 2, 6-$Et_2$-4-Me | Bn | 4) |

1) $^1$H NMR: described in the above Production Example.

2) $^1$H NMR ($CDCl_3$): δ ppm: 1.10 (6H, t, J = 7.7 Hz), 1.27 (3H, t, J = 7.6 Hz), 2.24-2.43 (4H, m), 2.66 (2H, q, J = 7.7 Hz), 3.36 (3H, s), 3.90 (3H, s), 7.03 (2H, s).

3) $^1$H NMR ($CDCl_3$): δ ppm: 1.10 (3H, t, J = 7.6 Hz), 2.07 (3H, s), 2.26-2.43 (2H, m), 2.33 (3H, s), 3.36 (3H, s), 3.90 (3H, s), 6.98 (1H, s). 7.00 (1H, s), 8.37 (1H, brs).

4) $^1$H NMR ($CDCl_3$): δ ppm: 1.14 (6H, t, J = 7.6 Hz), 2.30-2.48 (7H, m), 3.20 (3H, s), 3.88 (3H, s), 4.58 (2H, s), 7.03 (2H, s), 7.05-7.09 (2H, m), 7.25-7.30 (3H, m).

TABLE 4

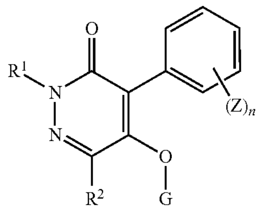

| No. | $R^1$ | $R^2$ | $(Z)_n$ | G | $^1$H NMR |
|---|---|---|---|---|---|
| (I-4-1) | Me | OMe | 2, 6-$Et_2$-4-Me | H | 1) |
| (I-4-2) | Me | OMe | 2, 4, 6-$Et_3$ | H | 2) |
| (I-4-3) | Me | OEt | 2, 6-$Et_2$-4-Me | H | 3) |
| (I-4-4) | Me | OEt | 2,4, 6-$Et_3$ | H | 4) |
| (I-4-5) | Me | OMe | 2-Et-4, 6-$Me_2$ | H | 5) |
| (I-4-6) | Me | OEt | 2-Et-4, 6-$Me_2$ | H | 6) |

1) $^1$H NMR: described in the above Production Example.

2) $^1$H NMR ($CDCl_3$): δ ppm: 1.09 (6H, t, J = 7.6 Hz), 1.26 (3H, t, J = 7.6 Hz), 2.28-2.47 (4H, m), 2.66 (2H, q, J = 7.6 Hz), 3.70 (3H, s), 3.99 (3H, s), 5.62 (1H, brs), 7.02 (2H, s).

3) $^1$H NMR ($CDCl_3$): δ ppm: 1.09 (6H, t, J = 7.6 Hz), 1.48 (3H, t, J = 7.1 Hz), 2.27-2.46 (4H, m), 2.35 (3H, s), 3.68 (3H, s), 4.36 (2H, q, J = 7.1 Hz), 5.67 (1H, brs), 7.00 (2H, s).

4) $^1$H NMR ($CDCl_3$): δ ppm: 1.10 (6H, t, J = 7.5 Hz), 1.27 (3H, t, J = 7.6 Hz), 1.48 (3H, t, J = 7.0 Hz), 2.28-2.47 (4H, m), 2.66 (2H, q, J = 7.6 Hz), 3.68 (3H, s), 4.36 (2H, q, J = 7.0 Hz), 5.67 (1H, brs), 7.02 (2H, s).

5) $^1$H NMR ($CDCl_3$): δ ppm: 1.09 (3H, t, J = 7.5 Hz), 2.07 (3H, s), 2.29-2.47 (2H, m), 2.33 (3H, s), 3.69 (3H, s), 3.99 (3H, s), 5.61 (1H, s), 6.97 (1H, s). 6.99 (1H, s).

6) $^1$H NMR ($CDCl_3$): δ ppm: 1.09 (3H, t, J = 7.7 Hz), 1.47 (3H, t, J = 7.1 Hz), 2.28-2.48 (2H, m), 2.07 (3H, s), 2.33 (3H, s), 3.68 (3H, s), 4.36 (2H, q, J = 7.1 Hz), 5.66 (1H, s), 6.96 (1H, s). 6.98 (1H, s).

Production Example 4

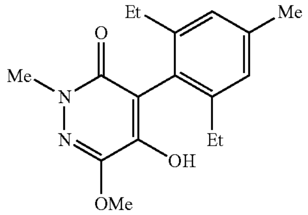

Production of 4-(2,6-diethyl-4-methylphenyl)-5-hydroxy-6-methoxy-2-methyl-3(2H)-pyridazinone (Compound (I-4-1))

To a solution of Compound (I-3-1) (5.34 g, 15.2 mmol) in dry DMF (130 ml) was added sodium methoxide (9.71 g, 180 mmol). The mixture was stirred at 105° C. for 20 minutes. After the reaction mixture was cooled to room temperature, 1N hydrochloric acid (300 ml) was added, and extracted with ethyl acetate 2 times. The combined organic layer was washed with water 2 times, saturated brine, dried over anhydrous magnesium sulfate, and concentrated under reduced pressure. The residue was purified by silica gel column chromatography (hexane:ethyl acetate=1:1 to 1:2 to ethyl acetate) to give 4.30 g of Compound (I-4-1) (yield: 93%).

$^1$H NMR ($CDCl_3$): δ ppm: 1.09 (6H, t, J=7.6 Hz), 2.27-2.46 (4H, m), 2.35 (3H, s), 3.70 (3H, s), 3.99 (3H, s), 5.62 (1H, brs), 7.00 (2H, s).

The present compounds produced according to Production Example 4 and Compound (I-4-1) are shown in Table 4.

Production Example 5

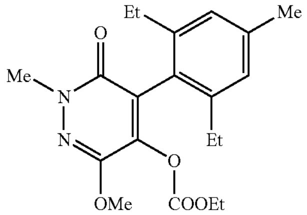 [SMILES: CCOC(=O)Oc1c(OC)nn(C)c(=O)c1-c1c(CC)cc(C)cc1CC]

Production of 4-(2,6-diethyl-4-methylphenyl)-5-ethoxycarbonyloxy-6-methoxy-2-methyl-3(2H)-pyridazinone (Compound (I-5-5))

To a solution of Compound (I-4-1) (0.201 g, 0.66 mmol) and triethylamine (0.106 g, 1.05 mmol) in THF (1.5 ml) was added a solution of ethyl chlorocarbonate (0.147 g, 1.35 mmol) in THF (1 ml) dropwise under ice-cooling. After ice-bath was removed, the mixture was stirred at room temperature for 16 hours. The reaction mixture was diluted with water (5 ml), and extracted with ethyl acetate 3 times. The combined organic layer was dried over anhydrous magnesium sulfate, and concentrated under reduced pressure. The residue was purified by silica gel column chromatography (hexane: ethyl acetate=3:2) to give 0.193 g of Compound (I-5-5) as solid.

$^1$H NMR ($CDCl_3$): δ ppm: 1.10 (6H, t, J=7.6 Hz), 1.24 (3H, t, J=7.1 Hz), 2.25-2.44 (4H, m), 2.34 (3H, s), 3.72 (3H, s), 3.92 (3H, s), 4.17 (2H, q, J=7.1 Hz), 6.96 (2H, s).

The present compounds produced according to Production Example 5 and Compound (I-5-5) are shown in Table 5.

TABLE 5

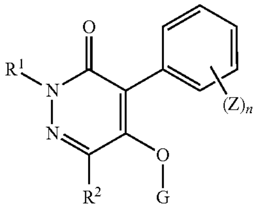

| No. | $R^1$ | $R^2$ | $(Z)_n$ | G | $^1$H NMR |
|---|---|---|---|---|---|
| (I-5-1) | Me | OMe | 2, 6-$Et_2$-4-Me | COMe | 1) |
| (I-5-2) | Me | OMe | 2, 6-$Et_2$-4-Me | COEt | 2) |
| (I-5-3) | Me | OMe | 2, 6-$Et_2$-4-Me | COt—Bu | 3) |
| (I-5-4) | Me | OMe | 2, 6-$Et_2$-4-Me | $CO_2Me$ | 4) |
| (I-5-5) | Me | OMe | 2, 6-$Et_2$-4-Me | $CO_2Et$ | 5) |
| (I-5-6) | Me | OMe | 2, 6-$Et_2$-4-Me | $CO_2CH_2CH{=}CH_2$ | 6) |
| (I-5-7) | Me | OMe | 2, 6-$Et_2$-4-Me | $CO_2Ph$ | 7) |
| (I-5-8) | Me | OMe | 2, 6-$Et_2$-4-Me | $SO_2Me$ | 8) |
| (I-5-9) | Me | OMe | 2-Br-4, 6-$Me_2$ | $CO_2Me$ | 9) |

1) $^1$H NMR ($CDCl_3$): δ ppm: 1.10 (6H, t, J = 7.6 Hz), 2.03 (3H, s), 2.24-2.43 (4H, m), 2.34 (3H, s), 3.72 (3H, s), 3.90 (3H, s), 6.95 (2H, s).
2) $^1$H NMR ($CDCl_3$): δ ppm: 0.95 (3H, t, J = 7.6 Hz), 1.09 (6H, t, J = 7.6 Hz), 2.23-2.43 (6H, m), 2.33 (3H, s), 3.72 (3H, s), 3.89 (3H, s), 6.94 (2H, s).
3) $^1$H NMR ($CDCl_3$): δ ppm: 0.90 (9H, s), 1.09 (6H, t, J = 7.6 Hz), 2.21-2.46 (4H, m), 2.29 (3H, s), 3.69 (3H, s), 3.97 (3H, s), 6.92 (2H, s).
4) $^1$H NMR ($CDCl_3$): δ ppm: 1.10 (6H, t, J = 7.6 Hz), 2.24-2.44 (4H, m), 2.34 (3H, s), 3.73 (3H, s), 3.76 (3H, s), 3.92 (3H, s), 6.96 (2H, s).
5) $^1$H NMR: described in the above Production Example.
6) $^1$H NMR ($CDCl_3$): δ ppm: 1.10 (6H, t, J = 7.6 Hz), 2.24-2.43 (4H, m), 2.34 (3H, s), 3.73 (3H, s), 3.91 (3H, s), 4.57-4.60 (2H, m), 5.17-5.30 (2H, m), 5.75-5.87 (1H, m), 6.95 (2H, s).
7) $^1$H NMR ($CDCl_3$): δ ppm: 1.11 (6H, t, J = 7.5 Hz), 2.28-2.46 (4H, m), 2.37 (3H, s), 3.74 (3H, s), 3.97 (3H, s), 6.96-7.05 (2H, m), 7.00 (2H, s), 7.21-7.29 (1H, m), 7.31-7.39 (2H, m).
8) $^1$H NMR ($CDCl_3$): δ ppm: 1.15 (6H, t, J = 7.6 Hz), 2.34 (3H, s), 2.39 (4H, q, J = 7.6 Hz), 2.54 (3H, s), 3.74 (3H, s), 3.98 (3H, s), 7.00 (2H, s).
9) $^1$H NMR ($CDCl_3$): δ ppm: 2.12 (3H, s), 2.31 (3H, s), 3.74 (3H, s), 3.80 (3H, s), 3.93 (3H, s), 7.01 (1H, s), 7.30 (1H, s).

Production Example 6

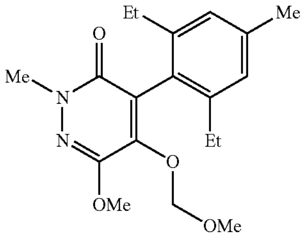 [SMILES: CCc1cc(C)cc(CC)c1-c1c(OCOC)c(OC)nn(C)c1=O]

Production of 4-(2,6-diethyl-4-methylphenyl)-6-methoxy-5-methoxymethoxy-2-methyl-3(2H)-pyridazinone (Compound (I-6-1))

To a mixture of 60% sodium hydride (0.070 g, 1.60 mmol) and dry DMF (0.5 ml) was added a solution of Compound (I-4-1) (0.201 g, 0.66 mmol) in DMF (2 ml) dropwise under ice-cooling. The mixture was stirred for 6 minutes under ice-cooling, and then a solution of chloromethyl methyl ether (0.122 g, 1.52 mmol) in DMF (0.5 ml) was added dropwise. The reaction solution was stirred at room temperature for 2 hours. The reaction mixture was diluted with water, and extracted with ethyl acetate 3 times. The combined organic layer was washed with water, then saturated brine, dried over anhydrous magnesium sulfate, and concentrated under reduced pressure. The residue was purified by silica gel column chromatography (hexane:ethyl acetate=2:1) to give 0.168 g of Compound (I-6-1) as solid.

$^1$H NMR ($CDCl_3$): δ ppm: 1.13 (6H, t, J=7.6 Hz), 2.28-2.50 (4H, m), 2.34 (3H, s), 3.03 (3H, s), 3.69 (3H, s), 3.92 (3H, s), 4.84 (2H, s), 6.95 (2H, s).

The present compounds produced according to Production Example 6 and Compound (I-6-1) are shown in Table 6.

TABLE 6

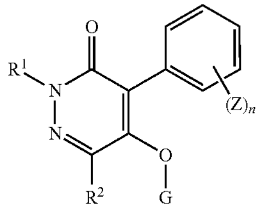

| No. | $R^1$ | $R^2$ | $(Z)_n$ | G | $^1$H NMR |
|---|---|---|---|---|---|
| (I-6-1) | Me | OMe | 2, 6-$Et_2$-4-Me | $CH_2OMe$ | 1) |
| (I-6-2) | Me | OMe | 2, 6-$Et_2$-4-Me | $CH_2OEt$ | 2) |

1) $^1$H NMR: described in the above Production Example.

2) $^1$H NMR ($CDCl_3$): δ ppm: 1.00 (3H, t, J = 7.1 Hz), 1.13 (6H, t, J = 7.6 Hz), 2.29-2.47 (4H, m), 2.34 (3H, s), 3.26 (2H, q, J = 7.1 Hz), 3.69 (3H, s), 3.91 (3H, s), 4.86 (2H, s), 6.95 (2H, s).

Production Example 7

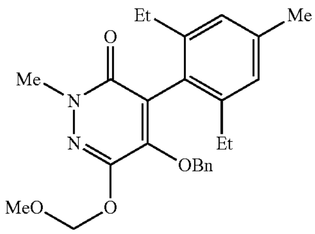 [SMILES: CCc1cc(C)cc(CC)c1-c1c(OCc2ccccc2)c(OCOC)nn(C)c1=O]

Production of 4-(2,6-diethyl-4-methylphenyl)-6-methoxymethoxy-5-benzyloxy-2-methyl-3(2H)-pyridazinone (Compound (I-7-1))

To a solution of 4-(2,6-diethyl-4-methylphenyl)-6-hydroxy-5-benzyloxy-2-methyl-3(2H)-pyridazinone (120 mg, 0.317 mmol) in dry DMF (2 ml) was added 60% sodium hydride (20 mg, 0.50 mmol) at 5° C. under nitrogen atmosphere. The mixture was stirred for 5 minutes, and then 80% chloromethyl methyl ether (0.04 ml, 0.47 mmol) was added. After ice-bath was removed, the mixture was stirred at room temperature for further 30 minutes. The reaction solution was diluted with water, and extracted with ethyl acetate 2 times. The combined organic layer was washed with water 2 times, washed with saturated brine, dried over anhydrous magnesium sulfate, and concentrated under reduced pressure to give 115 mg of Compound (I-7-1) as oil (yield: 85%).

$^1$H NMR ($CDCl_3$): δ ppm: 1.10 (6H, t, J=7.5 Hz), 2.22-2.48 (7H, m), 3.57 (3H, s), 3.68 (3H, s), 4.78 (2H, s), 5.46 (2H, s), 6.97 (2H, s), 6.99-7.04 (2H, m), 7.20-7.25 (3H, m).

The present compounds produced according to Production Example 7 and Compound (I-7-1) are shown in Table 7.

TABLE 7

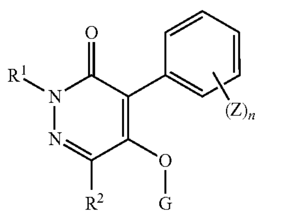

| No. | $R^1$ | $R^2$ | $(Z)_n$ | G | $^1H$ NMR |
|---|---|---|---|---|---|
| (I-7-1) | Me | $OCH_2OMe$ | 2, 6-$Et_2$-4-Me | Bn | 1) |
| (I-7-2) | Me | $OCH_2CH{=}CH_2$ | 2, 6-$Et_2$-4-Me | $CH_2$(4-OMe-Ph) | 2) |
| (I-7-3) | Me | $OCH_2C{\equiv}CH$ | 2, 6-$Et_2$-4-Me | $CH_2$(4-OMe-Ph) | 3) |
| (I-7-4) | Me | $OCH_2CN$ | 2, 6-$Et_2$-4-Me | $CH_2$(4-OMe-Ph) | 4) |

1) $^1H$ NMR: described in the above Production Example.

2) $^1H$ NMR ($CDCl_3$): δ ppm: 1.09 (6H, t, J = 7.6 Hz), 2.21-2.32 (2H, m), 2.34-2.46 (5H, m), 3.67 (3H, s), 3.77 (3H, s), 4.72 (2H, s), 4.76 (2H, d, J = 5.6 Hz), 5.32 (1H, d, J = 10.4 Hz), 5.45 (1H, d, J = 17.1 Hz), 6.04-6.18 (1H, m), 6.74 (2H, d, J = 8.5 Hz), 6.92 (2H, d, J = 8.5 Hz), 6.97 (2H, s).

3) $^1H$ NMR ($CDCl_3$): δ ppm: 1.09 (6H, t, J = 7.6 Hz), 2.19-2.31 (2H, m), 2.33-2.44 (5H, m), 2.56 (1H, t, J = 2.4 Hz), 3.68 (3H, s), 3.77 (3H, s), 4.73 (2H, s), 4.90 (2H, d, J = 2.4 Hz), 6.75 (2H, d, J = 8.5 Hz), 6.95 (2H, d, J = 8.5 Hz), 6.97 (2H, s).

4) $^1H$ NMR ($CDCl_3$): δ ppm: 1.12 (6H, t, J = 7.5 Hz), 2.24-2.47 (7H, m), 3.70 (3H, s), 3.77 (3H, s), 4.60 (2H, s), 4.92 (2H, s), 6.78 (2H, d, J = 8.5 Hz), 6.94 (2H, d, J = 8.7 Hz), 6.99 (2H, s).

Production Example 8

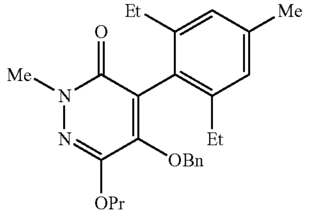

Production of 4-(2,6-diethyl-4-methylphenyl)-6-methoxy-5-benzyloxy-2-methyl-3(2H)-pyridazinone (Compound (I-8-1))

To a solution of 4-(2,6-diethyl-4-methylphenyl)-6-hydroxy-5-benzyloxy-2-methyl-3(2H)-pyridazinone (500 mg, 2.35 mmol) in acetone (10 ml) was added iodopropane (443 mg, 2.59 mmol) and cesium carbonate (920 mg, 2.59 mmol), and stirred under reflux for 2.5 hours. The reaction mixture was filtered, and then the filtrate was concentrated under reduced pressure. The residue was purified by silica gel column chromatography (hexane:ethyl acetate=2:1) to give 643 mg of Compound (I-8-1) (yield: 70%).

$^1H$ NMR ($CDCl_3$): δ ppm: 1.06 (3H, t, J=7.2 Hz), 1.09 (6H, t, J=7.6 Hz), 1.80-1.90 (2H, m), 2.22-2.33 (2H, m), 2.34-2.45 (5H, m), 3.68 (3H, s), 4.20 (2H, t, J=6.6 Hz), 4.80 (2H, s), 6.96 (2H, s), 6.98-7.01 (2H, m), 7.19-7.24 (3H, m).

The present compounds produced according to Production Example 8 and Compound (I-8-1) are shown in Table 8.

TABLE 8

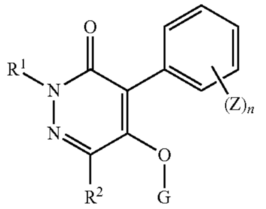

| No. | $R^1$ | $R^2$ | $(Z)_n$ | G | $^1H$ NMR |
|---|---|---|---|---|---|
| (I-8-1) | Me | OPr | 2, 6-$Et_2$-4-Me | Bn | 1) |
| (I-8-2) | Me | OBu | 2, 6-$Et_2$-4-Me | Bn | 2) |
| (I-8-3) | Me | Oi—Pr | 2, 6-$Et_2$-4-Me | Bn | 3) |
| (I-8-4) | Me | $OCH_2$c—Pr | 2, 6-$Et_2$-4-Me | Bn | 4) |
| (I-8-5) | Me | $OCH_2CHF_2$ | 2, 6-$Et_2$-4-Me | Bn | 5) |
| (I-8-6) | Me | $OCH_2CF_3$ | 2, 6-$Et_2$-4-Me | Bn | 6) |
| (I-8-7) | Me | $OCH_2COOMe$ | 2, 6-$Et_2$-4-Me | Bn | 7) |
| (I-8-8) | Me | $OCH_2SMe$ | 2, 6-$Et_2$-4-Me | Bn | 8) |
| (I-8-9) | Me | $OCH_2CH_2SMe$ | 2, 6-$Et_2$-4-Me | Bn | 9) |

1) $^1H$ NMR: described in the above Production Example.

2) $^1H$ NMR ($CDCl_3$): δ ppm: 0.99 (3H, t, J = 7.5 Hz), 1.09 (6H, t, J = 7.6 Hz), 1.44-1.55 (2H, m), 1.75-1.84 (2H, m), 2.22-2.32 (2H, m), 2.34-2.45 (5H, m), 3.68 (3H, s), 4.23 (2H, t, J = 6.6 Hz), 4.79 (2H, s), 6.96 (2H, s), 6.97-7.01 (2H, m), 7.19-7.24 (3H, m).

3) $^1H$ NMR ($CDCl_3$): δ ppm: 1.09 (6H, t, J = 7.5 Hz), 1.41 (6H, d, J = 6.1 Hz), 2.22-2.32 (2H, m), 2.34-2.45 (2H, m), 2.37 (3H, s), 3.67 (3H, s), 4.79 (2H, s), 5.07-5.14 (1H, m), 6.96 (2H, s), 6.97-7.01 (2H, m), 7.19-7.23 (3H, m).

4) $^1H$ NMR ($CDCl_3$): δ ppm: 0.37-0.42 (2H, m) , 0.63-0.69 (2H, m), 1.09 (6H, t, J = 7.6 Hz), 1.29-1.36 (1H, m), 2.22-2.32 (2H, m), 2.34-2.45 (2H, m), 2.37 (3H, s), 3.66 (3H, s), 4.08 (2H, d, J = 7.1 Hz), 4.84 (2H, s), 6.96 (2H, s), 7.02-7.06 (2H, m), 7.20-7.25 (3H, m).

5) $^1H$ NMR ($CDCl_3$): δ ppm: 1.10 (6H, t, J = 7.6 Hz), 2.22-2.33 (2H, m), 2.34-2.44 (2H, m), 2.38 (3H, s), 3.68 (3H, s), 4.45 (2H, td, J = 13.3, 4.2 Hz), 4.75 (2H, s), 6.14 (1H, tt, J = 55.2, 4.2 Hz), 6.97 (2H, s), 6.98-7.02 (2H, m), 7.21-7.25 (3H, m).

6) $^1H$ NMR ($CDCl_3$): δ ppm: 1.09 (6H, t, J = 7.6 Hz), 2.21-2.44 (7H, m), 3.68 (3H, s), 4.65 (2H, q, J = 8.3 Hz), 4.76 (2H, s), 6.96-7.02 (4H, m), 7.20-7.25 (3H, m).

7) $^1H$ NMR ($CDCl_3$): δ ppm: 1.08 (6H, t, J = 7.6 Hz), 2.19-2.31 (2H, m), 2.32-2.43 (2H, m), 2.37 (3H, s), 3.63 (3H, s), 3.84 (3H, s), 4.86 (4H, s), 6.96 (2H, s), 7.00-7.05 (2H, m), 7.20-7.24 (3H, m).

8) $^1H$ NMR ($CDCl_3$): δ ppm: 1.09 (6H, t, J = 7.5 Hz), 2.22-2.45 (10H, m), 3.69 (3H, s), 4.77 (2H, s), 5.39 (2H, s), 6.96 (2H, s), 6.99-7.03 (2H, m), 7.20-7.24 (3H, m).

9) $^1H$ NMR ($CDCl_3$): δ ppm: 1.10 (6H, t, J = 7.6 Hz), 2.19 (3H, s), 2.23-2.33 (2H, m), 2.35-2.46 (5H, m), 2.90 (2H, t, J = 6.7 Hz), 3.67 (3H, s), 4.42 (2H, t, J = 6.7 Hz), 4.78 (2H, s), 6.96 (2H, s), 6.99-7.02 (2H, m), 7.20-7.24 (3H, m).

Production Example 9

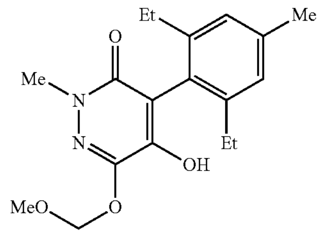 [SMILES: CCc1cc(C)cc(CC)c1-c1c(O)c(OCOC)nn(C)c1=O]

Production of 4-(2,6-diethyl-4-methylphenyl)-6-methoxymethoxy-5-hydroxy-2-methyl-3(2H)-pyridazinone (Compound (I-9-1))

A mixture of Compound (I-7-1) (110 mg, 0.26 mmol), 10% palladium-carbon (20 mg), and ethyl acetate (15 ml) was stirred under ambient-pressure hydrogen atmosphere at ° C. for 1 hour. The reaction mixture was filtered through Celite, and then the filtrate was concentrated under reduced pressure to give 70 mg of Compound (I-9-1) (yield: 80%).

$^1H$ NMR ($CDCl_3$): δ ppm: 1.08 (6H, t, J=7.6 Hz), 2.25-2.45 (7H, m), 3.59 (3H, s), 3.68 (3H, s), 5.48 (2H, s), 5.91 (1H, br s), 7.00 (2H, s).

The present compounds produced according to Production Example 9 and Compound (I-9-1) are shown in Table 9.

TABLE 9

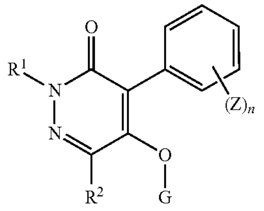

| No. | $R^1$ | $R^2$ | $(Z)_n$ | G | $^1$H NMR |
|---|---|---|---|---|---|
| (I-9-1) | Me | $OCH_2OMe$ | 2,6-$Et_2$-4-Me | H | 1) |
| (I-9-2) | Me | OPr | 2,6-$Et_2$-4-Me | H | 2) |
| (I-9-3) | Me | OBu | 2,6-$Et_2$-4-Me | H | 3) |
| (I-9-4) | Me | Oi—Pr | 2,6-$Et_2$-4-Me | H | 4) |
| (I-9-5) | Me | $OCH_2$c—Pr | 2,6-$Et_2$-4-Me | H | 5) |
| (I-9-6) | Me | $OCH_2CHF_2$ | 2,6-$Et_2$-4-Me | H | 6) |
| (I-9-7) | Me | $OCH_2CF_3$ | 2,6-$Et_2$-4-Me | H | 7) |
| (I-9-8) | Me | $OCH_2COOMe$ | 2,6-$Et_2$-4-Me | H | 8) |
| (I-9-9) | Me | $OCH_2CONH_2$ | 2,6-$Et_2$-4-Me | H | 9) |
| (1-9-10) | Me | $OCH_2CONMe_2$ | 2,6-$Et_2$-4-Me | H | 10) |

1) $^1$H NMR: described in the above Production Example.

2) $^1$H NMR ($CDCl_3$): δ ppm: 1.05 (3H, t, J = 7.0 Hz), 1.09 (6H, t, J = 7.6 Hz), 1.82-1.93 (2H, m), 2.27-2.46 (7H, m), 3.67 (3H, s), 4.25 (2H, t, J = 7.0 Hz), 5.66 (1H, br s), 7.00 (2H, s).

3) $^1$H NMR ($CDCl_3$): δ ppm: 1.00 (3H, t, J = 7.5 Hz), 1.09 (6H, t, J = 7.6 Hz), 1.44-1.55 (2H, m), 1.78-1.87 (2H, m), 2.27-2.46 (7H, m), 3.67 (3H, s), 4.29 (2H, t, J = 6.8 Hz), 5.67 (1H, br s), 6.99 (2H, s).

4) $^1$H NMR ($CDCl_3$): δ ppm: 1.09 (6H, t, J = 7.6 Hz), 1.43 (6H, d, J = 6.1 Hz), 2.27-2.45 (7H, m), 3.67 (3H, s), 5.11-5.22 (1H, m), 5.71 (1H, br s), 6.99 (2H, s).

5) $^1$H NMR ($CDCl_3$): δ ppm: 0.37-0.43 (2H, m), 0.64-0.72 (2H, m), 1.09 (6H, t, J = 7.6 Hz), 1.27-1.38 (1H, m), 2.28-2.46 (7H, m), 3.66 (3H, s), 4.11 (2H, d, J = 7.3 Hz), 5.77 (1H, br s), 7.00 (2H, s).

6) $^1$H NMR ($CDCl_3$): δ ppm: 1.09 (6H, t, J = 7.6 Hz), 2.26-2.45 (7H, m), 3.68 (3H, s), 4.50 (2H, td, J = 13.2, 4.2 Hz), 6.19 (1H, tt, J = 54.9, 4.2 Hz), 7.02 (2H, s).

7) $^1$H NMR ($CDCl_3$): δ ppm: 1.09 (6H, t, J = 7.6 Hz), 2.26-2.45 (7H, m), 3.68 (3H, s), 4.68 (2H, q, J = 8.3 Hz), 5.71 (1H, br s), 7.02 (2H, s).

8) $^1$H NMR ($CDCl_3$): δ ppm: 1.09 (6H, t, J = 7.6 Hz), 2.27-2.46 (7H, m), 3.65 (3H, s), 3.85 (3H, s), 4.87 (2H, s), 7.00 (2H, s).

9) $^1$H NMR ($CDCl_3$): δ ppm: 1.08 (6H, t, J = 7.6 Hz), 2.26-2.42 (7H, m), 3.67 (3H, s), 4.76 (2H, s), 5.43 (2H, br s), 6.52 (1H, br s), 7.02 (2H, s).

10) $^1$H NMR ($CDCl_3$): δ ppm: 1.07 (6H, t, J = 7.6 Hz), 2.26-2.44 (7H, m), 3.01 (3H, s), 3.05 (3H, s), 3.65 (3H, s), 4.87 (2H, s), 6.95 (2H, s).

Production Example 10

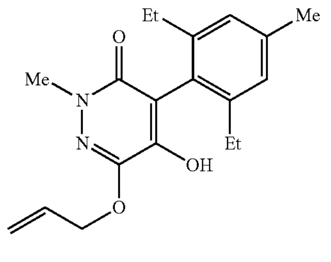 [SMILES: C=CCOc1nn(C)c(=O)c(-c2c(CC)cc(C)cc2CC)c1O]

Production of 4-(2,6-diethyl-4-methylphenyl)-6-allyloxy-5-hydroxy-2-methyl-3(2H)-pyridazinone (Compound (I-10-1))

To a solution of Compound (I-7-2) (240 mg, 0.53 mmol) in the mixed solvent of acetonitrile: water=4:1 (6 ml) was added ammonium cerium(IV) nitrate (740 mg, 1.28 mmol) under ice-cooling. After ice-bath was removed, the mixture was stirred overnight. The reaction solution was diluted with water, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=3:1) to give 107 mg of Compound (I-10-1) (yield: 61%) as yellow solid.

$^1$H NMR ($CDCl_3$): δ ppm: 1.09 (6H, t, J=7.5 Hz), 2.26-2.46 (7H, m), 3.68 (3H, s), 4.80 (2H, d, J=6.0 Hz), 5.36 (1H, d, J=10.4 Hz), 5.46 (1H, d, J=17.1 Hz), 5.84 (1H, br s), 6.06-6.18 (1H, m), 7.00 (2H, s).

The present compounds produced according to Production Example 10 and Compound (I-10-1) are shown in Table 10.

TABLE 10

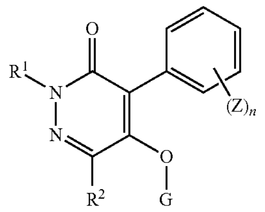

| No. | $R^1$ | $R^2$ | $(Z)_n$ | G | $^1$H NMR |
|---|---|---|---|---|---|
| (I-10-1) | Me | $OCH_2CH{=}CH_2$ | 2, 6-$Et_2$-4-Me | H | 1) |
| (I-10-2) | Me | $OCH_2C{\equiv}CH$ | 2, 6-$Et_2$-4-Me | H | 2) |
| (I-10-3) | Me | $OCH_2CN$ | 2, 6-$Et_2$-4-Me | H | 3) |

1) $^1$H NMR: described in the above Production Example.

2) $^1$H NMR ($CDCl_3$): δ ppm: 1.08 (6H, t, J = 7.6 Hz), 2.26-2.45 (7H, m), 2.59 (1H, t, J = 2.4 Hz), 3.69 (3H, s), 4.93 (2H, d, J = 2.4 Hz), 5.98 (1H, br s), 7.00 (2H, s).

3) $^1$H NMR ($CDCl_3$): δ ppm: 1.08 (6H, t, J = 7.6 Hz), 2.23-2.44 (7H, m), 3.70 (3H, s), 4.94 (2H, s), 6.07 (1H, br s), 7.02 (2H, s).

Production Example 11

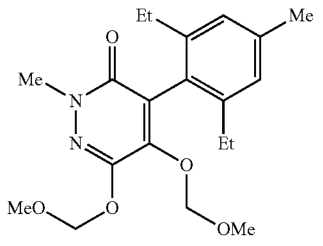 [SMILES: CCc1cc(C)cc(CC)c1-c1c(OCOC)c(OCOC)nn(C)c1=O]

Production of 4-(2,6-diethyl-4-methylphenyl)-5,6-bis(methoxymethoxy)-2-methyl-3(2H)-pyridazinone (Compound (I-11))

To a solution of 4-(2,6-diethyl-4-methylphenyl)-5,6-dihydroxy-2-methyl-3(2H)-pyridazinone (270 mg, 0.93 mmol) in dry DMF (3 ml) was added 60% sodium hydride (110 mg, 2.80 mmol) at 5° C. under nitrogen atmosphere. The mixture was stirred for 5 minutes, and then 80% chloromethyl methyl ether (0.27 ml, 2.8 mmol) was added. After ice-bath was removed, the mixture was stirred at room temperature for 30 minutes. The reaction solution was diluted with water, and extracted with ethyl acetate 2 times. The combined organic layer was washed with water 2 times, washed with saturated brine, dried over anhydrous magnesium sulfate, and concentrated under reduced pressure. The residue was purified by silica gel column chromatography (hexane:ethyl acetate=2:1) to give 20 mg of Compound (I-11) (yield: 5%) and 128 mg of Compound (I-9-1) as colorless solid (yield: 41%).

$^1$H NMR ($CDCl_3$): δ ppm: 1.13 (6H, t, J=7.6 Hz), 2.34 (7H, s), 3.04 (3H, s), 3.58 (3H, s), 3.68 (3H, s), 4.88 (2H, s), 5.45 (2H, s), 6.96 (2H, s).

Production Example 12

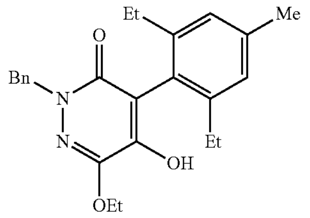 [SMILES: CCOc1nn(Cc2ccccc2)c(=O)c(-c2c(CC)cc(C)cc2CC)c1O]

Production of 4-(2,6-diethyl-4-methylphenyl)-6-ethoxy-5-hydroxy-2-benzyl-3(2H)-pyridazinone (Compound (I-12-1))

To a solution of potassium t-butoxide (12.4 g, 110 mmol) in dry THF (80 ml) was added a solution of ethyl 2-[2-(2,6-diethyl-4-methylphenyl)acetyl-2-benzylhydrazono]-2-(dodecylthio)acetate (16.4 g, 27.6 mmol) in dry THF (20 ml) dropwise at room temperature over 20 minutes. After being stirred for 10 minutes at room temperature, 1N hydrochloric acid (200 ml) was added, and extracted with tert-butyl methyl ether 2 times. The combined organic layer was washed with saturated brine, dried over anhydrous magnesium sulfate, and concentrated under reduced pressure. The residue was purified by silica gel column chromatography (hexane:ethyl acetate=2:1) to give 1.48 g of Compound (I-12-1) (yield: 13%) as solid and 2.71 g of 4-(2,6-diethyl-4-methylphenyl)-6-dodecylthio-5-hydroxy-2-benzyl-3(2H)-pyridazinone and Compound (I-12-1-B) (yield: 17%) as oil.

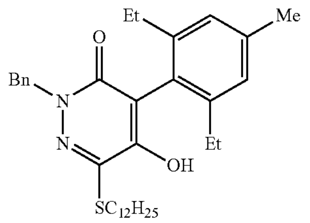

Compound (I-12-1): $^1$H NMR ($CDCl_3$): δ ppm: 1.05 (6H, t, J=7.6 Hz), 1.43 (3H, t, J=7.1 Hz), 2.24-2.43 (7H, m), 4.32 (2H, q, J=7.1 Hz), 5.22 (2H, s), 6.98 (2H, s), 7.23-7.34 (3H, m), 7.38-7.43 (2H, m).

Compound (I-12-1-B): $^1$H NMR ($CDCl_3$) δ ppm: 0.88 (3H, t, J=6.8 Hz), 1.03 (6H, t, J=7.5 Hz), 1.23-1.34 (16H, m), 1.37-1.47 (2H, m), 1.62-1.73 (2H, m), 2.22-2.39 (7H, m), 3.01 (2H, t, J=7.5 Hz), 5.32 (2H, s), 6.90 (1H, s), 7.00 (2H, s), 7.24-7.34 (3H, m), 7.37-7.42 (2H, m).

The present compounds produced according to Production Example 12 and Compound (I-12-1) are shown in Table 12.

TABLE 12

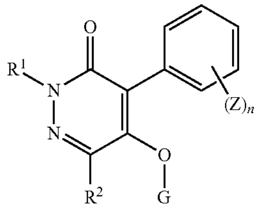

| No. | $R^1$ | $R^2$ | $(Z)_n$ | G | $^1$H NMR |
|---|---|---|---|---|---|
| (I-12-1) | Bn | OEt | 2, 6-$Et_2$-4-Me | H | 1) |
| (I-12-2) | Me | OEt | 2-Br-4, 6-$Me_2$ | H | 2) |
| (I-12-3) | $CH_2$c—Pr | OEt | 2, 6-$Et_2$-4-Me | H | 3) |
| (I-12-4) | $CH_2CH{=}CH_2$ | OEt | 2, 6-$Et_2$-4-Me | H | 4) |
| (I-12-1-B) | Bn | $SC_{12}H_{25}$ | 2, 6-$Et_2$-4-Me | H | 5) |
| (I-12-2-B) | Me | $SC_{12}H_{25}$ | 2-Br-4, 6-$Me_2$ | H | 6) |
| (I-12-3-B) | $CH_2$c—Pr | $SC_{12}H_{25}$ | 2, 6-$Et_2$-4-Me | H | 7) |

1) $^1$H NMR: described in the above Production Example.
2) $^1$H NMR ($CDCl_3$): δ ppm: 1.47 (3H, t, J = 7.1 Hz), 2.14 (3H, s), 2.32 (3H, s), 3.68 (3H, s), 4.37 (2H, q, J = 7.1 Hz), 7.05 (1H, s), 7.34 (1H, s).
3) $^1$H NMR ($CDCl_3$): δ ppm: 0.36-0.44 (2H, m), 0.46-0.53 (2H, m), 1.09 (6H, t, J = 7.5 Hz), 1.26-1.35 (1H, m), 1.48 (3H, t, J = 7.1 Hz), 2.28-2.47 (7H, m), 3.93 (2H, d, J = 7.0 Hz), 4.38 (2H, q, J = 7.1 Hz), 5.66 (1H, br s), 6.99 (2H, s).
4) $^1$H NMR ($CDCl_3$): δ ppm: 1.09 (6H, t, J = 7.6 Hz), 1.46 (3H, t, J = 7.1 Hz), 2.27-2.46 (7H, m), 4.36 (2H, q, J = 7.1 Hz), 4.63-4.68 (2H, m), 5.15-5.24 (2H, m), 5.72 (1H, s), 5.93-6.05 (1H, m), 6.99 (2H, s).
5) $^1$H NMR: described in the above Production Example.
6) $^1$H NMR ($CDCl_3$): δ ppm: 0.88 (3H, t, J = 6.8 Hz), 1.22-1.38 (18H, m), 1.38-1.77 (2H, m), 2.13 (3H, s), 2.33 (3H, s), 3.04 (2H, t, J = 7.3 Hz), 3.81 (3H, s), 5.96 (1H, brs), 7.08 (1H, s), 7.37 (1H, s).
7) $^1$H NMR ($CDCl_3$): δ ppm: 0.38-0.46 (2H, m), 0.48-0.55 (2H, m), 0.88 (3H, t, J = 6.9 Hz), 1.08 (6H, t, J = 7.5 Hz), 1.16-1.38 (17H, m), 1.41-1.51 (2H, m), 1.70-1.81 (2H, m), 2.26-2.44 (7H, m), 3.07 (2H, t, J = 7.4 Hz), 4.04 (2H, d, J = 7.2 Hz), 5.51 (1H, br s), 7.02 (2H, s).

Production Example 13

The procedure was performed by the method similar to Production Example 4 using 4-(2,6-diethyl-4-methylphenyl)-6-dodecylsulfonyl-5-hydroxy-2-methyl-3(2H)-pyridazinone as a starting material to give 4-(2,6-diethyl-4-methylphenyl)-6-methoxy-5-hydroxy-2-benzyl-3(2H)-pyridazinone (Compound (I-13-1)).

The present compounds produced according to Production Example 13 are shown in Table 13.

TABLE 13

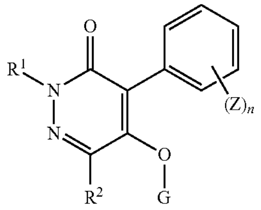

| No. | $R^1$ | $R^2$ | $(Z)_n$ | G | $^1$H NMR |
|---|---|---|---|---|---|
| (I-13-1) | Bn | OMe | 2, 6-$Et_2$-4-Me | H | 1) |
| (I-13-2) | Me | OMe | 2-Br-4, 6-$Me_2$ | H | 2) |
| (I-13-3) | $CH_2$c—Pr | OMe | 2, 6-$Et_2$-4-Me | H | 3) |
| (I-13-4) | Me | OMe | 2, 4, 6-$Me_3$ | H | 4) |
| (I-13-5) | Me | OMe | 2-$CF_3$-4-Cl | H | 5) |
| (I-13-6) | Me | OMe | 2-$OCF_3$ | H | 6) |

1) $^1$H NMR ($CDCl_3$): δ ppm: 1.05 (6H, t, J = 7.6 Hz), 2.23-2.42 (7H, m), 3.94 (3H, s), 5.24 (2H, s), 6.99 (2H, s), 7.24-7.34 (3H, m), 7.38-7.43 (2H, m).
2) $^1$H NMR ($CDCl_3$): δ ppm: 2.14 (3H, s), 2.32 (3H, s), 3.70 (3H, s), 3.99 (3H, s), 7.05 (1H, s), 7.34 (1H, s).
3) $^1$H NMR ($CDCl_3$): δ ppm: 0.39-0.45 (2H, m), 0.46-0.53 (2H, m), 1.09 (6H, t, J = 7.6 Hz), 1.26-1.37 (1H, m), 2.28-2.47 (7H, m), 3.95 (2H, d, J = 7.2 Hz), 4.00 (3H, s), 5.65 (1H, br s), 7.00 (2H, s).
4) $^1$H NMR ($CDCl_3$): δ ppm: 2.08 (6H, s), 2.30 (3H, s), 3.70 (3H, s), 3.99 (3H, s), 6.96 (2H, s).
5) $^1$H NMR ($CDCl_3$): δ ppm: 3.67 (3H, s), 3.99 (3H, s), 6.03 (1H, brs), 7.21 (1H, d, J = 8.4 Hz), 7.59 (1H, d, J = 8.4 Hz), 7.76 (1H, s).
6) $^1$H NMR ($CDCl_3$): δ ppm: 3.68 (3H, s), 3.99 (3H, s), 6.11 (1H, brs), 7.33-7.47 (4H, m).

Production Example 14

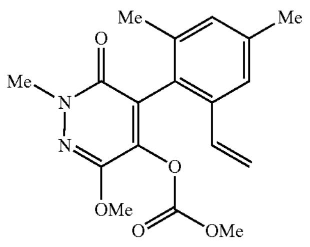 [SMILES: C=Cc1cc(C)cc(C)c1-c1c(OC(=O)OC)c(OC)nn(C)c1=O]

Production of 4-(2-vinyl-4,6-dimethylphenyl)-6-methoxy-5-methoxycarbonyloxy-2-methyl-3(2H)-pyridazinone (Compound (I-14))

To a solution of compound (I-5-9) (0.670 g, 1.69 mmol) and tributyl(vinyl)tin (0.656 g, 2.01 mmol) in toluene (25 ml) was added tetrakis(triphenylphosphine)palladium (0) (0.117 g, 0.101 mmol) under nitrogen atmosphere, and stirred at 95° C. for 5.5 hours. After the mixture was cooled to room temperature, the reaction solution was filtered through Celite. The filtrate was concentrated under reduced pressure. The residue was purified by silica gel column chromatography (hexane:ethyl acetate=2:1) to give 0.570 g of Compound (I-14) (yield: 98%).

$^1$H NMR ($CDCl_3$): δ ppm: 2.07 (3H, s), 2.34 (3H, s), 3.73 (3H, s), 3.75 (3H, s), 3.92 (3H, s), 5.14 (1H, dd, J=1.2, 11.0 Hz), 5.64 (1H, dd, J=1.2, 17.2 Hz), 6.42 (1H, dd, J=11.0, 17.2 Hz), 7.00 (1H, s), 7.27 (1H, s).

Production Example 15

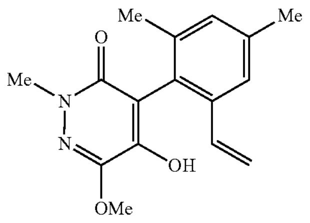 [SMILES: C=Cc1cc(C)cc(C)c1-c1c(O)c(OC)nn(C)c1=O]

Production of 4-(2-vinyl-4,6-dimethylphenyl)-6-methoxy-5-hydroxy-2-methyl-3(2H)-pyridazinone (Compound (I-15))

To a solution of Compound (I-14) (0.594 g, 1.69 mmol) in ethanol (12 ml) was added 1N aqueous sodium hydroxide solution (6 ml), and stirred at room temperature for 5 hours. The reaction solution was diluted with water (15 ml), and washed with t-butyl methyl ether. The aqueous layer was acidified with concentrated hydrochloric acid (1 ml), and extracted with chloroform 2 times. The combined organic layer was dried over anhydrous magnesium sulfate, and concentrated under reduced pressure. The residue was purified by silica gel column chromatography (hexane:ethyl acetate=30:70) to give 0.389 g of Compound (I-15) (yield: 71%) as colorless solid.

$^1$H NMR ($CDCl_3$): δ ppm: 2.09 (3H, s), 2.35 (3H, s), 3.70 (3H, s), 3.98 (3H, s), 5.15 (1H, dd, J=1.2, 11.0 Hz), 5.67 (1H, dd, J=1.2, 17.5 Hz), 5.71 (1H, brs), 6.45 (1H, dd, J=11.0, 17.5 Hz), 7.05 (1H, s), 7.32 (1H, s).

Production Example 16

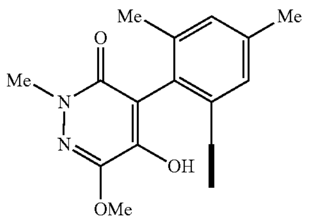

The procedure was performed by the method similar to Production Example 15 using 4-(2-trimethylsilylethynyl-4,6-dimethylphenyl)-6-methoxy-5-methoxycarbonyloxy-2-methyl-3(2H)-pyridazinone as a starting material to give 4-(2-ethynyl-4,6-dimethylphenyl)-6-methoxy-5-hydroxy-2-methyl-3(2H)-pyridazinone (Compound (I-16)) (yield: 68%).

$^1$H NMR ($CDCl_3$): δ ppm: 2.13 (3H, s), 2.32 (3H, s), 2.94 (1H, s), 3.70 (3H, s), 3.99 (3H, s), 5.88 (1H, brs), 7.12 (1H, s), 7.29 (1H, s).

Production Example 17

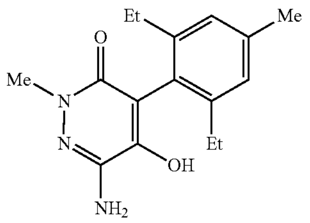

Production of 4-(2,6-diethyl-4-methylphenyl)-6-amino-5-hydroxy-2-methyl-3(2H)-pyridazinone (Compound (I-17))

To a solution of 4-(2,6-diethyl-4-methylphenyl)-6-bis(4-methoxybenzyl)amino-5-hydroxy-2-methyl-3(2H)-pyridazinone (10 g, 18.9 mmol) in methanol (250 ml) were added 10% palladium-carbon (824 mg) and concentrated hydrochloric acid (0.6 ml), and stirred under ambient-pressure hydrogen atmosphere at 35° C. for 4 hours. The reaction mixture was filtered through Celite, and then the filtrate was concentrated under reduced pressure. The resulting solid was washed with acetone (100 ml), and filtered to give 4.29 g of hydrochloride of Compound (I-17) (yield: 70%). The filtrate was concentrated, and the residue was purified by silica gel column chromatography to give 1.54 g of Compound (I-17) (yield: 28%) as solid.

$^1H$ NMR (DMSO-$d_6$) δ ppm: 0.96 (6H, t, J=7.6 Hz), 2.23 (4H, q, J=7.6 Hz), 2.28 (3H, s), 3.36 (3H, s), 5.31 (1H, br s), 6.86 (2H, s).

Production Example 18

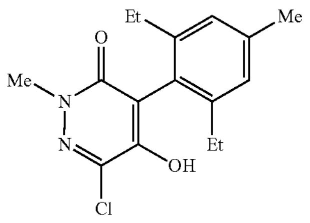 [SMILES: CCc1cc(C)cc(CC)c1-c1c(O)c(Cl)nn(C)c1=O]

Production of 4-(2,6-diethyl-4-methylphenyl)-6-chloro-5-hydroxy-2-methyl-3(2H)-pyridazinone (Compound (I-18))

Compound (I-17) (500 mg, 1.74 mmol) was dissolved in acetonitrile (3 ml), and then concentrated hydrochloric acid (2 ml) was added, and ice-cooled. To the solution was added sodium nitrite (323 mg, 4.68 mmol) portionwise. After the addition was complete, the mixture was stirred for 30 minutes. The reaction solution was diluted with water, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=3:1) to give 251 mg of Compound (I-18) (yield: 47%) as solid.

$^1H$ NMR ($CDCl_3$): δ ppm: 1.09 (6H, t, J=7.6 Hz), 2.24-2.43 (7H, m), 3.79 (3H, s), 5.72 (1H, s), 7.04 (2H, s).

Production Example 19

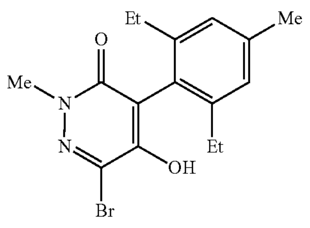 [SMILES: CCc1cc(C)cc(CC)c1-c1c(O)c(Br)nn(C)c1=O]

The procedure was performed by the method similar to Production Example 18 using 48% hydrobromic acid instead of concentrated hydrochloric acid as a starting material to give 4-(2,6-diethyl-4-methylphenyl)-6-bromo-5-hydroxy-2-methyl-3(2H)-pyridazinone (Compound (I-19)) (yield: 41%).

$^1H$ NMR ($CDCl_3$): δ ppm: 1.08 (6H, t, J=7.6 Hz), 2.24-2.42 (7H, m), 3.80 (3H, s), 5.64 (1H, s), 7.04 (2H, s).

Production Example 20

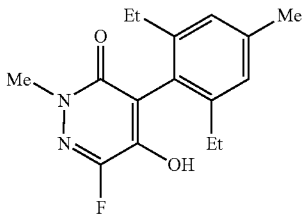 [SMILES: CCc1cc(C)cc(CC)c1-c1c(O)c(F)nn(C)c1=O]

Production of 4-(2,6-diethyl-4-methylphenyl)-6-fluoro-5-hydroxy-2-methyl-3(2H)-pyridazinone (Compound (I-20))

Compound (I-17) (500 mg, 1.74 mmol) was dissolved in 70% hydrogen fluoride-pyridine (3.5 ml), and cooled to −10° C. To the solution was added sodium nitrite (180 mg, 2.60 mmol) portionwise. After the addition was complete, the mixture was stirred for 10 minutes. To the reaction solution was diluted with water, and extracted with tert-butyl methyl ether 3 times. The combined organic layer was washed with saturated brine, dried over anhydrous magnesium sulfate, and concentrated under reduced pressure. The residue was purified by silica gel column chromatography (hexane:ethyl acetate=2:1) to give 387 mg of Compound (I-20) (yield: 76%) as solid.

$^1H$ NMR ($CDCl_3$): δ ppm: 1.09 (6H, t, J=7.6 Hz), 2.25-2.44 (7H, m), 3.70 (3H, s), 5.68 (1H, s), 7.04 (2H, s).

Production Example 21

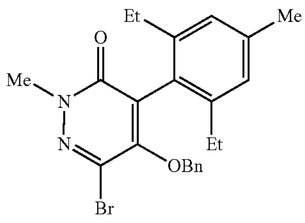 [SMILES: CCc1cc(C)cc(CC)c1-c1c(OCc2ccccc2)c(Br)nn(C)c1=O]

Production of 4-(2,6-diethyl-4-methylphenyl)-6-bromo-5-benzyloxy-2-methyl-3(2H)-pyridazinone (Compound (I-21-1))

To a solution of Compound (I-19) (953 mg, 2.71 mmol) in acetone (20 ml) was added benzyl bromide (510 mg, 2.98 mmol) and potassium carbonate (450 mg, 3.25 mmol), and refluxed for 2 hours. After cooling to room temperature, the mixture was filtered, and then the filtrate was concentrated under reduced pressure. The residue was purified by silica gel column chromatography (hexane:ethyl acetate=4:1) to give 980 mg of Compound (I-21) (yield: 81%) as solid.

$^1H$ NMR ($CDCl_3$): δ ppm: 1.13 (6H, t, J=7.6 Hz), 2.28-2.48 (7H, m), 3.79 (3H, s), 4.52 (2H, s), 7.00 (2H, s), 7.05-7.10 (2H, m), 7.25-7.31 (3H, m).

The present compounds produced according to Production Example 21 and Compound (I-21-1) are shown in Table 21.

TABLE 21

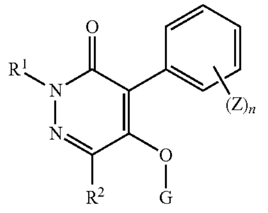

| No. | $R^1$ | $R^2$ | $(Z)_n$ | G | $^1$H NMR |
|---|---|---|---|---|---|
| (I-21-1) | Me | Br | 2, 6-$Et_2$-4-Me | Bn | 1) |
| (I-21-2) | Me | OMe | 2, 6-$Et_2$-4-Me | Bn | 2) |
| (I-21-3) | Me | OEt | 2, 6-$Et_2$-4-Me | Bn | 3) |
| (I-21-4) | Me | SMe | 2, 6-$Et_2$-4-Me | Bn | 4) |

1) $^1$H NMR: described in the above Production Example.

2) $^1$H NMR ($CDCl_3$): δ ppm: 1.09 (6H, t, J = 7.5 Hz), 2.22-2.47 (7H, m), 3.69 (3H, s), 3.93 (3H, s), 4.75 (2H, s), 6.95-7.02 (4H, m), 7.20-7.25 (3H, m).

3) $^1$H NMR ($CDCl_3$): δ ppm: 1.09 (6H, t, J = 7.6 Hz), 1.44 (3H, t, J = 7.1 Hz), 2.22-2.33 (2H, m), 2.34-2.45 (5H, m), 3.67 (3H, s), 4.30 (2H, q, J = 7.1 Hz), 4.79 (2H, s), 6.96 (2H, s), 6.98-7.02 (2H, m), 7.20-7.24 (3H, m).

4) $^1$H NMR ($CDCl_3$): δ ppm: 1.13 (6H, t, J = 7.6 Hz), 2.27-2.53 (10H, m), 3.78 (3H, s), 4.47 (2H, s), 6.98 (2H, s), 7.07-7.13 (2H, m), 7.24-7.31 (3H, m).

Production Example 22

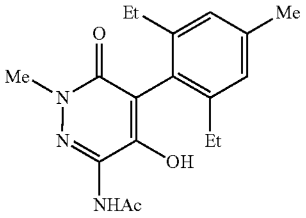 [SMILES: CCc1cc(C)cc(CC)c1-c1c(O)c(NC(C)=O)nn(C)c1=O]

Production of 4-(2,6-diethyl-4-methylphenyl)-6-acetamido-5-hydroxy-2-methyl-3(2H)-pyridazinone (Compound (I-22))

To a mixture of Compound (I-17) (750 mg, 2.61 mmol) and acetonitrile (10 ml) was added triethylamine (1.7 ml, 12.2 mmol), and ice-cooled. To the mixture was slowly added acetyl chloride (0.6 ml, 6.92 mmol). After ice-bath was removed, the mixture was stirred at room temperature for 30 minutes. To the reaction mixture was added 2N aqueous sodium hydroxide solution (10 ml), and stirred at room temperature for further 15 minutes. To the reaction solution was added 2N hydrochloric acid (15 ml), and extracted with ethyl acetate 2 times. The combined organic layer was washed with saturated brine, dried over anhydrous magnesium sulfate, and concentrated under reduced pressure. The resulting solid was washed with tert-butyl methyl ether to give 590 mg of Compound (I-22) (yield: 68%) as solid.

$^1$H NMR ($CDCl_3$): δ ppm: 1.09 (6H, t, J=7.6 Hz), 2.20 (3H, s), 2.28-2.44 (7H, m), 3.72 (3H, s), 6.98 (2H, s), 8.24 (1H, s), 11.53 (1H, s).

Production Example 23

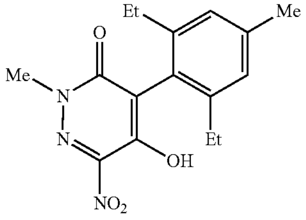 [SMILES: CCc1cc(C)cc(CC)c1-c1c(O)c([N+](=O)[O-])nn(C)c1=O]

Production of 4-(2,6-diethyl-4-methylphenyl)-6-nitro-5-hydroxy-2-methyl-3(2H)-pyridazinone (Compound (I-23))

To a solution of Compound (I-17) (500 mg, 1.74 mmol) in methanol (15 ml) was added sodium tungstate dihydrate (57 mg, 0.17 mmol) and 30% aqueous hydrogen peroxide solution (1.2 ml), and refluxed for 3 hours. After cooling to room temperature, the reaction solution was diluted with saturated brine, and extracted with ethyl acetate 2 times. The combined organic layer was dried over anhydrous magnesium sulfate, and concentrated under reduced pressure. The residue was purified by silica gel column chromatography (hexane:ethyl acetate=2:1) to give 215 mg of Compound (I-23) (yield: 39%) as solid.

$^1$H NMR ($CDCl_3$): δ ppm: 1.10 (6H, t, J=7.6 Hz), 2.26-2.42 (7H, m), 3.96 (3H, s), 7.03 (2H, s), 9.50 (1H, br s).

Production Example 24

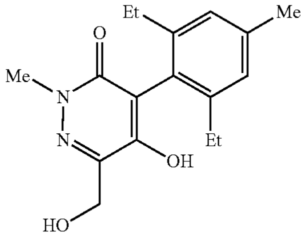 [SMILES: CCc1cc(C)cc(CC)c1-c1c(O)c(CO)nn(C)c1=O]

Production of 4-(2,6-diethyl-4-methylphenyl)-6-hydroxymethyl-5-hydroxy-2-methyl-3(2H)-pyridazinone (Compound (I-24-1))

To a solution of 4-(2,6-diethyl-4-methylphenyl)-6-hydroxymethyl-5-(4-methylphenylsulfonyl)-2-methyl-3(2H)-pyridazinone (2.58 g, 5.85 mmol) in 1,3-dimethylimidazolidinone (30 ml) was added 2N aqueous sodium hydroxide solution (15 ml), and stirred at 70° C. for 12 hours. After cooling to room temperature, 2N hydrochloric acid (25 ml) was added, and extracted with ethyl acetate 2 times. The combined organic layer was washed with water 2 times, washed with saturated brine, dried over anhydrous magnesium sulfate, and concentrated under reduced pressure. The residue was purified by silica gel column chromatography (hexane:ethyl acetate=1:1 to 1:2) to give 842 mg of Compound (I-24-1) (yield: 47%) as solid.

$^1$H NMR ($CDCl_3$): δ ppm: 1.07 (6H, t, J=7.6 Hz), 2.23-2.43 (7H, m), 3.79 (3H, s), 4.68 (2H, s), 7.02 (2H, s).

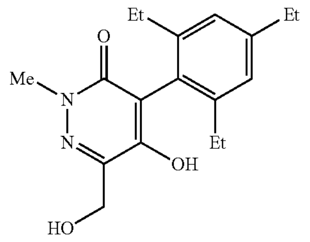

The procedure was performed according to Production Example 24 to give 4-(2,4,6-triethylphenyl)-6-hydroxymethyl-5-hydroxy-2-methyl-3(2H)-pyridazinone (Compound (I-24-2)).

$^1$H NMR ($CDCl_3$): δ ppm: 1.08 (6H, t, J=7.6 Hz), 1.27 (3H, t, J=7.6 Hz), 2.25-2.48 (4H, m), 2.66 (2H, q, J=7.6 Hz), 3.81 (3H, s), 4.72 (2H, d, J=3.4 Hz), 7.05 (2H, s).

Production Example 25

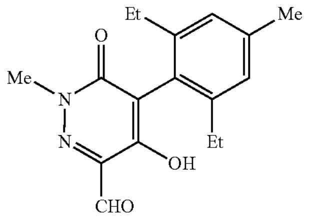 [SMILES: CCc1cc(C)cc(CC)c1-c1c(O)c(C=O)nn(C)c1=O]

Production of 4-(2,6-diethyl-4-methylphenyl)-6-formyl-5-hydroxy-2-methyl-3(2H)-pyridazinone (Compound (I-25-1))

To a solution of Compound (I-24-1) (681 mg, 2.25 mmol) in chloroform (10 ml) was added 2,2,6,6-tetramethylpiperidine 1-oxyl (35 mg, 0.224 mmol) and iodobenzene diacetate (798 mg, 2.47 mmol), and stirred at room temperature for 5 minutes. To the reaction solution was added 1N hydrochloric acid (10 ml), and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=70:30) to give 422 mg of Compound (I-25-1) (yield: 62%) as solid.

$^1$H NMR ($CDCl_3$): δ ppm: 1.08 (6H, t, J=7.6 Hz), 2.26-2.43 (7H, m), 3.95 (3H, s), 6.99 (2H, s), 9.82 (1H, s), 10.03 (1H, s).

The procedure was performed according to Production Example 25 to give 4-(2,4,6-triethylphenyl)-6-formyl-5-hydroxy-2-methyl-3(2H)-pyridazinone (Compound (I-25-2)).

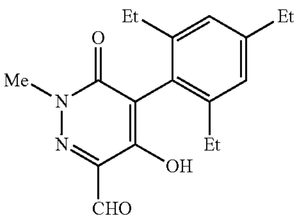 [SMILES: CCc1cc(CC)c(-c2c(O)c(C=O)nn(C)c2=O)c(CC)c1]

$^1$H NMR ($CDCl_3$): δ ppm: 1.09 (6H, t, J=7.6 Hz), 1.26 (3H, t, J=7.6 Hz), 2.27-2.44 (4H, m), 2.66 (2H, q, J=7.6 Hz), 3.95 (3H, s), 7.01 (2H, s), 9.82 (1H, s), 10.04 (1H, s).

Production Example 26

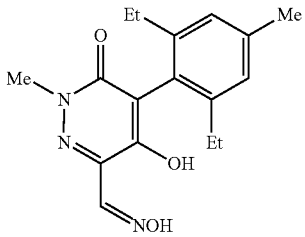

Production of 4-(2,6-diethyl-4-methylphenyl)-6-hydroxyiminomethyl-5-hydroxy-2-methyl-3(2H)-pyridazinone (Compound (I-26-1))

To a solution of Compound (I-25-1) (438 mg, 1.45 mmol) in THF (16 ml) was added hydroxylamine hydrochloride (152 mg, 2.18 mmol), sodium formate (246 mg, 3.62 mmol) and water (10 ml), and stirred at room temperature for 30 minutes. To the reaction solution was added 1N hydrochloric acid (10 ml), and extracted with ethyl acetate 2 times. The combined organic layer was washed with saturated brine, dried over anhydrous magnesium sulfate, and concentrated under reduced pressure to give 460 mg of Compound (I-26-1) (yield: 100%) as solid.

$^1$H NMR ($CDCl_3$): δ ppm: 1.08 (6H, t, J=7.6 Hz), 2.26-2.43 (7H, m), 3.84 (3H, s), 6.98 (2H, s), 8.16 (1H, s), 8.20 (1H, s), 9.91 (1H, s).

The procedure was performed according to Production Example 26 to give 4-(2,4,6-triethylphenyl)-6-hydroxyiminomethyl-5-hydroxy-2-methyl-3(2H)-pyridazinone (Compound (I-26-2)).

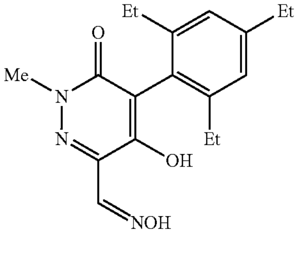

$^1$H NMR ($CDCl_3$): δ ppm: 1.07 (6H, t, J=7.6 Hz, Et), 1.25 (3H, t, J=7.6 Hz, Et), 2.18-2.48 (4H, m, Et), 2.63 (2H, q, J=7.6

Hz, Et), 3.83 (3H, s, N-Me), 6.99 (2H, s, Ph), 8.13 (1H, s), 8.51 (1H, brs, OH), 10.00 (1H, brs, OH).

Production Example 27

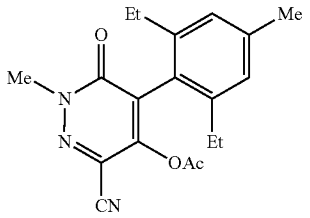 [SMILES: CCc1cc(C)cc(CC)c1-c1c(OC(C)=O)c(C#N)nn(C)c1=O]

Production of 4-(2,6-diethyl-4-methylphenyl)-6-cyano-5-acetoxy-2-methyl-3(2H)-pyridazinone (Compound (I-27-1))

Compound (I-26-1) (433 mg, 1.37 mmol) was added to acetic anhydride (3 ml), and stirred at 130° C. for 14 hours. The reaction solution was concentrated under reduced pressure. The residue was purified by silica gel column chromatography (hexane:ethyl acetate=4:1) to give 374 mg of Compound (I-27-1) (yield: 75%) as solid.

$^1$H NMR ($CDCl_3$): δ ppm: 1.10 (6H, t, J=7.5 Hz), 2.07 (3H, s), 2.29 (4H, q, J=7.5 Hz), 2.35 (3H, s), 3.91 (3H, s), 6.97 (2H, s).

The procedure was performed according to Production Example 27 to give 4-(2,4,6-triethylphenyl)-6-cyano-5-acetoxy-2-methyl-3(2H)-pyridazinone (Compound (I-27-2)).

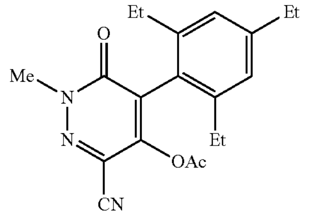 [SMILES: CCc1cc(CC)c(-c2c(OC(C)=O)c(C#N)nn(C)c2=O)c(CC)c1]

$^1$H NMR ($CDCl_3$): δ ppm: 1.10 (6H, t, J=7.6 Hz), 1.26 (3H, t, J=7.6 Hz), 2.07 (3H, s), 2.31 (4H, q, J=7.6 Hz), 2.65 (2H, q, J=7.6 Hz), 3.91 (3H, s), 6.99 (2H, s).

Production Example 28

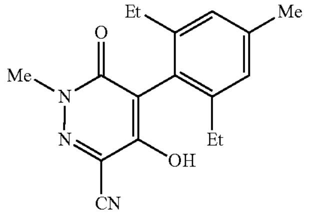 [SMILES: CCc1cc(C)cc(CC)c1-c1c(O)c(C#N)nn(C)c1=O]

Production of 4-(2,6-diethyl-4-methylphenyl)-6-cyano-5-hydroxy-2-methyl-3(2H)-pyridazinone (Compound (I-28-1))

To a solution of Compound (I-27-1) (302 mg, 0.889 mmol) in ethanol (4 ml) was added 2N aqueous sodium hydroxide solution (1.3 ml), and stirred at room temperature overnight. To the reaction solution was added 2N hydrochloric acid (4 ml), and extracted with ethyl acetate 2 times. The combined organic layer was washed with water 2 times and saturated brine, dried over anhydrous magnesium sulfate, and concentrated under reduced pressure. The residue was washed with a mixed solvent of hexane:tert-butyl methyl ether 2:1 to give 190 mg of Compound (I-28-1) (yield: 71%) as solid.

$^1$H NMR ($CDCl_3$): δ ppm: 1.07 (6H, t, J=7.6 Hz), 2.23-2.43 (7H, m), 3.79 (3H, s), 4.68 (1H, s), 7.02 (2H, s).

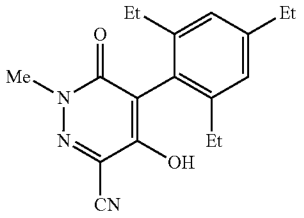 [SMILES: CCc1cc(CC)c(-c2c(O)c(C#N)nn(C)c2=O)c(CC)c1]

The procedure was performed according to Production Example 28 to give 4-(2,4,6-triethylphenyl)-6-cyano-5-hydroxy-2-methyl-3(2H)-pyridazinone (Compound (I-28-2)).

$^1$H NMR ($CDCl_3$): δ ppm: 1.09 (6H, t, J=7.6 Hz), 1.27 (3H, t, J=7.7 Hz), 2.25-2.42 (4H, m), 2.67 (2H, q, J=7.7 Hz), 3.88 (3H, s), 6.13 (1H, brs), 7.08 (2H, s).

Production Example 29

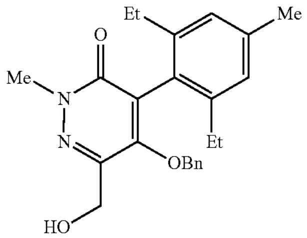 [SMILES: CCc1cc(C)cc(CC)c1-c1c(OCc2ccccc2)c(CO)nn(C)c1=O]

Production of 4-(2,6-diethyl-4-methylphenyl)-6-hydroxymethyl-5-benzyloxy-2-methyl-3(2H)-pyridazinone (Compound (I-29))

To a solution of 4-(2,6-diethyl-4-methylphenyl)-6-methoxymethoxymethyl-5-benzyloxy-2-methyl-3(2H)-pyridazinone (2.3 g, 4.91 mmol) in methanol (15 ml) was added concentrated hydrochloric acid (2 ml) and water (1 ml), and stirred at 65° C. for 75 minutes. After cooling to room temperature, the mixture was neutralized with 2N aqueous sodium hydroxide solution, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=1:1) to give 1.64 g of Compound (I-29) (yield: 85%) as solid.

$^1$H NMR ($CDCl_3$): δ ppm: 1.15 (6H, t, J=7.6 Hz), 2.32-2.53 (7H, m), 2.74 (1H, t, J=5.9 Hz), 3.79 (3H, s), 4.43 (2H, s), 4.61 (2H, d, J=5.9 Hz), 6.99 (2H, s), 7.03-7.08 (2H, m), 7.28-7.32 (3H, m).

Production Example 30

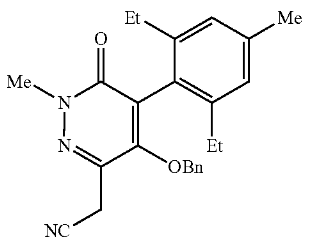 [SMILES: CCc1cc(C)cc(CC)c1-c1c(OCc2ccccc2)c(CC#N)nn(C)c1=O]

Production of 4-(2,6-diethyl-4-methylphenyl)-6-cyanomethyl-5-benzyloxy-2-methyl-3(2H)-pyridazinone (Compound (I-30))

To a solution of 4-(2,6-diethyl-4-methylphenyl)-6-bromomethyl-5-benzyloxy-2-methyl-3(2H)-pyridazinone (675 mg, 1.48 mmol) in DMSO (4 ml) was added sodium cyanide (80 mg, 1.63 mmol), and stirred at room temperature for 30 minutes. The reaction solution was diluted with water, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=2:1) to give 405 mg of Compound (I-30) (yield: 66%) as solid.

$^1$H NMR ($CDCl_3$): δ ppm: 1.16 (6H, t, J=7.6 Hz), 2.32-2.51 (7H, m), 3.65 (2H, s), 3.78 (3H, s), 4.47 (2H, s), 7.00 (2H, s), 7.07-7.12 (2H, m), 7.29-7.34 (3H, m).

Production Example 31

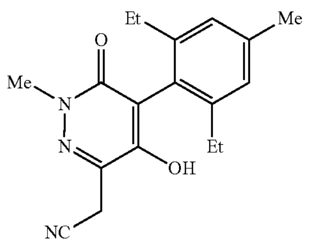 [SMILES: CCc1cc(C)cc(CC)c1-c1c(O)c(CC#N)nn(C)c1=O]

Production of 4-(2,6-diethyl-4-methylphenyl)-6-cyanomethyl-5-hydroxy-2-methyl-3(2H)-pyridazinone (Compound (I-31))

A mixture of Compound (I-30) (400 mg, 0.996 mmol), ethyl acetate (10 ml), and 10% palladium-carbon (30 mg) was stirred under ambient-pressure hydrogen atmosphere for 1 hour. The resulting reaction solution was filtered through Celite, and then the filtrate was concentrated under reduced pressure. The residue was purified by silica gel column chromatography (ethyl acetate) to give 291 mg of Compound (I-31) (yield: 93%) as solid.

$^1$H NMR ($CDCl_3$): δ ppm: 1.07 (6H, t, J=7.7 Hz), 2.22-2.42 (7H, m), 3.78 (2H, s), 3.81 (3H, s), 5.83 (1H, br s), 7.04 (2H, s).

Production Example 32

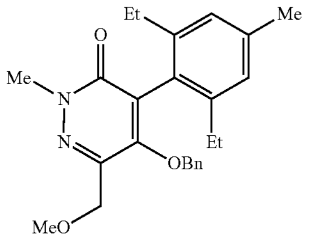 [SMILES: CCc1cc(C)cc(CC)c1-c1c(OCc2ccccc2)c(COC)nn(C)c1=O]

Production of 4-(2,6-diethyl-4-methylphenyl)-6-methoxymethyl-5-benzyloxy-2-methyl-3(2H)-pyridazinone (Compound (I-32))

To a solution of Compound (I-29) (500 mg, 1.27 mmol) in dry THF (8 ml) was added methyl iodide (0.16 ml) and 60% sodium hydride (56 mg, 1.4 mmol) at 5° C. After ice-bath was removed, the mixture was stirred at room temperature for 30 minutes. The reaction solution was diluted with water, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=2:1) to give 506 mg of Compound (I-32) (yield: 97%) as oil.

$^1$H NMR ($CDCl_3$): δ ppm: 1.13 (6H, t, J=7.6 Hz), 2.31-2.52 (7H, m), 3.41 (3H, s), 3.80 (3H, s), 4.40 (2H, s), 4.45 (2H, s), 6.99 (2H, s), 7.04-7.08 (2H, m), 7.26-7.31 (3H, m).

Production Example 33

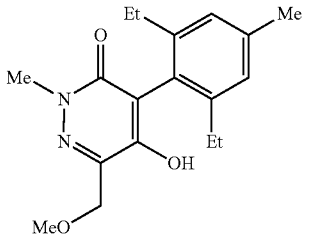 [SMILES: CCc1cc(C)cc(CC)c1-c1c(O)c(COC)nn(C)c1=O]

Production of 4-(2,6-diethyl-4-methylphenyl)-6-methoxymethyl-5-hydroxy-2-methyl-3(2H)-pyridazinone (Compound (I-33-1))

To a solution of Compound (I-32) (500 mg, 1.23 mmol) in glacial acetic acid (4 ml) was added 48% hydrobromic acid (0.5 ml), and stirred at 70° C. for 1 hour. After cooling to room temperature, water was added, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=2:1) to give 292 mg of Compound (I-33-1) (yield: 74%) as solid.

$^1$H NMR ($CDCl_3$): δ ppm: 1.08 (6H, t, J=7.6 Hz), 2.26-2.44 (7H, m), 3.50 (3H, s), 3.79 (3H, s), 4.59 (2H, s), 6.81 (1H, s), 7.01 (2H, s).

Production Example 34

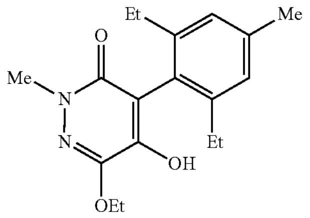 [SMILES: CCOc1nn(C)c(=O)c(-c2c(CC)cc(C)cc2CC)c1O]

Production of Compound (I-4-3)

The procedure was performed by the method similar to Production Example 12 using ethyl 2-[2-(2,6-diethyl-4-methylphenyl)acetyl-2-methylhydrazono]-2-(dodecylthio)acetate (2:1 mixture of geometric isomers) as a starting material to give Compound (I-4-3) (yield: 20%) and 4-(2,6-diethyl-4-methylphenyl)-6-dodecylthio-5-hydroxy-2-methyl-3(2H)-pyridazinone (yield: 31%).

$^1$H NMR ($CDCl_3$) for 4-(2,6-diethyl-4-methylphenyl)-6-dodecylthio-5-hydroxy-2-methyl-3(2H)-pyridazinone: δ ppm: 0.88 (3H, t, J=6.8 Hz), 1.08 (6H, t, J=7.6 Hz), 1.19-1.38 (16H, m), 1.41-1.51 (2H, m), 1.69-1.79 (2H, m), 2.25-2.44 (7H, m), 3.06 (2H, t, J=7.4 Hz), 3.79 (3H, s), 5.55 (1H, br s), 7.02 (2H, s).

Production Example 35

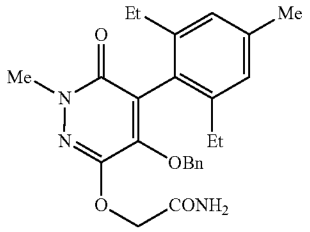 [SMILES: CCc1cc(C)cc(CC)c1-c1c(OCc2ccccc2)c(OCC(N)=O)nn(C)c1=O]

Production of 4-(2,6-diethyl-4-methylphenyl)-6-carbamoylmethoxy-5-benzyloxy-2-methyl-3(2H)-pyridazinone (Compound (I-35-1))

A solution of (4-(2,6-diethyl-4-methylphenyl)-5-benzyloxy-2-methyl-3(2H)-pyridazinone-6-yl)oxyacetic acid (530 mg, 1.53 mmol), thionyl chloride (290 mg, 2.43 mmol) and DMF (10 mg) in toluene (15 ml) was stirred at 50° C. for 45 minutes. The reaction solution was cooled to room temperature, and then concentrated under reduced pressure. The residue was dissolved in THF (5 ml), and aqueous ammonia (2 ml) was slowly added under ice-cooling. After the reaction solution was stirred at room temperature for 30 minutes, the reaction solution was diluted with water, and extracted with ethyl acetate. The organic layer was washed with saturated brine, and concentrated under reduced pressure to give 500 mg of Compound (I-35-1) (yield: 94%).

$^1$H NMR ($CDCl_3$): δ ppm: 1.15 (6H, t, J=7.6 Hz), 2.30-2.51 (7H, m), 3.67 (3H, s), 4.62 (2H, s), 4.70 (2H, s), 5.33 (1H, br s), 6.11 (1H, br s), 7.00 (2H, s), 7.06-7.10 (2H, m), 7.27-7.31 (3H, m).

The procedure was performed by the method similar to Production Example 35 to give 4-(2,6-diethyl-4-methylphenyl)-6-dimethylaminocarbonylmethoxy-5-benzyloxy-2-methyl-3(2H)-pyridazinone (Compound (I-35-2))(yield: 73%).

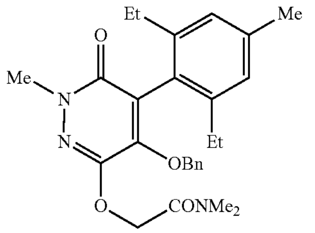

$^1$H NMR ($CDCl_3$): δ ppm: 1.08 (6H, t, J=7.6 Hz), 2.20-2.30 (2H, m), 2.32-2.43 (2H, m), 2.36 (3H, s), 3.04 (3H, s), 3.07 (3H, s), 3.64 (3H, s), 4.96 (2H, s), 4.96 (2H, s), 6.95 (2H, s), 7.00-7.04 (2H, m), 7.18-7.22 (3H, m).

Production Example 36

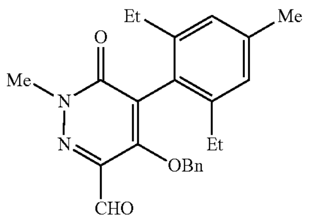 [SMILES: CCc1cc(C)cc(CC)c1-c1c(OCc2ccccc2)c(C=O)nn(C)c1=O]

Production of 4-(2,6-diethyl-4-methylphenyl)-6-formyl-5-benzyloxy-2-methyl-3(2H)-pyridazinone (Compound (I-36))

The procedure was performed by the method similar to Production Example 25 to give Compound (I-36) (yield: 54%).

$^1$H NMR ($CDCl_3$): δ ppm: 1.12 (6H, t, J=7.6 Hz), 2.29-2.47 (7H, m), 3.93 (3H, s), 4.60 (2H, s), 7.01 (2H, s), 7.03 (2H, m), 7.24-7.30 (3H, m), 9.92 (1H, s).

The production examples of a compound of the formula (II) are shown in Reference Example 1 and Reference Example 2.

Reference Example 1

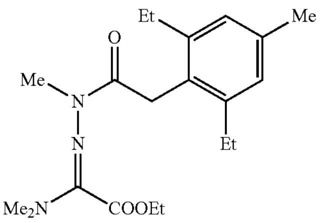 [SMILES: CCOC(=O)C(=NN(C)C(=O)Cc1c(CC)cc(C)cc1CC)N(C)C]

Production of ethyl 2-[2-(2,6-diethyl-4-methylphenyl)acetyl-2-methylhydrazono]-2-dimethylaminoacetate (Compound (II-2))

Reference Example 1-1

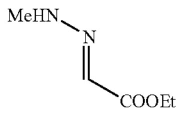

E-Ethyl 2-(2-methylhydrazono)acetate (Compound (XVI-1))

47% ethyl glyoxylate in toluene (polymer type) (467.84 g, 2.15 mol) was dissolved in THF (620 ml), to the solution was slowly added methylhydrazine (103 g, 1.02 eq) under ice-cooled. After the addition was complete, the mixture was stirred at 0° C. for 30 minutes and at room temperature for 16 hours. The reaction solution was concentrated under reduced pressure. The residue was dissolved in toluene (400 ml), and concentrated under reduced pressure. The resulting solid was washed with tert-butyl methyl ether (200 ml), and allowed to stand at 0° C. for 30 minutes. Then, the mixture was filtered, and washed with cooled tert-butyl methyl ether (100 ml) to give 223.91 g of Compound (XVI-1) (yield: 78.8%) as solid.

$^1$H NMR ($CDCl_3$): δ ppm: 1.34 (3H, t, J=7.1 Hz), 2.97 (3H, d, J=4.4 Hz), 4.29 (2H, q, J=7.1 Hz), 6.57 (1H, brs), 6.69 (1H, s).

Reference Example 1-2

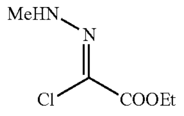

Z-Ethyl 2-chloro-2-(2-methylhydrazono)acetate (Compound (XVII-1))

Compound (XVI-1) (24.01 g, 184 mmol) was dissolved in DMF (100 ml) and heated to 50° C. N-chlorosuccinimide (27.15 g, 203 mmol) was slowly added with keeping the internal temperature 50-60° C. After the addition was complete, the mixture was stirred for 30 minutes. The reaction solution was diluted with water (300 ml), and extracted with tert-butyl methyl ether 2 times. The combined organic layer was washed with water and saturated brine, dried over sodium sulfate, and concentrated in vacuo. The residue was purified by silica gel column chromatography (hexane:ethyl acetate=3:1) to give 22.97 g of Compound (XVII-1) (yield: 75.6%) as solid.

$^1$H NMR ($CDCl_3$): δ ppm: 1.36 (3H, t, J=7.1 Hz), 3.29 (3H, d, J=3.9 Hz), 4.35 (2H, q, J=7.1 Hz), 6.44 (1H, brs).

Reference Example 1-3

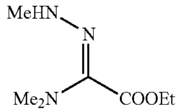

Z-Ethyl 2-dimethylamino-2-(2-methylhydrazono)acetate (Compound (VI-1))

To a solution of Compound (XVII-1) (1.33 g, 8.09 mmol) in THF (30 ml) was added 50% aqueous dimethylamine solution (15 ml, 166 mmol) at room temperature. The mixture was refluxed for 9 hours. After the reaction mixture was cooled to room temperature, water (30 ml) was added, and extracted with ethyl acetate 2 times. The combined organic layer was washed with saturated brine, dried over anhydrous magnesium sulfate, and concentrated under reduced pressure to give 1.34 g of Compound (VI-1) (yield: 95%) as an oil.

$^1$H NMR ($CDCl_3$): δ ppm: 1.34 (3H, t, J=7.1 Hz), 2.58 (6H, s), 3.15 (3H, d, J=4.4 Hz), 4.27 (2H, q, J=7.1 Hz), 6.28 (1H, brs).

Reference Example 1-4

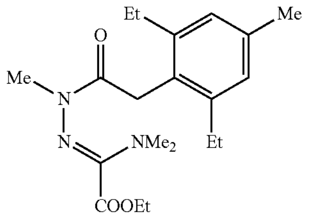 [SMILES: CCOC(=O)/C(=N/N(C)C(=O)Cc1c(CC)cc(C)cc1CC)N(C)C]

Ethyl 2-[2-(2,6-diethyl-4-methylphenyl)acetyl-2-methylhydrazono]-2-dimethylaminoacetate (Compound (II-2))

To a solution of Compound (VI-1) (365 mg, 2.10 mmol) in THF (8 ml) was added pyridine (195 mg, 2.46 mmol), and ice-cooled. To the solution was slowly added a solution of 2-(2,6-diethyl-4-methylphenyl)acetyl chloride (Compound (V-1)) (474 mg, 2.11 mmol) in THF (3 ml) dropwise. The reaction solution was stirred at room temperature for 2 hours. The reaction solution was diluted with water, and extracted with ethyl acetate 2 times. The combined organic layer was washed with saturated aqueous sodium hydrogen carbonate solution, then saturated brine, dried over anhydrous magnesium sulfate, and concentrated under reduced pressure to give 750 mg of Compound (II-2) (2.07 mmol) as oil.

$^1$H NMR ($CDCl_3$): δ ppm: 1.14-1.21 (6H, m), 1.34-1.40 (3H, m), 2.28 (3H, s), 2.47-2.58 (4H, m), 3.01 (6H, s), 3.08 (3H, s), 3.66 (2H, s), 4.30-4.34 (2H, m), 6.88 (2H, s).

The following compounds were produced by the method similar to Reference Example 1.

Ethyl 2-dimethylamino-2-[2-methyl-2-(2,4,6-trimethylphenyl)acetylhydrazono]acetate (Compound (II-1))

$^1$H NMR ($CDCl_3$): δ ppm: 1.37 (3H, t, J=7.1 Hz), 2.21 (6H, s), 2.23 (3H, s), 3.01 (6H, s), 3.08 (3H, s), 3.62 (2H, s), 4.36 (2H, q, J=7.1 Hz), 6.82 (2H, s).

Ethyl 2-dimethylamino-2-[2-methyl-2-(2,4,6-triethylphenyl)acetylhydrazono]acetate (Compound (II-3))

$^1$H NMR ($CDCl_3$): δ ppm: 1.12-1.28 (9H, m), 1.33-1.42 (3H, m), 2.51-2.68 (6H, m), 3.01 (6H, s), 3.08 (3H, s), 3.67 (2H, s), 4.32-4.41 (2H, m), 6.87 (2H, s).

Reference Example 2

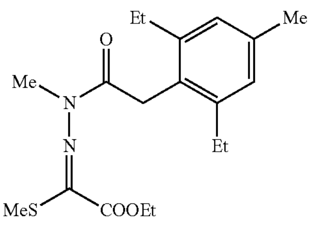 [SMILES: CCOC(=O)C(=NN(C)C(=O)Cc1c(CC)cc(C)cc1CC)SC]

Production of ethyl 2-[2-(2,6-diethyl-4-methylphenyl)acetyl-2-methylhydrazono]-2-(methylthio)acetate (Compound (II-5))

Reference Example 2-1

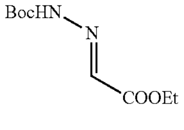 [SMILES: CCOC(=O)/C=N/NC(=O)OC(C)(C)C]

E-Ethyl 2-[2-(t-butoxycarbonyl)hydrazono]acetate (Compound (X-1))

To a solution of t-butyl carbazate (25.5 g, 193 mmol) in THF (60 ml) was added 47% ethyl glyoxylate in toluene (polymer type) (46.1 g, 212 mmol), and stirred at 60° C. for minutes. The reaction solution was cooled to room temperature, and concentrated under reduced pressure. The resulting solid was washed with a mixed solvent of hexane:ethyl acetate=5:1 to give 33.9 g of Compound (X-1) (yield: 80%) as colorless solid.

$^1$H NMR ($CDCl_3$): δ ppm: 1.34 (3H, t, J=7.2 Hz), 1.53 (9H, s), 4.31 (2H, q, J=7.2 Hz), 7.54 (1H, brs), 8.25 (1H, s).

Reference Example 2-2

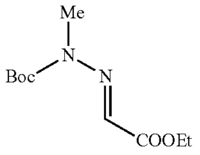 [SMILES: CCOC(=O)/C=N/N(C)C(=O)OC(C)(C)C]

E-Ethyl 2-(2-t-butoxycarbonyl-2-methylhydrazono) acetate (Compound (XII-1))

To a mixture of 55% sodium hydride (6.98 g, 160 mmol) and DMF (180 ml) was added Compound (X-1) (31.22 g, 144 mmol) over 13 minutes under ice-cooling. To the resulting mixture was added iodomethane (30.73 g, 217 mmol) dropwise over 14 minutes. The mixture was stirred at room temperature for 3.5 hours. The reaction mixture was diluted with water, and extracted with ethyl acetate 3 times. The combined organic layer was washed with water, dried over anhydrous magnesium sulfate, and concentrated under reduced pressure to give 31.35 g of the crude Compound (XII-1) as oil. The product was used in the next reaction without purification.

$^1$H NMR ($CDCl_3$): δ ppm: 1.36 (3H, t, J=7.2 Hz), 1.57 (9H, s), 3.28 (3H, s), 4.33 (2H, q, J=7.2 Hz), 6.97 (1H, s).

Reference Example 2-3

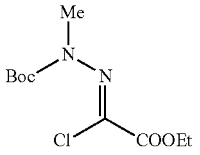 [SMILES: CCOC(=O)/C(Cl)=N/N(C)C(=O)OC(C)(C)C]

Z-Ethyl 2-(2-t-butoxycarbonyl-2-methylhydrazono)-2-chloroacetate (Compound (XIII-1))

To a solution of Compound (XII-1) (1.1 g, 4.77 mmol) in ethyl acetate (10 ml) was added N-chlorosuccinimide (2.45 g, 18.3 mmol), and stirred at 50° C. for 9 hours. The reaction mixture was cooled to room temperature, and concentrated under reduced pressure. The residue was washed with a mixed solvent of hexane:ethyl acetate=3:1, and filtered. The filtrate was concentrated. The residue was purified by silica gel column chromatography (hexane:ethyl acetate=3:1) to give 1.0 g of Compound (XIII-1) (yield: 79%) (pale yellow oil).

$^1$H NMR ($CDCl_3$): δ ppm: 1.38 (3H, t, J=7.2 Hz), 1.54 (9H, s), 3.55 (3H, s), 4.37 (2H, q, J=7.2 Hz).

Reference Example 2-4

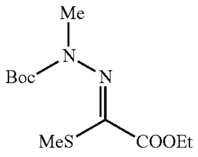 [SMILES: CCOC(=O)/C(=N/N(C)C(=O)OC(C)(C)C)SC]

Z-Ethyl 2-[2-(t-butoxycarbonyl)-2-methylhydrazono]-2-(methylthio)acetate (Compound (XV-1))

To a solution of 15% aqueous methyl mercaptan solution (1.94 g, 4.15 mmol) in THF (10 ml) was added a solution of Compound (XIII-1) (1.0 g, 3.77 mmol) in THF (5 ml) dropwise under ice-cooling. After being stirred at room temperature for 1 hour, the reaction solution was diluted with water, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=2:1) to give 900 mg of Compound (XV-1) (yield: 86%).

$^1$H NMR ($CDCl_3$): δ ppm: 1.39 (3H, t, J=7.1 Hz), 1.49 (9H, s), 2.39 (3H, s), 3.20 (3H, s), 4.38 (2H, q, J=7.2 Hz).

Reference Example 2-5

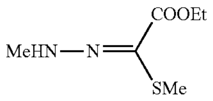 [SMILES: CCOC(=O)C(=NNC)SC]

Ethyl 2-(2-methylhydrazono)-2-(methylthio)acetate (Compound (VI-2))

To a solution of Compound (XV-1) (4.47 g, 16.1 mmol) in dioxane (13 ml) was added 4.0 M hydrogen chloride in dioxane (23 ml, 92 mmol). The mixture was stirred at room temperature for 2 hours. The reaction solution was poured into saturated aqueous sodium hydrogen carbonate solution to be alkalified, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=3:1) to give 1.95 g of the E isomer of Compound (VI-2) (yield: 68%) (pale yellow solid) and 0.63 g of the Z isomer of Compound (VI-2) (yield: 22%).

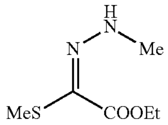 [SMILES: CCOC(=O)/C(=N\NC)SC]

E-Ethyl 2-(2-methylhydrazono)-2-(methylthio)acetate $^1$H NMR ($CDCl_3$): δ ppm: 1.35 (3H, t, J=7.1 Hz), 2.29 (3H, s), 3.21 (3H, d, J=3.9 Hz), 4.26 (2H, q, J=7.1 Hz), 9.96 (1H, brs).

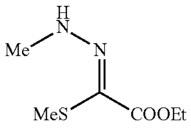

Z-Ethyl 2-(2-methylhydrazono)-2-(methylthio)acetate $^1$H NMR ($CDCl_3$): δ ppm: 1.36 (3H, t, J=7.2 Hz, OEt), 2.28 (3H, s), 3.33 (3H, d, J=4.1 Hz), 4.33 (2H, q, J=7.2 Hz), 7.32 (1H, brs).

Reference Example 2-6

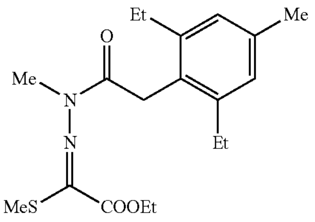 [SMILES: CCOC(=O)C(=NN(C)C(=O)Cc1c(CC)cc(C)cc1CC)SC]

Ethyl 2-[2-(2,6-diethyl-4-methylphenyl)acetyl-2-methylhydrazono]-2-(methylthio)acetate (Compound (II-5))

The E isomer of Compound (VI-2) was reacted with Compound (V-1) according to Reference Example 1-4 to give Compound (II-5) as oil (about 2:1 mixture of geometric isomers).

$^1$H NMR ($CDCl_3$) for main product: δ ppm: 1.17 (6H, t, J=7.6 Hz), 1.40 (3H, t, J=7.2 Hz), 2.29 (3H, s), 2.49 (3H, s), 2.54 (4H, q, J=7.6 Hz), 3.39 (3H, s), 3.84 (2H, s), 4.40 (3H, q, J=7.2 Hz), 6.88 (2H, s).

Reference Example 2-7

To a solution of the Z isomer of Compound (VI-2) (540 mg, 2.83 mmol) in toluene (5 ml) was added Compound (V-1) (780 mg, 3.47 mmol), pyridine (0.3 ml) and 4-dimethylaminopyridine (3 mg), and refluxed for 1 hour. After the reaction solution was cooled to room temperature, tert-butyl methyl ether was added, washed with 2N hydrochloric acid, saturated aqueous sodium hydrogen carbonate solution, then saturated brine, dried over anhydrous magnesium sulfate, and concentrated under reduced pressure. The residue was purified by silica gel column chromatography (hexane:ethyl acetate=4:1) to give 1.11 g of Compound (II-5) (yield: 99%) as oil. The ratio of geometric isomers of the product was about 2:1 which was the same as that in Reference Example 2-6.

The following compounds were produced according to Reference Example 2.

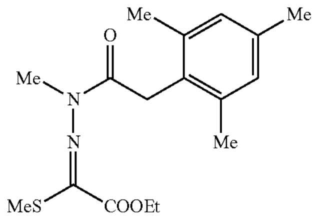

Ethyl 2-[2-methyl-2-(2,4,6-trimethylphenyl)acetylhydrazono]-2-(methylthio)acetate (Compound (II-4))

$^1$H NMR ($CDCl_3$): δ ppm: 1.38 (3H, t, J=7.1 Hz), 2.21 (6H, s), 2.25 (3H, s), 2.49 (3H, s), 3.25 (3H, s), 3.94 (2H, s), 4.36 (2H, q, J=7.1 Hz), 6.86 (2H, s).

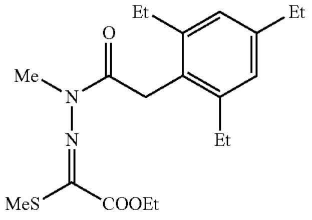 [SMILES: CCOC(=O)C(=NN(C)C(=O)Cc1c(CC)cc(CC)cc1CC)SC]

Ethyl 2-[2-methyl-2-(2,4,6-triethylphenyl)acetylhydrazono]-2-(methylthio)acetate (Compound (II-6)) (about 3:1 mixture of geometric isomers)

$^1$H NMR ($CDCl_3$) for main product: δ ppm: 1.13-1.29 (9H, m), 1.33-1.42 (3H, m), 2.49 (3H, s), 2.51-2.66 (6H, m), 3.26 (3H, s), 4.01 (2H, s), 4.30-4.43 (2H, m), 6.91 (2H, s).

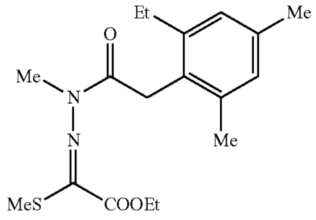 [SMILES: CCOC(=O)C(=NN(C)C(=O)Cc1c(C)cc(C)cc1CC)SC]

Ethyl 2-[2-methyl-2-(2-ethyl-4,6-dimethylphenyl)acetylhydrazono]-2-(methylthio)acetate (mixture of geometric isomers)

$^1$H NMR ($CDCl_3$): δ ppm: 1.11-1.22 (3H, m), 1.33-1.45 (3H, m), 2.21 (3H, s), 2.27 (3H, s), 2.49 (3H, s), 2.46-2.66 (2H, m), 3.26 (3H, s), 3.96 (2H, s), 4.26-4.45 (2H, m), 6.87 (2H, s).

Reference Example 3

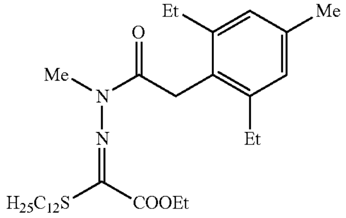

Production of ethyl 2-[2-(2,6-diethyl-4-methylphenyl)acetyl-2-methylhydrazono]-2-(dodecylthio)acetate

Reference Example 3-1

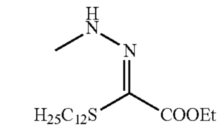

Z-Ethyl 2-(2-methylhydrazono)-2-(dodecylthio)acetate

To a solution of Compound (XVII-1) (2.61 g, 15.8 mmol) in tert-butyl methyl ether (15 ml) was added 1-dodecanethiol (3.21 g, 15.8 mmol), and ice-cooled. To the solution was added 60% sodium hydride (698 mg, 17.4 mmol), and stirred for 5 minutes. The reaction solution was diluted with water, and extracted with tert-butyl methyl ether 2 times. The combined organic layer was washed with saturated brine, dried over anhydrous magnesium sulfate, and concentrated under reduced pressure. The residue was purified by silica gel column chromatography (hexane:ethyl acetate=4:1) to give 4.52 g of Z-ethyl 2-(2-methylhydrazono)-2-(dodecylthio)acetate (yield: 86%) as oil.

$^1$H NMR ($CDCl_3$): δ ppm: 0.88 (3H, t, J=6.8 Hz), 1.18-1.39 (18H, m), 1.48-1.59 (5H, m), 2.76 (2H, t, J=7.4 Hz), 3.33 (3H, d, J=4.1 Hz), 4.32 (2H, q, J=7.2 Hz), 7.39 (1H, d, J=4.1 Hz).

Reference Example 3-2

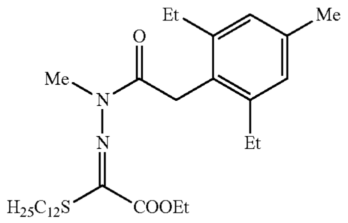

Ethyl 2-[2-(2,6-diethyl-4-methylphenyl)acetyl-2-methylhydrazono]-2-(dodecylthio)acetate The procedure was performed according to Reference Example 2-7 to give ethyl 2-[2-(2,6-diethyl-4-methylphenyl) acetyl-2-methylhydrazono]-2-(dodecylthio)acetate (about 2:1 mixture of geometric isomers).

$^1$H NMR ($CDCl_3$): δ ppm: 0.84-0.91 (3H, m), 1.11-1.45 (27H, m), 1.60-1.77 (2H, m), 2.29 (2H, s), 2.30 (1H, s), 2.49-2.59 (4H, m), 2.92-3.09 (2H, m), 3.24 (1H, s), 3.39 (2H, s), 3.84 (1.4H, s), 3.95 (0.6H, s), 4.32-4.43 (2H, m), 6.87 (1.4H, s), 6.89 (0.6H, s).

The following compounds were produced according to Reference Example 3.

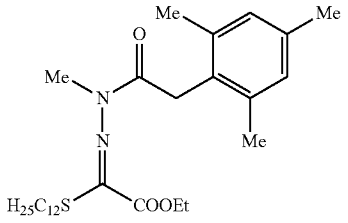

Ethyl 2-[2-(2,4,6-trimethylphenyl)acetyl-2-methylhydrazono]-2-(dodecylthio)acetate (about 2:1 mixture of geometric isomers)

$^1$H NMR ($CDCl_3$): δ ppm: 0.84-0.92 (3H, m), 1.17-1.44 (21H, m), 1.55-1.80 (2H, m), 2.18 (2H, s), 2.21 (4H, s), 2.25 (2H, s), 2.28 (1H, s), 2.95 (1.4H, t, J=7.4 Hz), 3.05 (0.6H, t, J=7.4 Hz), 3.24 (1H, s), 3.39 (2H, s), 3.79 (1.4H, s), 3.90 (0.6H, s), 4.31-4.43 (2H, m), 6.84 (1.4H, s), 6.86 (0.6H, s).

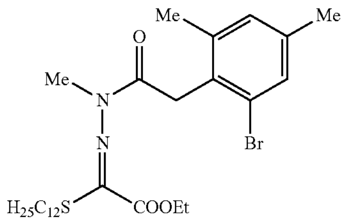

Ethyl 2-[2-(2-bromo-4,6-dimethylphenyl)acetyl-2-methylhydrazono]-2-(dodecylthio)acetate (about 2:1 mixture of geometric isomers)

$^1$H NMR ($CDCl_3$): δ ppm: 0.85-0.91 (3H, m), 1.17-1.44 (21H, m), 1.55-1.80 (2H, m), 2.25 (2H, s), 2.26 (2H, s), 2.27 (1H, s), 2.28 (1H, s), 2.96 (1.4H, t, J=7.4 Hz), 3.07 (0.6H, t, J=7.3 Hz), 3.25 (1H, s), 3.41 (2H, s), 3.98 (0.6H, s), 3.99 (1.4H, s), 4.32-4.43 (2H, m), 6.93 (0.7H, s), 6.95 (0.3H, s), 7.25 (0.7H, s), 7.26 (0.3H, s).

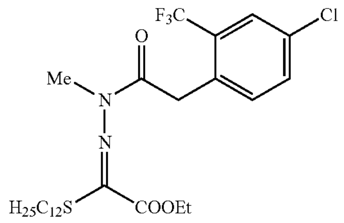

Ethyl 2-[2-(4-chloro-2-trifluoromethylphenyl)acetyl-2-methylhydrazono]-2-(dodecylthio)acetate (about 3:1 mixture of geometric isomers)

$^1$H NMR ($CDCl_3$): δ ppm: 0.84-0.92 (3H, m), 1.19-1.41 (21H, m), 1.48-1.71 (2H, m), 2.84-3.00 (2H, m), 3.23 (0.75H, s), 3.39 (2.25H, s), 3.98 (1.5H, s), 4.08 (0.5H, s), 4.31-4.39 (2H, m), 7.23-7.32 (1H, m), 7.43-7.51 (1H, m), 7.61-7.65 (1H, m).

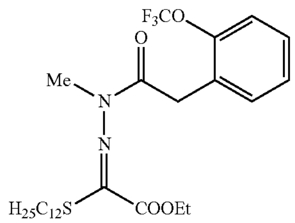

Ethyl 2-[2-(2-trifluoromethoxyphenyl)acetyl-2-methylhydrazono]-2-(dodecylthio)acetate (about 3:1 mixture of geometric isomers)

$^1$H NMR ($CDCl_3$): δ ppm: 0.85-0.92 (3H, m), 1.18-1.41 (21H, m), 1.48-1.71 (2H, m), 2.84-3.00 (2H, m), 3.24 (0.75H, s), 3.39 (2.25H, s), 3.89 (1.5H, s), 3.99 (0.5H, s), 4.29-4.41 (2H, m), 7.14-7.50 (4H, m).

Reference Example 4

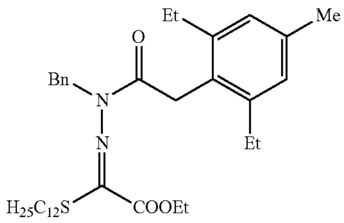

Production of Ethyl 2-[2-(2,6-diethyl-4-methylphenyl)acetyl-2-benzylhydrazono]-2-(dodecylthio)acetate

Reference Example 4-1

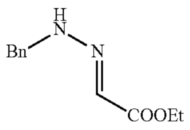 [SMILES: CCOC(=O)/C=N/NCc1ccccc1]

Ethyl 2-(2-benzylhydrazono)acetate

47% ethyl glyoxylate in toluene (polymer type) (29.2 g, 134.5 mmol) was dissolved in THF (200 ml), and to the solution was added benzylhydrazine monohydrochloride (21.3 g, 134.5 mmol) and triethylamine (20.6 ml, 148 mmol), and stirred at room temperature overnight. The reaction solution was diluted with ethyl acetate, washed with water, washed with saturated brine, dried over anhydrous magnesium sulfate, and concentrated under reduced pressure. The residue was purified by silica gel column chromatography (hexane:ethyl acetate=2:1) to give 14.9 g of E-ethyl 2-(2-benzylhydrazono)acetate (mixture of E:Z=4:1) (yield: 53%) as oil.

$^1$H NMR ($CDCl_3$) for E isomer: δ ppm: 1.32 (3H, t, J=7.1 Hz), 4.26 (2H, q, J=7.1 Hz), 4.40 (2H, d, J=4.3 Hz), 6.77 (1H, s), 6.84 (1H, br s), 7.23-7.40 (5H, m).

Reference Example 4-2

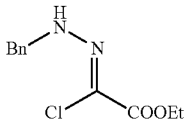 [SMILES: CCOC(=O)/C(Cl)=N/NCc1ccccc1]

Ethyl 2-chloro-2-(2-benzylhydrazono)acetate

The procedure was performed according to Reference Example 1-2 to give as an oily mixture of E:Z=8:1 (yield: 56%).

$^1$H NMR ($CDCl_3$) for Z isomer: δ ppm: 1.37 (3H, t, J=7.2 Hz), 4.35 (2H, q, J=7.2 Hz), 4.70 (2H, d, J=4.8 Hz), 6.71 (1H, brs), 7.28-7.40 (5H, m).

Reference Example 4-3

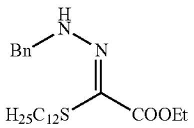

Z-Ethyl 2-(2-benzylhydrazono)-2-(dodecylthio)acetate

The procedure was performed according to Reference Example 3-1 to give Z-ethyl 2-(2-benzylhydrazono)-2-(dodecylthio)acetate as an oily mixture (yield: 78%).

$^1$H NMR ($CDCl_3$): δ ppm: 0.88 (3H, t, J=6.6 Hz), 1.14-1.53 (23H, m), 2.76 (2H, t, J=7.4 Hz), 4.33 (2H, q, J=7.2 Hz), 4.76 (2H, d, J=4.8 Hz), 7.24-7.39 (5H, m), 7.63 (1H, t, J=4.8 Hz).

Reference Example 4-4

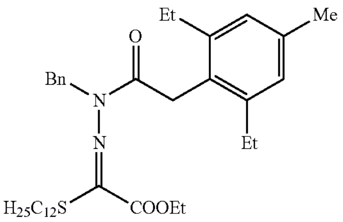

Ethyl 2-[2-(2,6-diethyl-4-methylphenyl)acetyl-2-benzylhydrazono]-2-(dodecylthio)acetate The procedure was performed according to Reference Example 2-7 to give ethyl 2-[2-(2,6-diethyl-4-methylphenyl)acetyl-2-benzylhydrazono]-2-(dodecylthio)acetate as an oily mixture of geometric isomers (yield: 83%).

$^1$H NMR ($CDCl_3$) for E isomer: δ ppm: 0.88 (3H, t, J=6.8 Hz), 1.07-1.71 (29H, m), 2.28 (2.4H, s), 2.32 (0.6H, s), 2.51 (3.2H, q, J=7.5 Hz), 2.65 (0.8H, q, J=7.6 Hz), 2.86 (1.6H, t, J=7.4 Hz), 2.97 (0.4H, t, J=7.4 Hz), 3.79 (0.4H, s), 3.80 (1.6H, s), 4.15 (0.4H, q, J=7.0 Hz), 4.36 (1.6H, q, J=7.2 Hz), 5.11 (1.6H, s), 5.29 (0.4H, s), 6.87 (1.6H, s), 6.93 (0.4H, s), 7.19-7.40 (5H, m).

Reference Example 5

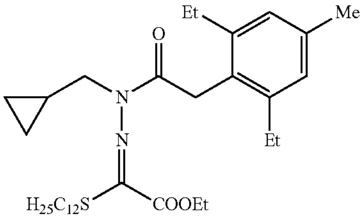

Production of ethyl 2-[2-(2,6-diethyl-4-methylphenyl)acetyl-2-(cyclopropylmethyl)hydrazono]-2-(dodecylthio)acetate Reference Example 5-1

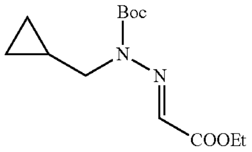 [SMILES: CCOC(=O)/C=N/N(CC1CC1)C(=O)OC(C)(C)C]

E-Ethyl 2-(2-t-butoxycarbonyl-2-(cyclopropylmethyl)hydrazono)acetate

60% sodium hydride (2.10 g, 52.5 mmol) was suspended in a mixed solvent of dry THF (50 ml) and dry DMF (50 ml), and (bromomethyl)cyclopropane (7.04 g, 52.1 mmol) was added, and ice-cooled. To the mixture was slowly added Compound (X-1) (10.2 g, 47.4 mmol). The resulting mixture was stirred at 65° C. for 3.5 hours. After the reaction solution was cooled to room temperature, the reaction solution was diluted with water, and extracted with tert-butyl methyl ether 2 times. The combined organic layer was washed with water, dried over anhydrous magnesium sulfate, and concentrated under reduced pressure. The residue was purified by silica gel column chromatography (hexane:ethyl acetate=3:1) to give 9.38 g of E-ethyl 2-(2-t-butoxycarbonyl-2-(cyclopropylmethyl)hydrazono)acetate (yield: 73%) as oil.

$^1$H NMR ($CDCl_3$): δ ppm: 0.31-0.37 (2H, m), 0.48-0.55 (2H, m), 0.98-1.11 (1H, m), 1.36 (3H, t, J=7.1 Hz), 1.56 (9H, s), 3.74 (2H, d, J=6.8 Hz), 4.32 (2H, q, J=7.1 Hz), 7.32 (1H, s).

Reference Example 5-2

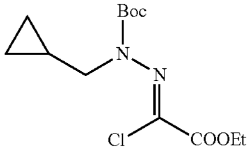 [SMILES: CCOC(=O)/C(Cl)=N/N(CC1CC1)C(=O)OC(C)(C)C]

Z-Ethyl 2-chloro-2-(2-t-butoxycarbonyl-2-(cyclopropylmethyl)hydrazono)acetate

The procedure was performed according to Reference Example 1-2 to give Z-ethyl 2-chloro-2-(2-t-butoxycarbonyl-2-(cyclopropylmethyl)hydrazono)acetate as oil (yield: 70%).

$^1$H NMR ($CDCl_3$): δ ppm: 0.28-0.34 (2H, m), 0.47-0.53 (2H, m), 1.07-1.18 (1H, m), 1.39 (3H, t, J=7.2 Hz), 1.52 (9H, s), 3.83 (2H, d, J=7.0 Hz), 4.38 (2H, q, J=7.2 Hz).

Reference Example 5-3

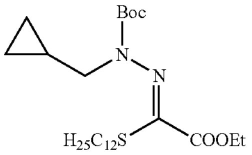

Z-Ethyl 2-(2-t-butoxycarbonyl-2-(cyclopropylmethyl)hydrazono)-2-(dodecylthio)acetate The procedure was performed according to Reference Example 3-1 to give Z-ethyl 2-(2-t-butoxycarbonyl-2-(cyclopropylmethyl)hydrazono)-2-(dodecylthio)acetate as an oil (yield: 87%).

$^1$H NMR ($CDCl_3$): δ ppm: 0.23-0.29 (2H, m), 0.43-0.50 (2H, m), 0.88 (3H, t, J=6.9 Hz), 1.02-1.12 (1H, m), 1.21-1.64 (23H, m), 1.49 (9H, s), 2.85 (2H, t, J=7.5 Hz), 3.49 (2H, d, J=7.2 Hz), 4.37 (2H, q, J=7.1 Hz).

Reference Example 5-4

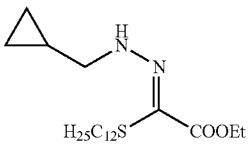

Ethyl 2-(2-(cyclopropylmethyl)hydrazono)-2-(dodecylthio)acetate

To a solution of Z-ethyl 2-(2-t-butoxycarbonyl-2-(cyclopropylmethyl)hydrazono)-2-(dodecylthio)acetate (10.0 g, 21.3 mmol) in dioxane (10 ml) was added a 4M solution of hydrogen chloride in dioxane (10 ml), and stirred at room temperature for 2 hours. The reaction solution was added to saturated aqueous sodium hydrogen carbonate solution, and extracted with tert-butyl methyl ether 2 times. The combined organic layer was washed with saturated brine, dried over anhydrous magnesium sulfate, and concentrated under reduced pressure. The residue was purified by silica gel column chromatography (hexane:ethyl acetate=9:1) to give 1.26 g of E-ethyl 2-(2-(cyclopropylmethyl)hydrazono)-2-(dodecylthio)acetate (yield: 16%) and 1.34 g of Z-ethyl 2-(2-(cyclopropylmethyl)hydrazono)-2-(dodecylthio)acetate (yield: 17%).

$^1$H NMR ($CDCl_3$) for E isomer: δ ppm: 0.20-0.27 (2H, m), 0.49-0.56 (2H, m), 0.88 (3H, t, J=6.9 Hz), 0.98-1.09 (1H, m), 1.18-1.44 (21H, m), 1.56-1.67 (2H, m), 2.78 (2H, t, J=7.4 Hz), 3.31 (2H, dd, J=7.0, 4.6 Hz), 4.26 (2H, q, J=7.2 Hz), 10.26 (1H, t, J=4.6 Hz).

$^1$H NMR ($CDCl_3$) for Z isomer: δ ppm: 0.22-0.28 (2H, m), 0.52-0.59 (2H, m), 0.88 (3H, t, J=6.7 Hz), 1.00-1.11 (1H, m), 1.18-1.40 (21H, m), 1.48-1.59 (2H, m), 2.78 (2H, t, J=7.3 Hz), 3.44 (2H, dd, J=7.1, 4.7 Hz), 4.32 (2H, q, J=7.1 Hz), 7.58 (1H, t, J=4.7 Hz).

Reference Example 5-5

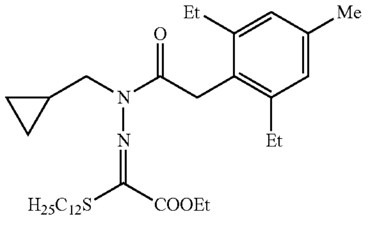

Ethyl 2-[2-(2,6-diethyl-4-methylphenyl)acetyl-2-(cyclopropylmethyl)hydrazono]-2-(dodecylthio)acetate The procedure was performed according to Reference Example 2-7 to give ethyl 2-[2-(2,6-diethyl-4-methylphenyl)acetyl-2-(cyclopropylmethyl)hydrazono]-2-(dodecylthio)acetate (ratio of geometric isomers=about 5:1) as oil (yield: 84%).

$^1$H NMR ($CDCl_3$) for main product: δ ppm: 0.25-0.31 (2H, m), 0.43-0.50 (2H, m), 0.88 (3H, t, J=6.7 Hz), 1.12-1.20 (7H, m), 1.22-1.34 (19H, m), 1.36-1.44 (2H, m), 1.60-1.70 (2H, m), 2.29 (3H, s), 2.55 (4H, q, J=7.6 Hz), 2.96 (2H, t, J=7.3 Hz), 3.76 (2H, s), 3.78 (2H, d, J=7.1 Hz), 4.40 (2H, q, J=7.2 Hz), 6.87 (2H, s).

Reference Example 6

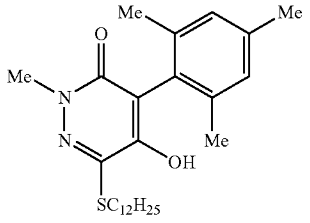

4-(2,4,6-trimethylphenyl)-6-dodecylthio-5-hydroxy-2-methyl-3(2H)-pyridazinone

The procedure was performed by the method similar to Production Example 12 using ethyl 2-[2-(2,4,6-trimethylphenyl)acetyl-2-methylhydrazono]-2-(dodecylthio)acetate as a starting material to give 4-(2,4,6-trimethylphenyl)-6-dodecylthio-5-hydroxy-2-methyl-3(2H)-pyridazinone (yield: 17%).

$^1$H NMR ($CDCl_3$): δ ppm: 0.88 (3H, t, J=6.8 Hz), 1.19-1.38 (16H, m), 1.41-1.50 (2H, m), 1.69-1.79 (2H, m), 2.07 (6H, s), 2.31 (3H, s), 3.06 (2H, t, J=7.3 Hz), 3.79 (3H, s), 5.82 (1H, brs), 6.98 (2H, s).

The following compounds were produced by the method similar to Reference Example 6.

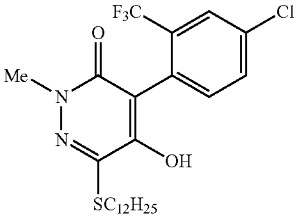

4-(2-trifluoromethyl-4-chlorophenyl)-6-dodecylthio-5-hydroxy-2-methyl-3(2H)-pyridazinone $^1$H NMR ($CDCl_3$): δ ppm: 0.88 (3H, t, J=6.8 Hz), 1.19-1.35 (16H, m), 1.38-1.48 (2H, m), 1.63-1.75 (2H, m), 2.99 (2H, t, J=7.3 Hz), 3.77 (3H, s), 7.20-7.24 (1H, m), 7.59-7.62 (1H, m), 7.76-7.78 (1H, m).

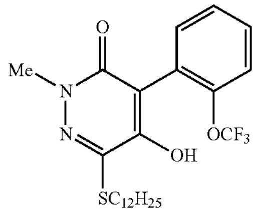

4-(2-trifluoromethoxyphenyl)-6-dodecylthio-5-hydroxy-2-methyl-3(2H)-pyridazinone $^1$H NMR ($CDCl_3$): δ ppm: 0.88 (3H, t, J=6.7 Hz), 1.21-1.36 (16H, m), 1.37-1.48 (2H, m), 1.65-1.75 (2H, m), 3.00 (2H, t, J=7.3 Hz), 3.80 (3H, s), 7.36-7.43 (3H, m), 7.45-7.51 (1H, m).

Reference Example 7

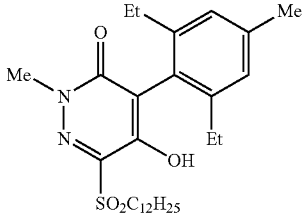

Production of 4-(2,6-diethyl-4-methylphenyl)-6-dodecylsulfonyl-5-hydroxy-2-methyl-3(2H)-pyridazinone To a solution of 4-(2,6-diethyl-4-methylphenyl)-6-dodecylthio-5-hydroxy-2-methyl-3(2H)-pyridazinone (4.0 g, 8.46 mmol) in DMF (20 ml) was added a solution of sodium tungstate dihydrate (279 mg, 0.846 mmol) in water (10 ml). To the solution was slowly added 30% aqueous hydrogen peroxide solution (2.87 g, 25.3 mmol) at 60° C. After the addition was complete, the mixture was stirred for 1 hour, and cooled to room temperature. To the reaction solution was added 1M aqueous sodium hydrogen sulfite solution (9 ml), and stirred for 5 minutes. To the solution was added 2N hydrochloric acid (10 ml), and extracted with ethyl acetate 2 times. The combined organic layer was washed with water 2 times, washed with saturated brine, dried over anhydrous magnesium sulfate, and concentrated under reduced pressure to give 4.27 g of 4-(2,6-diethyl-4-methylphenyl)-6-dodecylsulfonyl-5-hydroxy-2-methyl-3(2H)-pyridazinone (yield: 100%) as oil.

$^1$H NMR ($CDCl_3$): δ ppm: 0.88 (3H, t, J=6.8 Hz), 1.09 (6H, t, J=7.6 Hz), 1.20-1.37 (16H, m), 1.40-1.50 (2H, m), 1.77-1.89 (2H, m), 2.25-2.42 (7H, m), 3.38-3.46 (2H, m), 3.90 (3H, s), 7.00 (2H, s), 8.90 (1H, brs).

The following compounds were produced by the method similar to Reference Example 7.

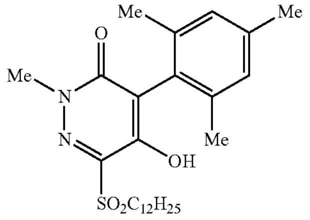

4-(2,4,6-trimethylphenyl)-6-dodecylsulfonyl-5-hydroxy-2-methyl-3(2H)-pyridazinone $^1$H NMR ($CDCl_3$): δ ppm: 0.88 (3H, t, J=6.8 Hz), 1.19-1.36 (16H, m), 1.40-1.50 (2H, m), 1.79-1.89 (2H, m), 2.07 (6H, s), 2.31 (3H, s), 3.37-3.44 (2H, m), 3.90 (3H, s), 6.95 (2H, s).

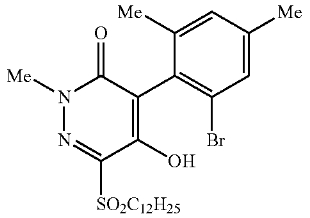

4-(2-bromo-4,6-dimethylphenyl)-6-dodecylsulfonyl-5-hydroxy-2-methyl-3(2H)-pyridazinone $^1$H NMR ($CDCl_3$): δ ppm: 0.88 (3H, t, J=6.8 Hz), 1.20-1.35 (16H, m), 1.38-1.52 (2H, m), 1.75-1.92 (2H, m), 2.13 (3H, s), 2.32 (3H, s), 3.33-3.47 (2H, m), 3.91 (3H, s), 7.06 (1H, s), 7.34 (1H, s).

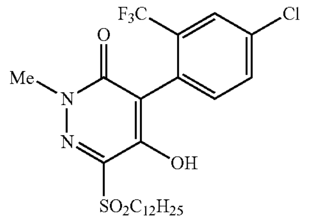

4-(2-trifluoromethyl-4-chlorophenyl)-6-dodecylsulfonyl-5-hydroxy-2-methyl-3(2H)-pyridazinone $^1$H NMR ($CDCl_3$): δ ppm: 0.88 (3H, t, J=6.8 Hz), 1.17-1.51 (16H, m), 1.40-1.52 (2H, m), 1.72-1.94 (2H, m), 3.30-3.47 (2H, m), 3.89 (3H, s), 7.18-7.23 (1H, m), 7.58-7.65 (1H, m), 7.74-7.80 (1H, m).

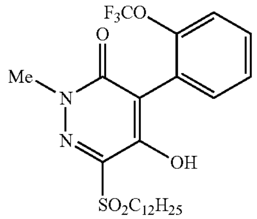

4-(2-trifluoromethoxyphenyl)-6-dodecylsulfonyl-5-hydroxy-2-methyl-3(2H)-pyridazinone $^1$H NMR ($CDCl_3$): δ ppm: 0.84-0.91 (3H, m), 1.16-1.50 (16H, m), 1.39-1.51 (2H, m), 1.74-1.94 (2H, m), 3.31-3.47 (2H, m), 3.90 (3H, s), 7.32-7.41 (3H, m), 7.43-7.51 (1H, m).

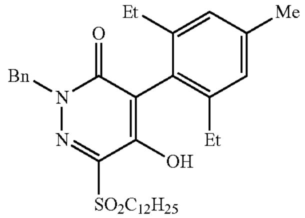

4-(2,6-diethyl-4-methylphenyl)-6-dodecylsulfonyl-5-hydroxy-2-benzyl-3(2H)-pyridazinone $^1$H NMR ($CDCl_3$): δ ppm: 0.89 (3H, t, J=6.9 Hz), 1.02 (6H, t, J=7.6 Hz), 1.16-1.38 (16H, m), 1.65-1.75 (2H, m), 2.23-2.36 (5H, m), 2.61 (2H, t, J=7.6 Hz), 3.30-3.37 (2H, m), 5.41 (2H, s), 6.90 (1H, s), 6.98 (2H, s), 7.29-7.36 (3H, m), 7.38-7.43 (2H, m).

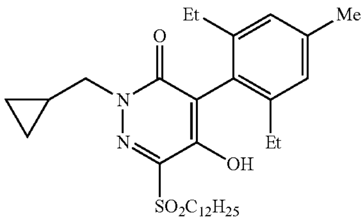

4-(2,6-diethyl-4-methylphenyl)-6-dodecylsulfonyl-5-hydroxy-2-cyclopropylmethyl-3(2H)-pyridazinone $^1$H NMR ($CDCl_3$): δ ppm: 0.42-0.47 (2H, m), 0.54-0.60 (2H, m), 0.88 (3H, t, J=6.8 Hz), 1.09 (6H, t, J=7.6 Hz), 1.21-1.49 (19H, m), 1.78-1.88 (2H, m), 2.27-2.42 (7H, m), 3.38-3.44 (2H, m), 4.14 (2H, d, J=7.3 Hz), 7.00 (2H, s), 8.77 (1H, br s).

Reference Example 8

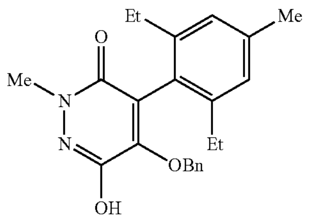

Production of 4-(2,6-diethyl-4-methylphenyl)-6-hydroxy-5-benzyloxy-2-methyl-3(2H)-pyridazinone To a solution of Compound (I-3-4) (500 mg, 1.13 mmol) in 1,3-dimethylimidazolidinone (5 ml) was added 2N aqueous sodium hydroxide solution (2.3 ml), and stirred at 70° C. for 4 hours. After the reaction solution was cooled to room temperature, to the reaction solution was added 2N hydrochloric acid (5 ml), and extracted with tert-butyl methyl ether 2 times. The combined organic layer was washed with water 2 times, washed with saturated brine, dried over anhydrous magnesium sulfate, and concentrated under reduced pressure. The residue was purified by silica gel column chromatography (hexane:ethyl acetate=1:1) to give 309 mg of 4-(2,6-diethyl-4-methylphenyl)-6-hydroxy-5-benzyloxy-2-methyl-3(2H)-pyridazinone (yield: 72%) as solid.

$^{1}$H NMR ($CDCl_3$): δ ppm: 1.14 (6H, t, J=7.6 Hz), 2.29-2.52 (7H, m), 3.67 (3H, s), 4.61 (2H, s), 6.91 (1H, br s), 6.98 (2H, s), 7.04-7.09 (2H, m), 7.27-7.33 (3H, m).

Reference Example 9

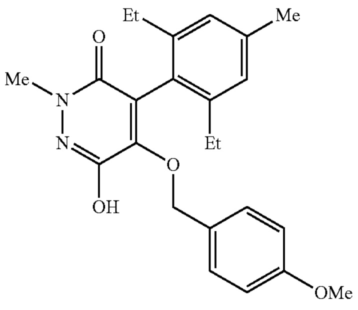 [SMILES: CCc1cc(C)cc(CC)c1-c1c(OCc2ccc(OC)cc2)c(O)nn(C)c1=O]

Production of 4-(2,6-diethyl-4-methylphenyl)-6-hydroxy-5-(4-methoxybenzyl)oxy-2-methyl-3(2H)-pyridazinone Reference Example 9-1

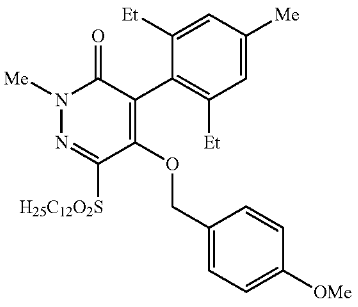

The procedure was performed by the method similar to Production Example 21 using 4-(2,6-diethyl-4-methylphenyl)-6-dodecylsulfonyl-5-hydroxy-2-methyl-3(2H)-pyridazinone and 4-methoxybenzyl chloride as a starting material to give 4-(2,6-diethyl-4-methylphenyl)-6-dodecylsulfonyl-5-(4-methoxybenzyl)oxy-2-methyl-3(2H)-pyridazinone (yield: 57%).

$^{1}$H NMR ($CDCl_3$): δ ppm: 0.88 (3H, t, J=6.8 Hz), 1.14 (6H, t, J=7.5 Hz), 1.17-1.35 (18H, m), 1.67-1.78 (2H, m), 2.30-2.49 (7H, m), 3.21-3.30 (2H, m), 3.78 (3H, s), 3.90 (3H, s), 4.48 (2H, s), 6.79 (2H, d, J=8.5 Hz), 6.98 (2H, d, J=8.5 Hz), 7.05 (2H, s).

Reference Example 9-2

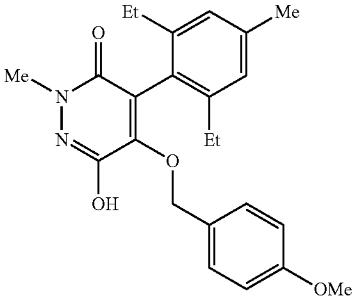 [SMILES: CCc1cc(C)cc(CC)c1-c1c(OCc2ccc(OC)cc2)c(O)nn(C)c1=O]

4-(2,6-diethyl-4-methylphenyl)-6-hydroxy-5-(4-methoxybenzyl)oxy-2-methyl-3(2H)-pyridazinone The procedure was performed by the method similar to Reference Example 8 to give 4-(2,6-diethyl-4-methylphenyl)-6-hydroxy-5-(4-methoxybenzyl)oxy-2-methyl-3(2H)-pyridazinone (yield: 15%).

$^1H$ NMR ($CDCl_3$): δ ppm: 1.15 (6H, t, J=7.6 Hz), 2.30-2.40 (5H, m), 2.41-2.52 (2H, m), 3.67 (3H, s), 3.79 (3H, s), 4.53 (2H, s), 6.81 (2H, d, J=8.8 Hz), 6.99 (2H, s), 6.99 (2H, d, J=8.8 Hz).

Reference Example 10

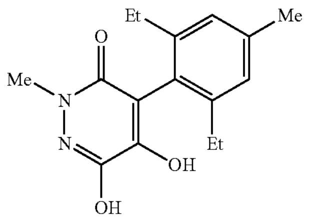

Production of 4-(2,6-diethyl-4-methylphenyl)-5,6-dihydroxy-2-methyl-3(2H)-pyridazinone To a mixture of Compound (I-4-3) (660 mg, 2.08 mmol) and toluene (10 ml) was added aluminum chloride (832 mg, 6.34 mmol). The mixture was refluxed for 30 minutes. After the reaction solution was cooled to room temperature, 2N hydrochloric acid was added, and extracted with ethyl acetate. The organic layer was washed with saturated brine, dried over anhydrous magnesium sulfate, and concentrated under reduced pressure. The residue was purified by ODS silica gel column chromatography (methanol:0.5% aqueous formic acid solution=60:40) to give 200 mg of 4-(2,6-diethyl-4-methylphenyl)-5,6-dihydroxy-2-methyl-3(2H)-pyridazinone (yield: 33%) as solid.

$^1H$ NMR ($CDCl_3$): δ ppm: 1.05 (6H, t, J=7.6 Hz), 2.22-2.39 (7H, m), 3.60 (3H, s), 5.59 (1H, br s), 6.95 (2H, s), 7.93 (1H, s).

Reference Example 11

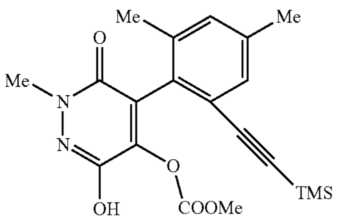 [SMILES: COC(=O)Oc1c(O)nn(C)c(=O)c1-c1c(C)cc(C)cc1C#C[Si](C)(C)C]

Production of 4-(2-trimethylsilylethinyl-4,6-dimethylphenyl)-6-methoxy-5-methoxycarbonyloxy-2-methyl-3(2H)-pyridazinone The procedure was performed by the method similar to Production Example 14 using tributyl(trimethylsilylethinyl) tin as a starting material to give 4-(2-trimethylsilylethinyl-4,6-dimethylphenyl)-6-methoxy-5-methoxycarbonyloxy-2-methyl-3(2H)-pyridazinone (yield: 74%).

$^1H$ NMR ($CDCl_3$): δ ppm: 0.07 (9H, s), 2.12 (3H, s), 2.29 (3H, s), 3.73 (3H, s), 3.77 (3H, s), 3.91 (3H, s), 7.01 (1H, s), 7.19 (1H, s).

Reference Example 12

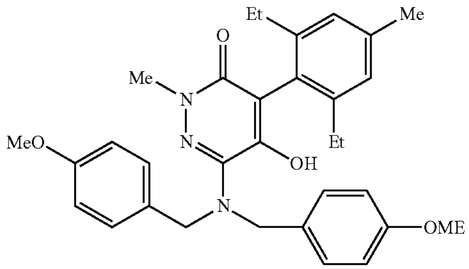

Production of 4-(2,6-diethyl-4-methylphenyl)-6-bis(4-methoxybenzyl)amino-5-hydroxy-2-methyl-3(2H)-pyridazinone Reference Example 12-1

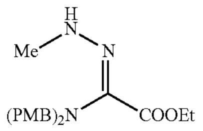

Z-Ethyl 2-(2-methylhydrazono)-2-(bis(4-methoxybenzyl)amino)acetate

To a solution of Compound (XVII-1) (17.6 g, 107 mmol) and bis(4-methoxybenzyl)amine (12.3 g, 47.7 mmol) in tert-butyl methyl ether (100 ml) was slowly added DBU (16.8 g, 110 mmol) under ice-cooling. The solution was stirred at room temperature for 2 hours. The reaction solution was washed with water, then saturated brine, dried over anhydrous magnesium sulfate, and concentrated under reduced pressure to give 18.3 g of Z-ethyl 2-(2-methylhydrazono)-2-(bis(4-methoxybenzyl)amino)acetate (yield: 99%) as oil.

$^1H$ NMR ($CDCl_3$): δ ppm: 1.32 (3H, t, J=7.2 Hz), 2.87 (3H, d, J=4.1 Hz), 3.78 (6H, s), 3.94 (4H, s), 4.26 (2H, q, J=7.2 Hz), 6.81 (4H, d, J=8.5 Hz), 7.04 (1H, q, J=4.1 Hz), 7.15 (4H, d, J=8.5 Hz).

Reference Example 12-2

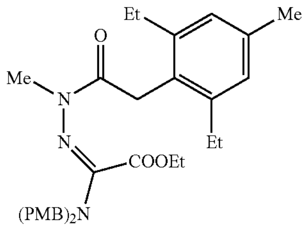

Ethyl 2-[2-(2,6-diethyl-4-methylphenyl)acetyl-2-methylhydrazono]-2-(bis(4-methoxybenzyl)amino)acetate The procedure was performed according to Reference Example 2-7 to give ethyl 2-[2-(2,6-diethyl-4-methylphenyl)acetyl-2-methylhydrazono]-2-(bis(4-methoxybenzyl)amino)acetate as oil (yield: 100%).

$^1$H NMR ($CDCl_3$): δ ppm: 1.18 (6H, t, J=7.6 Hz), 1.32 (3H, t, J=7.2 Hz), 2.29 (3H, s), 2.55 (4H, q, J=7.6 Hz), 3.15 (3H, s), 3.71 (2H, s), 3.79 (6H, s), 4.28-4.42 (6H, m), 6.87 (4H, d, J=8.8 Hz), 6.87 (2H, s), 7.19 (4H, d, J=8.8 Hz).

Reference Example 12-3

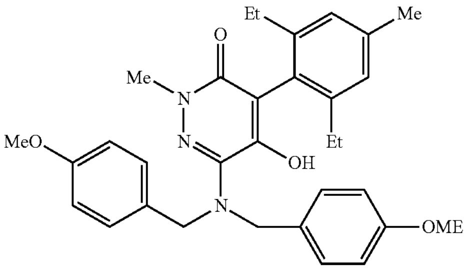

4-(2,6-diethyl-4-methylphenyl)-6-bis(4-methoxybenzyl)amino-5-hydroxy-2-methyl-3(2H)-pyridazinone The procedure was performed by the method similar to Production Example 12 to give 4-(2,6-diethyl-4-methylphenyl)-6-bis(4-methoxybenzyl)amino-5-hydroxy-2-methyl-3(2H)-pyridazinone (yield: 80%).

$^1$H NMR ($CDCl_3$): δ ppm: 0.89 (6H, t, J=7.6 Hz), 1.93-2.12 (4H, m), 2.28 (3H, s), 3.74 (3H, s), 3.77 (6H, s), 4.17 (4H, s), 6.51 (1H, s), 6.79 (4H, d, J=8.5 Hz), 6.88 (2H, s), 7.15 (4H, d, J=8.5 Hz).

Reference Example 13

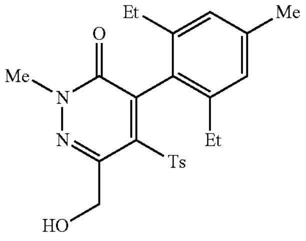

Production of 4-(2,6-diethyl-4-methylphenyl)-6-hydroxymethyl-5-(4-methylphenylsulfonyl)-2-methyl-3(2H)-pyridazinone Reference Example 13-1

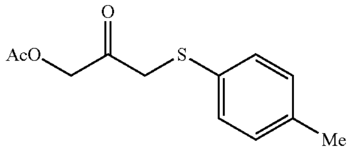 [SMILES: CC(=O)OCC(=O)CSc1ccc(C)cc1]

1-acetoxy-3-(4-methylphenylthio)acetone

To a solution of 1-acetoxy-3-chloroacetone (5.0 g, 33.2 mmol) and 4-methylthiophenol (4.12 g, 33.2 mmol) in tert-butyl methyl ether (100 ml) was slowly added triethylamine (5.1 ml, 36.6 mmol) under ice-cooling. The solution was stirred at room temperature for 30 minutes. The reaction solution was washed with water, saturated aqueous sodium hydrogen carbonate solution, then saturated brine, dried over anhydrous magnesium sulfate, and concentrated under reduced pressure. The residue was purified by silica gel column chromatography (hexane:ethyl acetate=7:3) to give 7.72 g of 1-acetoxy-3-(4-methylphenylthio)acetone (yield: 97%) as oil.

$^1$H NMR ($CDCl_3$): δ ppm: 2.14 (3H, s), 2.32 (3H, s), 3.65 (2H, s), 4.84 (2H, s), 7.12 (2H, d, J=8.1 Hz), 7.28 (2H, d, J=8.1 Hz).

Reference Example 13-2

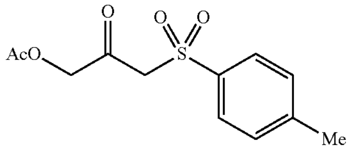 [SMILES: CC(=O)OCC(=O)CS(=O)(=O)c1ccc(C)cc1]

1-acetoxy-3-(4-methylphenylsulfonyl)acetone

To a solution of 1-acetoxy-3-(4-methylphenylthio)acetone (22.2 g, 93.5 mmol) in chloroform (200 ml) was slowly added 70% m-chloroperbenzoic acid (50.7 g, 205 mmol) under ice-cooling. The reaction solution was stirred at room temperature for 1 hour, and concentrated under reduced pressure. The residue was dissolved in ethyl acetate, washed with aqueous sodium hydrogen sulfite solution, saturated aqueous sodium hydrogen carbonate solution, then saturated brine, dried over anhydrous magnesium sulfate, concentrated under reduced pressure to give 22.7 g of 1-acetoxy-3-(4-methylphenylsulfonyl)acetone (yield: 90%) as solid.

$^1$H NMR ($CDCl_3$): δ ppm: 2.16 (3H, s), 2.46 (3H, s), 4.19 (2H, s), 4.92 (2H, s), 7.38 (2H, d, J=8.2 Hz), 7.77 (2H, d, J=8.2 Hz).

Reference Example 13-3

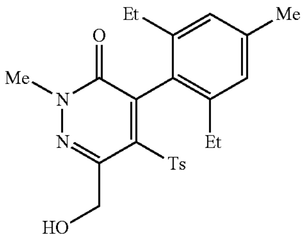

1-acetoxy-3-(4-methylphenylsulfonyl)acetone (17.5 g, 64.7 mmol) was dissolved in THF (60 ml), and ice-cooled. To the solution was slowly added methylhydrazine (2.98 g, 64.7 mmol) dropwise. After ice-bath was removed, the mixture was stirred at room temperature overnight. To the reaction solution was added triethylamine (10.8 ml, 77.5 mmol), and then a solution of (2,6-diethyl-4-methylphenyl)glyoxyl chloride (15.4 g, 64.7 mmol) in THF. (30 ml) was slowly added. The reaction mixture was stirred at room temperature for 3 hours, then stirred under reflux for 1.5 hours. After the reaction solution was cooled to room temperature, the reaction solution was diluted with water, and extracted with tert-butyl methyl ether. The organic layer was washed with saturated aqueous sodium hydrogen carbonate solution, then saturated brine, dried over anhydrous magnesium sulfate, and concentrated under reduced pressure. The residue was dissolved in methanol (70 ml), and ice-cooled. To the solution was added lithium hydroxide monohydrate (8.14 g, 194 mmol), and stirred at 0° C. for 5 hours. To the reaction solution was added 2N hydrochloric acid (150 ml), concentrated under reduced pressure to remove methanol. The residue was extracted with ethyl acetate 2 times. The combined organic layer was washed with saturated aqueous sodium hydrogen carbonate solution, then saturated brine, dried over anhydrous magnesium sulfate, and concentrated under reduced pressure. The residue was purified by silica gel column chromatography (hexane:ethyl acetate=1:1) to give 2.58 g of 4-(2,6-diethyl-4-methylphenyl)-6-hydroxymethyl-5-(4-methylphenylsulfonyl)-2-methyl-3(2H)-pyridazinone (yield: 9%) as solid.

$^1$H NMR ($CDCl_3$): δ ppm: 0.95 (6H, t, J=7.5 Hz), 1.94 (4H, q, J=7.5 Hz), 2.32 (3H, s), 2.39 (3H, s), 3.73 (1H, t, J=7.0 Hz), 3.82 (3H, s), 5.06 (2H, d, J=7.0 Hz), 6.71 (2H, s), 7.04 (2H, d, J=8.3 Hz), 7.20 (2H, d, J=8.3 Hz).

The following compound was produced by the method similar to Reference Example 13.

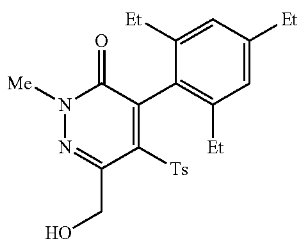 [SMILES: CCc1cc(CC)c(-c2c(S(=O)(=O)c3ccc(C)cc3)c(CO)nn(C)c2=O)c(CC)c1]

4-(2,4,6-triethylphenyl)-6-hydroxymethyl-5-(4-methylphenylsulfonyl)-2-methyl-3(2H)-pyridazinone

$^1$H NMR ($CDCl_3$): δ ppm: 0.95 (6H, t, J=7.5 Hz), 1.27 (3H, t, J=7.6 Hz), 1.88-1.98 (4H, m), 2.38 (3H, s), 2.61 (2H, q, J=7.6 Hz), 3.74 (1H, t, J=6.6 Hz), 3.82 (3H, s), 5.07 (2H, d, J=6.6 Hz), 6.72 (2H, s), 7.02 (2H, d, J=8.5 Hz), 7.17 (2H, d, J=8.5 Hz).

Reference Example 14

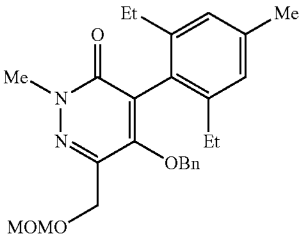

Production of 4-(2,6-diethyl-4-methylphenyl)-6-methoxymethoxymethyl-5-benzyloxy-2-methyl-3 (2H)-pyridazinone Reference Example 14-1

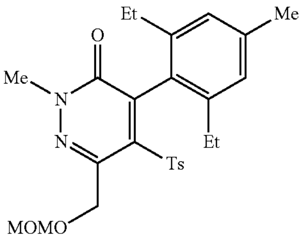

4-(2,6-diethyl-4-methylphenyl)-6-methoxymethoxymethyl-5-(4-methylphenylsulfonyl)-2-methyl-3(2H)-pyridazinone To a solution of 4-(2,6-diethyl-4-methylphenyl)-6-hydroxymethyl-5-(4-methylphenylsulfonyl)-2-methyl-3(2H)-pyridazinone (2.40 g, 5.45 mmol) and diisopropylethylamine (10 ml, 57.4 mmol) in THF (20 ml) was added chloromethyl methyl ether (2.4 ml, 31.6 mmol), and refluxed for 4 hours. After the reaction solution was cooled to room temperature, to the reaction solution was added saturated aqueous sodium hydrogen carbonate solution, and extracted with ethyl acetate 2 times. The combined organic layer was washed with saturated brine, dried over anhydrous magnesium sulfate, and concentrated under reduced pressure. The residue was purified by silica gel column chromatography (hexane:ethyl acetate=2:1) to give 2.11 g of 4-(2,6-diethyl-4-methylphenyl)-6-methoxymethoxymethyl-5-(4-methylphenylsulfonyl)-2-methyl-3(2H)-pyridazinone (yield: 80%) as solid.

$^1$H NMR ($CDCl_3$): δ ppm: 0.93 (6H, t, J=7.6 Hz), 1.82-1.95 (4H, m), 2.33 (3H, s), 2.39 (3H, s), 3.50 (3H, s), 3.82 (3H, s), 4.87 (2H, s), 5.10 (2H, s), 6.73 (2H, s), 7.04 (2H, d, J=8.3 Hz), 7.25 (2H, d, J=8.3 Hz).

Reference Example 14-2

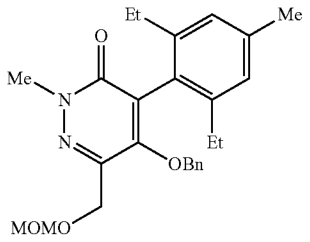

4-(2,6-diethyl-4-methylphenyl)-6-methoxymethoxymethyl-5-benzyloxy-2-methyl-3(2H)-pyridazinone To a solution of 4-(2,6-diethyl-4-methylphenyl)-6-methoxymethoxymethyl-5-(4-methylphenylsulfonyl)-2-methyl-3(2H)-pyridazinone (2.38 g, 4.91 mmol) and benzylalcohol (797 mg, 7.37 mmol) in dry DMF (10 ml) was added 60% sodium hydride (294 mg, 7.35 mmol) at 5° C. The reaction solution was stirred at 0° C. for 1 hour. The reaction solution was diluted with water, and extracted with tert-butyl methyl ether 2 times. The combined organic layer was washed with saturated brine, dried over anhydrous magnesium sulfate, and concentrated under reduced pressure. The residue was purified by silica gel column chromatography (hexane:ethyl acetate=2:1) to give 2.12 g of 4-(2,6-diethyl-4-methylphenyl)-6-methoxymethoxymethyl-5-benzyloxy-2-methyl-3(2H)-pyridazinone (yield: 99%) as oil.

$^1$H NMR ($CDCl_3$): δ ppm: 1.14 (6H, t, J=7.6 Hz), 2.32-2.53 (7H, m), 3.30 (3H, s), 3.79 (3H, s), 4.45 (2H, s), 4.51 (2H, s), 4.63 (2H, s), 6.99 (2H, s), 7.03-7.09 (2H, m), 7.24-7.33 (3H, m).

Reference Example 15

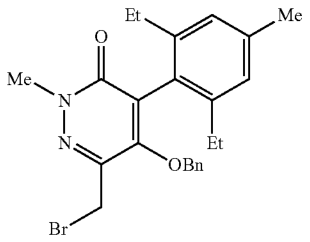

Production of 4-(2,6-diethyl-4-methylphenyl)-6-bromomethyl-5-benzyloxy-2-methyl-3(2H)-pyridazinone To a solution of Compound (I-29) (600 mg, 1.53 mmol) in THF (8 ml) was added a solution of phosphorus tribromide (166 mg, 0.613 mmol) in THF (0.5 ml) dropwise at 0° C. The reaction solution was stirred at 0° C. for 30 minutes. To the reaction solution was added saturated aqueous sodium hydrogen carbonate solution, and extracted with tert-butyl methyl ether 3 times. The combined organic layer was washed with saturated brine, dried over anhydrous magnesium sulfate, and concentrated under reduced pressure to give 681 g of 4-(2,6-diethyl-4-methylphenyl)-6-bromomethyl-5-benzyloxy-2-methyl-3(2H)-pyridazinone (yield: 97%) as oil.

$^1$H NMR ($CDCl_3$): δ ppm: 1.15 (6H, t, J=7.6 Hz), 2.32-2.54 (7H, m), 3.78 (3H, s), 4.42 (2H, s), 4.50 (2H, s), 7.00 (2H, s), 7.11-7.15 (2H, m), 7.28-7.32 (3H, m).

Reference Example 16

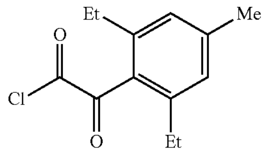 [SMILES: CCc1cc(C)cc(CC)c1C(=O)C(=O)Cl]

Production of (2,6-diethyl-4-methylphenyl)glyoxyl chloride

Reference Example 16-1

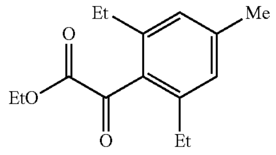 [SMILES: CCOC(=O)C(=O)c1c(CC)cc(C)cc1CC]

ethyl (2,6-diethyl-4-methylphenyl)glyoxylate

To a 3 L volume four-necked flask, magnesium (turnings, 35.31 g), tetrahydrofuran (anhydrous, 600 ml) were added under nitrogen atmosphere at room temperature. After the stirring was started, the mixture was heated to about 30° C. of the internal temperature, and then dibromoethane (25.4 g) was added dropwise over 20 minutes. The resulting mixture was stirred for 30 minutes, and heated to about 50° C. of the internal temperature. To the mixture was added a solution of 2,6-diethyl-4-methylbromobenzene (300.18 g) in tetrahydrofuran (150 ml) dropwise over 2 hours. The resulting mixture was stirred at 50° C. for 1 hour, and then diethyl oxalate (192.5 g) was added dropwise at about 0° C. over 15 minutes. The resulting mixture was stirred at room temperature for 2 hours. To the mixture was added 3.5 weight % of hydrochloric acid (1000 ml) and concentrated hydrochloric acid (60 ml) with cooling. Then, the organic layer was evaporated, and the aqueous layer was extracted with tert-butyl methyl ether. The organic layer was concentrated under reduced pressure to give 320.82 g of ethyl (2,6-diethyl-4-methylphenyl)glyoxylate.

$^1$H NMR ($CDCl_3$) δ ppm: 6.92 (2H, s), 4.36 (2H, q, J=7.1 Hz), 2.52 (4H, q, J=7.6 Hz), 2.34 (3H, s), 1.36 (3H, t, J=7.1 Hz), 1.16 (6H, t, J=7.6 Hz)

Reference Example 16-2

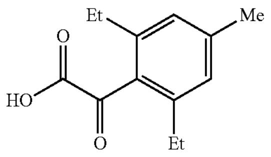 [SMILES: CCc1cc(C)cc(CC)c1C(=O)C(=O)O]

(2,6-diethyl-4-methylphenyl)glyoxylic acid

To a solution of ethyl (2,6-diethyl-4-methylphenyl)glyoxylate (320.82 g) in tetrahydrofuran (600 ml) was added 10.7 weight % of aqueous sodium hydroxide solution (900 ml) dropwise at 10° C. of the internal temperature over 2 hours. The resulting mixture was stirred at room temperature for 1 hour. Then, the organic layer was evaporated, and the aqueous layer was washed with tert-butyl methyl ether. To the aqueous layer was added concentrated hydrochloric acid (180 ml) dropwise, and extracted with tert-butyl methyl ether. The organic layer was concentrated under reduced pressure to give 166.55 g of (2,6-diethyl-4-methylphenyl)glyoxylic acid.

$^1$H NMR ($CDCl_3$) δ ppm: 6.95 (2H, s), 2.49 (4H, q, J=7.5 Hz), 2.35 (3H, s), 1.16 (6H, t, J=7.5 Hz)

Reference Example 16-3

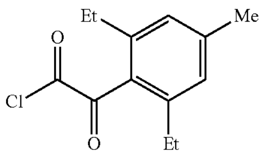 [SMILES: CCc1cc(C)cc(CC)c1C(=O)C(=O)Cl]

(2,6-diethyl-4-methylphenyl)glyoxyl chloride

To a solution of (2,6-diethyl-4-methylphenyl)glyoxylic acid (0.94 g) in toluene (anhydrous, 3.0 ml) was added dimethylformamide (anhydrous, 0.2 ml) under nitrogen atmosphere at room temperature. The mixture was heated to about 50° C. of the internal temperature, and then thionyl chloride (0.45 ml) was added. The resulting mixture was stirred at 50° C. for 2 hours, concentrated under reduced pressure to give 0.96 g of (2,6-diethyl-4-methylphenyl)glyoxyl chloride.

$^1$H NMR ($CDCl_3$) δ ppm: 6.96 (2H, s), 2.53 (4H, q, J=7.6 Hz), 2.38 (3H, s), 1.18 (6H, t, J=7.6 Hz).

Reference Example 17

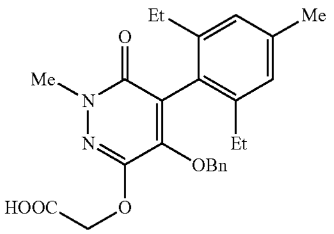 [SMILES: CCc1cc(C)cc(CC)c1-c1c(OCc2ccccc2)c(OCC(=O)O)nn(C)c1=O]

Production of (4-(2,6-Diethyl-4-methylphenyl)-5-benzyloxy-2-methyl-3(2H)-pyridazinon-6-yl)oxyacetic acid The procedure was performed by the method similar to Production Example 28 using Compound (I-8-7) as a starting material to give (4-(2,6-Diethyl-4-methylphenyl)-5-benzyloxy-2-methyl-3(2H)-pyridazinon-6-yl)oxyacetic acid (yield: 88%) as solid.

$^1$H NMR ($CDCl_3$): δ ppm: 1.08 (6H, t, J=7.6 Hz), 2.20-2.30 (2H, m), 2.32-2.43 (2H, m), 2.37 (3H, s), 3.66 (3H, s), 4.85 (2H, s), 4.87 (2H, s), 6.96 (2H, s), 7.00-7.04 (2H, m), 7.20-7.24 (3H, m).

Reference Example 18

Production of ethyl 2-[2-(2,6-diethyl-4-methylphenyl)acetyl-2-allylhydrazono]-2-(dodecylthio)acetate

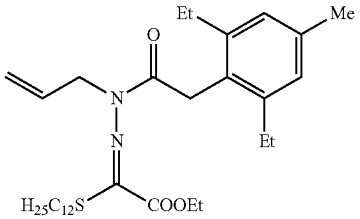

Reference Example 18-1

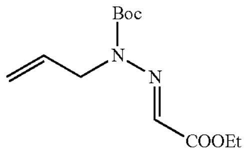 [SMILES: C=CCN(/N=C/C(=O)OCC)C(=O)OC(C)(C)C]

E-Ethyl 2-(2-t-butoxycarbonyl-2-allylhydrazono)acetate

The procedure was performed by the method similar to Reference Example 5-1 to give E-ethyl 2-(2-t-butoxycarbonyl-2-allylhydrazono)acetate (yield: 73%) as oil.

$^1H$ NMR ($CDCl_3$): δ ppm: 1.35 (3H, t, J=7.2 Hz), 1.56 (9H, s), 4.30 (2H, q, J=7.2 Hz), 4.44-4.50 (2H, m), 5.06-5.15 (1H, m), 5.19-5.27 (1H, m), 5.64-5.77 (1H, m), 7.03 (1H, s).

Reference Example 18-2

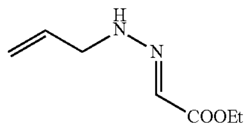

E-Ethyl 2-(2-allylhydrazono)acetate

To a solution of E-ethyl 2-(2-t-butoxycarbonyl-2-allylhydrazono)acetate (8.65 g, 33.7 mmol) in dichloromethane (60 ml) was added trifluoroacetic acid (15 ml) at 3° C. After being stirred at room temperature for 1 hour, concentrated in vacuo. The residue was added to a saturated aqueous sodium hydrogen carbonate solution (300 ml), and extracted with ethyl acetate. The combined organic layer was washed with saturated brine, dried over anhydrous magnesium sulfate, and concentrated under reduced pressure. The residue was purified by silica gel column chromatography (hexane:ethyl acetate=2:1) to give 1.87 g of E-ethyl 2-(2-allylhydrazono) acetate (yield 35%) as oil.

$^1H$ NMR ($CDCl_3$): δ ppm: 1.33 (3H, t, J=7.2 Hz), 3.89 (2H, t, J=5.1 Hz), 4.28 (2H, q, J=7.2 Hz), 5.25-5.34 (2H, m), 5.80-5.91 (1H, m), 6.51 (1H, br s), 6.76 (1H, s).

Reference Example 18-3

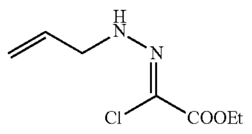

Z-Ethyl 2-chloro-2-(2-allylhydrazono)acetate

The procedure was performed by the method similar to Reference Example 1-2 to give Z-ethyl 2-chloro-2-(2-allylhydrazono)acetate (yield: 38%) as oil.

$^1H$ NMR ($CDCl_3$): δ ppm: 1.36 (3H, t, J=7.2 Hz), 4.11-4.17 (2H, m), 4.35 (2H, q, J=7.2 Hz), 5.19-5.29 (2H, m), 5.86-5.99 (1H, m), 6.51 (1H, brs).

Reference Example 18-4

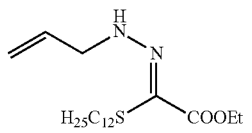

Ethyl 2-(2-allylhydrazono)-2-(dodecylthio)acetate

The procedure was performed by the method similar to Reference Example 3-1 to give ethyl 2-(2-allylhydrazono)-2-(dodecylthio)acetate (yield: 40%) as oil.

$^1H$ NMR ($CDCl_3$): δ ppm: 0.88 (3H, t, J=6.9 Hz), 1.17-1.42 (21H, m), 1.48-1.59 (2H, m), 2.79 (2H, t, J=7.4 Hz), 4.16-4.23 (2H, m), 4.32 (2H, q, J=7.1 Hz), 5.16-5.28 (2H, m), 5.86-5.99 (1H, m), 7.46 (1H, t, J=4.7 Hz).

Reference Example 18-5

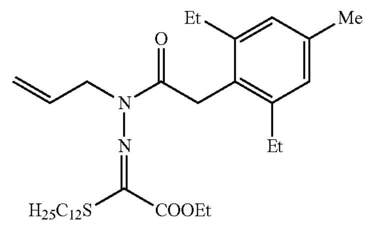

Ethyl 2-[2-(2,6-diethyl-4-methylphenyl)acetyl-2-allylhydrazono]-2-(dodecylthio)acetate The procedure was performed by the method similar to Reference Example 3-1 to give ethyl 2-[2-(2,6-diethyl-4-methylphenyl)acetyl-2-allylhydrazono]-2-(dodecylthio)acetate as an oily mixture of geometric isomers (yield: 81%).

$^1H$ NMR ($CDCl_3$) for main product: δ ppm: 0.88 (3H, t, J=6.8 Hz), 1.10-1.45 (27H, m), 1.57-1.69 (2H, m), 2.29 (3H, s), 2.54 (4H, q, J=7.6 Hz), 2.95 (2H, t, J=7.6 Hz), 3.82 (2H, s), 4.38 (2H, q, J=7.2 Hz), 4.57 (2H, d, J=5.3 Hz), 5.09-5.27 (2H, m), 5.77-5.93 (1H, m), 6.87 (2H, s).

Formulation Examples will be shown below.

Formulation Example 1

Wettable Powder

| | |
|---|---|
| Compound (I-1-1) | 50% by weight |
| Sodium lignin sulfonate | 5% by weight |
| Polyoxyethylenealkylether | 5% by weight |
| White carbon | 5% by weight |
| Clay | 35% by weight |

The above ingredients are mixed and ground to obtain a wettable powder.

In the same manner, each of Compound (I-1-2)-Compound (I-1-7), Compound (I-2-1)-Compound (I-2-3), Compound (I-3-1)-Compound (I-3-4), Compound (I-4-1)-Compound (I-4-6), Compound (I-5-1)-Compound (I-5-9), Compound (I-6-1), Compound (I-6-2), Compound (I-7-1)-Compound (I-7-4), Compound (I-8-1)-Compound (I-8-9), Compound (I-9-1)-Compound (I-9-10), Compound (I-10-1)-Compound (I-10-3), Compound (I-11), Compound (I-12-1)-Compound (I-12-4), Compound (I-13-1)-Compound (I-13-6), Compound (I-14)-Compound (I-20), Compound (I-21-1)-Compound (I-21-4), Compound (I-22), Compound (I-23), Compound (I-24-1), Compound (I-24-2), Compound (I-25-1), Compound (I-25-2), Compound (I-26-1), Compound (I-26-2), Compound (I-27-1), Compound (I-27-2), Compound (I-28-1), Compound (I-28-2), Compound (I-29)-Compound (I-32), Compound (I-33-1), Compound (I-35-1), Compound (I-35-2) and Compound (I-36) is used instead of Compound (I-1-1) to obtain a wettable powder of each compound.

Formulation Example 2

Granule

| | | |
|---|---|---|
| Compound (I-1-1) | 1.5% | by weight |
| Sodium lignin sulfonate | 2% | by weight |
| Talc | 40% | by weight |
| bentonite | 56.5% | by weight |

The above ingredients are mixed, kneaded with water, and then granulated and dried to obtain a granule.

In the same manner, each of Compound (I-1-2)-Compound (I-1-7), Compound (I-2-1)-Compound (I-2-3), Compound (I-3-1)-Compound (I-3-4), Compound (I-4-1)-Compound (I-4-6), Compound (I-5-1)-Compound (I-5-9), Compound (I-6-1), Compound (I-6-2), Compound (I-7-1)-Compound (I-7-4), Compound (I-8-1)-Compound (I-8-9), Compound (I-9-1)-Compound (I-9-10), Compound (I-10-1)-Compound (I-10-3), Compound (I-11), Compound (I-12-1)-Compound (I-12-4), Compound (I-13-1)-Compound (I-13-6), Compound (I-14)-Compound (I-20), Compound (I-21-1)-Compound (I-21-4), Compound (I-22), Compound (I-23), Compound (I-24-1), Compound (I-24-2), Compound (I-25-1), Compound (I-25-2), Compound (I-26-1), Compound (I-26-2), Compound (I-27-1), Compound (I-27-2), Compound (I-28-1), Compound (I-28-2), Compound (I-29)-Compound (I-32), Compound (I-33-1), Compound (I-35-1), Compound (I-35-2) and Compound (I-36) is used instead of Compound (I-1-1) to obtain a granule of each compound.

Formulation Example 3

Flowable Formulation

| | |
|---|---|
| Compound (I-1-1) | 10% by weight |
| Polyoxyethylene alkyl ether sulfate ammonium salt | 50% by weight |
| White carbon | 35% by weight |
| Water | 55% by weight |

The above ingredients are mixed and finely ground by a wet grinding method to obtain a flowable formulation.

In the same manner, each of Compound (I-1-2)-Compound (I-1-7), Compound (I-2-1)-Compound (I-2-3), Compound (I-3-1)-Compound (I-3-4), Compound (I-4-1)-Compound (I-4-6), Compound (I-5-1)-Compound (I-5-9), Compound (I-6-1), Compound (I-6-2), Compound (I-7-1)-Compound (I-7-4), Compound (I-8-1)-Compound (I-8-9), Compound (I-9-1)-Compound (I-9-10), Compound (I-10-1)-Compound (I-10-3), Compound (I-11), Compound (I-12-1)-Compound (I-12-4), Compound (I-13-1)-Compound (I-13-6), Compound (I-14)-Compound (I-20), Compound (I-21-1)-Compound (I-21-4), Compound (I-22), Compound (I-23), Compound (I-24-1), Compound (I-24-2), Compound (I-25-1), Compound (I-25-2), Compound (I-26-1), Compound (I-26-2), Compound (I-27-1), Compound (I-27-2), Compound (I-28-1), Compound (I-28-2), Compound (I-29)-Compound (I-32), Compound (I-33-1), Compound (I-35-1), Compound (I-35-2) and Compound (I-36) is used instead of Compound (I-1-1) to obtain a flowable formulation of each compound.

Test Example 1-1

Post-Emergence Treatment Test in Dry Field

A plastic cup with a diameter of 8 cm and a depth of 6.5 cm was filled with commercially available soil. Seeds of *Echinochloa crus-galli* were sowed in the cup, covered with soil about 0.5 cm thick and then grown in a greenhouse. When the plants were grown in the first to second leaf stage, a diluted liquid formulation containing a prescribed amount of Compound (I-1-1) was sprayed onto the whole plants uniformly. The diluted liquid formulation was prepared by dissolving a prescribed amount of Compound (I-1-1) in a 2% solution of Tween 20 (polyoxyethylene sorbitan fatty acid ester, MP Biomedicals, Inc.) in dimethylformamide and then diluting the solution with deionized water. After the treatment, the plants were grown in a greenhouse. Twenty days after treatment, the controlling effect of the compound on *Echinochloa crus*-galli was visually evaluated. The effect was rated in 11 levels, from 0 to 10 (0 represents “no effect”; 10 represents “complete death”; and a state of the plant t The other present compounds were similarly tested.

As a result, Compounds (I-1-1), (I-1-2), (I-1-3), (I-1-4), (I-1-5), (I-1-6), (I-1-7), (I-2-1), (I-2-2), (I-2-3), (I-3-3), (I-4-1), (I-4-2), (I-4-3), (I-4-4), (I-4-5), (I-4-6), (I-5-1), (I-5-2), (I-5-3), (I-5-4), (I-5-5), (I-5-6), (I-5-7), (I-5-8), (I-6-1), (I-6-2), (I-9-1), (I-9-2), (I-9-3), (I-9-4), (I-9-5), (I-9-6), (I-9-7), (I-9-9), (I-9-10), (I-10-1), (I-10-2), (I-10-3), (I-11), (I-12-2), (I-12-3), (I-13-2), (I-13-3), (I-13-4), (I-13-5), (I-13-6), (I-15), (I-16), (I-17), (I-18), (I-19), (I-20), (I-21-2), (I-21-3), (I-22), (I-23), (I-24-1), (I-24-2), (I-25-1), (I-26-1), (I-26-2), (I-27-1), (I-27-2), (I-28-1), (I-28-2), (I-31) and (I-33-1) showed an effect of 9 or more at a treatment amount of 1,000 g/10,000 $m^2$.

Test Example 1-2

Post-Emergence Treatment Test in Dry Field

A plastic cup with a diameter of 8 cm and a depth of 6.5 cm was filled with commercially available soil. Seeds of Galium aparine were sowed in the cup, covered with soil about 0.5 cm thick and then grown in a greenhouse. When the plants were grown in the first to second leaf stage, a diluted liquid formulation containing a prescribed amount of Compound (I-1-1) was sprayed onto the whole plants uniformly. The diluted liquid formulation was prepared by the method similar to that in Test Example 1-1. After the treatment, the plants were grown in a greenhouse. Twenty days after treatment, the controlling effect of the compound on Galium aparine was visually evaluated. The effect was rated in 11 levels, from 0 to 10 (0 represents “no effect”; 10 represents “complete death”; and a state of the plant t The other present compounds were similarly tested.

As a result, Compounds (I-1-1), (I-1-2), (I-1-3), (I-1-4), (I-1-5), (I-1-6), (I-1-7), (I-2-1), (I-2-2), (I-2-3), (I-4-1), (I-4-2), (I-4-5), (I-5-1), (I-5-2), (I-5-3), (I-5-4), (I-5-5), (I-5-6), (I-5-7), (I-6-1), (I-6-2), (I-13-2), (I-13-4), (I-13-5), (I-15), (I-16), (I-18), (I-19), (I-20), (I-23), (I-24-2), (I-26-1), (I-26-2), (I-27-1), (I-27-2), (I-28-1), (I-28-2), (I-31) showed an effect of 9 or more at a treatment amount of 1,000 g/10,000 $m^2$.

Test Example 2-1

Pre-Emergence Treatment Test in Dry Field

A plastic cup with a diameter of 8 cm and a depth of 6.5 cm was filled with commercially available soil. Seeds of *Lolium*

*multiflorum* were sowed in the cup, covered with soil about 0.5 cm thick. Then, a diluted liquid formulation containing a prescribed amount of Compound (I-1-1) was sprayed onto the soil surface uniformly. The diluted liquid formulation was prepared by the method similar to that in Test Example 1-1. After the treatment, the plants were grown in a greenhouse. Twenty days after treatment, the controlling effect of the compound on *Lolium multiflorum* was visually evaluated. The effect was rated in 11 levels, from 0 to 10 similarly to Test example 1-1.

The other present compounds were similarly tested.

As a result, Compounds (I-1-1), (I-1-3), (I-1-4), (I-1-5), (I-1-6), (I-1-7), (I-2-1), (I-2-2), (I-2-3), (I-3-3), (I-4-1), (I-4-2), (I-4-3), (I-4-4), (I-4-5), (I-4-6), (I-5-1), (I-5-2), (I-5-3), (I-5-4), (I-5-5), (I-5-6), (I-5-7), (I-5-8), (I-6-1), (I-6-2), (I-9-2), (I-9-3), (I-9-4), (I-9-5), (I-9-6), (I-9-7), (I-9-9), (I-9-10), (I-10-1), (I-10-2), (I-10-3), (I-12-2), (I-12-3), (I-13-1), (I-13-2), (I-13-3), (I-13-4), (I-13-5), (I-13-6), (I-15), (I-16), (I-17), (I-18), (I-19), (I-20), (I-22), (I-24-1), (I-24-2), (I-25-1), (I-28-2), (I-31) and (I-33-1) showed an effect of 9 or more at a treatment amount of 1,000 g/10,000 $m^2$.

INDUSTRIAL APPLICABILITY

The present compound has an activity of controlling weeds and an activity of controlling noxious arthropods.

The invention claimed is:

1. A pyridazinone compound of the formula (I):

(I)

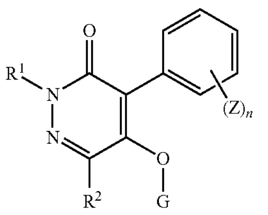

wherein:

$R^1$ represents hydrogen, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl)$C_{3-8}$ cycloalkyl group, a ($C_{3-8}$ cycloalkyl)$C_{1-6}$ alkyl group, a ($C_{3-8}$ cycloalkyl)$C_{3-8}$ cycloalkyl group, a ($C_{3-8}$ halocycloalkyl)$C_{1-6}$ alkyl group, a {($C_{1-6}$ alkyl)$C_{3-8}$ cycloalkyl}$C_{1-6}$ alkyl group, a ($C_{1-6}$ alkoxy)$C_{1-6}$ alkyl group, a ($C_{3-8}$ cycloalkoxy)$C_{1-6}$ alkyl group, a {($C_{1-6}$ alkoxy)$C_{1-6}$ alkoxy}$C_{1-6}$ alkyl group, a ($C_{1-6}$ alkylthio)$C_{1-6}$ alkyl group, a ($C_{1-6}$ alkylsulfinyl)$C_{1-6}$ alkyl group, a ($C_{1-6}$ alkylsulfonyl)$C_{1-6}$ alkyl group, a phenyl$C_{1-6}$ alkyl group optionally substituted with one or more substituents selected from Group A, a $C_{3-6}$ alkenyl group, a $C_{3-6}$ alkynyl group, or a tetrahydropyranyl group;

$R^2$ represents halogen, a cyano group, a nitro group, a $C_{1-6}$ alkoxy group, a $C_{1-6}$ haloalkoxy group, a $C_{1-6}$ alkylthio group, a $C_{1-6}$ alkylsulfinyl group, a $C_{1-6}$ alkylsulfonyl group, a $C_{1-6}$ haloalkylthio group, a $C_{1-6}$ haloalkylsulfinyl group, a $C_{1-6}$ haloalkylsulfonyl group, a $C_{3-8}$ cycloalkoxy group, a ($C_{3-8}$ cycloalkyl)$C_{1-6}$ alkoxy group, a $C_{1-6}$ alkylthio$C_{1-6}$ alkoxy group, a $C_{1-6}$ alkoxy$C_{1-6}$ alkoxy group, a $C_{3-6}$ alkenyloxy group, a $C_{3-6}$ alkynyloxy group, a cyano$C_{1-6}$ alkoxy group, a ($C_{1-6}$ alkoxycarbonyl)$C_{1-6}$ alkoxy group, a carbamoyl$C_{1-6}$ alkoxy group, a ($C_{1-6}$ alkylaminocarbonyl)$C_{1-6}$ alkoxy group, a (di$C_{1-6}$ alkylaminocarbonyl)$C_{1-6}$ alkoxy group, an amino group, a $C_{1-6}$ alkylamino group, a di($C_{1-6}$ alkyl)amino group, a formylamino group, a ($C_{1-6}$ alkyl)carbonylamino group, a hydroxy$C_{1-6}$ alkyl group, a ($C_{1-6}$ alkoxy)$C_{1-6}$ alkyl group, a ($C_{1-6}$ haloalkoxy)$C_{1-6}$ alkyl group, a ($C_{3-8}$ cycloalkoxy)$C_{1-6}$ alkyl group, a {($C_{3-8}$ cycloalkyl)$C_{1-6}$ alkoxy}$C_{1-6}$ alkyl group, a ($C_{1-6}$ alkylthio)$C_{1-6}$ alkyl group, a ($C_{1-6}$ haloalkylthio)$C_{1-6}$ alkyl group, a cyano$C_{1-6}$ alkyl group, a hydroxyimino$C_{1-6}$ alkyl group, a ($C_{1-6}$ alkoxyimino)$C_{1-6}$ alkyl group, a formyl group, or a ($C_{1-6}$ alkyl)carbonyl group;

G represents hydrogen or a group of the following formula:

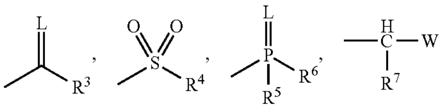

wherein, L represents oxygen or sulfur;

$R^3$ represents a $C_{1-6}$ alkyl group, a $C_{3-8}$ cycloalkyl group, a $C_{2-6}$alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl)$C_{1-6}$ alkoxy group, a di($C_{1-6}$ alkyl)amino group, a di($C_{3-6}$ alkenyl)amino group, a ($C_{1-6}$ alkyl)($C_{6-10}$ aryl)amino group, or a 5-6 membered heteroaryl group;

$R^4$ represents a $C_{1-6}$ alkyl group, a $C_{6-10}$ aryl group, or a di($C_{1-6}$ alkyl)amino group;

$R^5$ and $R^6$ may be same or different and represent independently a $C_{1-6}$ alkyl group, a $C_{3-8}$ cycloalkyl group, a $C_{6-10}$ aryl group, a $C_{1-6}$ alkoxy group, a $C_{3-8}$ cycloalkoxy group, a $C_{6-10}$ aryloxy group, a ($C_{6-10}$ aryl)$C_{1-6}$ alkoxy group, a $C_{1-6}$ alkylthio group, or a di($C_{1-6}$ alkyl)amino group;

$R^7$ represents hydrogen or a $C_{1-6}$ alkyl group; and

W represents a $C_{1-6}$ alkoxy group, a $C_{1-6}$ alkylthio group, a $C_{1-6}$ alkylsulfinyl group, a $C_{1-6}$ alkylsulfonyl group, or a phenyl group optionally substituted with one or more substituents selected from Group A: provided that any of $R^3$, $R^4$, $R^5$, $R^6$, and W may be optionally substituted with halogens, and any of the $C_{3-8}$ cycloalkyl group, the $C_{6-10}$ aryl group, the aryl part of the ($C_{6-10}$ aryl)$C_{1-6}$ alkyl group, the $C_{3-8}$ cycloalkoxy group, the $C_{6-10}$ aryloxy group, the aryl part of the ($C_{6-10}$ aryl)$C_{1-6}$ alkoxy group, the aryl part of the ($C_{1-6}$ alkyl)($C_{6-10}$ aryl)amino group, and the 5-6 membered heteroaryl group may be optionally substituted with a $C_{1-6}$ alkyl group;

Z represents halogen, a cyano group, a nitro group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, or a $C_{3-8}$ cycloalkyl group: provided that for the Z group, the $C_{1-6}$ alkyl group, the $C_{2-6}$ alkenyl group, the $C_{2-6}$ alkynyl group, the $C_{1-6}$ alkoxy group, and the $C_{1-6}$ alkylthio group may be optionally substituted with halogens, and the $C_{3-8}$ cycloalkyl group may be optionally substituted with at least one group selected from the group consisting of halogen and a $C_{1-6}$ alkyl group;

n represents an integer of 1-5: provided that when n is 2 or more, each of Z may be same or different; and the Group A consists of halogen, a $C_{1-6}$ alkyl group, or a $C_{1-6}$ alkoxy group.

2. The pyridazinone compound according to claim 1 wherein $R^1$ is hydrogen, a $C_{1-3}$ alkyl group, a $C_{1-3}$ haloalkyl group, a ($C_{3-6}$ cycloalkyl)methyl group, a $C_{3-6}$ alkenyl group, a $C_{3-6}$ alkynyl group, or a benzyl group;

$R^2$ is a $C_{1-3}$ alkoxy group, a $C_{1-3}$ alkylthio group, a $C_{1-3}$ alkylsulfinyl group, a $C_{1-3}$ alkylsulfonyl group, a di($C_{1-3}$ alkyl)amino group, a halogen, a cyano group, a nitro group, a $C_{1-3}$ haloalkoxy group, a cyclopropyl$C_{1-3}$ alkoxy group, a ($C_{1-3}$ alkylthio)$C_{1-3}$ alkoxy group, a ($C_{1-3}$ alkoxy)$C_{1-3}$ alkoxy group, a $C_{3-6}$ alkenyloxy group, a $C_{3-6}$ alkynyloxy group, a cyano$C_{1-3}$ alkoxy group, an amino group, a formylamino group, a ($C_{1-3}$ alkyl)carbonylamino group, a hydroxy$C_{1-3}$ alkyl group, a ($C_{1-3}$ alkoxy)$C_{1-3}$ alkyl group, a cyano$C_{1-3}$ alkyl group, a hydroxyiminomethyl group, a methoxyiminomethyl group, or a formyl group;

G is hydrogen or a group of the following formula:

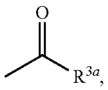

—$CH_2W^a$ wherein, $R^{3a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group, or a $C_{6-10}$ aryloxy group; and $W^a$ is a $C_{1-3}$ alkoxy group;

Z is a $C_{1-3}$ alkyl group, a $C_{2-6}$ alkenyl group, or a $C_{2-6}$ alkynyl group; and n is an integer of 1-3: wherein when n is 2 or more, each of Z may be same or different.

3. The pyridazinone compound according; to claim 2 wherein R is a methyl group;

$R^2$ is a methoxy group, an ethoxy group, a methylthio group, a methylsulfinyl group, a methylsulfonyl group, a dimethylamino group, a fluorine atom, a chlorine atom, a bromine atom, a cyano group, a nitro group, a cyclopropylmethyloxy group, a methylthiomethoxy group, a methoxymethoxy group, an allyloxy group, a propargyloxy group, a cyanomethyloxy group, an amino group, an acetamide group, a hydroxymethyl group, a methoxymethyl group, a cyanomethyl group, a hydroxyiminomethyl group, or a formyl group;

G is hydrogen, an acetyl group, a propionyl group, a benzoyl group, a methoxycarbonyl group, an ethoxycarbonyl group, an allyloxycarbonyl group, a phenoxycarbonyl group, a methoxymethyl group, or an ethoxymethyl group; and Z is a methyl group, an ethyl group, a vinyl group, or an ethynyl group.

4. The pyridazinone compound according to claim 1 wherein G is hydrogen.

5. A herbicide comprising the pyridazinone compound according to claim 1 as an active ingredient.

6. A method of controlling a weed which comprises applying an effective amount of the pyridazinone compound according to claim 1 to a weed or soil where a weed is grown.

7. A noxious arthropod controlling agent which comprises the pyridazinone compound according to claim 1 as an active ingredient.

8. A method of controlling a noxious arthropod which comprises applying an effective amount of the pyridazinone compound according to claim 1 to a noxious arthropod or to a habitat of a noxious arthropod.

* * * * *